United States Patent
Hong et al.

(10) Patent No.: US 9,698,358 B2
(45) Date of Patent: Jul. 4, 2017

(54) NITROGEN-CONTAINING POLYCYCLIC COMPOUND AND ORGANIC ELECTROLUMINESCENT DEVICE USING THE SAME

(71) Applicant: LG CHEM, LTD., Seoul (KR)

(72) Inventors: Wanpyo Hong, Daejeon (KR); Kongkyeom Kim, Daejeon (KR); Hyok Joon Kwon, Daejeon (KR); Hoyong Lee, Daejeon (KR); Minjun Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 77 days.

(21) Appl. No.: 14/941,194

(22) Filed: Nov. 13, 2015

(65) Prior Publication Data
US 2016/0141518 A1  May 19, 2016

(30) Foreign Application Priority Data

Nov. 18, 2014 (KR) .................. 10-2014-0160811
Oct. 19, 2015 (KR) .................. 10-2015-0145445

(51) Int. Cl.
| | |
|---|---|
| H01L 51/50 | (2006.01) |
| H01L 51/00 | (2006.01) |
| C07D 403/14 | (2006.01) |
| C09K 11/02 | (2006.01) |
| C09K 11/06 | (2006.01) |
| C07D 409/14 | (2006.01) |
| C07D 405/14 | (2006.01) |
| C07D 401/04 | (2006.01) |
| C07D 401/14 | (2006.01) |
| C07D 403/10 | (2006.01) |
| H05B 33/14 | (2006.01) |

(52) U.S. Cl.
CPC ........ *H01L 51/0072* (2013.01); *C07D 401/04* (2013.01); *C07D 401/14* (2013.01); *C07D 403/10* (2013.01); *C07D 403/14* (2013.01); *C07D 405/14* (2013.01); *C07D 409/14* (2013.01); *C09K 11/02* (2013.01); *C09K 11/06* (2013.01); *H01L 51/0052* (2013.01); *H01L 51/0054* (2013.01); *H01L 51/0067* (2013.01); *H01L 51/0073* (2013.01); *H01L 51/0074* (2013.01); *H05B 33/14* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *H01L 51/5012* (2013.01); *H01L 51/5016* (2013.01)

(58) Field of Classification Search
None
See application file for complete search history.

(56) References Cited

U.S. PATENT DOCUMENTS

2014/0183413 A1* 7/2014 Ober .................. H01L 51/0071
                                                          252/500

FOREIGN PATENT DOCUMENTS

| KR | 10-2000-0051826 A | 8/2000 |
|---|---|---|
| KR | 10-2014-0103393 A | 8/2014 |

* cited by examiner

*Primary Examiner* — Gregory Clark
(74) *Attorney, Agent, or Firm* — Dentons US LLP

(57) ABSTRACT

Disclosed are a nitrogen-containing polycyclic compound and an organic electroluminescent device including the same.

19 Claims, 2 Drawing Sheets

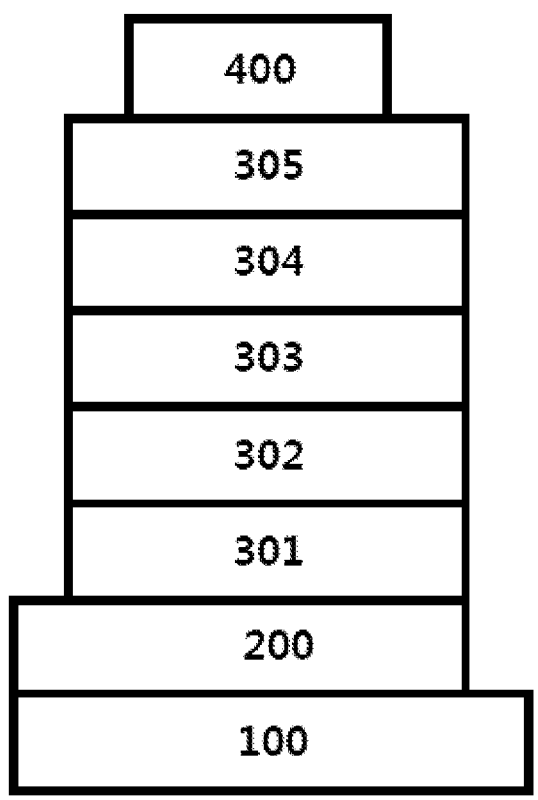

NITROGEN-CONTAINING POLYCYCLIC COMPOUND AND ORGANIC ELECTROLUMINESCENT DEVICE USING THE SAME

CROSS-REFERENCE TO RELATED APPLICATIONS

This application claims priority to and the benefit of Korean Patent Application No. 10-2014-0160811 filed in the Korean Intellectual Property Office on Nov. 18, 2014 and Korean Patent Application No. 10-2015-0145445 filed in the Korean Intellectual Property Office on Oct. 19, 2015, the entire contents of which are incorporated herein by reference.

TECHNICAL FIELD

The present specification relates to an organic electroluminescent device material and an organic electroluminescent device including the same.

BACKGROUND ART

An electroluminescent device is a kind of self-emitting type display device, and has an advantage in that the viewing angle is wide, the contrast is excellent, and the response speed is fast.

An organic light emitting device has a structure in which an organic thin film is disposed between two electrodes. When a voltage is applied to an organic light emitting device having the structure, electrons and holes injected from the two electrodes combine with each other in an organic thin film to make a pair, and then, emit light while being extinguished. The organic thin film may be composed of a single layer or multi layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition to the material, as the material for the organic thin film, it is also possible to use a compound, which may serve as hole injection, hole transport, electron blocking, hole blocking, electron transport or electron injection.

In order to improve the performance, service life or efficiency of an organic electroluminescent device, there is a continuous need for developing a material for an organic thin film.

CITATION LIST

Patent Document

Official Gazette of Korean Patent Application Laid-Open No. 2000-0051826

SUMMARY OF THE INVENTION

The present specification provides a nitrogen-containing polycyclic compound and an organic electroluminescent device including the same.

An exemplary embodiment of the present specification provides a compound represented by the following Formula 1:

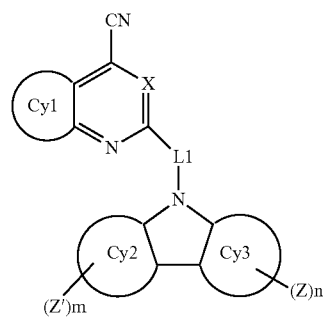

[Formula 1]

in Formula 1,

Cy1 to Cy3 are the same as or different from each other, and are each independently a substituted or unsubstituted aromatic hydrocarbon ring having 6 to 30 carbon atoms; or a substituted or unsubstituted heterocyclic group, X is N or CR, L1 is a direct bond; a substituted or unsubstituted divalent aromatic hydrocarbon ring group having 6 to 30 carbon atoms; or a substituted or unsubstituted divalent heterocyclic group having 6 to 30 carbon atoms, Z and Z' are the same as or different from each other, at least one of Z and Z' is represented by any one of the following Formulae 2 to 6,

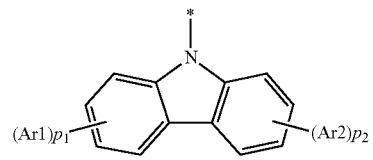

[Formula 2]

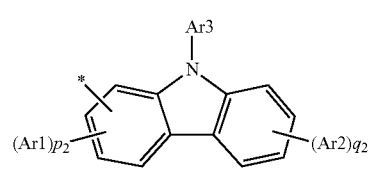

[Formula 3]

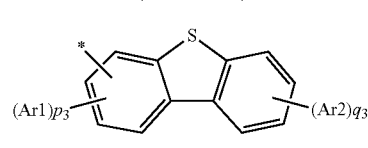

[Formula 4]

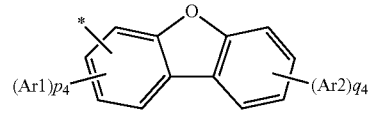

[Formula 5]

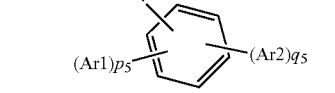

[Formula 6]

n and m are each independently 0 or 1, at least one of n and m is 1, $p_1$ and $q_1$ are each independently an integer of 1 to 4, $p_2$ to $p_4$ are each independently an integer of 1 to 3, and $q_2$ to $q_4$ are each independently an integer of 1 to 4, $p_5$ and $q_5$ are each independently an integer of 1 to 5, and p+q is 5 or less, when $p_1$ to $p_5$ are each independently an integer of 2 or more, a plurality of Ar1's is the same as or different from each other, when $q_1$ to $q_5$ are each independently an integer of 2 or more, a plurality of Ar2's is the same as or different from each other, and R and An to Ar3 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphineoxide group; a substituted or unsubstituted aryl group; or a substituted or unsubstituted heterocyclic group, or optionally combine with an adjacent group to form a ring.

The present specification provides an organic electroluminescent device including: a first electrode; a second electrode provided to face the first electrode; and one or more organic material layers provided between the first electrode and the second electrode, in which one or more layers of the organic material layers include the compound of Formula 1.

The compound according to the present specification may be used as a material for the organic material layer of the organic electroluminescent device. The compound may serve as a hole injection material, a hole transporting material, a light emitting material, an electron transporting material, an electron injection material, and the like. The compound according to an exemplary embodiment may also be used as a light emitting host material of an organic electroluminescent device, for example, a phosphorescent host material, particularly, a red phosphorescent host material. The compound according to another exemplary embodiment may also be used as a material for an electron transporting layer of an organic electroluminescent device.

BRIEF DESCRIPTION OF THE DRAWINGS

FIGS. 1 to 3 illustrate a stacking sequence of electrodes and organic material layers of an organic electroluminescent device according to exemplary embodiments of the present invention.

DETAILED DESCRIPTION

Figure 1:
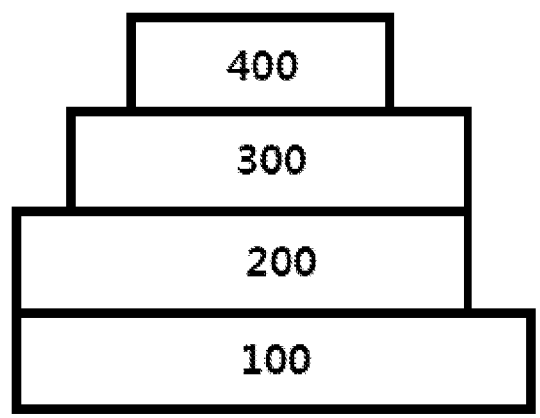

Hereinafter, the present specification will be described in more detail.

The present specification provides a compound represented by Formula 1.

In the present specification, * and

mean a position in which the compound is bonded to another substituent.

In the present specification, the term "substituted or unsubstituted" means being unsubstituted or substituted with one or more substituents selected from the group consisting of deuterium; a halogen group; a nitrile group; a nitro group; an amino group; a phosphineoxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an arylamine group; or a substituted or unsubstituted carbazole group; a substituted or unsubstituted dibenzofuran group; or a substituted or unsubstituted dibenzothiophene group, or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine. In the present specification, the number of carbon atoms of a carbonyl group is not particularly limited, but is preferably 1 to 40.

Specifically, the substituent may be a compound having the following structures, but is not limited thereto.

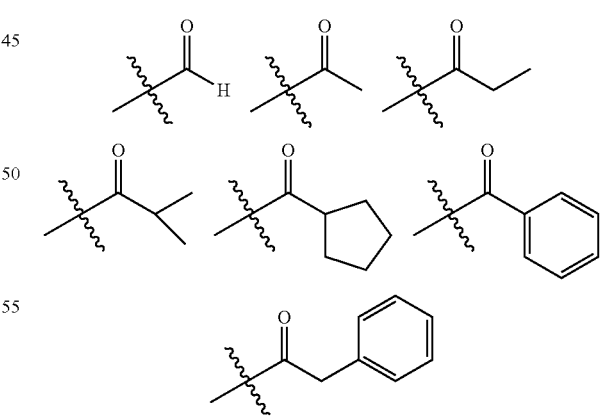

In the present specification, in an ester group, the oxygen of the ester group may be substituted with a straight-chained, branched, or cyclic alkyl group having 1 to 25 carbon atoms, or an aryl group having 6 to 25 carbon atoms. Specifically, the ester group may be a compound having the following structural formulae, but is not limited thereto.

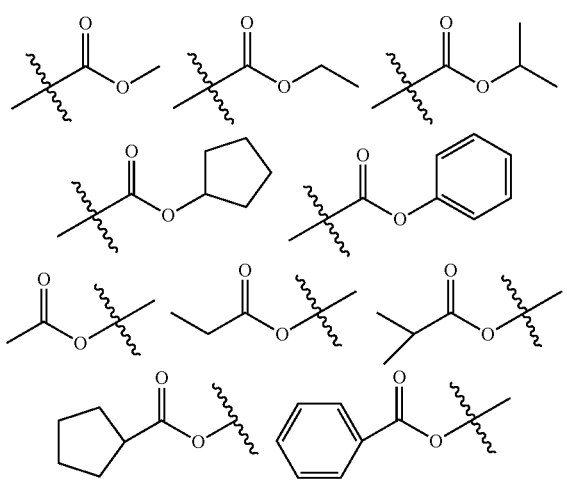

In the present specification, the number of carbon atoms of an imide group is not particularly limited, but is preferably 1 to 25. Specifically, the imide group may be a compound having the following structures, but is not limited thereto.

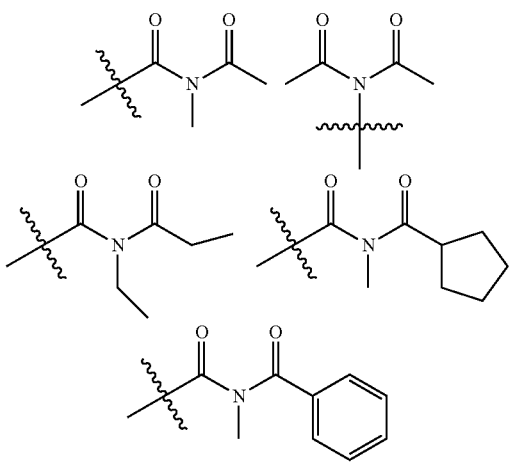

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, specific examples of a boron group include a trimethylboron group, a triethylboron group, a t-butyldimethylboron group, a triphenylboron group, a phenylboron group, and the like, but are not limited thereto.

In the present specification, the alkyl group may be straight-chained or branched, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohectylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto. In the present specification, a cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to still another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branched, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the number of carbon atoms of an amine group is not particularly limited, but is preferably 1 to 30. Specific examples of the amine group include a methylamine group, a dimethylamine group, an ethylamine group, a diethylamine group, and the like, but are not limited thereto.

In the present specification, the aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and two substituents may combine with each other to form a spiro structure.

When the fluorenyl group is substituted, the group may be

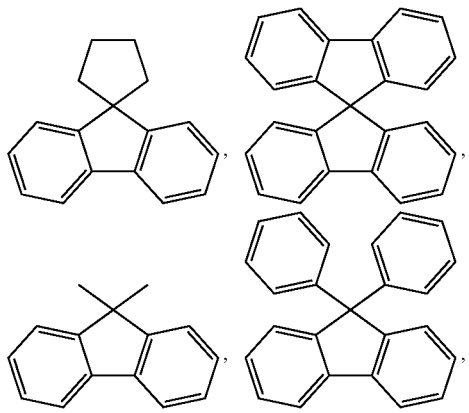

and the like. However, the group is not limited thereto.

In the present specification, a heterocyclic group is a heterocyclic group including one or more of O, N, and S as a hetero element, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aryloxy group, the arylthioxy group, the arylsulfoxy group, the arylphosphine group, the aralkyl group, the aralkylamine group, the aralkenyl group, the alkylaryl group, and the arylamine group is the same as the above-described examples of the aryl group.

In the present specification, the alkyl group in the alkylthioxy group, the alkylsulfoxy group, the aralkyl group, the aralkylamine group, the alkylaryl group, and the alkylamine group is the same as the above-described examples of the alkyl group.

In the present specification, the above-described description on the heterocyclic group may be applied to a heteroaryl group of a heteroaryl group and a heteroarylamine group.

In the present specification, the alkenyl group in the aralkenyl group is the same as the above-described examples of the alkenyl group.

In the present specification, the meaning of combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; or a substituted or unsubstituted aromatic hetero ring.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as "an adjacent group" to each other.

In the present specification, the aliphatic hydrocarbon ring means a ring composed only of carbon and hydrogen atoms as a ring which is not an aromatic group. In the present specification, examples of the aromatic hydrocarbon ring include a phenyl group, a naphthyl group, an anthracenyl group, and the like, but are not limited thereto.

In the present specification, the aliphatic hetero ring means an aliphatic ring including one or more of N, O, and S atoms as a hetero atom.

In the present specification, the aromatic hetero ring means an aromatic ring including one or more of N, O, and S atoms as a hetero atom.

In the present specification, the aliphatic hydrocarbon ring, the aromatic hydrocarbon ring, the aliphatic hetero ring, and the aromatic hetero ring may be monocyclic or polycyclic.

In an exemplary embodiment of the present specification, Cy1 is a substituted or unsubstituted monocyclic aromatic hydrocarbon ring having 6 to 30 carbon atoms; or a substituted or unsubstituted monocyclic heterocyclic group including one or more N atoms.

In an exemplary embodiment of the present specification, Cy1 is a substituted or unsubstituted benzene.

In an exemplary embodiment of the present specification, Cy1 is a benzene which is unsubstituted or substituted with one or two or more substituents selected from the group consisting of a halogen group; an alkyl group; a substituted or unsubstituted aryl group having 6 to 30 carbon atoms; or a substituted or unsubstituted heterocyclic group having 2 to 30 atoms.

In an exemplary embodiment of the present specification, Cy1 is a benzene which is unsubstituted or substituted with one or two or more substituents selected from the group consisting of a halogen group; an alkyl group; a substituted or unsubstituted phenyl group; or a substituted or unsubstituted pyridine group.

In an exemplary embodiment of the present specification, Cy1 is a benzene.

In an exemplary embodiment of the present specification, Cy2 is a substituted or unsubstituted aromatic hydrocarbon ring having 6 to 30 carbon atoms.

In an exemplary embodiment of the present specification, Cy2 is a substituted or unsubstituted naphthalene; or a substituted or unsubstituted benzene.

In an exemplary embodiment of the present specification, Cy2 is a substituted or unsubstituted benzene.

In an exemplary embodiment of the present specification, Cy2 is a benzene.

In an exemplary embodiment of the present specification, Cy2 is a substituted or unsubstituted naphthalene.

In an exemplary embodiment of the present specification, Cy2 is a naphthalene.

In an exemplary embodiment of the present specification, Cy3 is a substituted or unsubstituted aromatic hydrocarbon ring having 6 to 30 carbon atoms.

In an exemplary embodiment of the present specification, Cy3 is a substituted or unsubstituted naphthalene; or a substituted or unsubstituted benzene.

In an exemplary embodiment of the present specification, Cy3 is a substituted or unsubstituted benzene.

In an exemplary embodiment of the present specification, Cy3 is a benzene.

In an exemplary embodiment of the present specification, Cy3 is a substituted or unsubstituted naphthalene.

In an exemplary embodiment of the present specification, Cy2 is a naphthalene.

In an exemplary embodiment of the present specification, Cy2 and Cy3 are a substituted or unsubstituted aromatic hydrocarbon ring having 6 to 30 carbon atoms.

In another exemplary embodiment, Cy2 and Cy3 are a substituted or unsubstituted benzene.

In an exemplary embodiment of the present specification, Cy2 is a substituted or unsubstituted naphthalene, and Cy3 is a substituted or unsubstituted benzene.

In an exemplary embodiment of the present specification, Cy2 is a substituted or unsubstituted benzene, and Cy3 is a substituted or unsubstituted naphthalene.

In an exemplary embodiment of the present specification, m is 0.

In an exemplary embodiment of the present specification, n is 1.

In an exemplary embodiment of the present specification, m is 0, and n is 1.

In an exemplary embodiment of the present specification, X is CR.

In an exemplary embodiment of the present specification, X is CR, and R is hydrogen or a substituted or unsubstituted aryl group.

In an exemplary embodiment of the present specification, X is CR, and R is hydrogen.

In an exemplary embodiment of the present specification, X is CR, and R is a substituted or unsubstituted benzene.

In an exemplary embodiment of the present specification, X is N.

In an exemplary embodiment of the present specification, L1 is a direct bond; or a substituted or unsubstituted divalent aromatic hydrocarbon ring group having 6 to 30 carbon atoms.

In an exemplary embodiment of the present specification, L1 is a direct bond; a substituted or unsubstituted phenylene group; or a substituted unsubstituted divalent naphthalene group.

In another exemplary embodiment, L1 is a direct bond.

In an exemplary embodiment of the present specification, L1 is a substituted or unsubstituted divalent aromatic hydrocarbon ring group having 6 to 30 carbon atoms.

In an exemplary embodiment of the present specification, L1 is a substituted or unsubstituted phenylene group; or a substituted unsubstituted divalent naphthalene group.

In an exemplary embodiment of the present specification, at least one of Z and Z' is represented by Formula 2 or 3.

In another exemplary embodiment, at least one of Z and Z' is represented by any one of Formulae 4 to 6.

In an exemplary embodiment of the present specification, at least one of Z and Z' is represented by Formula 7.

In an exemplary embodiment of the present specification, at least one of Z and Z' is a substituted or unsubstituted carbazole group; or a substituted or unsubstituted benzocarbazole group.

In an exemplary embodiment of the present specification, at least one of Z and Z' is a carbazole group which is unsubstituted or substituted with a substituted or unsubstituted aryl group having 6 to 30 carbon atoms; or a benzocarbazole group which is unsubstituted or substituted with a substituted or unsubstituted aryl group having 6 to 30 carbon atoms.

In the present specification, the (benzo)carbazole group means a carbazole group or a benzocarbazole group.

In an exemplary embodiment of the present specification, at least one of Z and Z' is a (benzo)carbazole group which is unsubstituted or substituted with one or more substituents selected from the group consisting of a substituted or unsubstituted phenyl group, a substituted or unsubstituted biphenyl group, or a substituted or unsubstituted fluorenyl group.

In an exemplary embodiment of the present specification, at least one of Z and Z' is a (benzo)carbazole group which is unsubstituted or substituted with a naphthyl group or deuterium.

In another exemplary embodiment, Z and Z' are a substituted or unsubstituted carbazole group.

In an exemplary embodiment of the present specification, Z and Z' are a carbazole group which is unsubstituted or substituted with an aryl group having 6 to 30 carbon atoms.

In an exemplary embodiment of the present specification, Z and Z' are a carbazole group which is unsubstituted or substituted with a substituted or unsubstituted phenyl group.

In an exemplary embodiment of the present specification, Formula 6 may be represented by a substituted or unsubstituted phenyl group; a substituted or unsubstituted naphthyl group; a substituted or unsubstituted fluorenyl group; or a substituted or unsubstituted phenanthrene group.

In an exemplary embodiment of the present specification, at least one of Z and Z' is represented by any one of Formulae 2 and 6 and the following Formulae 7 to 18.

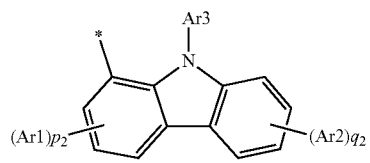

[Formula 7]

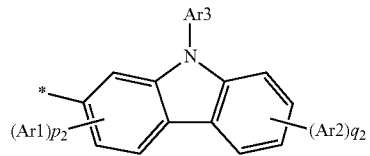

[Formula 8]

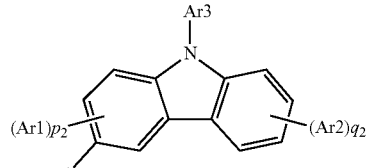

[Formula 9]

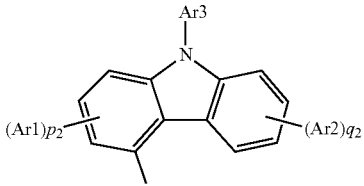

[Formula 10]

[Formula 11]

[Formula 12]

[Formula 13]

[Formula 14]

[Formula 15]

[Formula 16]

[Formula 17]

[Formula 18]

In Formulae 7 to 18|[x1], $p_2$ to $p_4$, $q_2$ to $q_4$, and Ar1 to Ar3 are the same as those described above.

In an exemplary embodiment of the present specification, $p_2$ is 1 or 2.

In an exemplary embodiment of the present specification, $p_2$ is 1.

In an exemplary embodiment of the present specification, $q_2$ is an integer of 1 to 3.

In an exemplary embodiment of the present specification, $q_2$ is 1 or 2.

In an exemplary embodiment of the present specification, $q_2$ is 1.

In another exemplary embodiment, $p_3$ is 1 or 2.

In an exemplary embodiment of the present specification, $p_3$ is 1.

In an exemplary embodiment of the present specification, $q_3$ is an integer of 1 to 3.

In an exemplary embodiment of the present specification, $q_3$ is 1 or 2.

In an exemplary embodiment of the present specification, $q_3$ is 1.

In an exemplary embodiment of the present specification, $p_4$ is 1 or 2.

In another exemplary embodiment, $p_4$ is 1.

In an exemplary embodiment of the present specification, $q_4$ is an integer of 1 to 3.

In an exemplary embodiment of the present specification, $q_4$ is 1 or 2.

In an exemplary embodiment of the present specification, $q_4$ is 1.

In Formulae 7 to 18, p, q, and An to Ar3 are the same as those defined in Formula 1.

In an exemplary embodiment of the present specification, m is 0, and Formula 1 is represented by any one of the following Formulae 1-1 to 1-7.

[Formula 1-1]

[Formula 1-2]

[Formula 1-3]

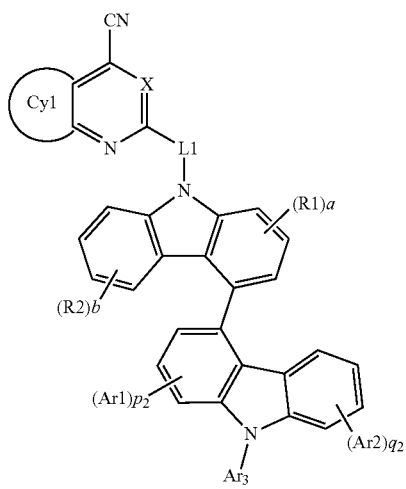

[Formula 1-4]

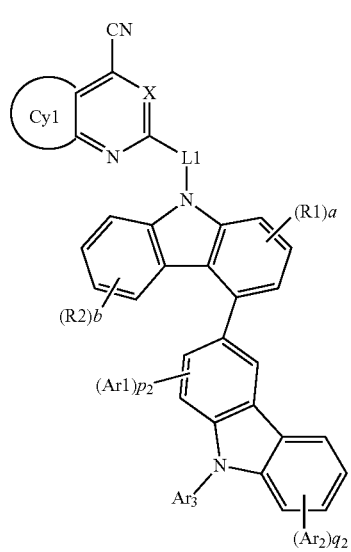

[Formula 1-5]

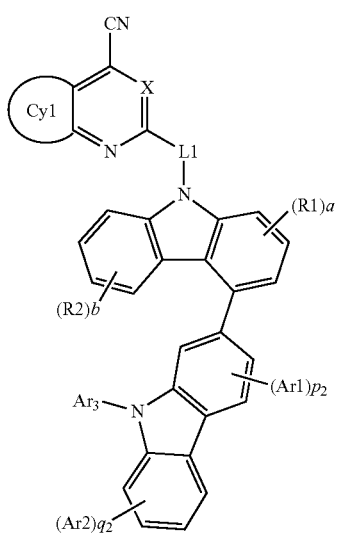

[Formula 1-6]

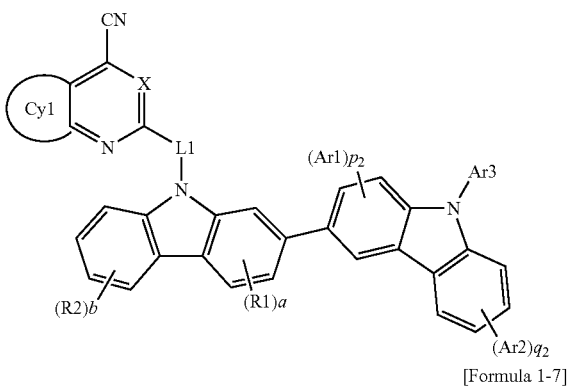

[Formula 1-7]

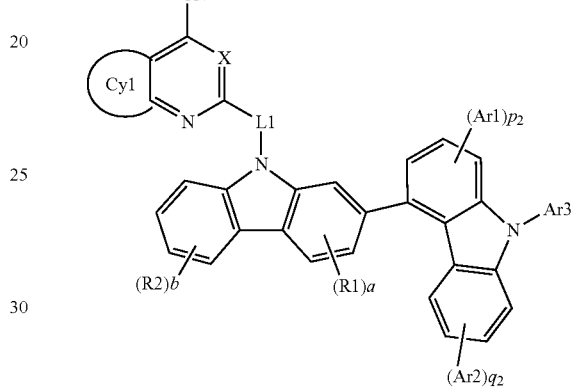

In Formulae 1-1 to 1-7,

Cy1, X, L1, Ar1 to Ar3, $p_2$ and $q_2$ are the same as those defined in Formula 1, R1 and R2 are the same as or different from each other, and the same as the definition of Ar1 to Ar3, a is an integer of 1 to 3, when a is an integer of 2 or more, a plurality of R1's is the same as or different from each other, b is an integer of 1 to 4, and when b is an integer of 2 or more, a plurality of R2's is the same as or different from each other.

In an exemplary embodiment of the present specification, Formula 1 is represented by the following Formula 1-8 or 1-9.

[Formula 1-8]

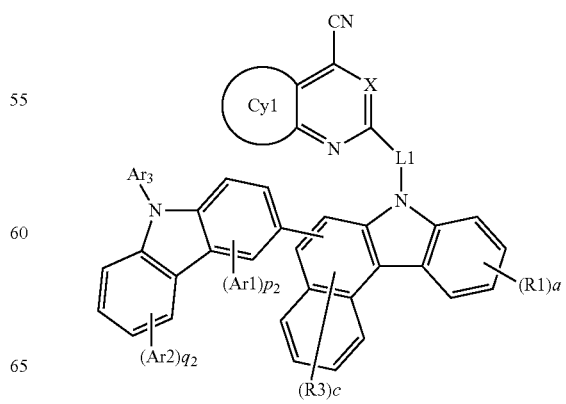

[Formula 1-9]

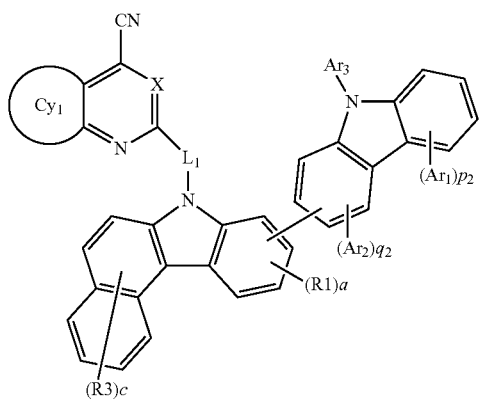

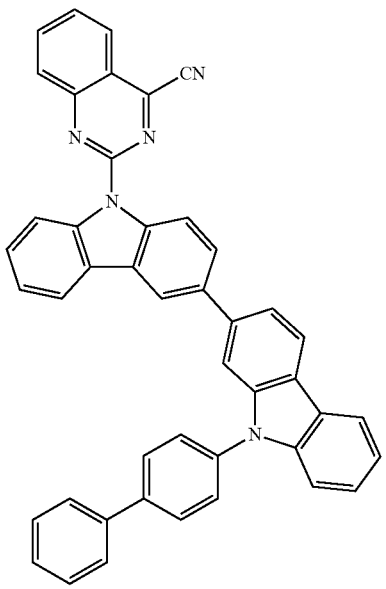

In Formulae 1-8 and 1-9,

Cy1, X, L1, Ar1 to Ar3, $p_2$, and $q_2$ are the same as those defined in Formula 1, R1 and R3 are the same as or different from each other, and the same as the definition of Ar1 to Ar3, a is an integer of 1 to 4, when a is an integer of 2 or more, a plurality of R1's is the same as or different from each other, c is an integer of 1 to 5, and when c is an integer of 2 or more, a plurality of R3's is the same as or different from each other.

In an exemplary embodiment of the present specification, the compound represented by Formula 1 may be represented by any one of the following structures.

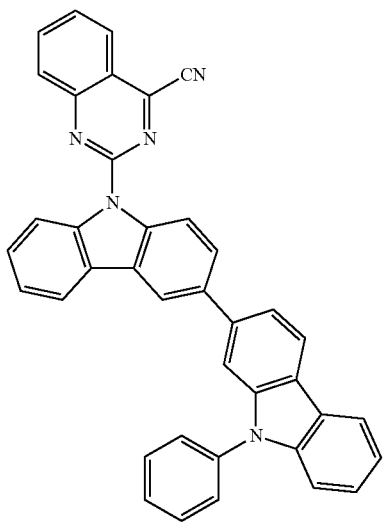

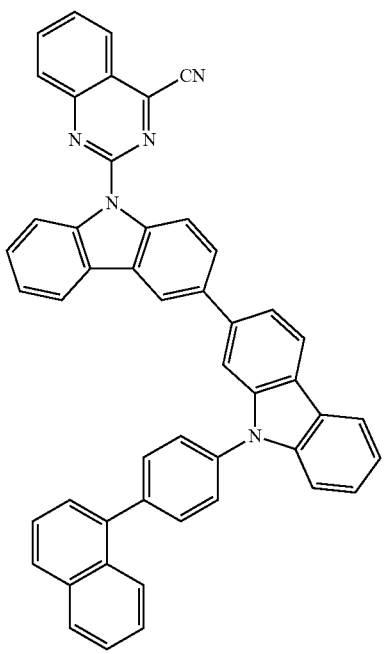

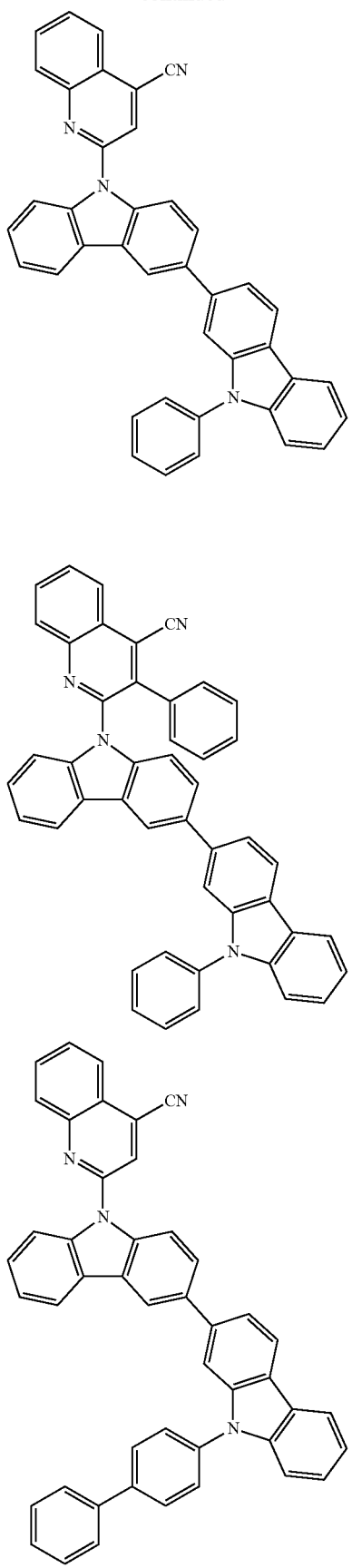
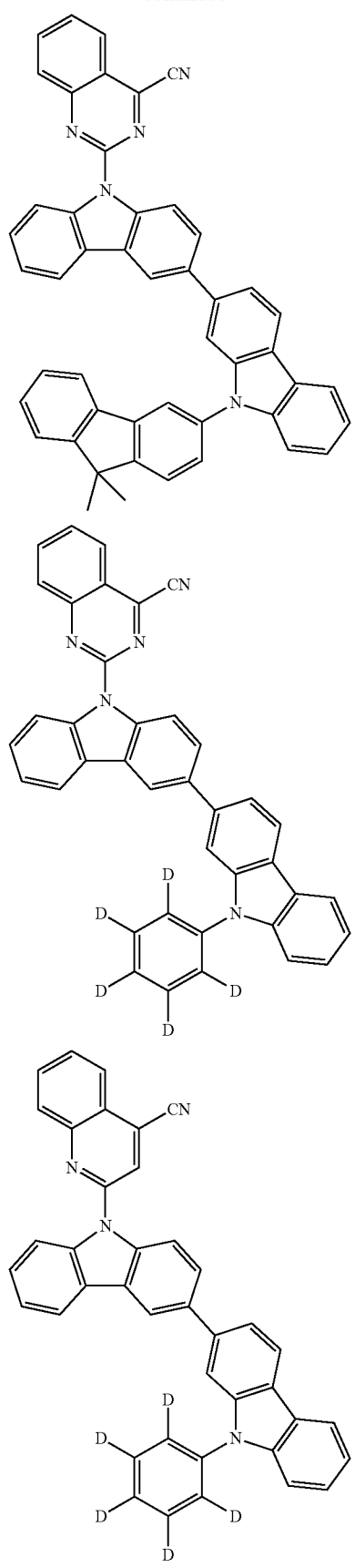

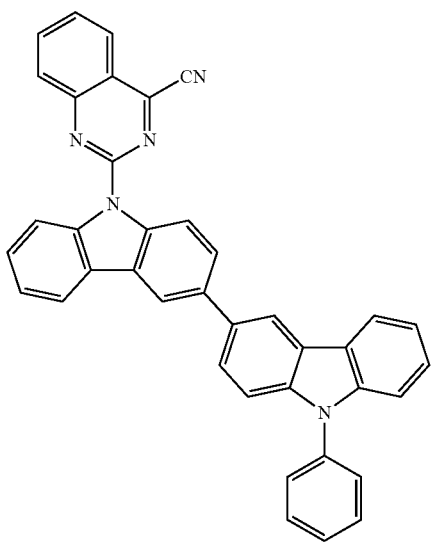
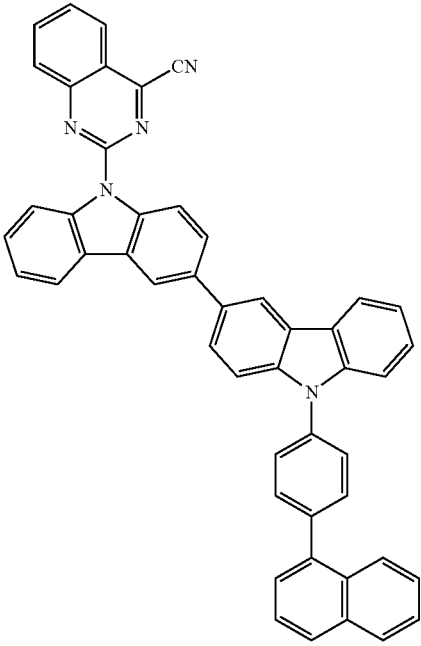
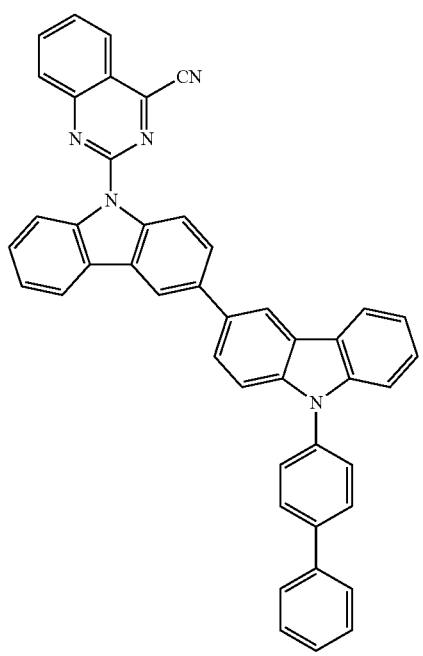
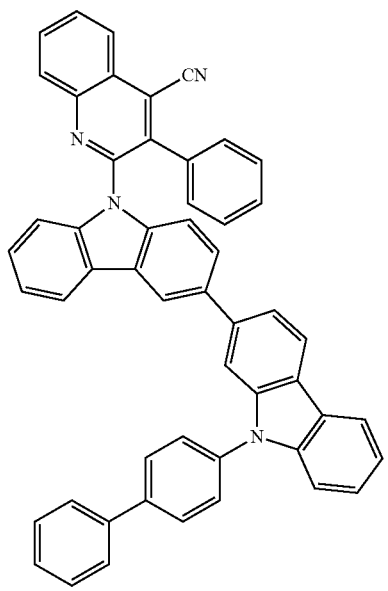

-continued
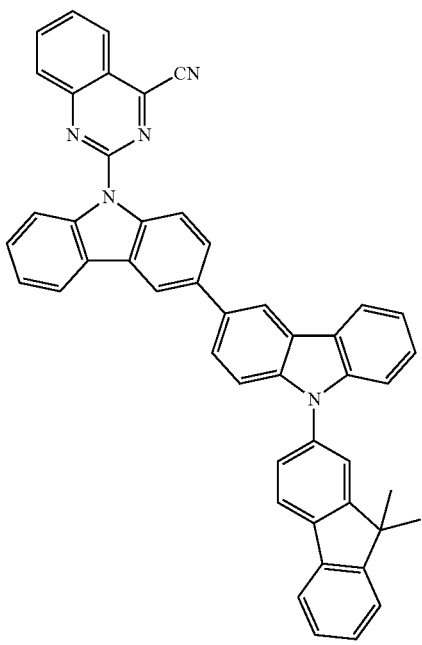
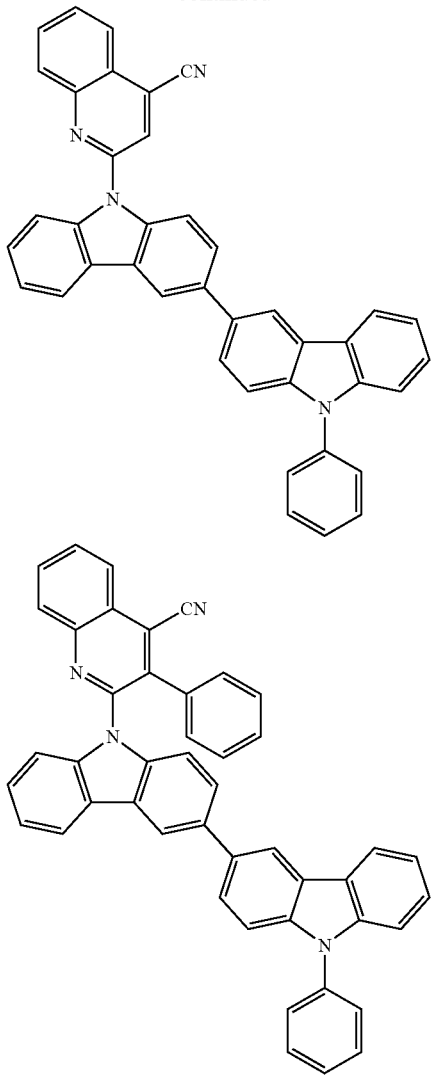
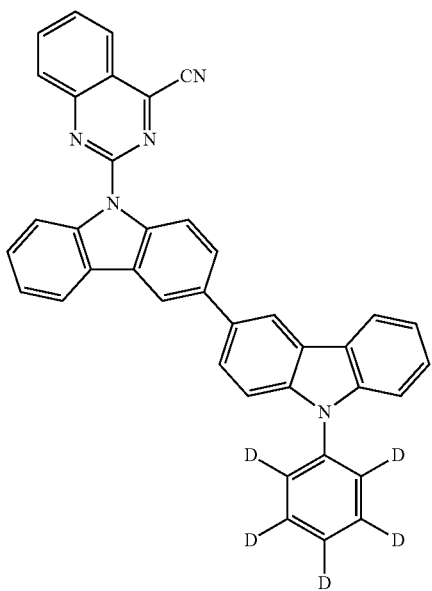
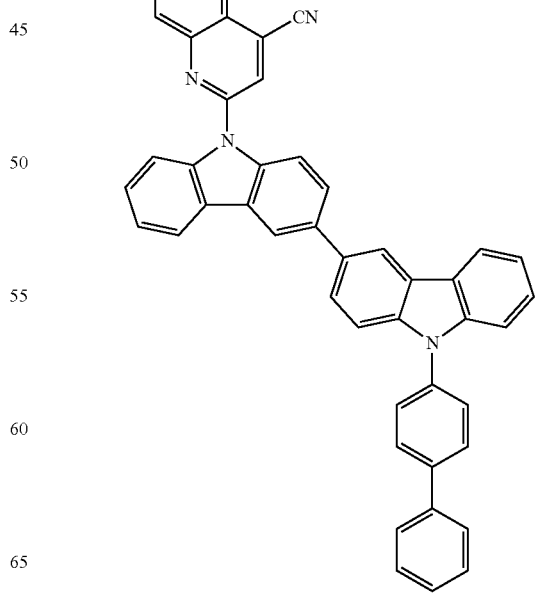

23
-continued
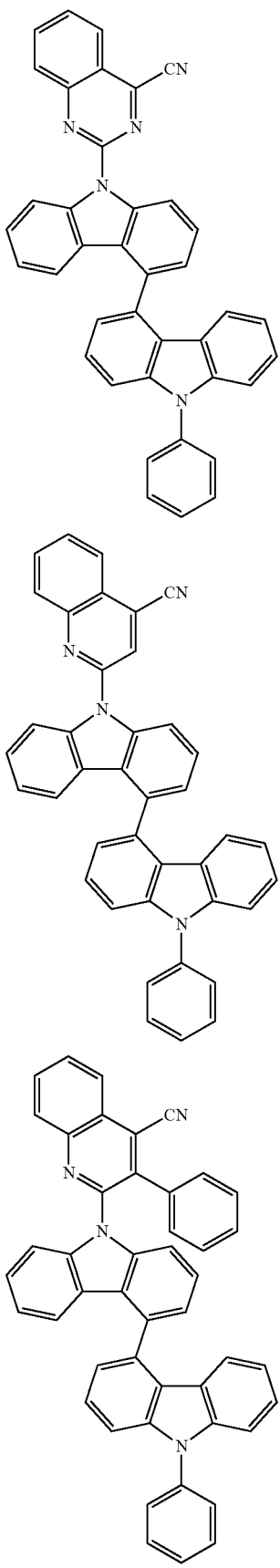 [SMILES: N#Cc1nc(-n2c3ccccc3c3c(-c4cccc5c4c4ccccc4n5-c4ccccc4)cccc32)nc2ccccc12 ; N#Cc1cc(-n2c3ccccc3c3c(-c4cccc5c4c4ccccc4n5-c4ccccc4)cccc32)nc2ccccc12 ; N#Cc1c(-c2ccccc2)c(-n2c3ccccc3c3c(-c4cccc5c4c4ccccc4n5-c4ccccc4)cccc32)nc2ccccc12]
24
-continued
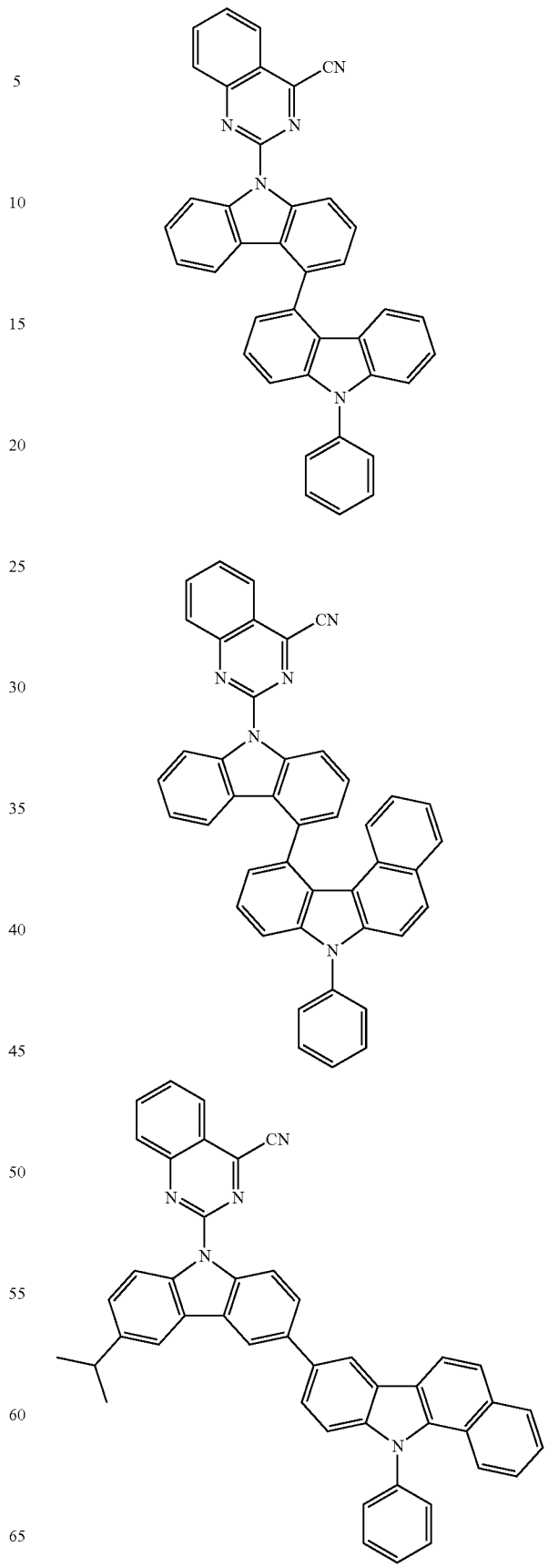

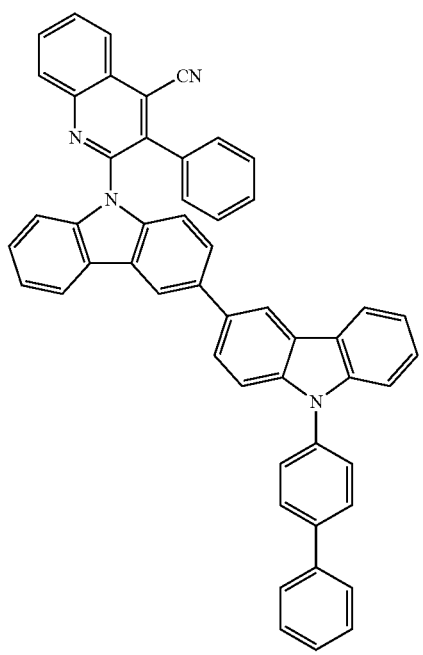
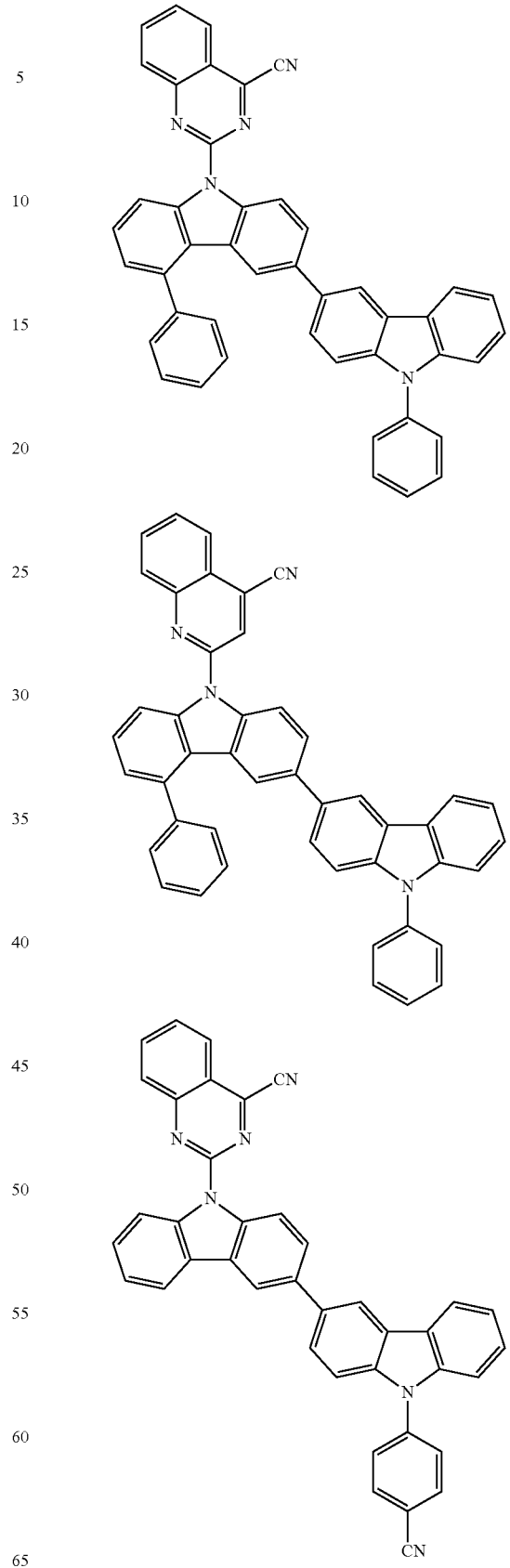

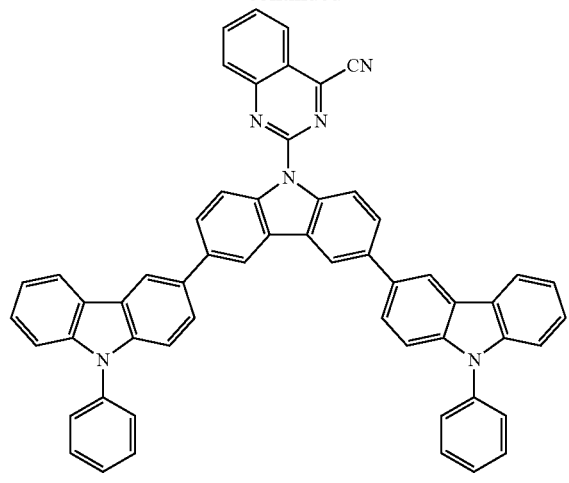
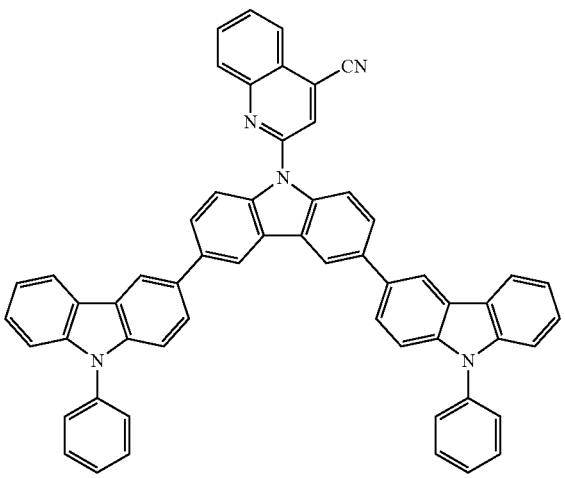

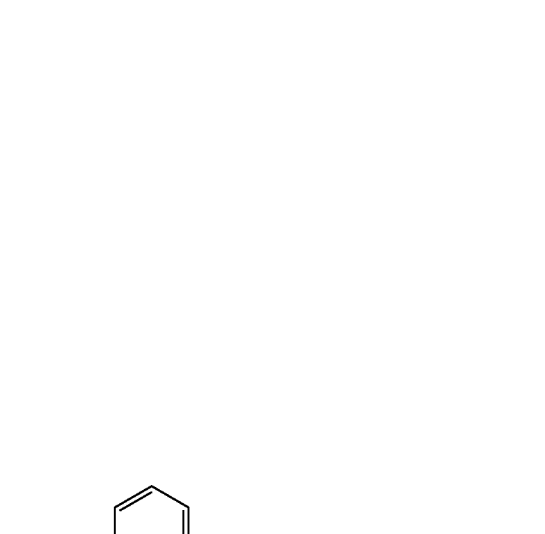
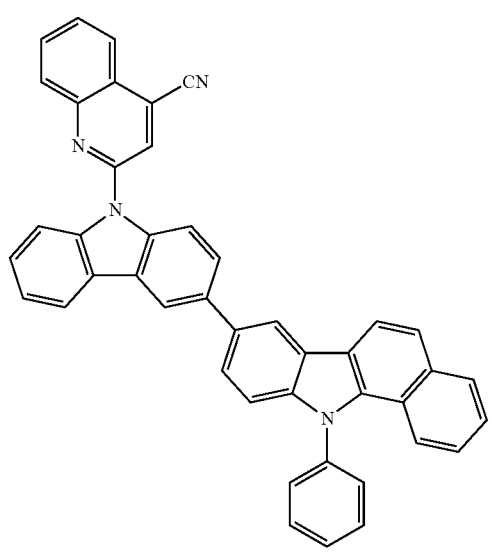
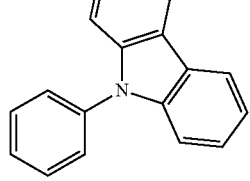

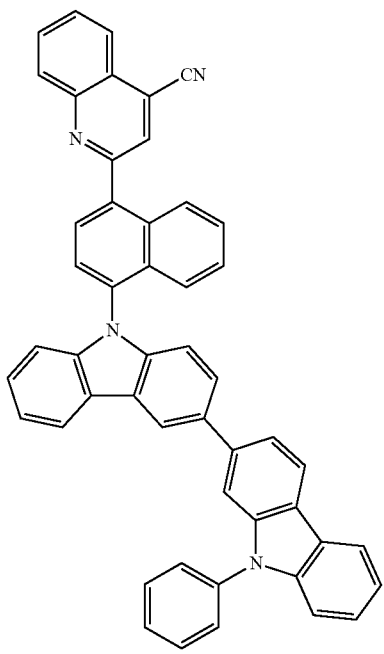
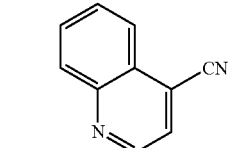
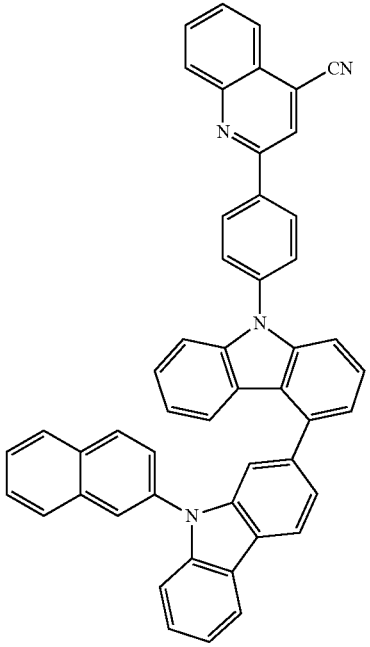
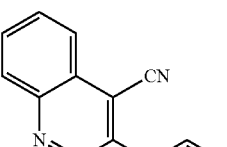

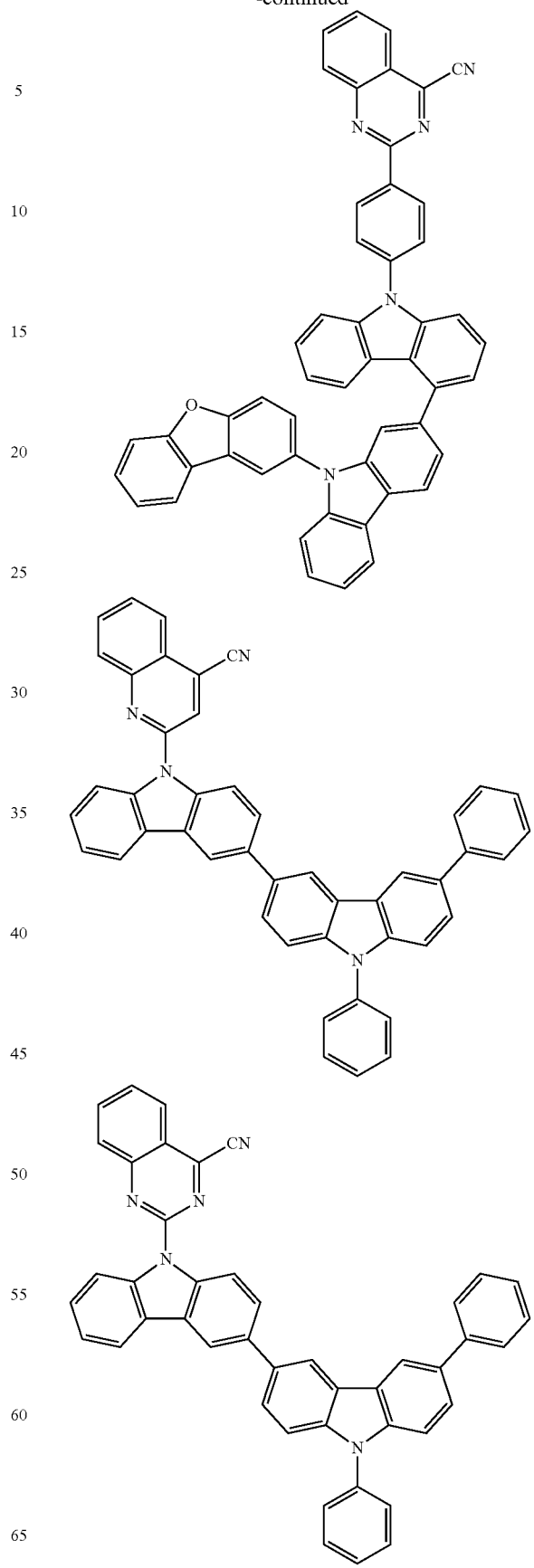

33
-continued
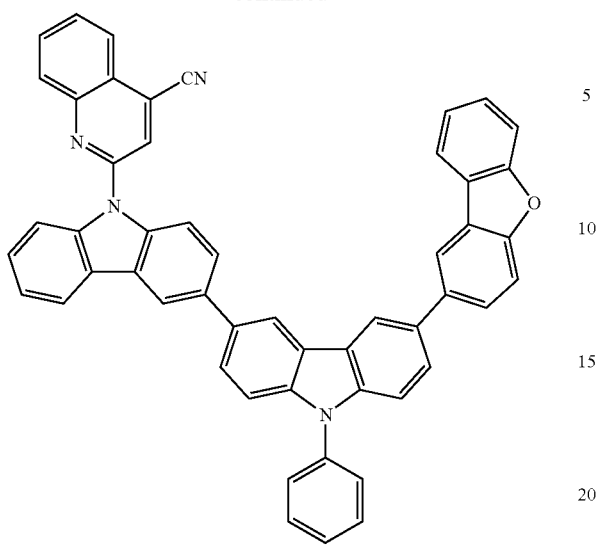
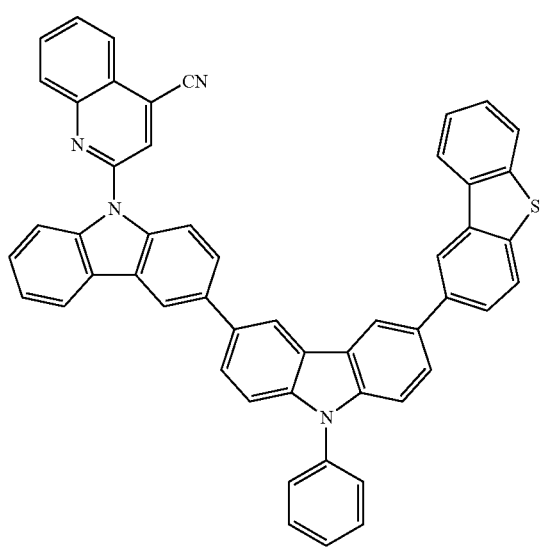
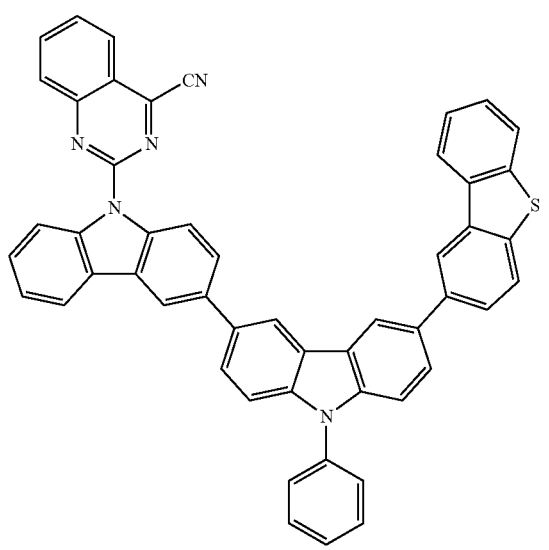
34
-continued
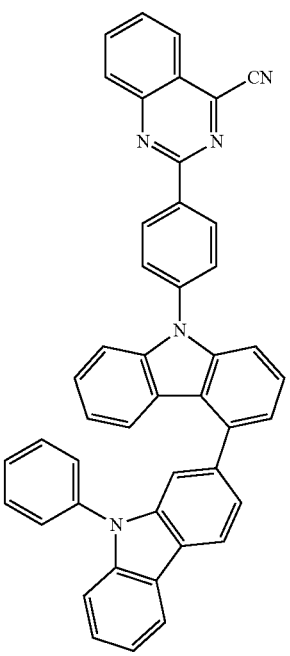
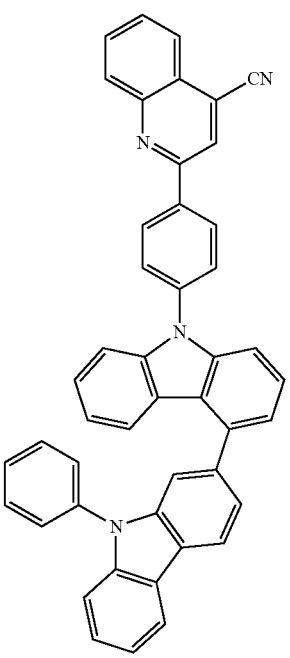

35
-continued
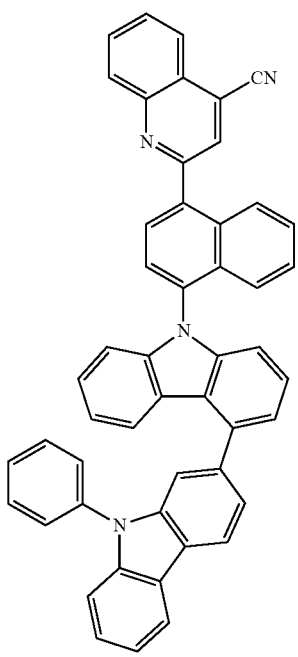
36
-continued
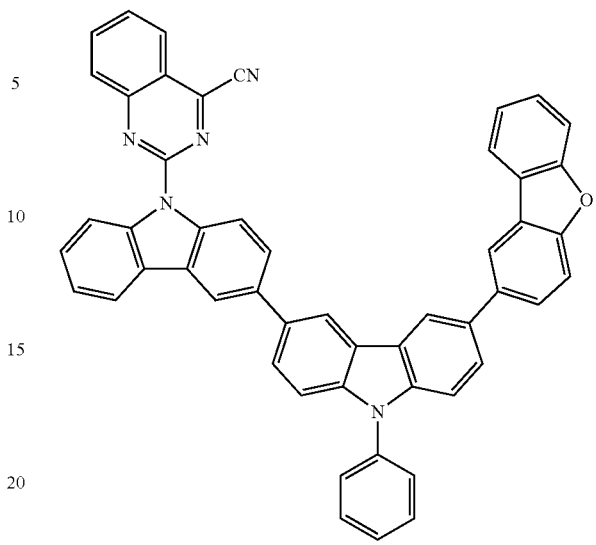
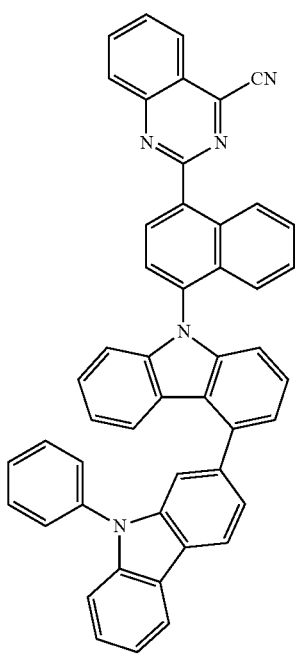

37
-continued
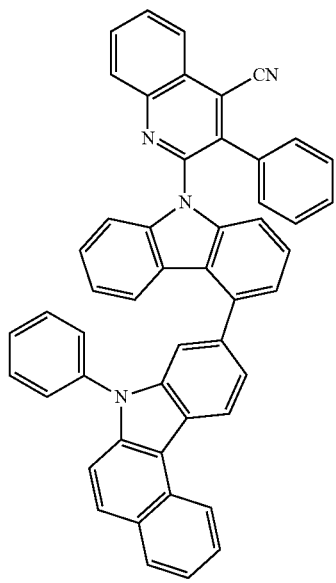
38
-continued
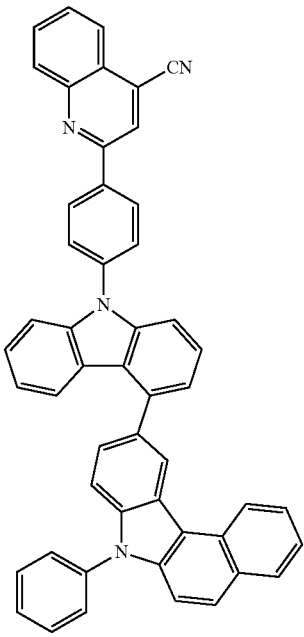
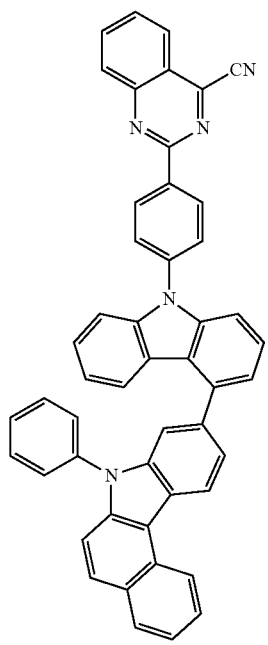
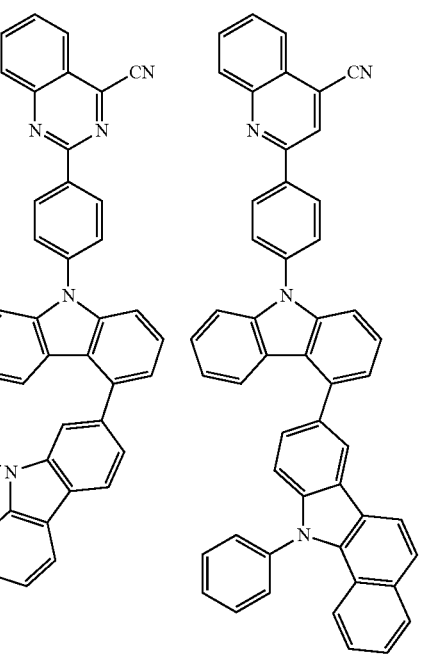

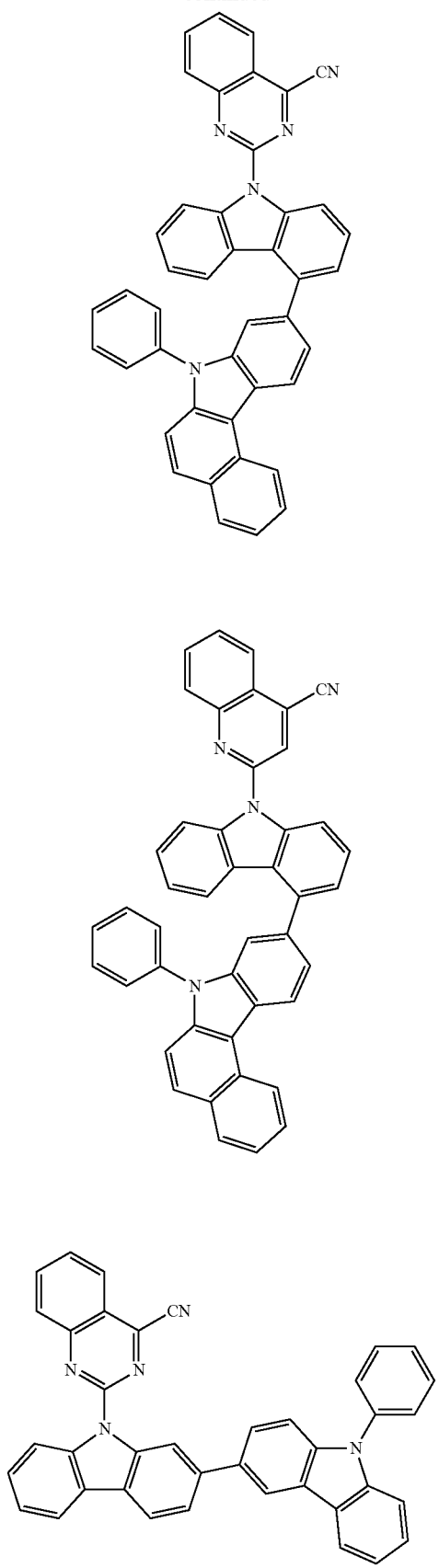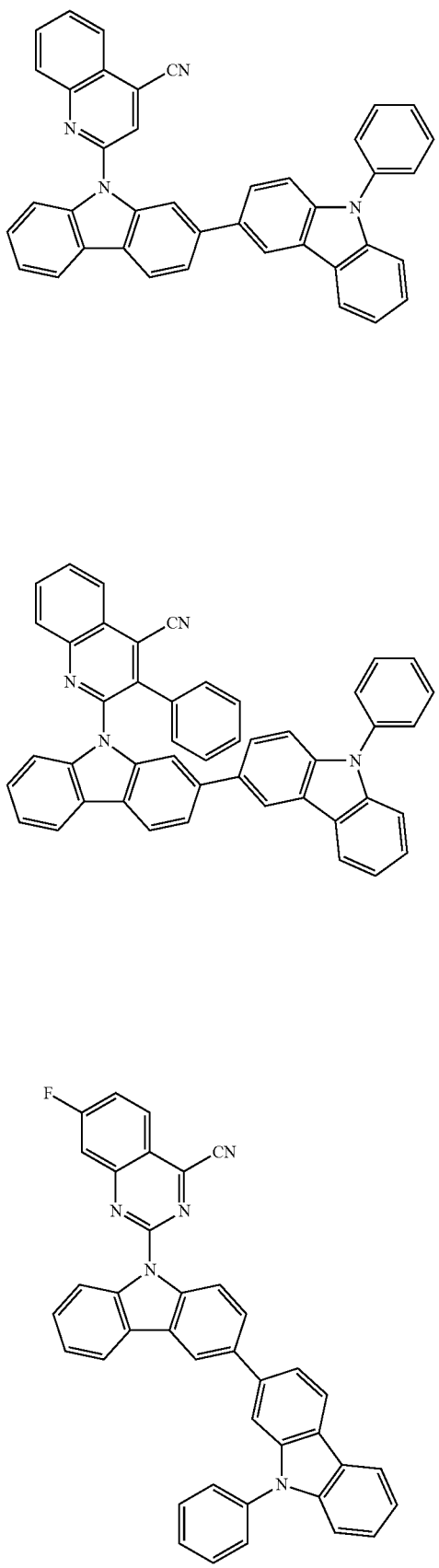

41
-continued
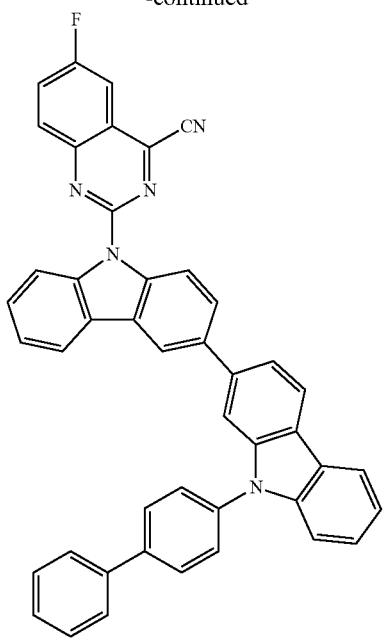
42
-continued
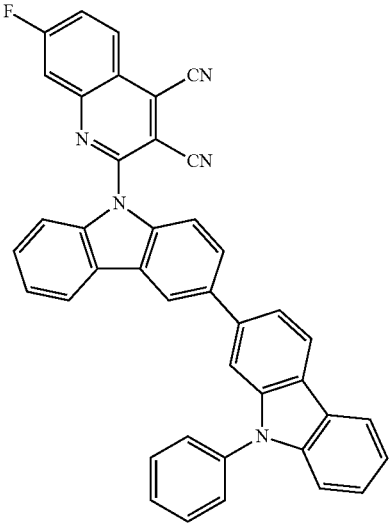
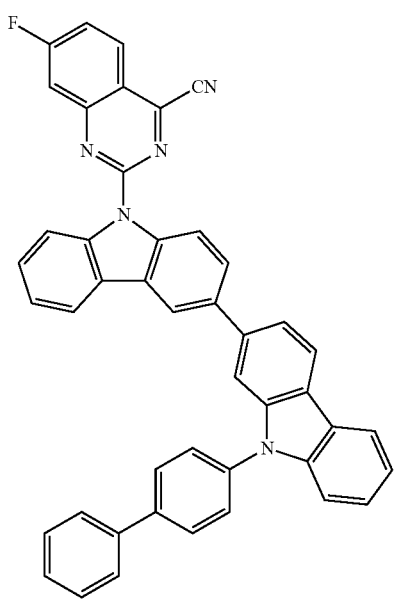
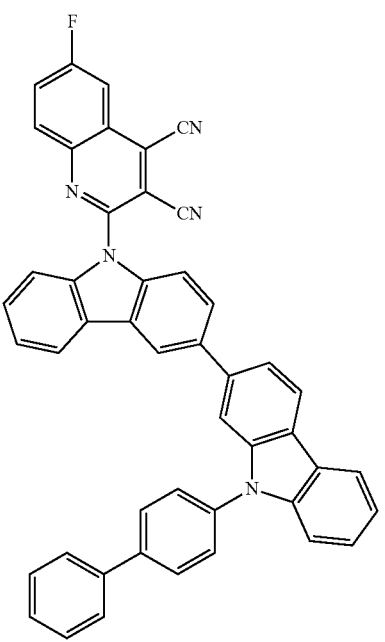

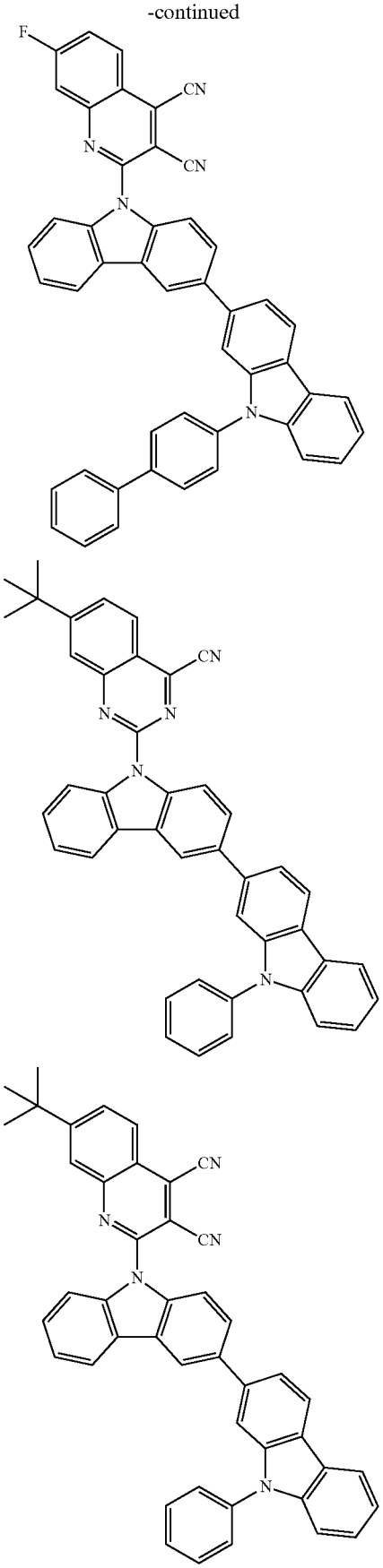
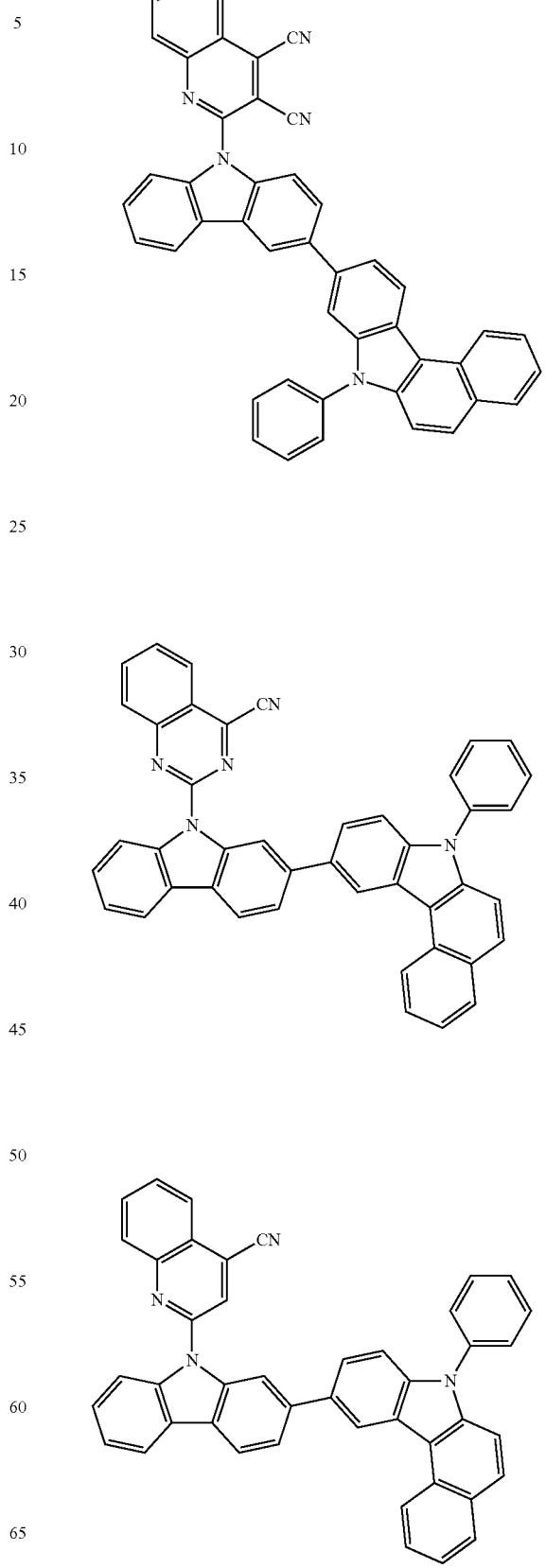

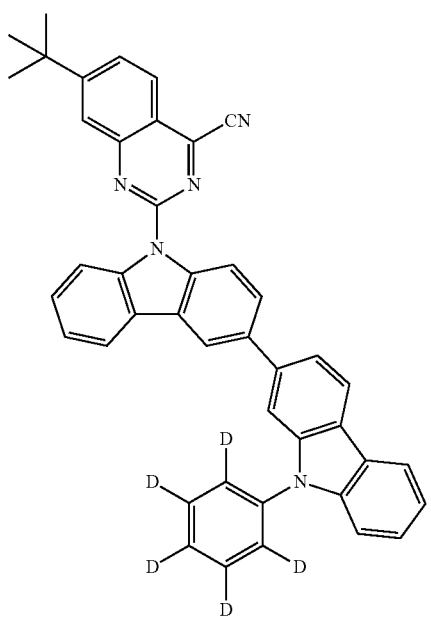
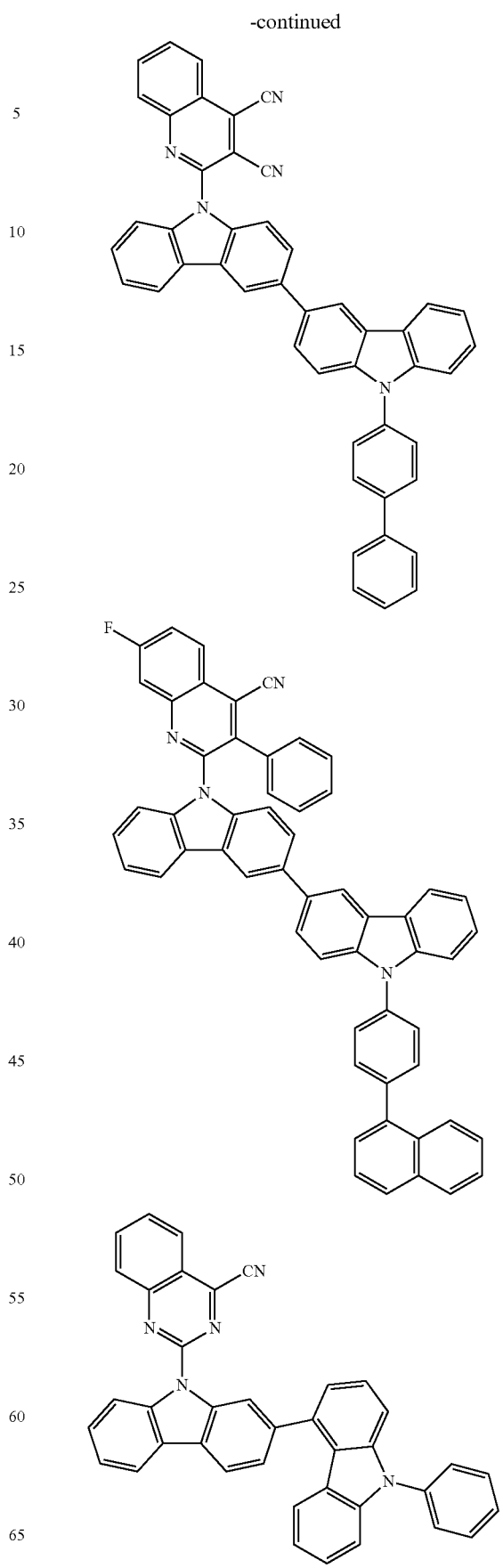

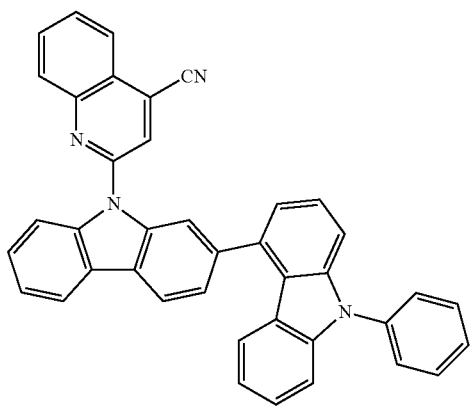
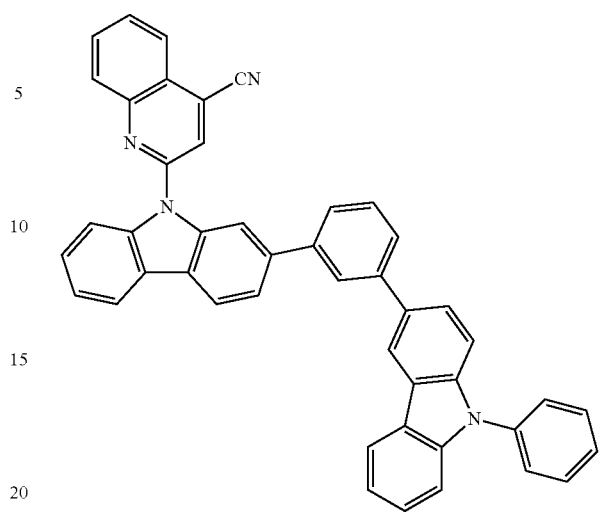
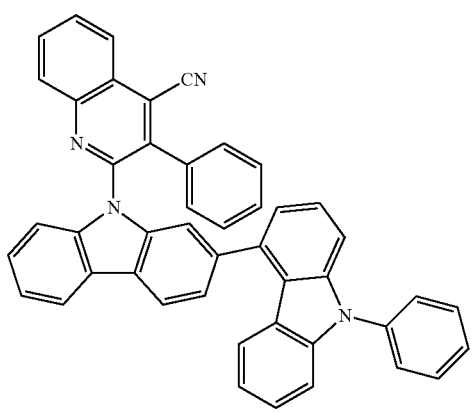
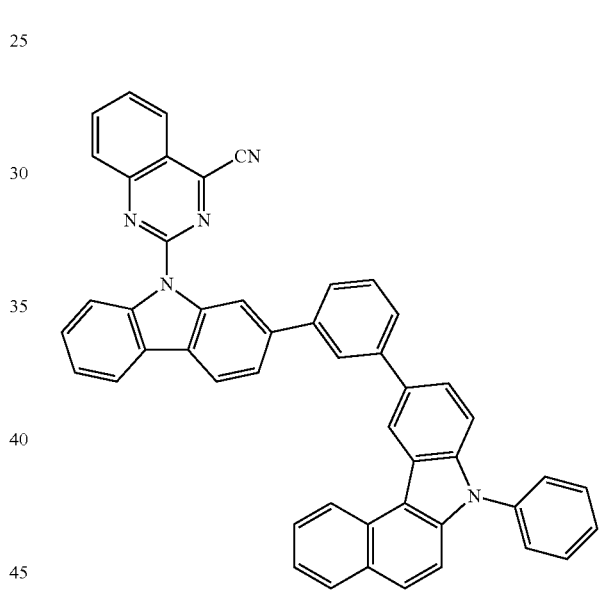
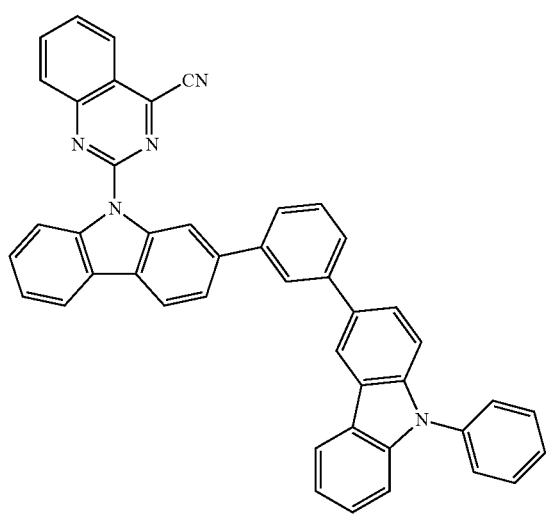
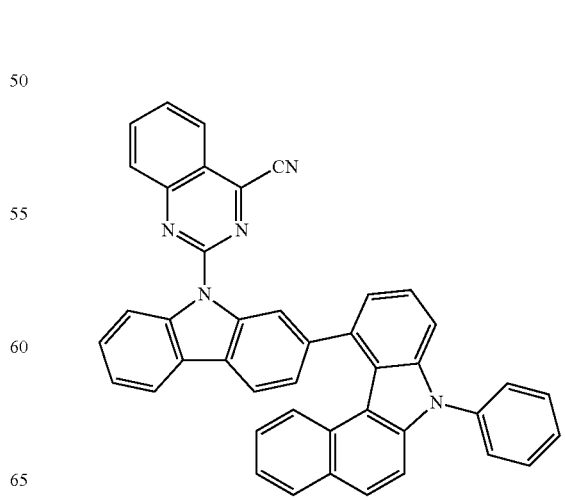

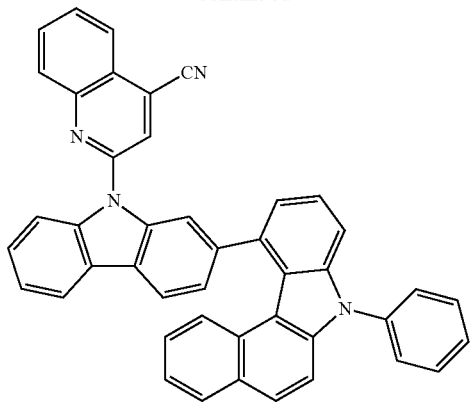
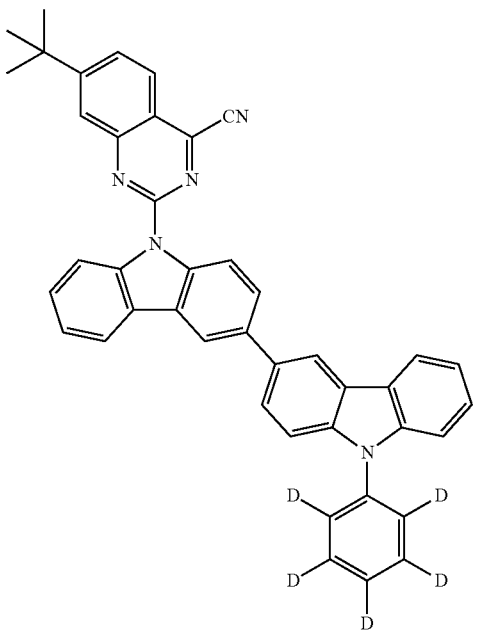
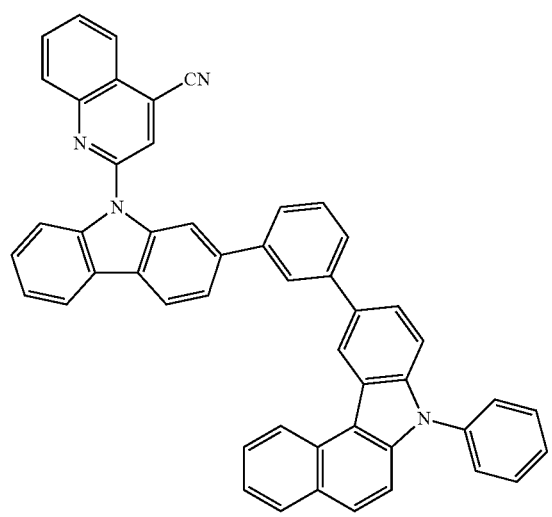
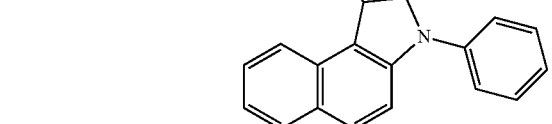
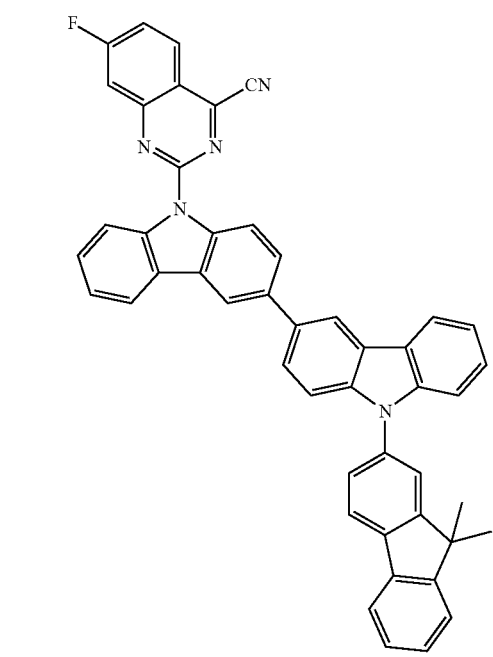

51
-continued
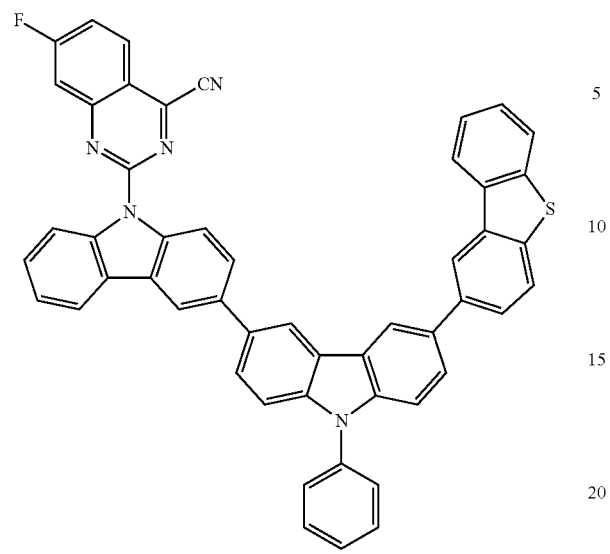
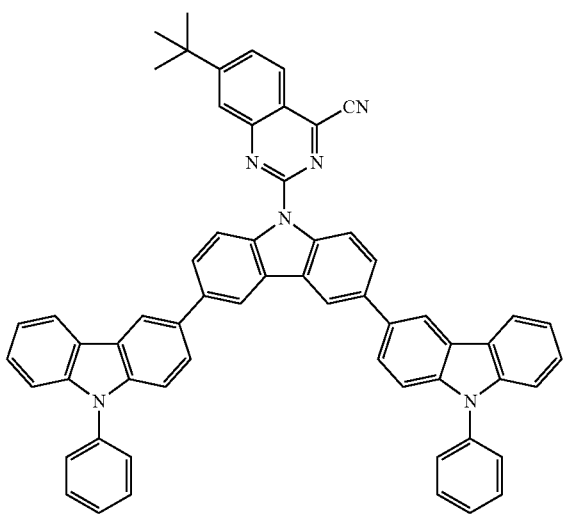
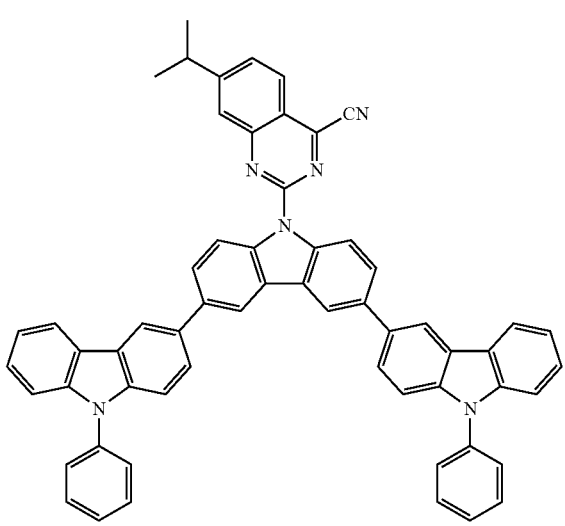
52
-continued
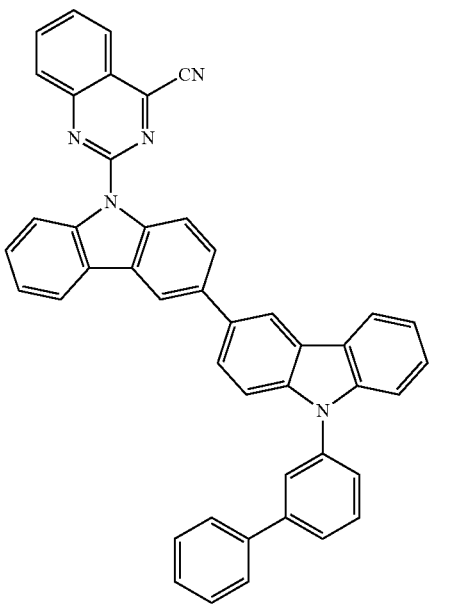
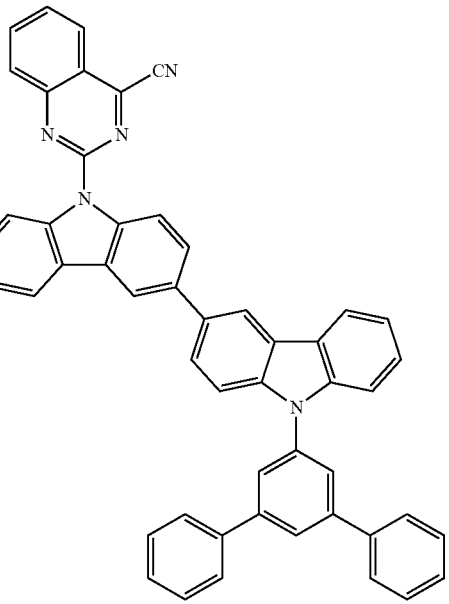

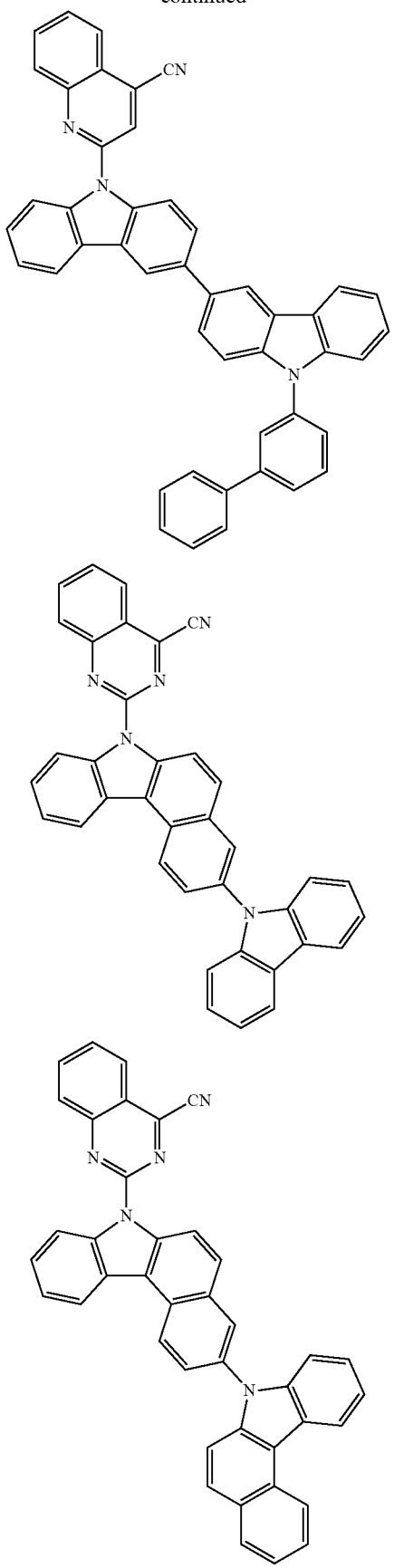
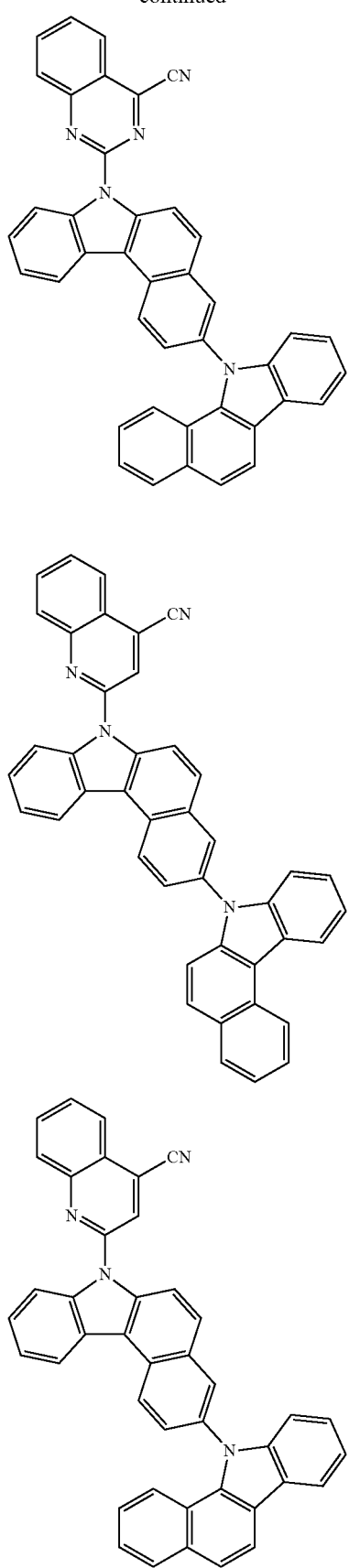

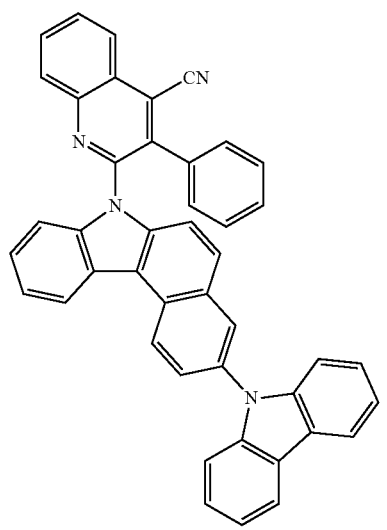
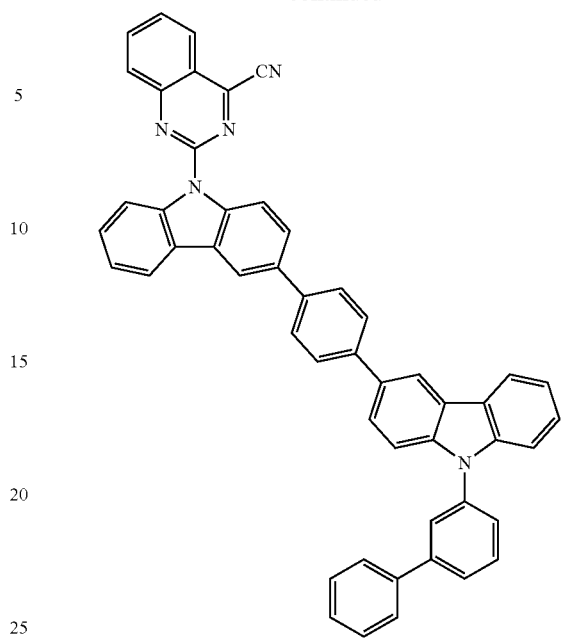
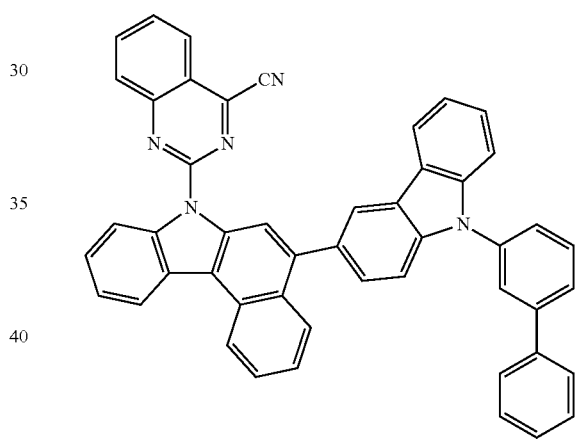
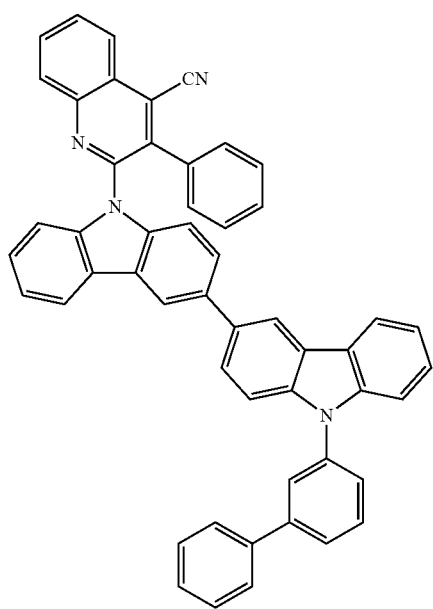

-continued
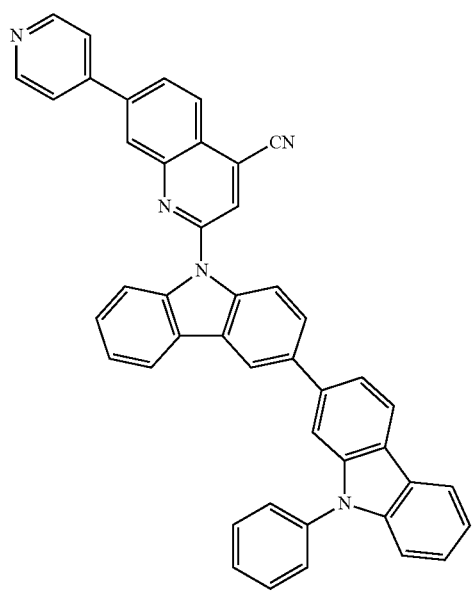
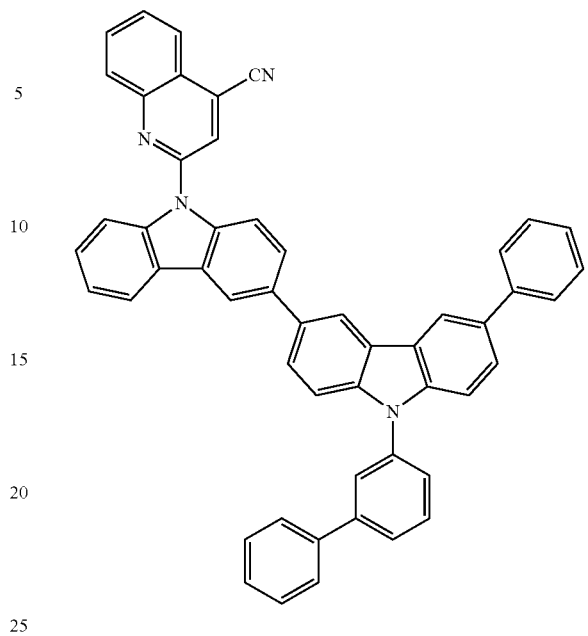
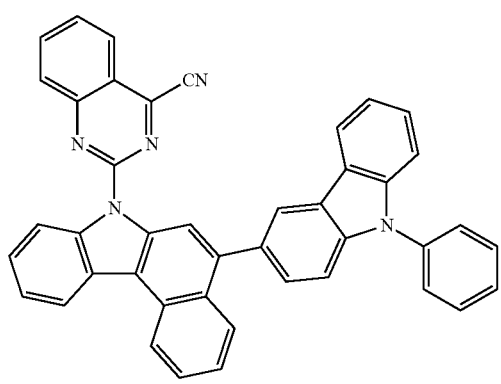
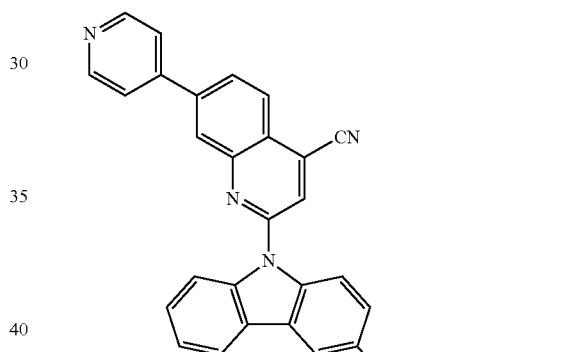
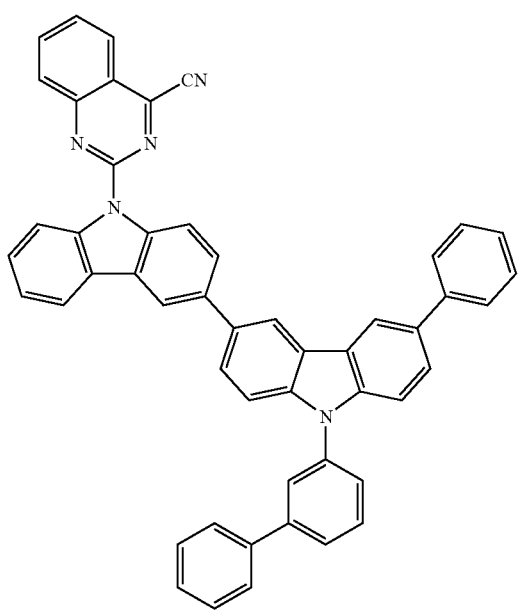
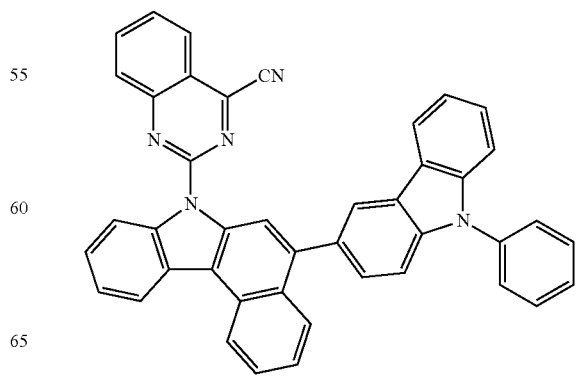

-continued
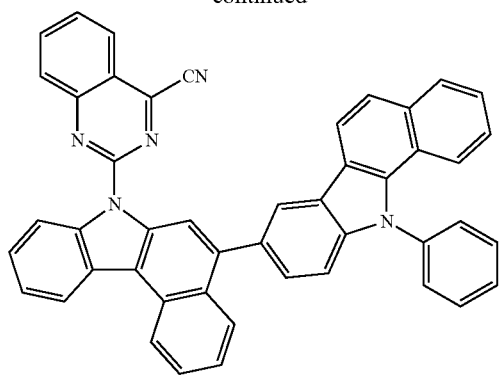
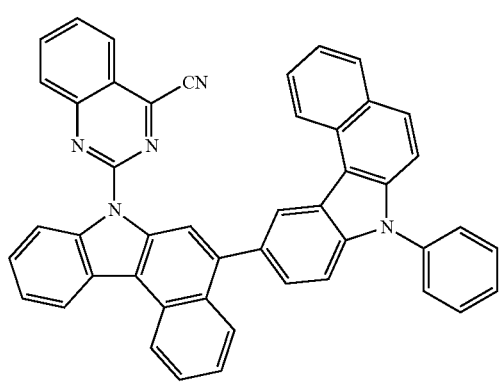
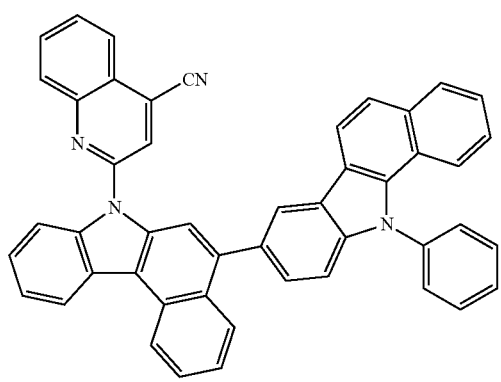
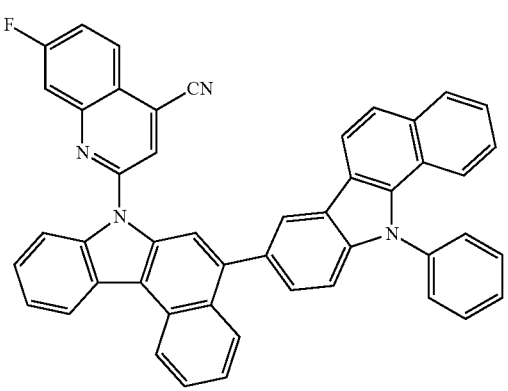
-continued
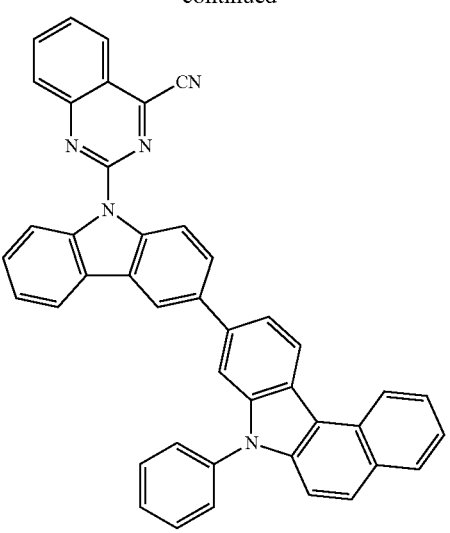
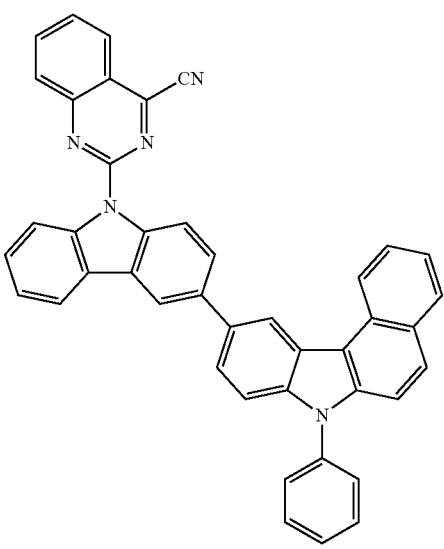
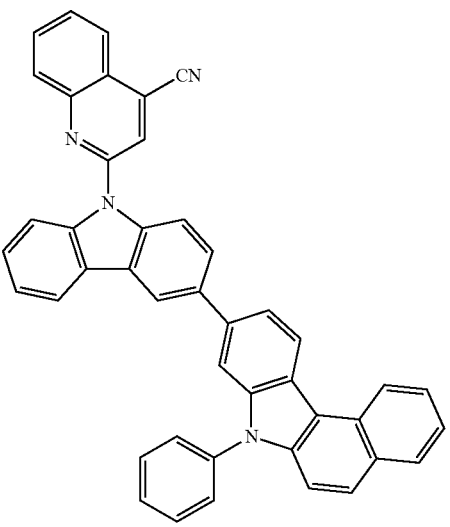

61
-continued
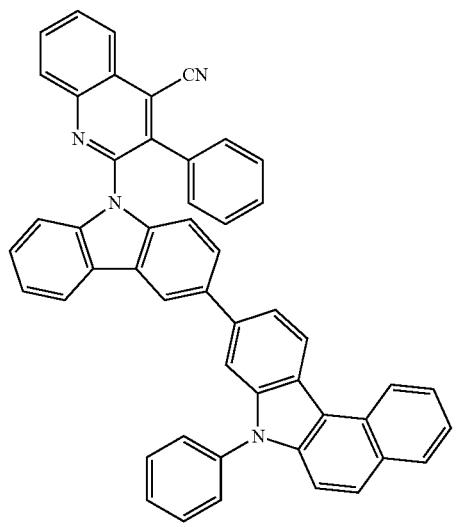
62
-continued
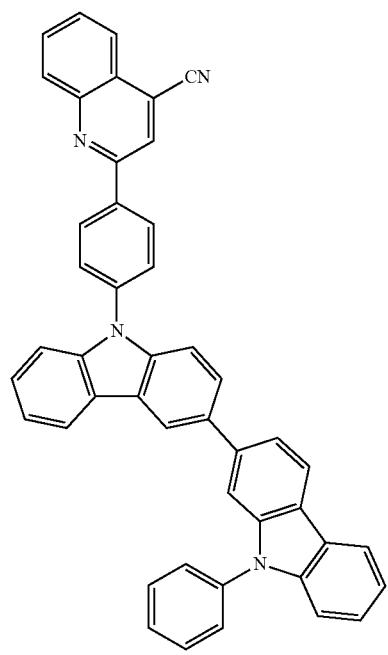
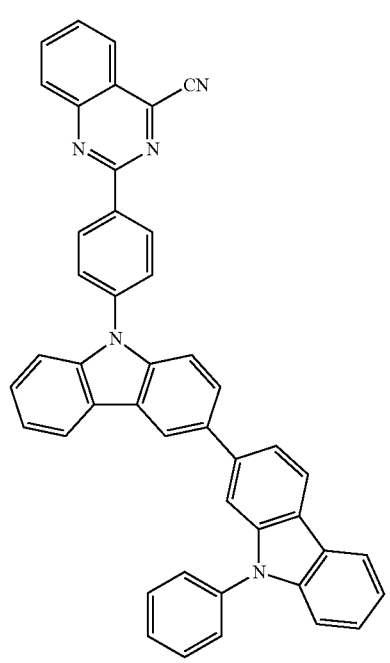
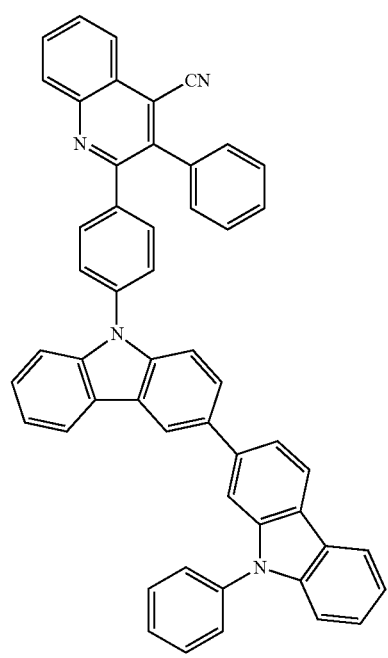

63
-continued
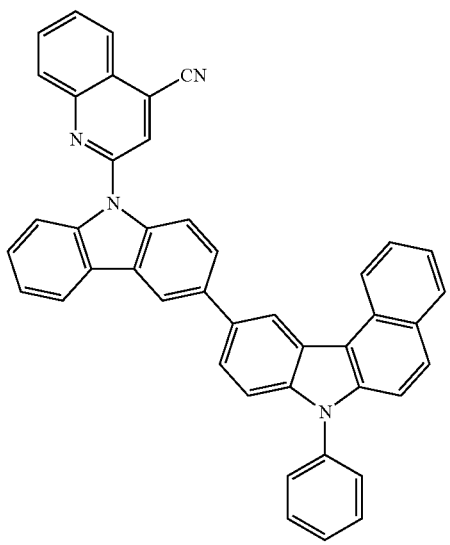
64
-continued
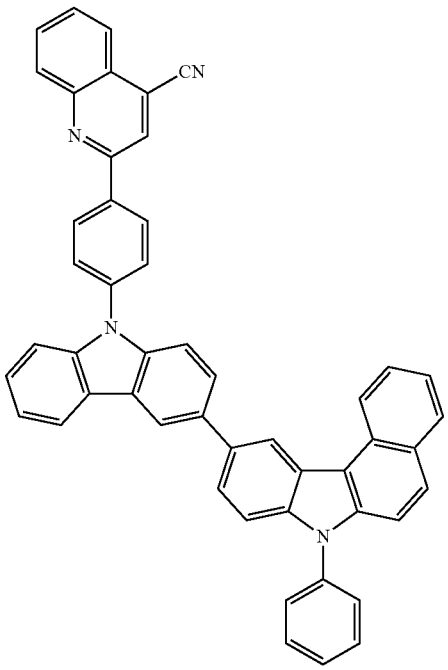
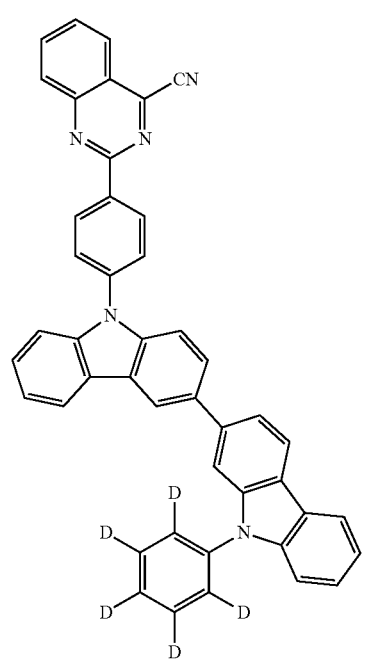
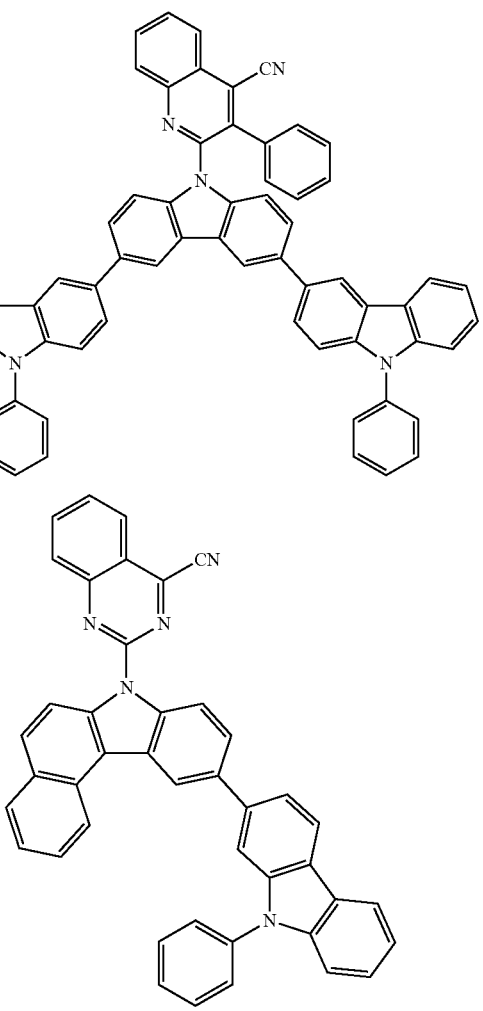

65
-continued
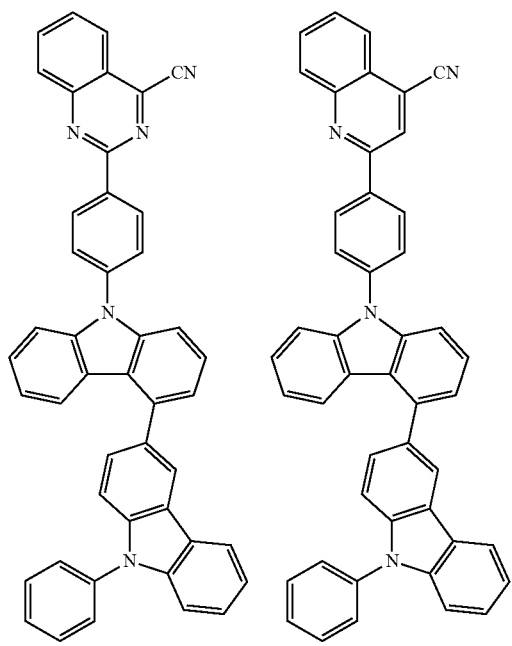
66
-continued
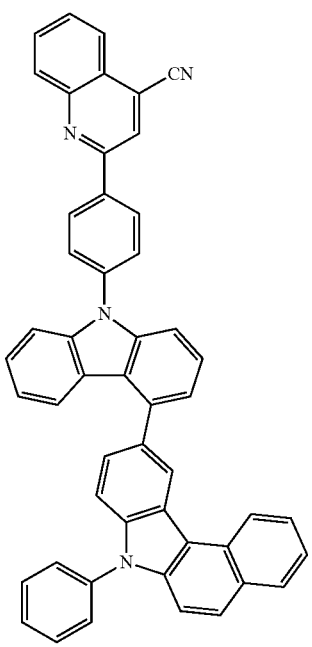
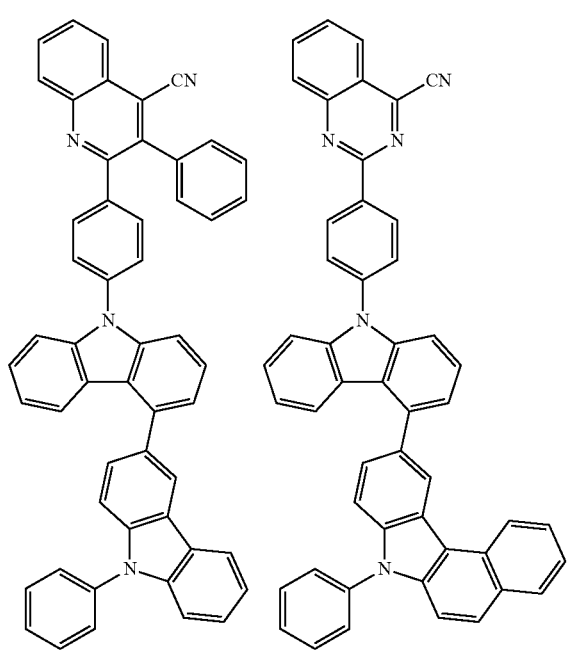
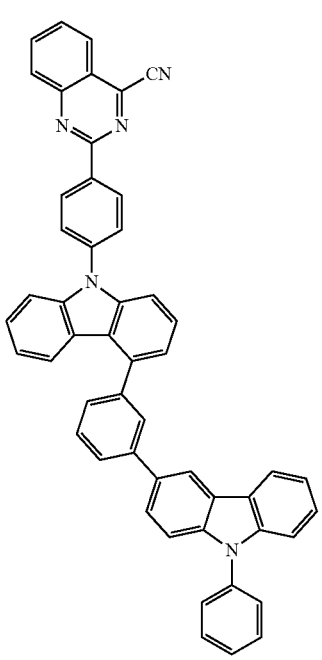 [SMILES: N#Cc1nc(-c2ccc(-n3c4ccccc4c4c(-c5cccc(-c6ccc7c(c6)c6ccccc6n7-c6ccccc6)c5)cccc43)cc2)nc2ccccc12]

67
-continued
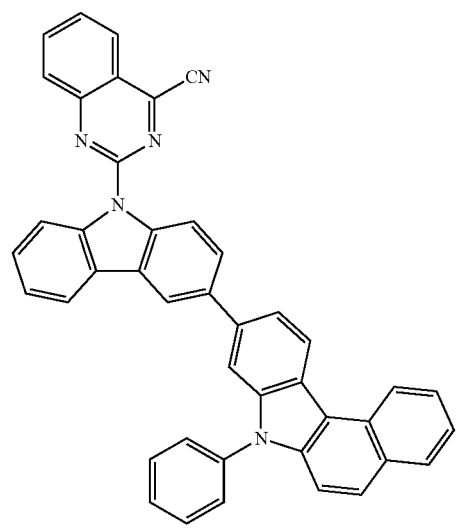
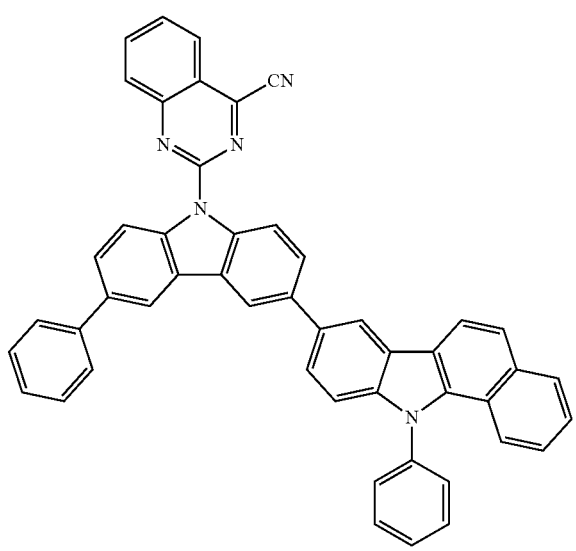
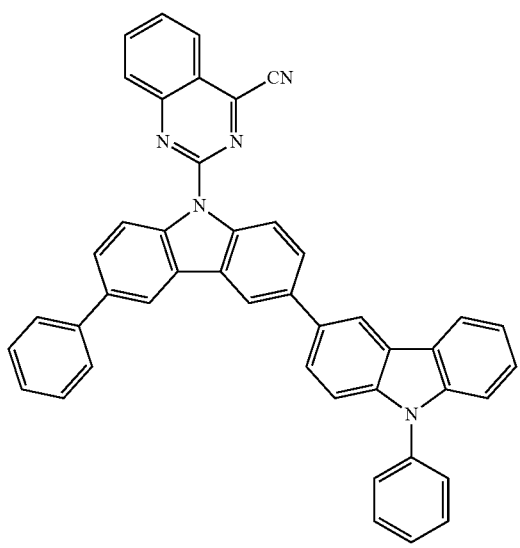
68
-continued
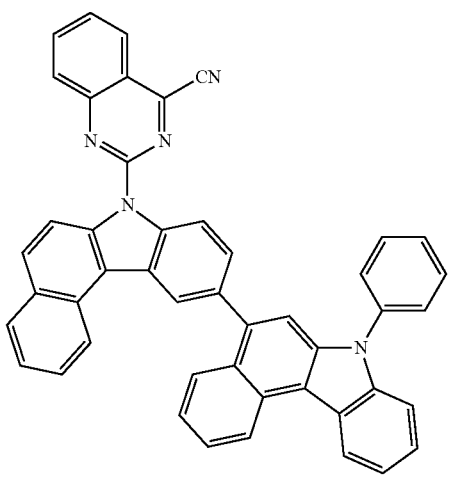
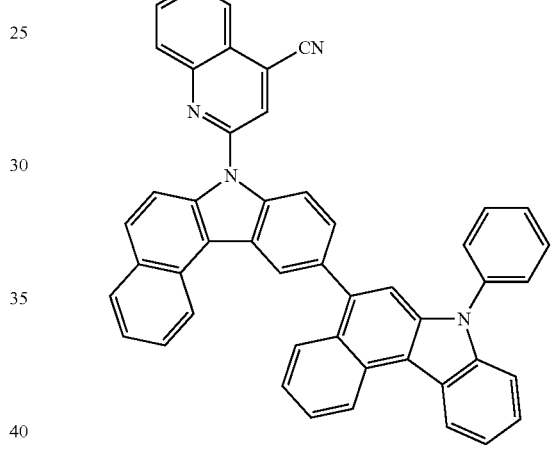
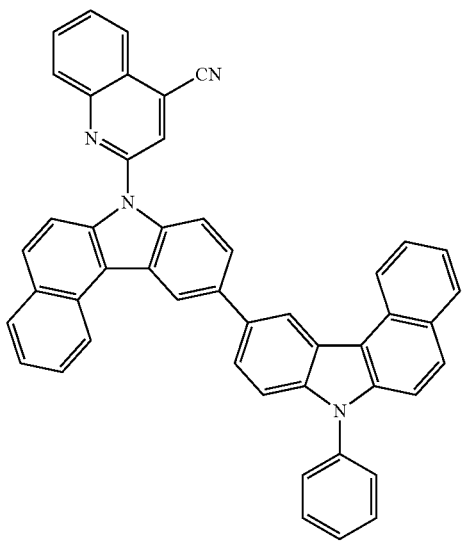

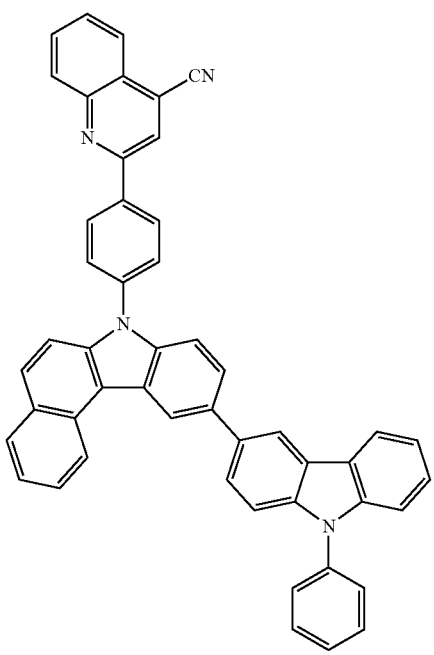
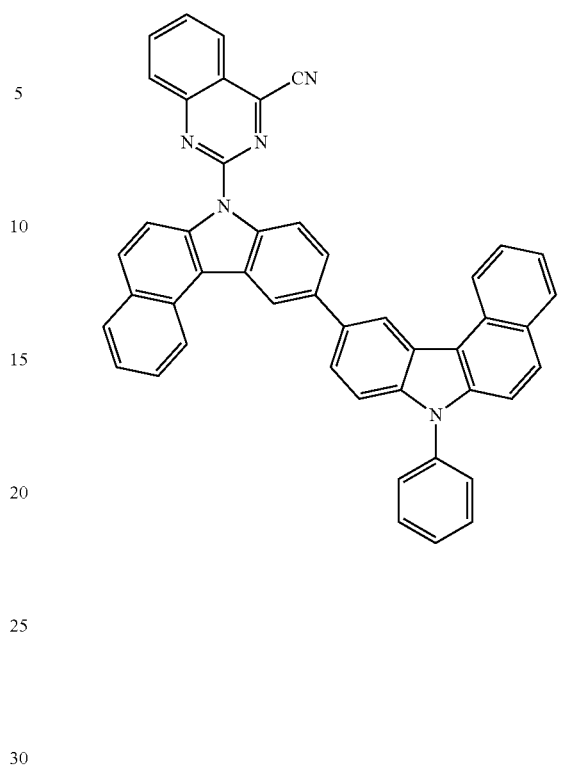
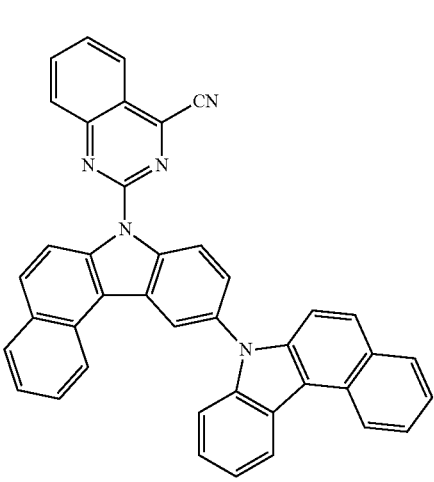
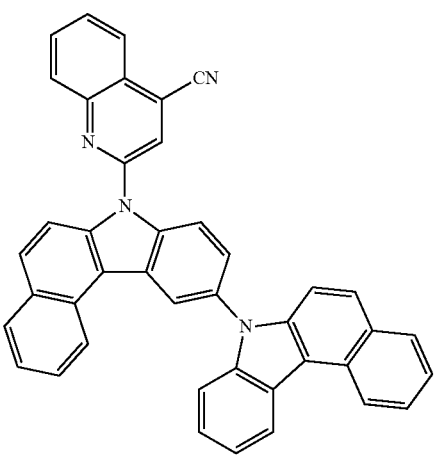
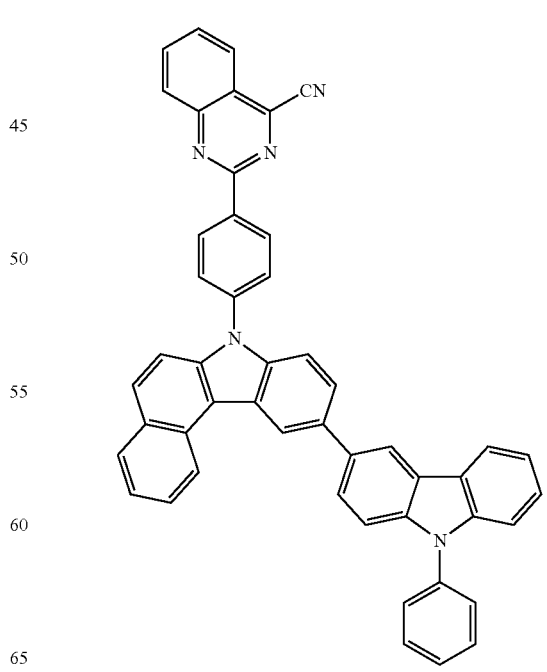

71
-continued
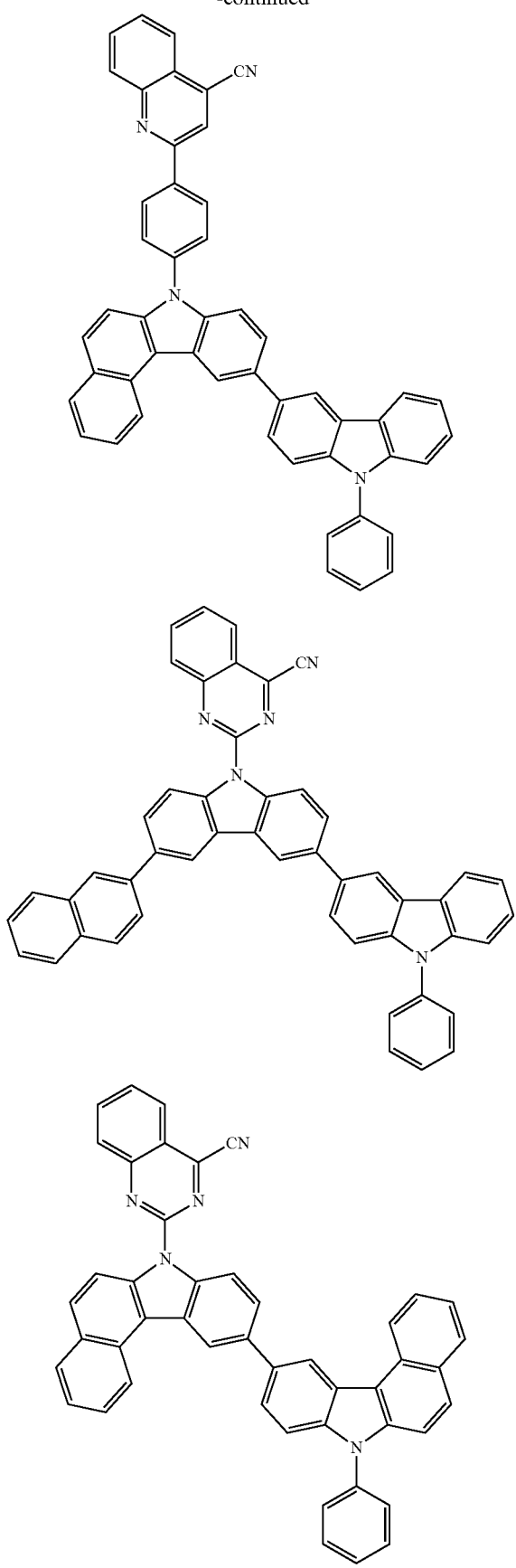
72
-continued
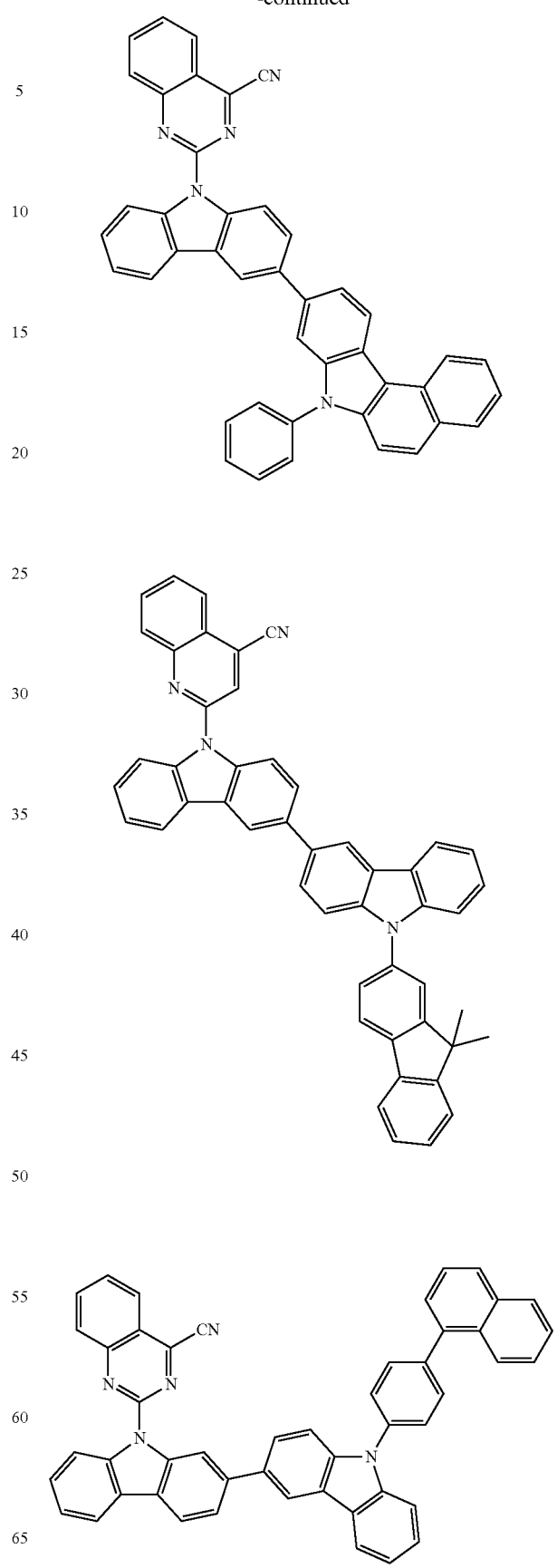

73
-continued
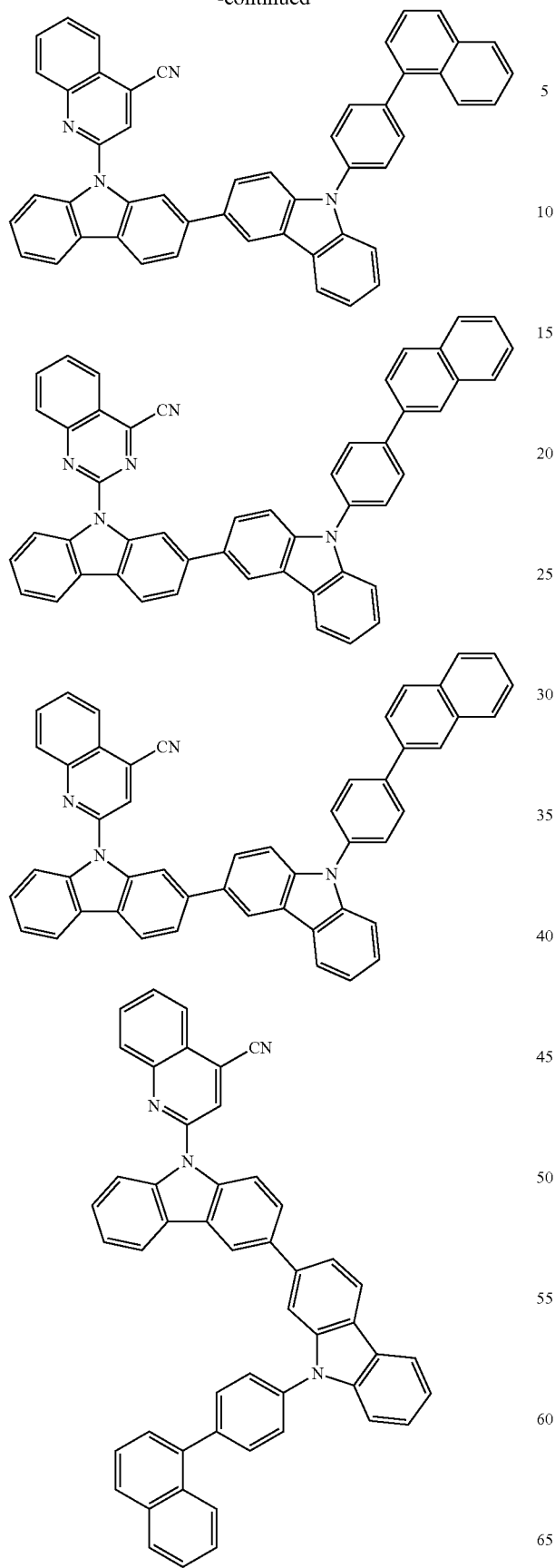
74
-continued

75
-continued
76
-continued
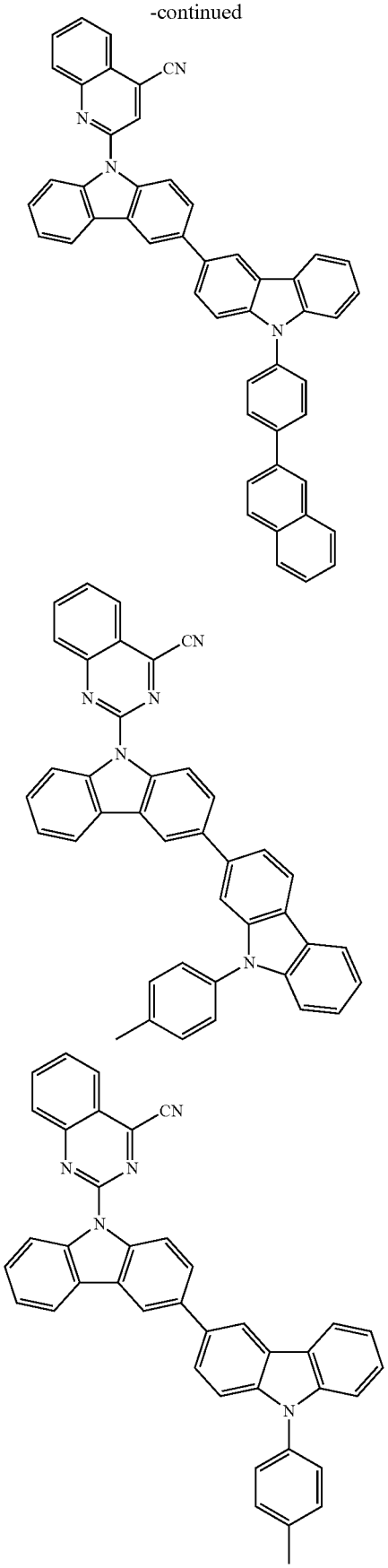
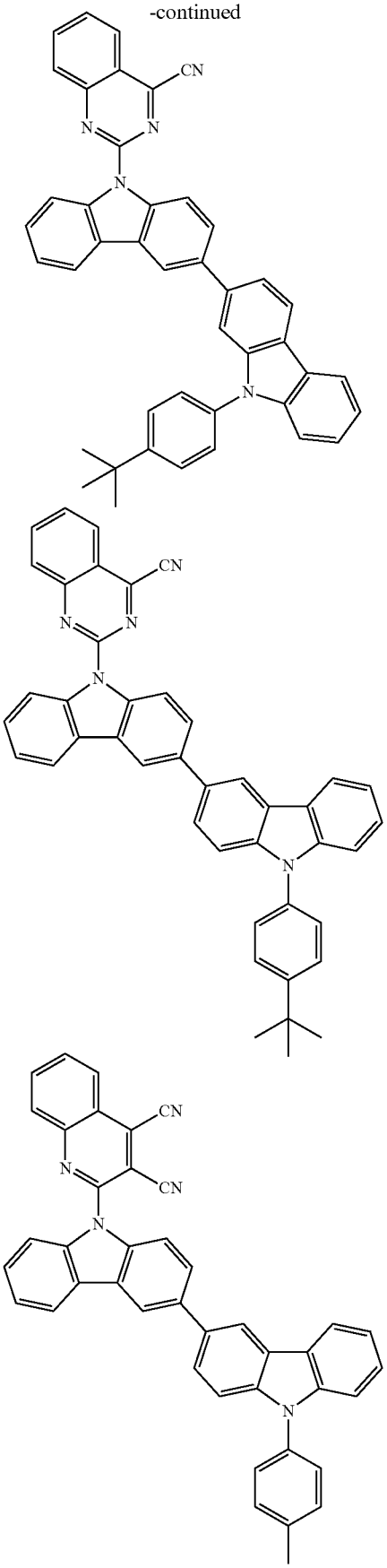

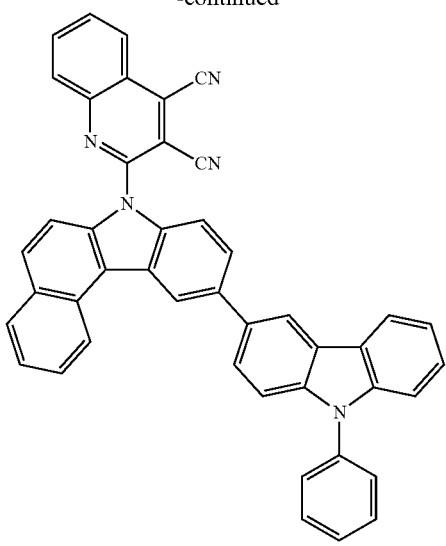
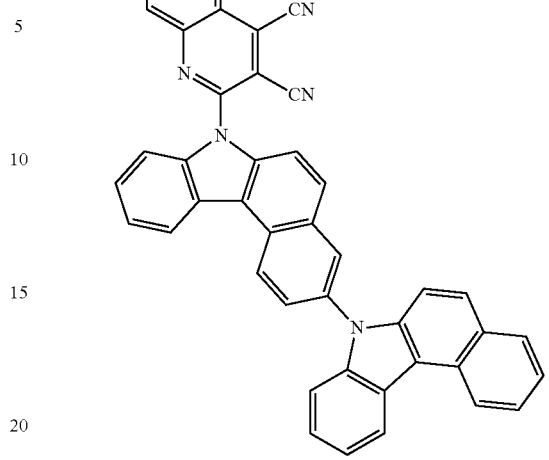
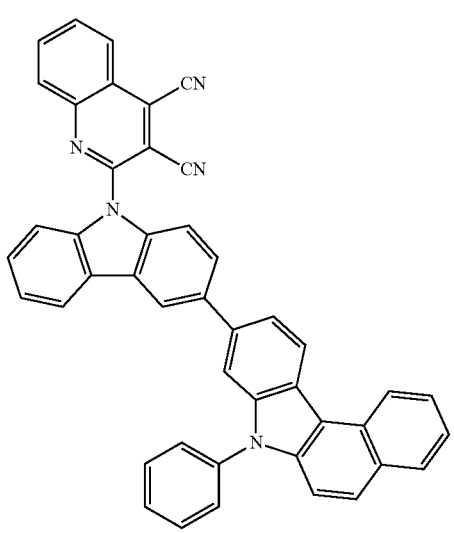
In an exemplary embodiment of the present specification, the compound represented by Formula 1 may be represented by any one of the following structures.
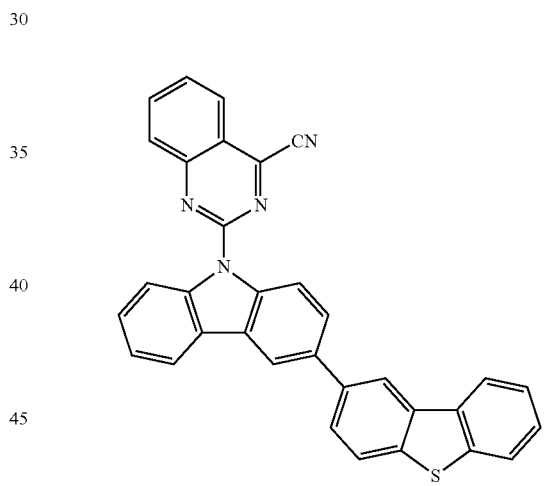
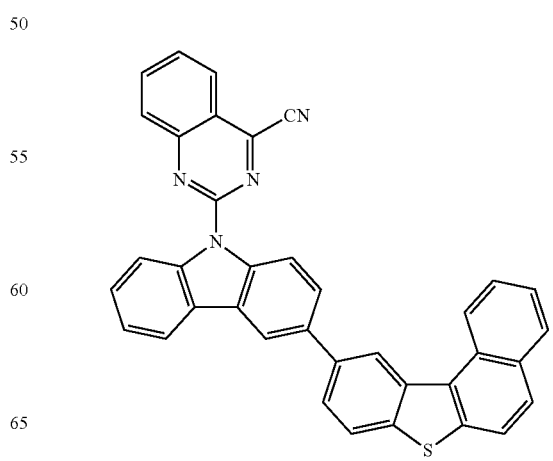

-continued
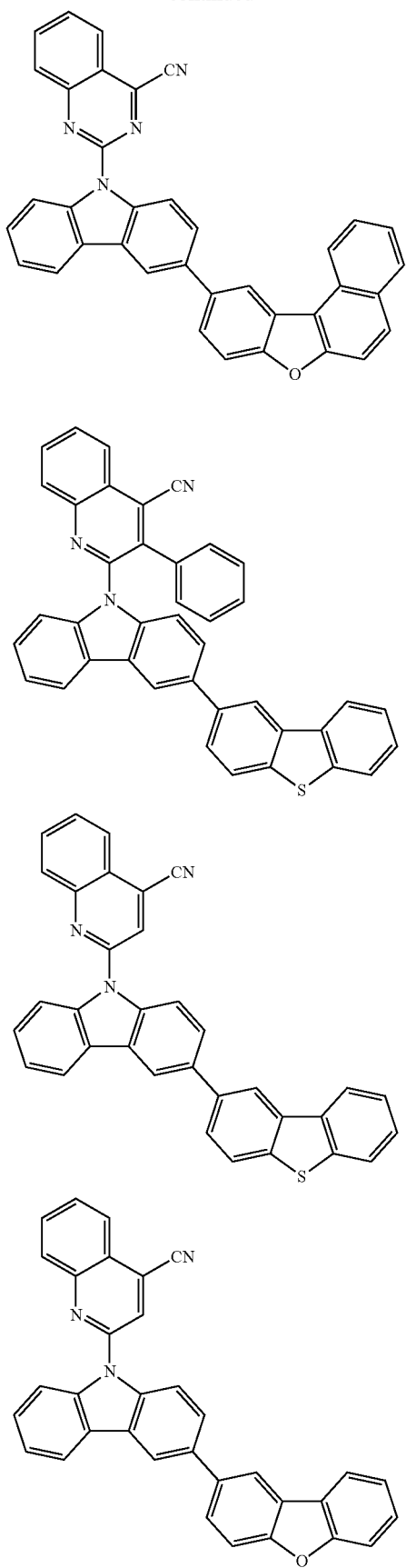
-continued
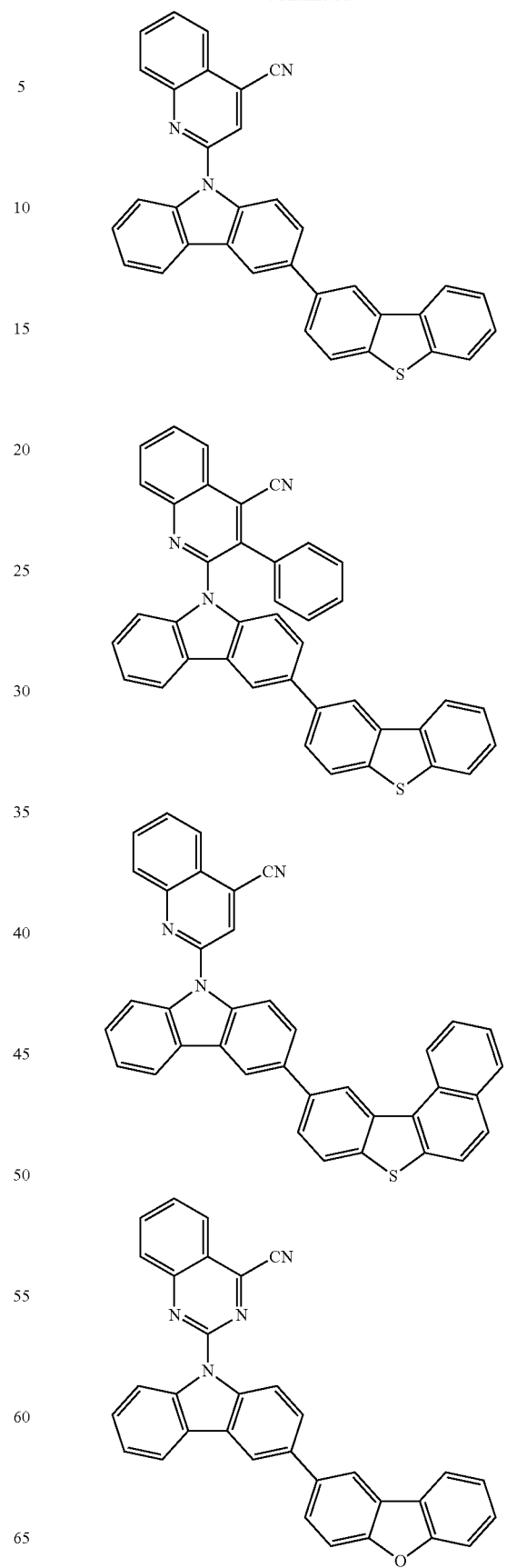

-continued
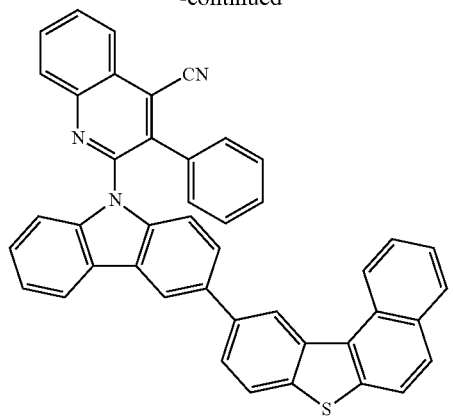
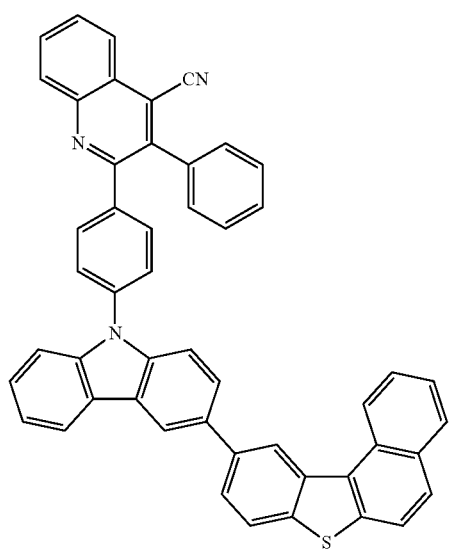
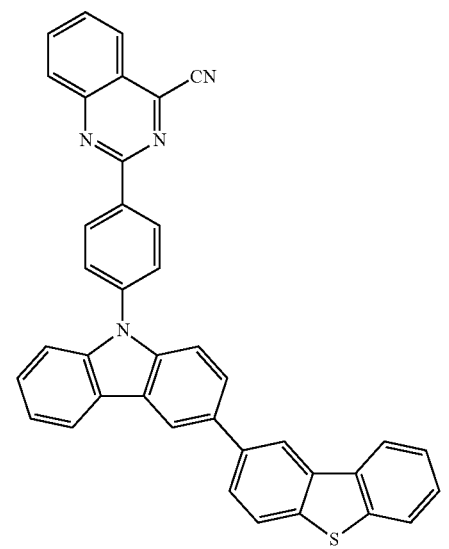
-continued
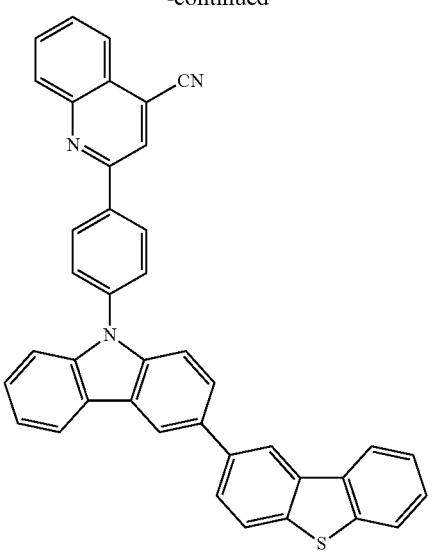
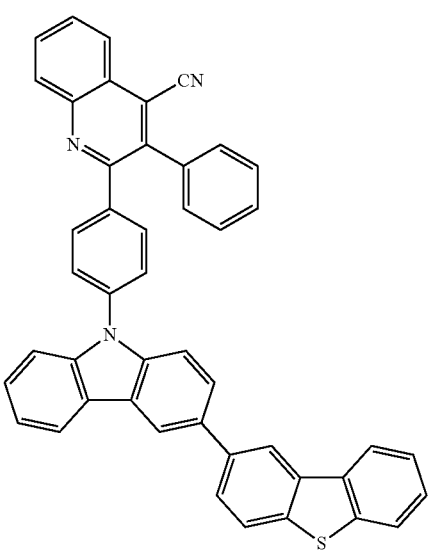
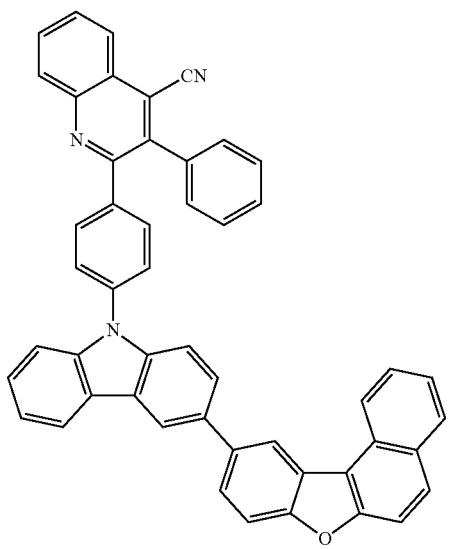

-continued
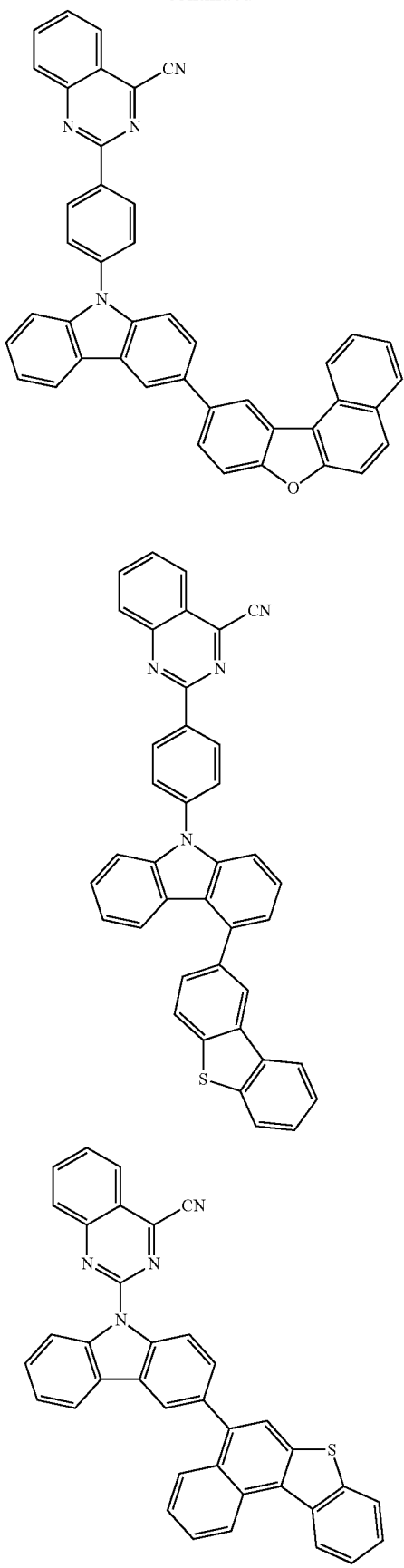
-continued
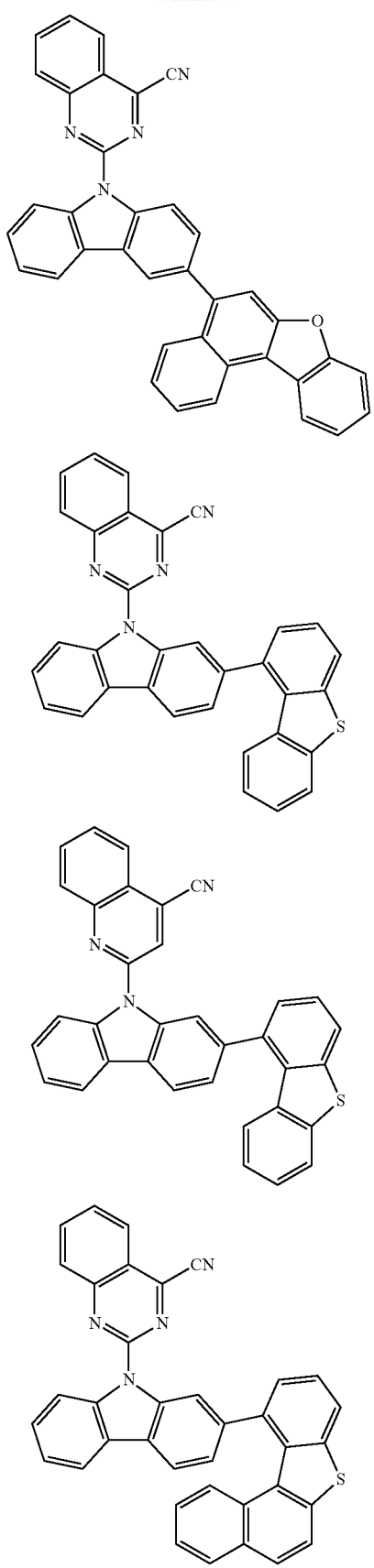

85
-continued
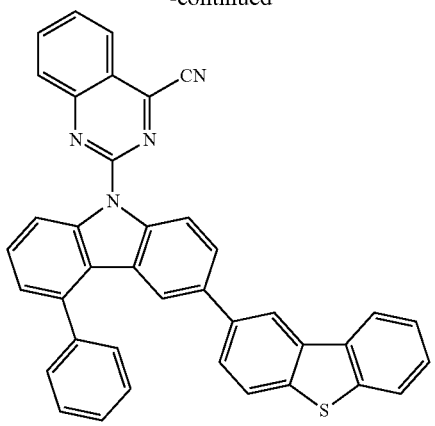
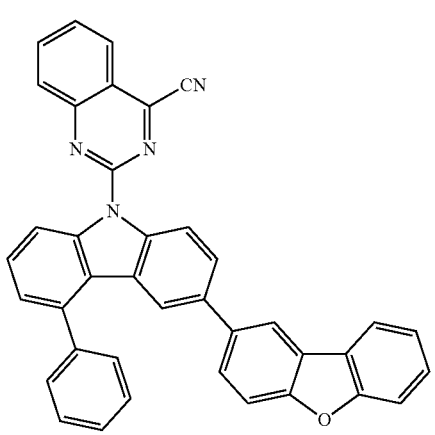
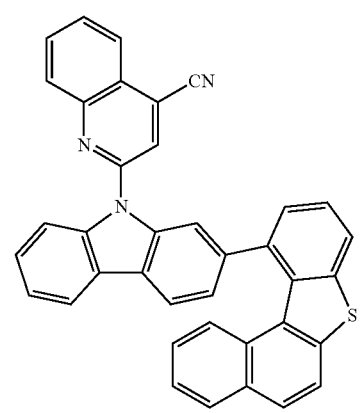
86
-continued
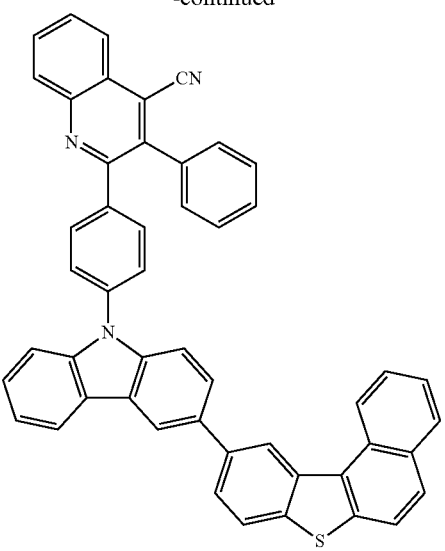
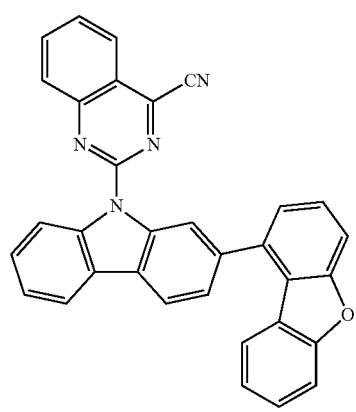

-continued
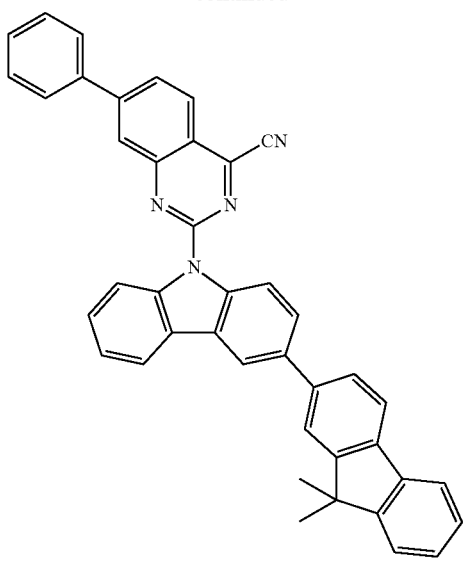
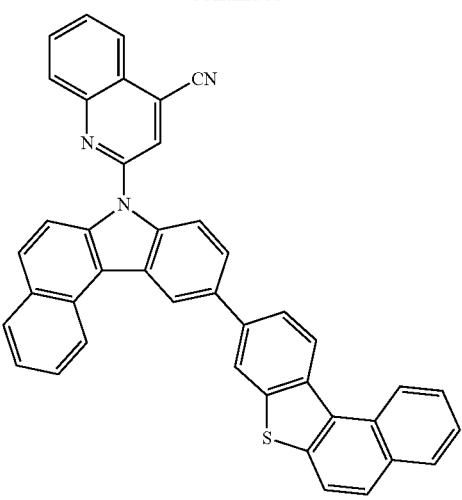
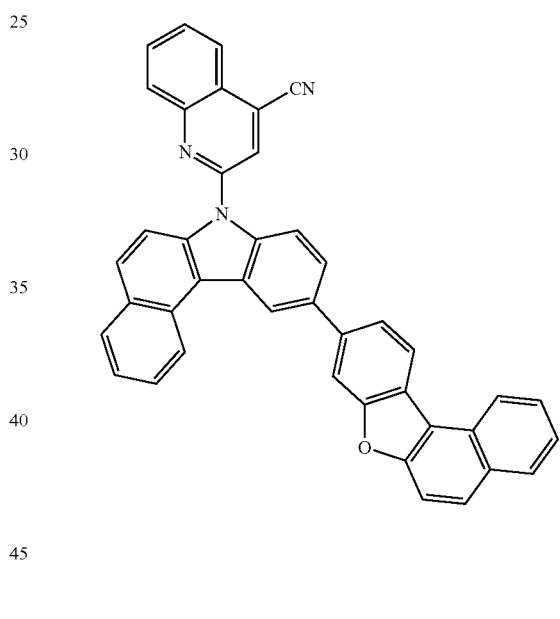
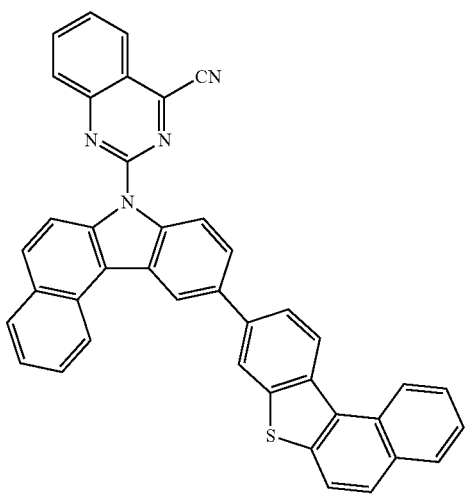
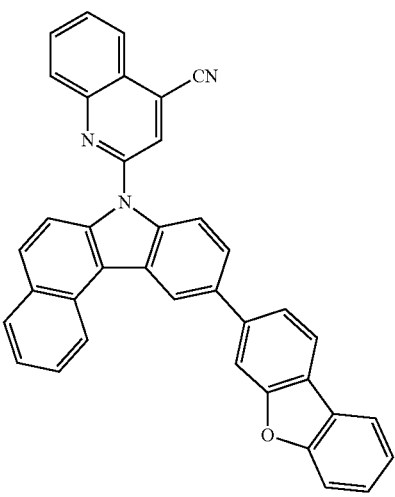

-continued
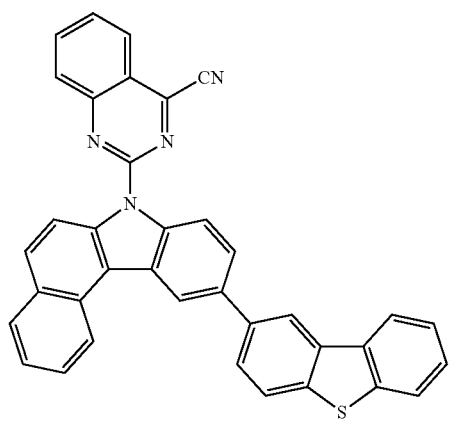
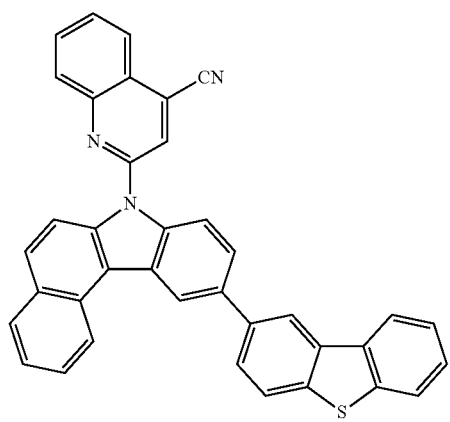
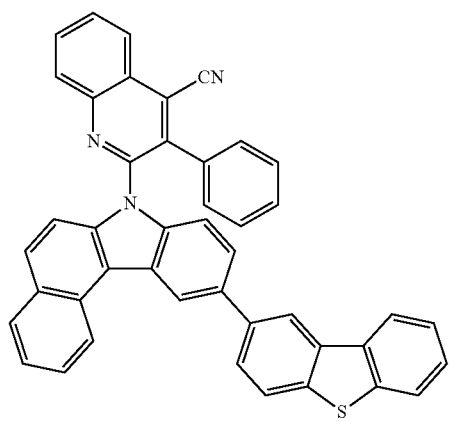
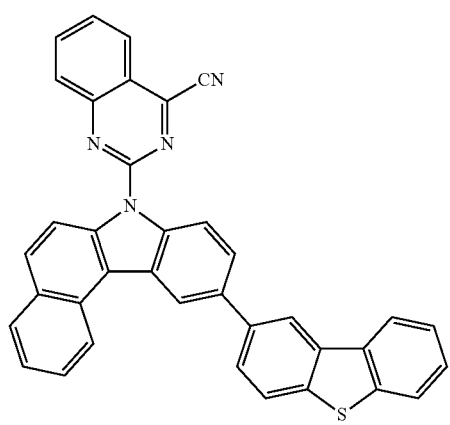
-continued
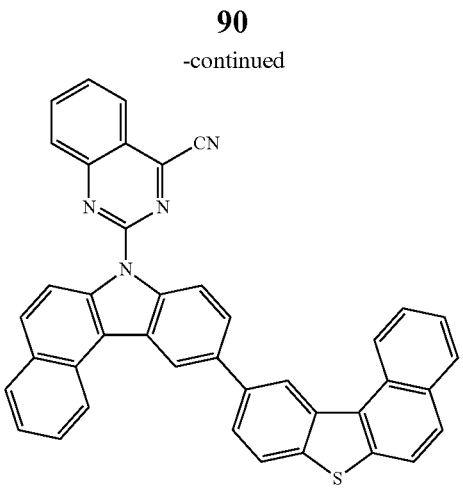
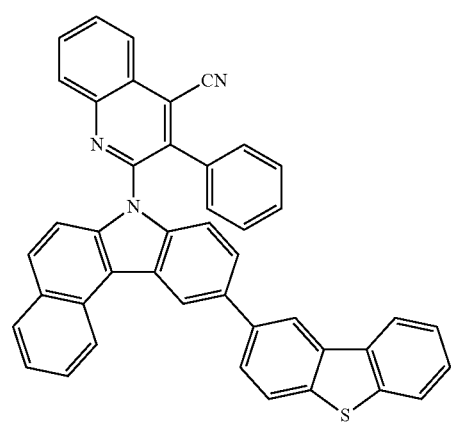
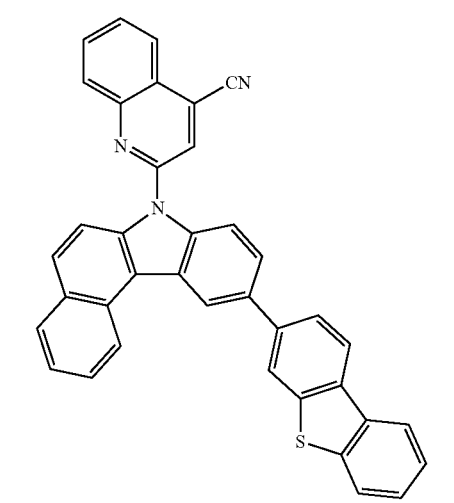

91
-continued
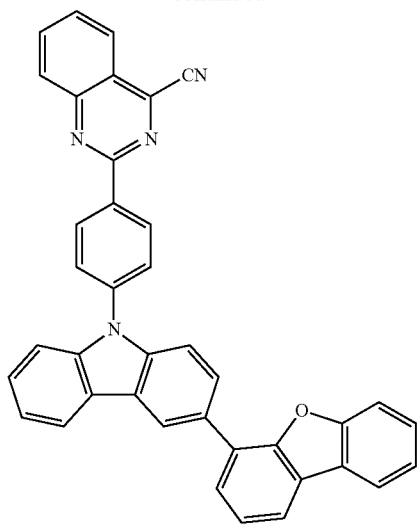
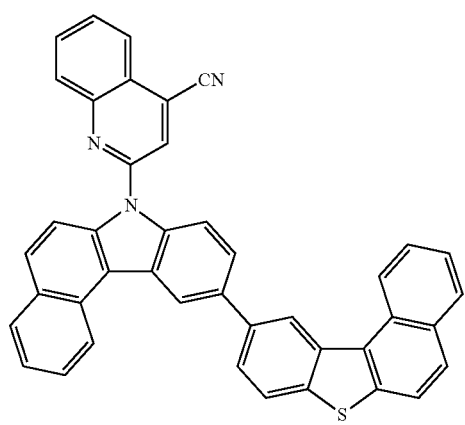
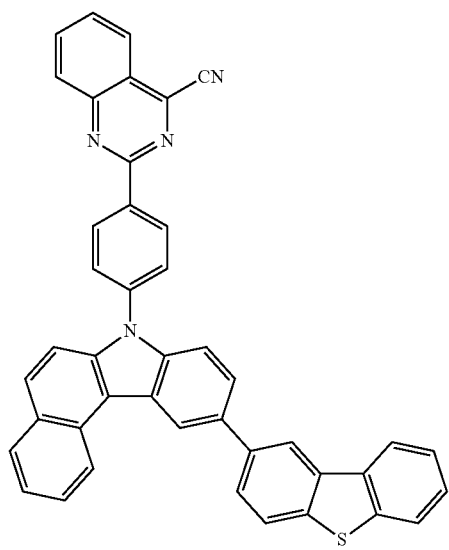
92
-continued
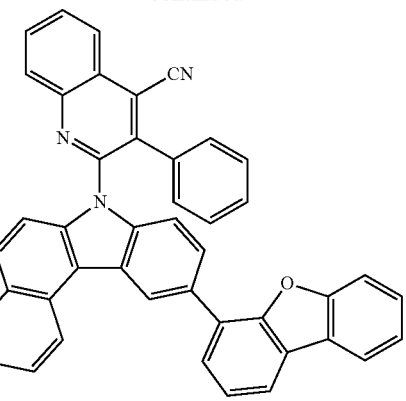
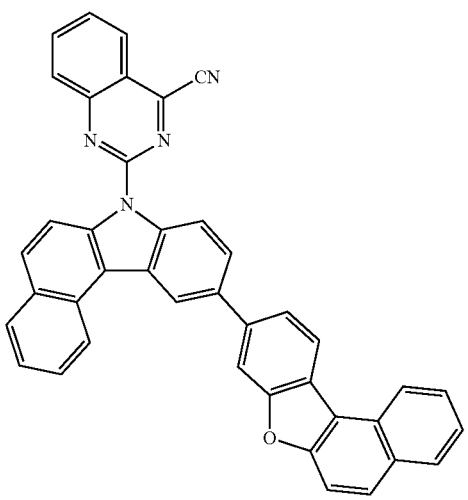
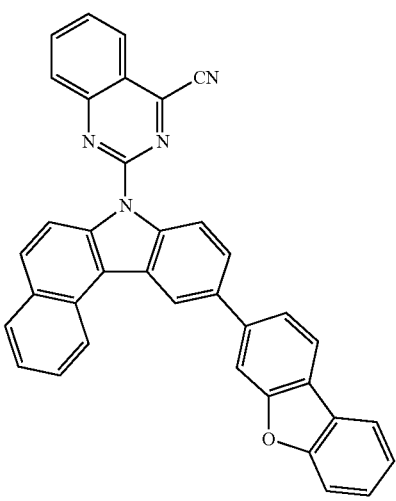

93
-continued
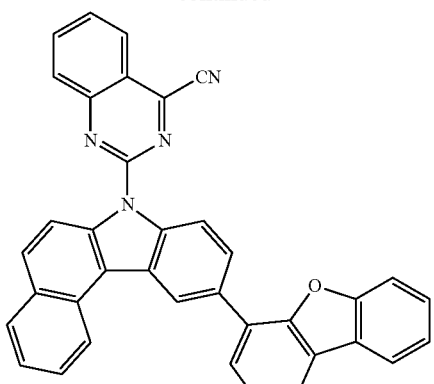
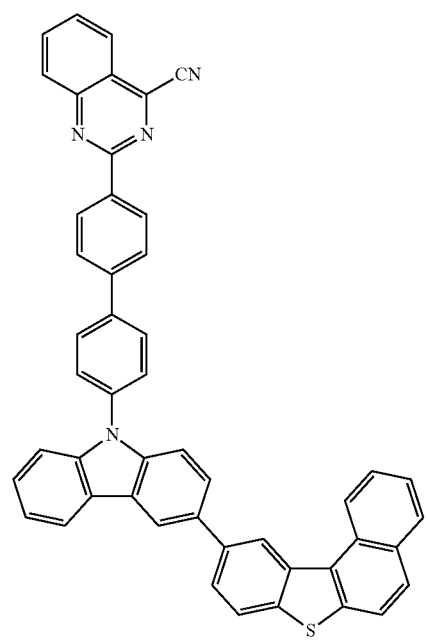
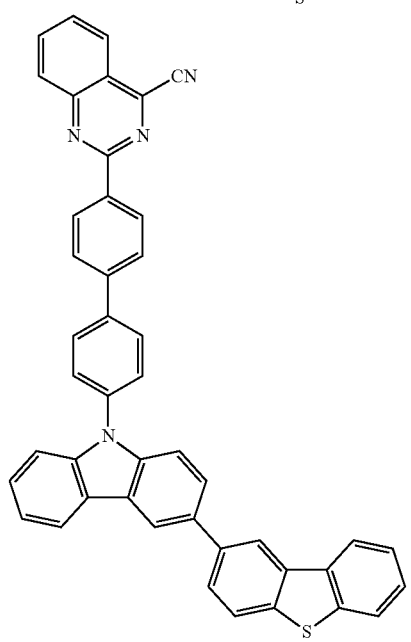
94
-continued
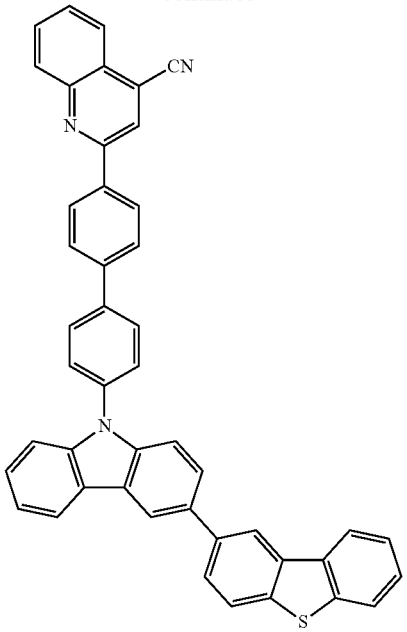
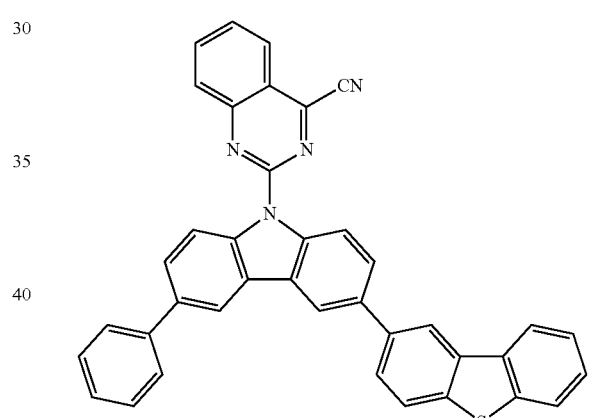
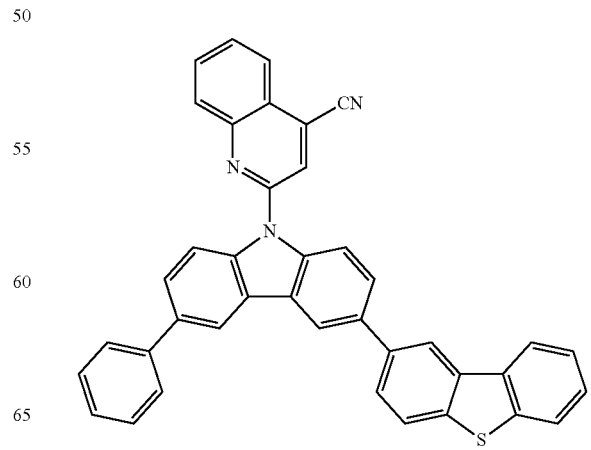

95
-continued
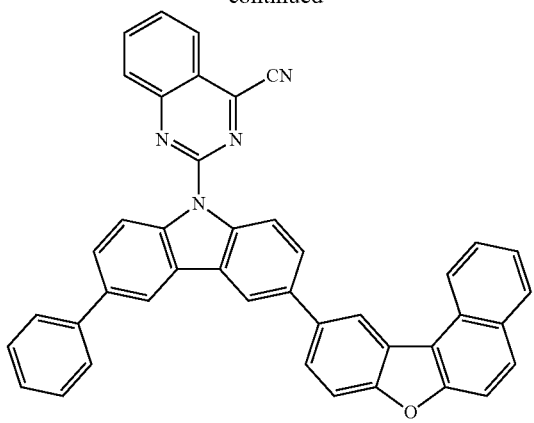
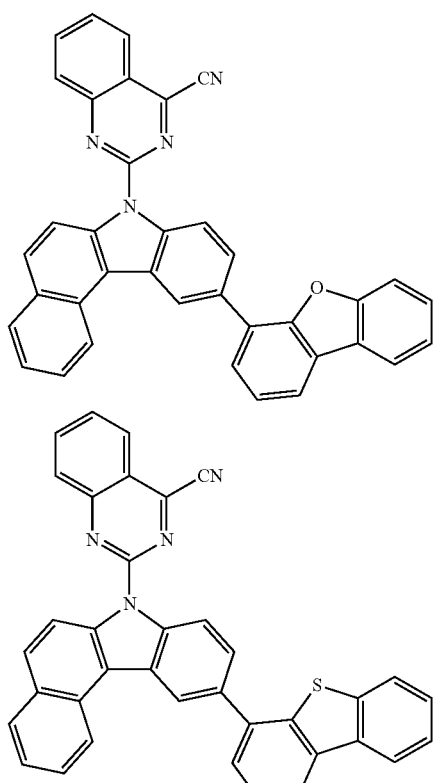
96
-continued
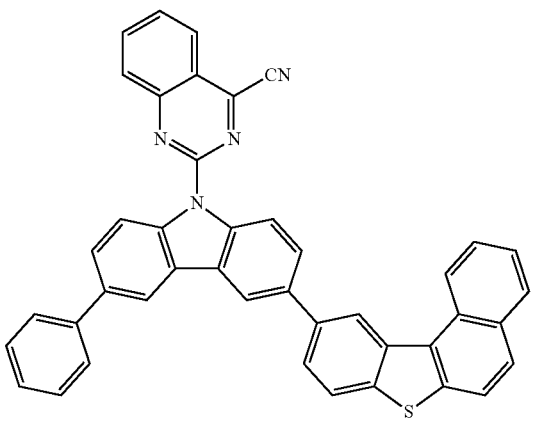
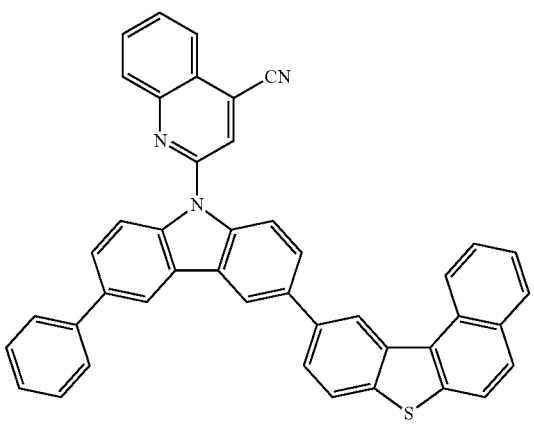
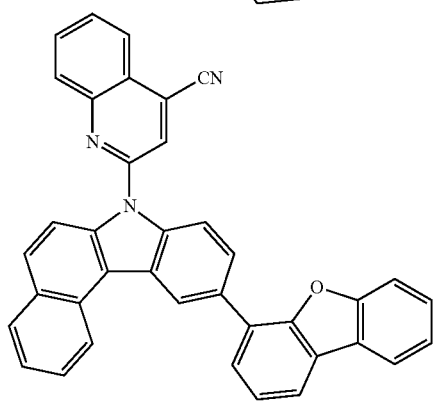
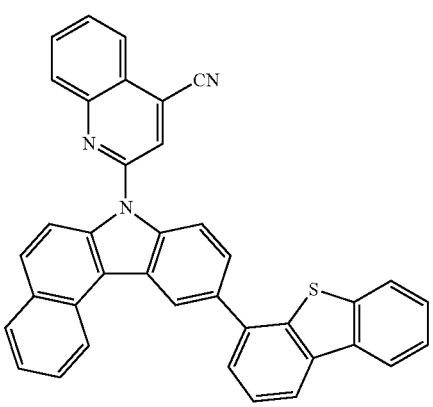

97
-continued
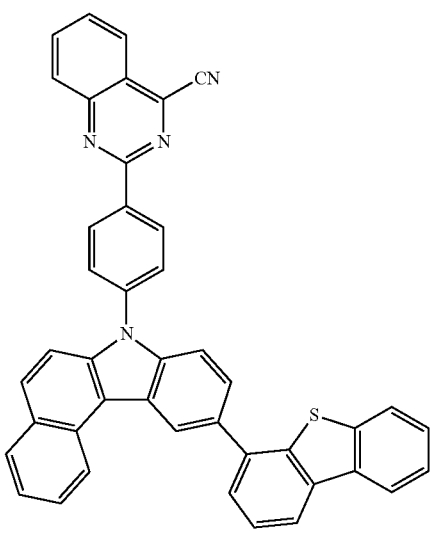
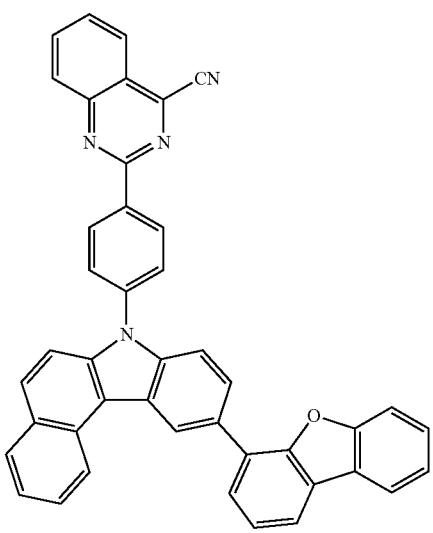
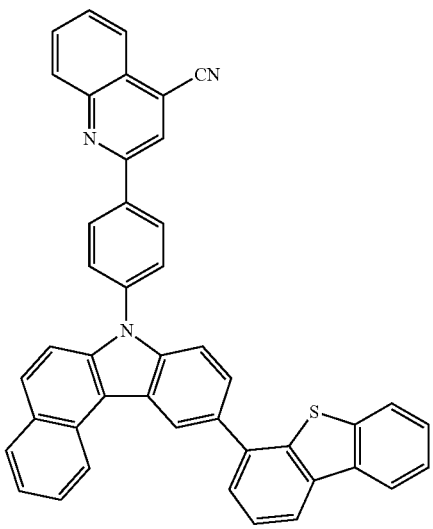
98
-continued
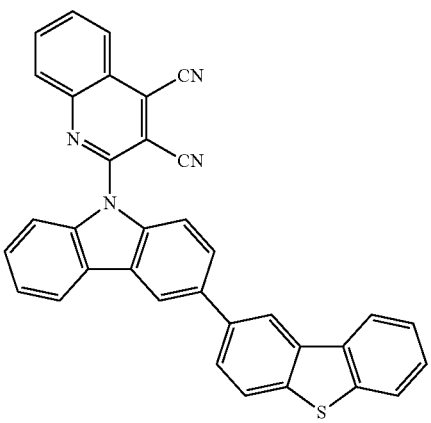
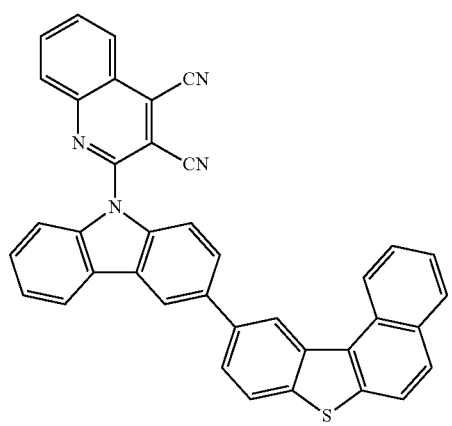
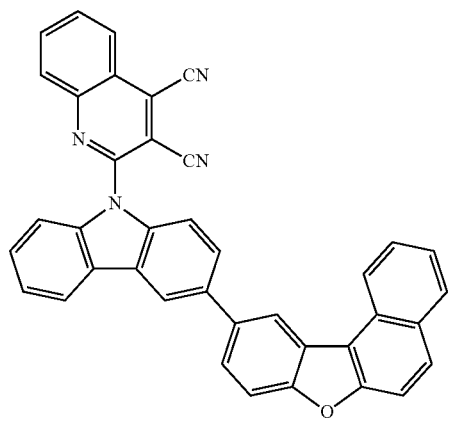

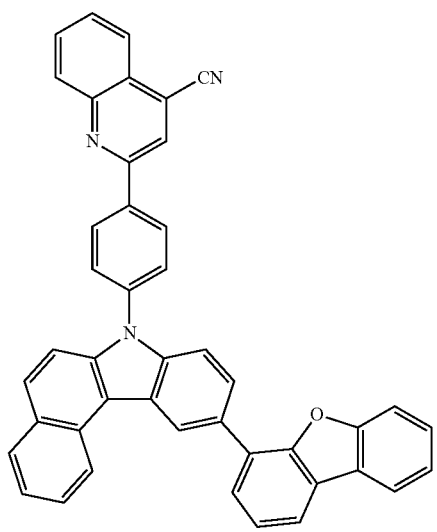
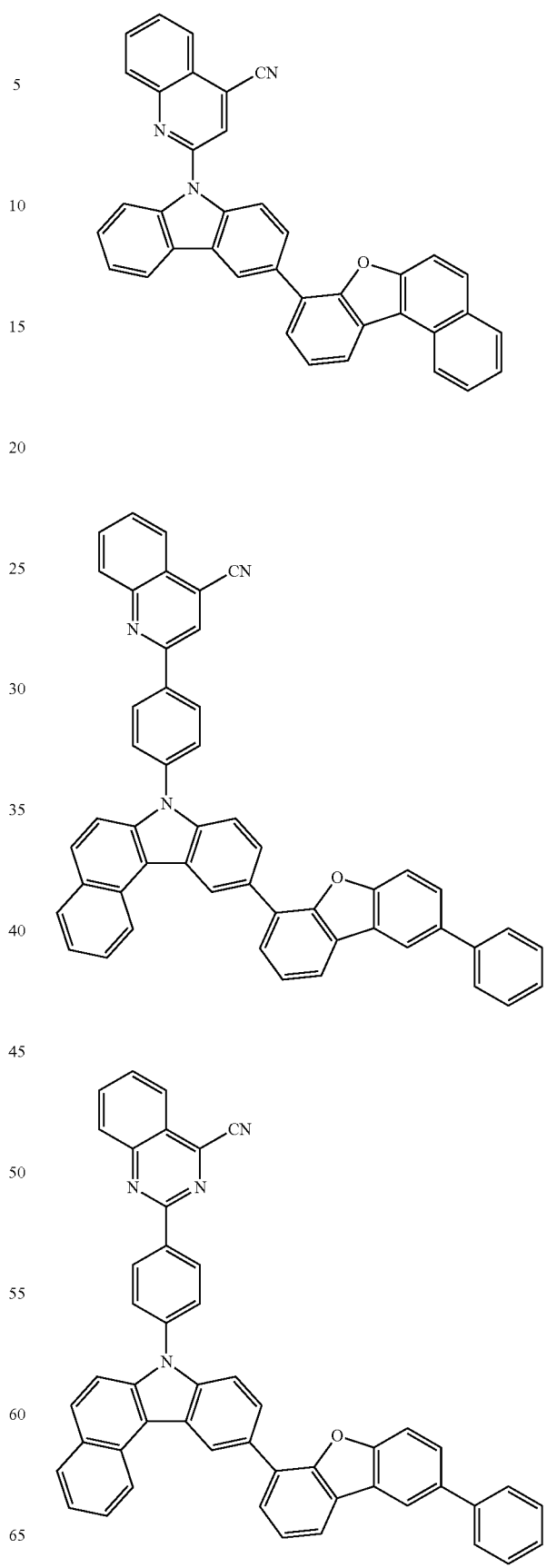

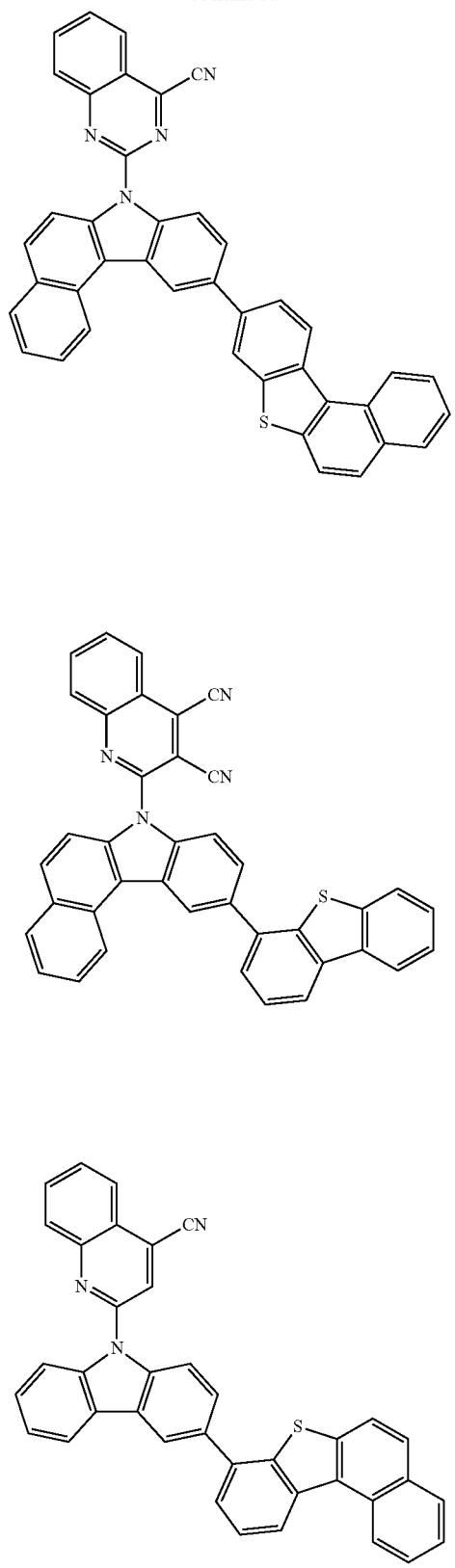
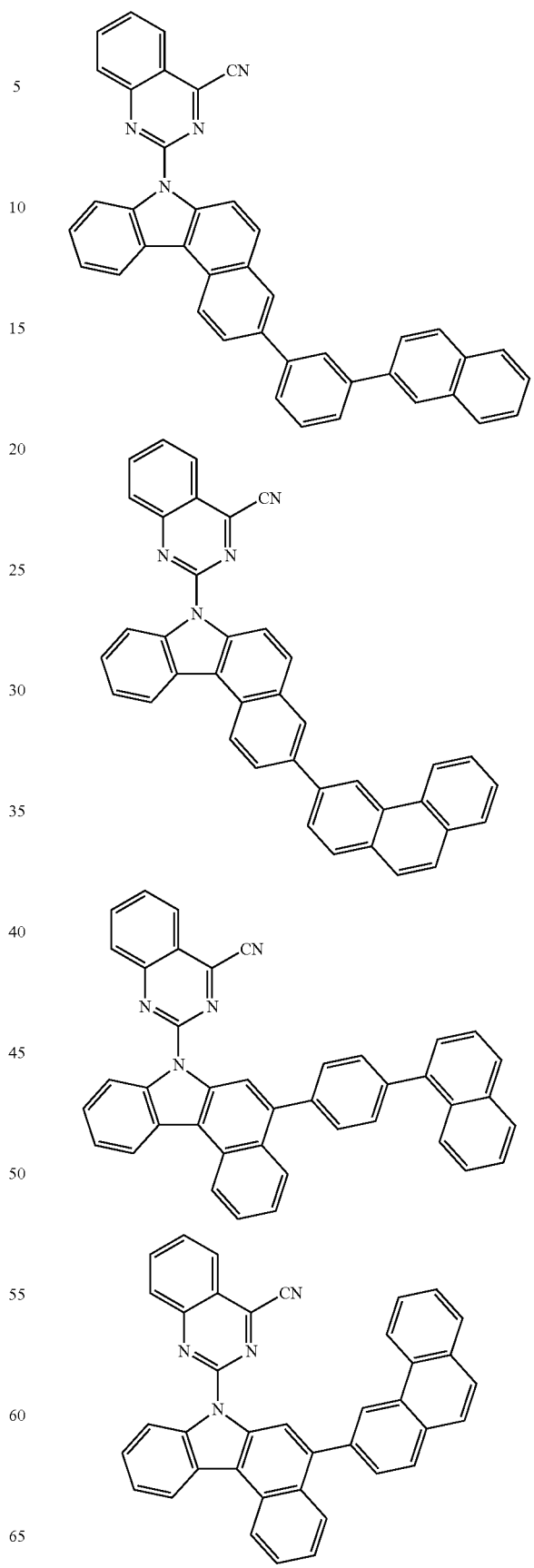
In an exemplary embodiment of the present specification, the compound represented by Formula 1 may be represented by any one of the following structures.

103
-continued
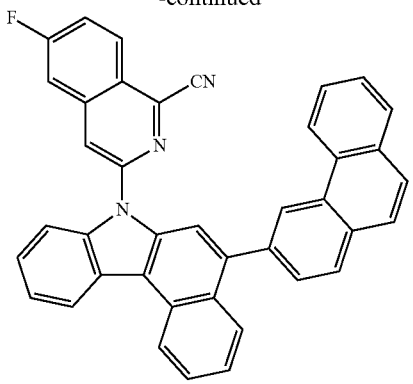
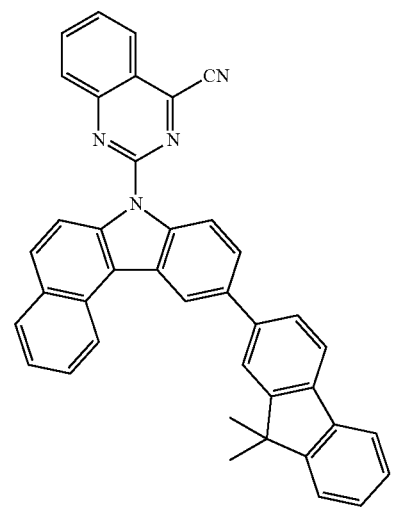
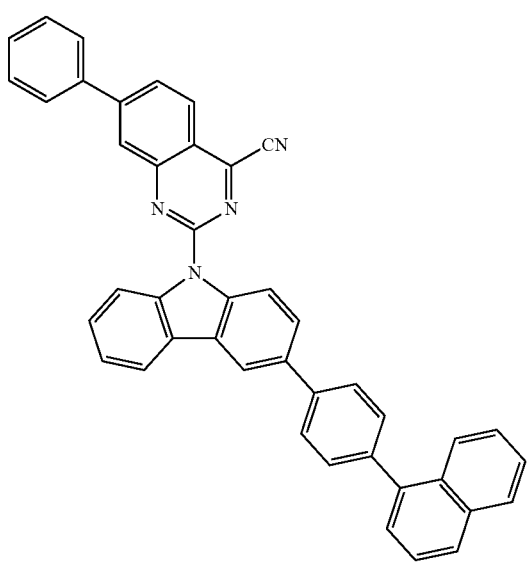
104
-continued
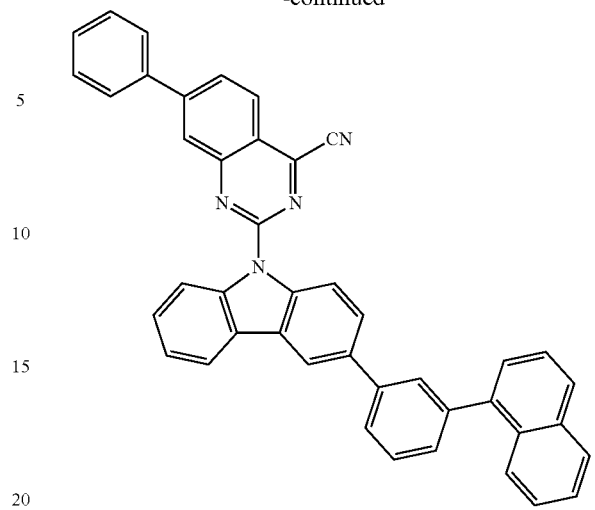
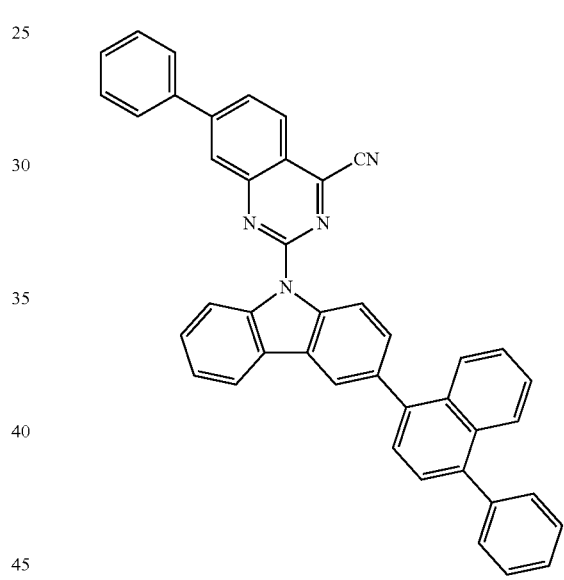
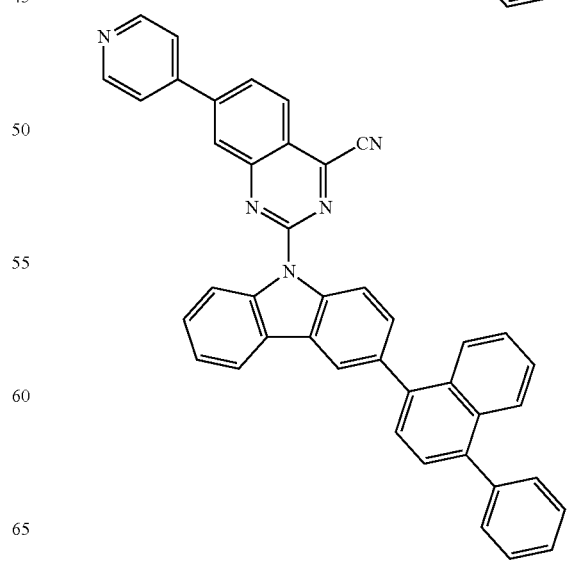

105
-continued
106
-continued
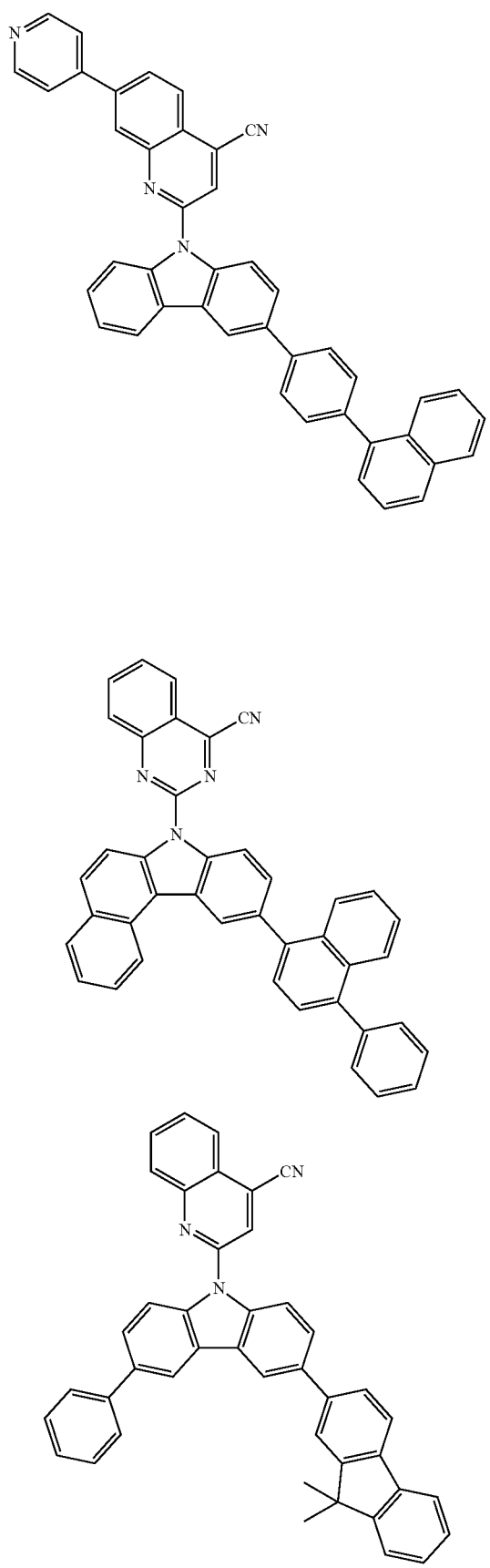
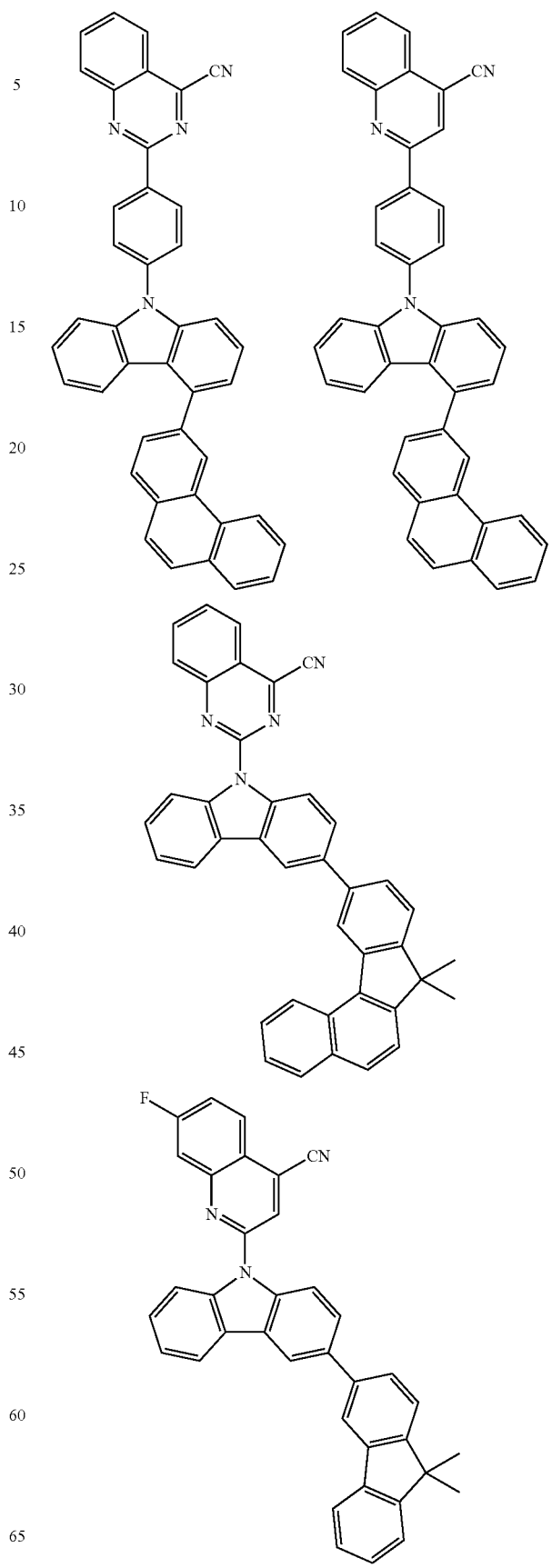

107
-continued
108
-continued
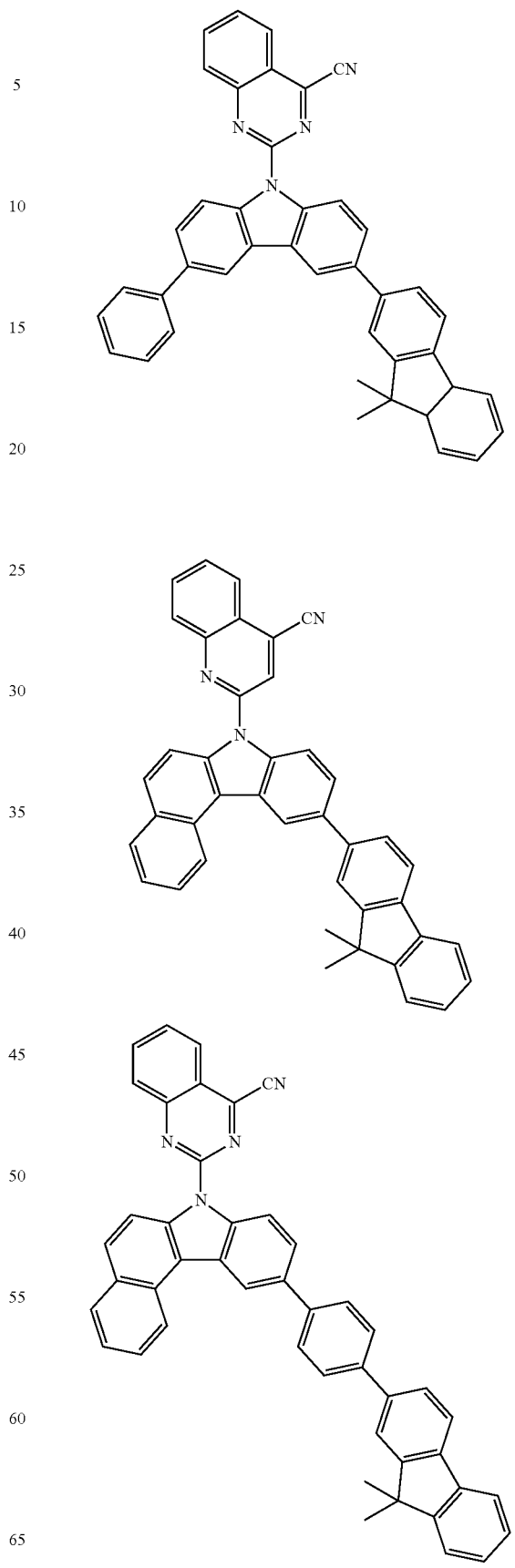

109
-continued
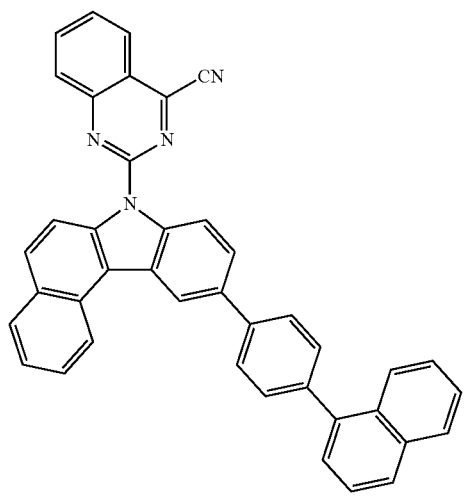
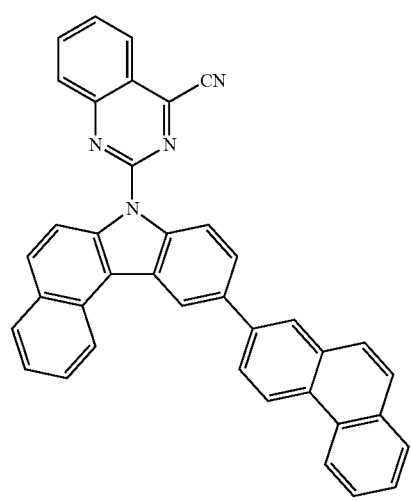
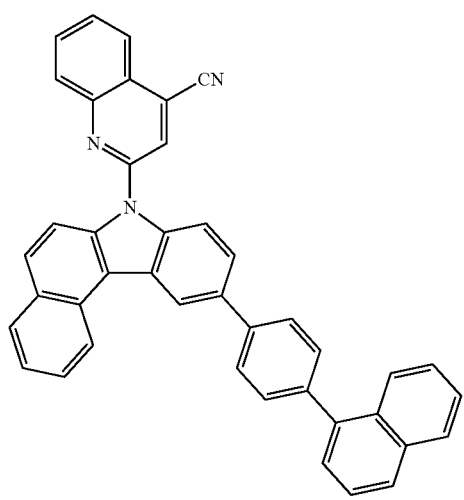
110
-continued
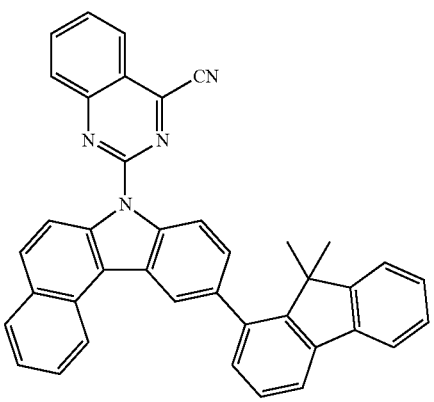
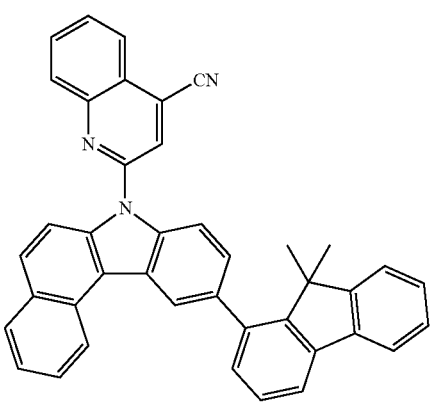
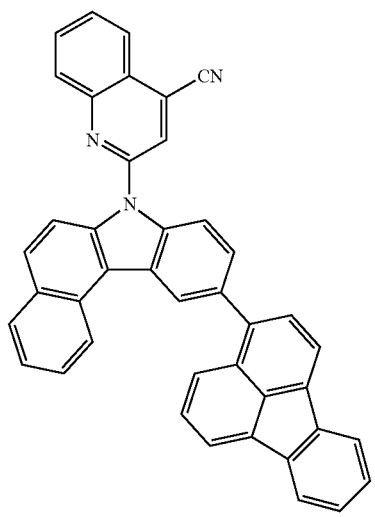

111
-continued
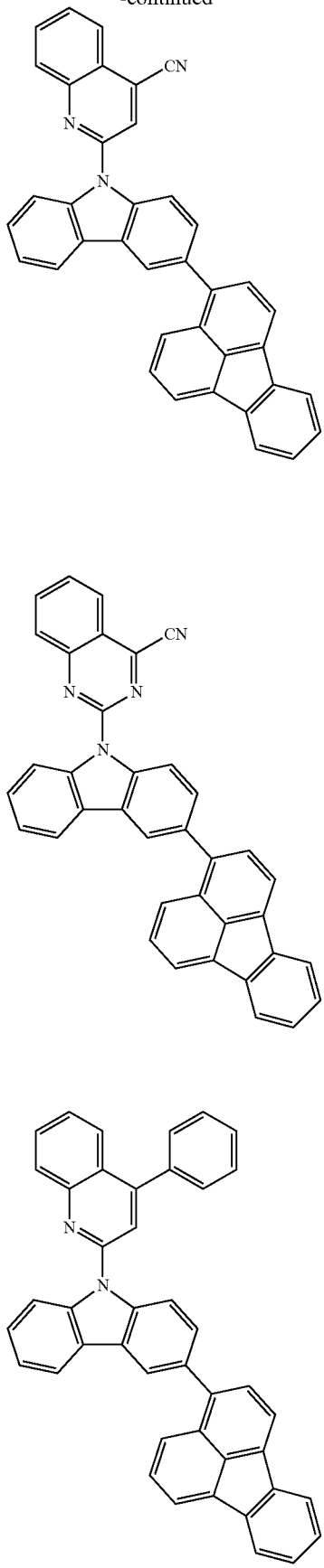
112
-continued

113
-continued
114
-continued
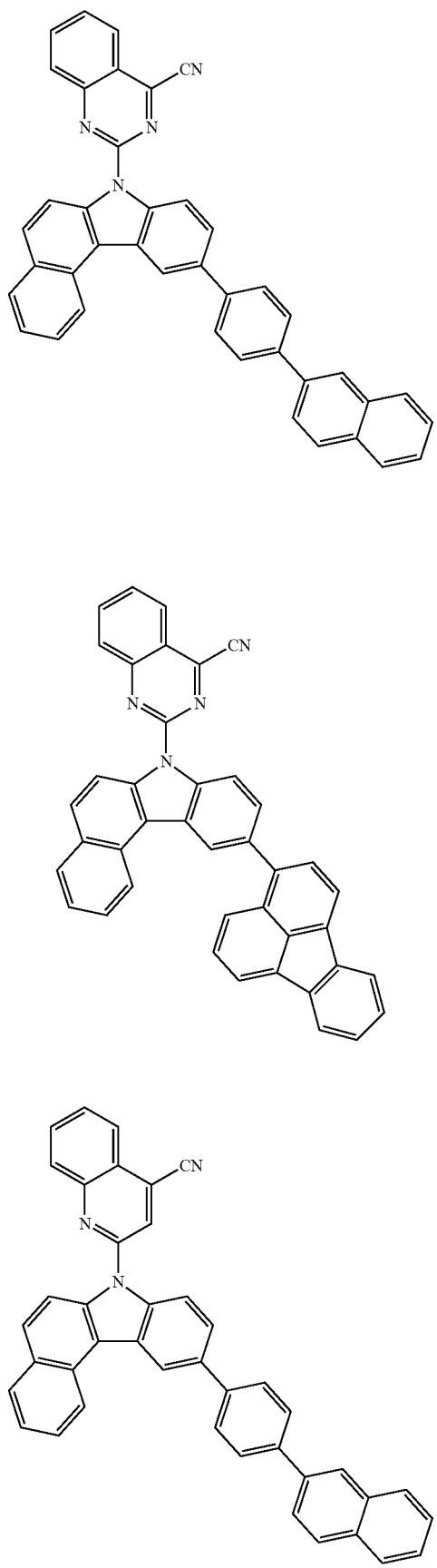
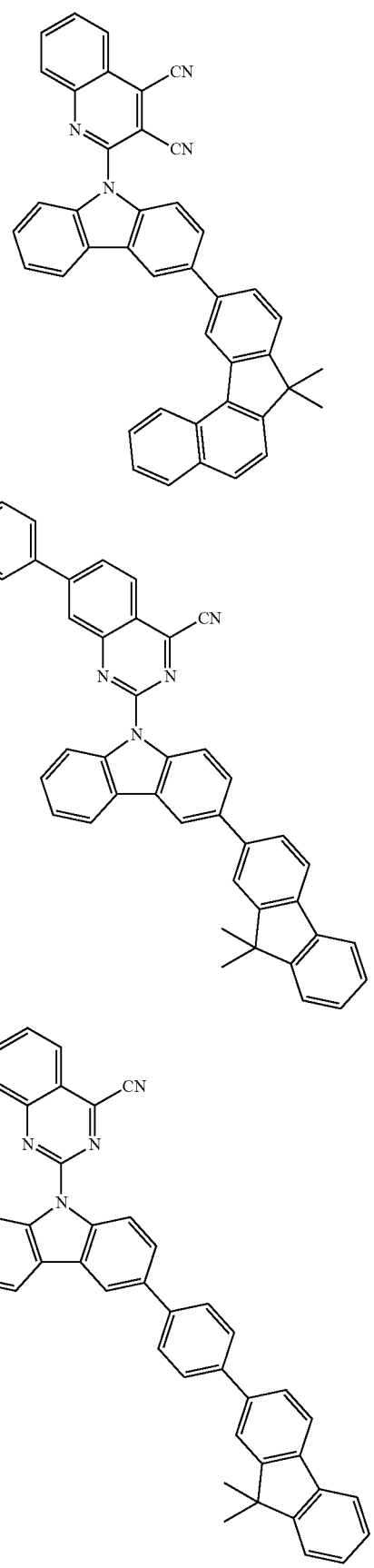

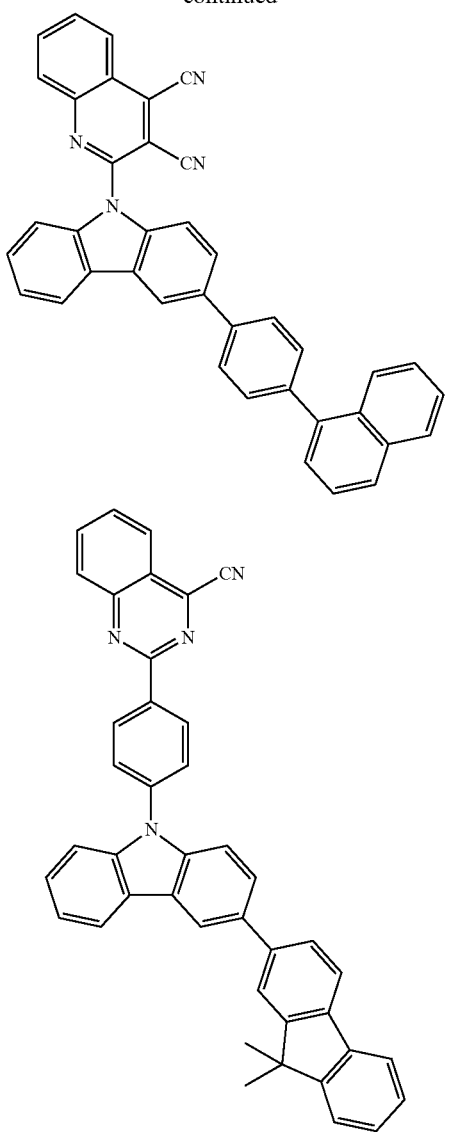

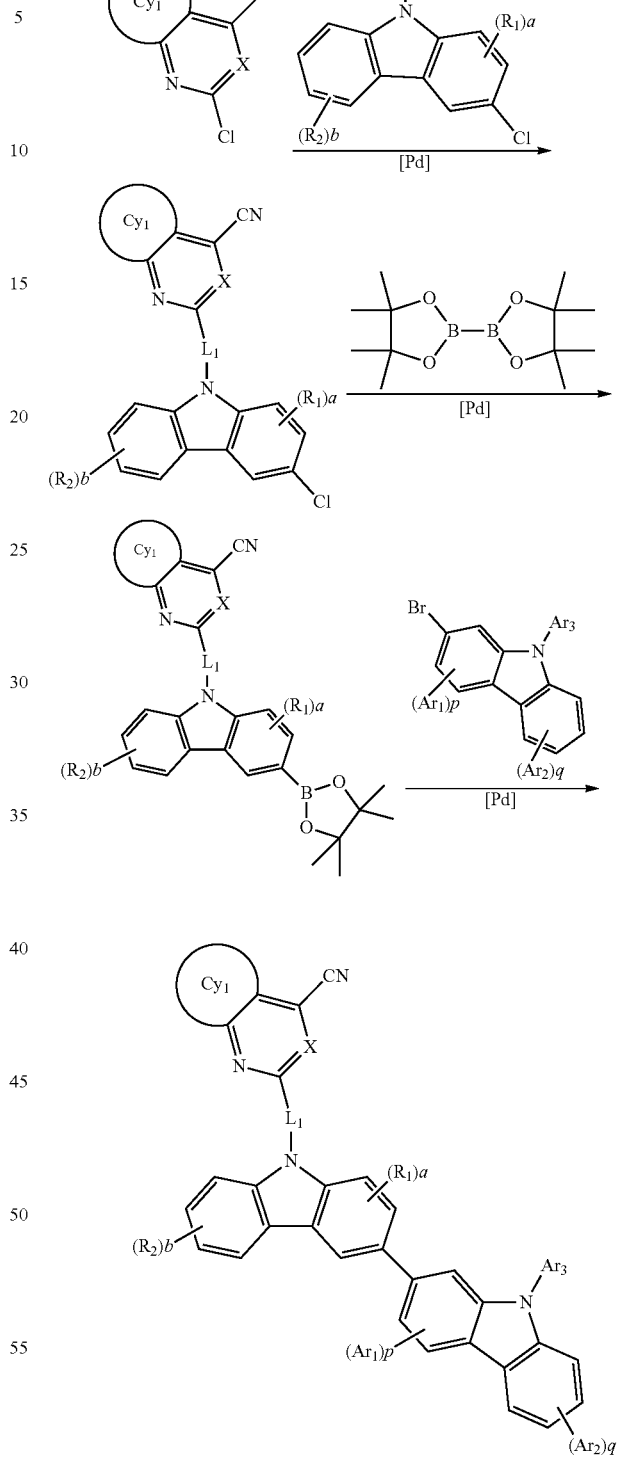

The compound according to the present specification may be easily prepared by a publicly known method. For example, when L1 in Formula 1-1 is a substituted or unsubstituted divalent aromatic hydrocarbon ring group having 6 to 30 carbon atoms, the compound may be prepared by the following Reaction Formula 1 with reference to the Synthesis Examples shown in [the paper *J. Med. Chem.* 1973, 16, 528], [the paper *Archiv der Pharmazie* 1936, 274, 8], and [the paper *Chem. Rev.* 1995, 95, 2457].

[Reaction Formula 1]

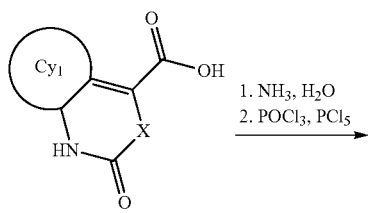

When L1 in Formula 1-1 is a direct bond, the compound may be prepared by the following Reaction Formula 2 with reference to the Synthesis Examples shown in [the paper Rec. Tray. Chim. 1961, 80, 149], [the paper J. Med. Chem. 1973, 16, 528], and [the paper Chem. Rev. 1995, 95, 2457].

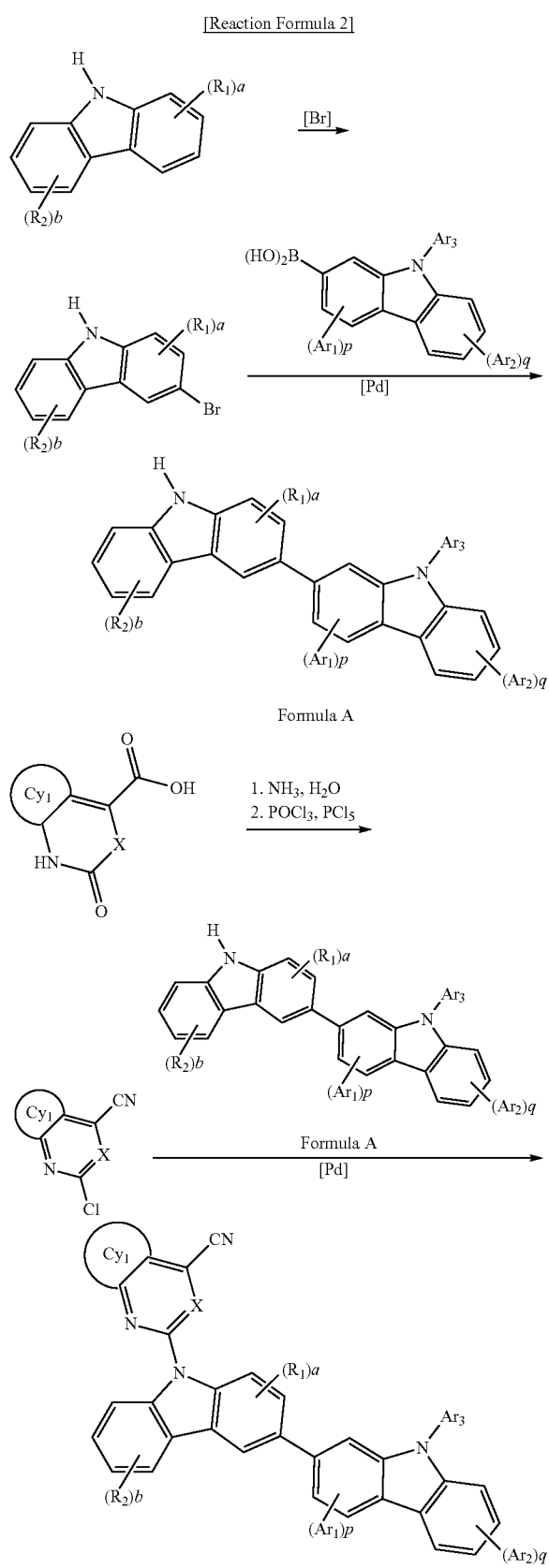

In an exemplary embodiment of the present specification, provided is an organic electroluminescent device including:

a first electrode; a second electrode provided to face the first electrode; and one or more organic material layers provided between the first electrode and the second electrode, in which one or more layers of the organic material layers include the compound of Formula 1.

The organic material layer of the organic electroluminescent device of the present specification may also be composed of a single-layered structure, but may be composed of a multi-layered structure in which two or more organic material layers are stacked. For example, the organic light emitting device of the present invention may have a structure including a hole injection layer, a hole transporting layer, a light emitting layer, an electron transporting layer, an electron injection layer, and the like as organic material layers. However, the structure of the organic electroluminescent device is not limited thereto, and may include a fewer number of organic layers.

In an exemplary embodiment of the present specification, the organic material layer includes a hole injection layer, a hole transporting layer, or a layer which simultaneously injects and transports holes, and the hole injection layer, the hole transporting layer, or the layer which simultaneously injects and transports holes includes the compound of Formula 1.

In another exemplary embodiment, the organic material layer includes a light emitting layer, and the light emitting layer includes the compound of Formula 1.

In an exemplary embodiment of the present specification, the compound of Formula 1 is a phosphorescent host material or a fluorescent host material.

In an exemplary embodiment of the present specification, the compound of Formula 1 is a red phosphorescent host material.

In an exemplary embodiment of the present specification, the organic material layer includes an electron transporting layer or an electron injection layer, and the electron transporting layer or the electron injection layer includes the compound of Formula 1.

In an exemplary embodiment of the present specification, the electron transporting layer, the electron injection layer, or the layer which simultaneously transports and injects electrons includes the compound of Formula 1.

In another exemplary embodiment, the organic material layer includes a light emitting layer and an electron transporting layer, and the electron transporting layer includes the compound of Formula 1.

In still another exemplary embodiment, the organic electroluminescent device may be an organic electroluminescent device having a structure (normal type) in which a positive electrode, one or more organic material layers, and a negative electrode are sequentially stacked on a substrate.

In yet another exemplary embodiment, the organic electroluminescent device may be an organic light emitting device having a reverse-direction structure (inverted type) in which a negative electrode, one or more organic material layers, and a positive electrode are sequentially stacked on a substrate.

Figure 2:
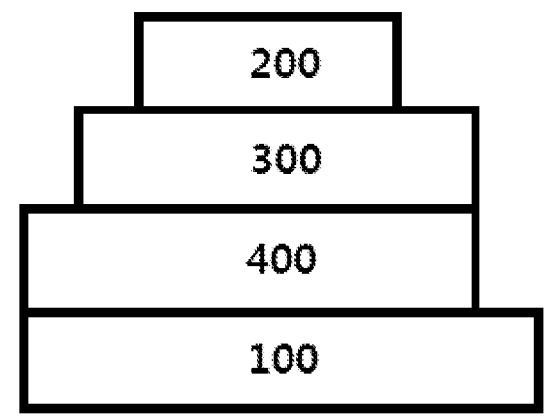

FIGS. 1 to 3 illustrate the stacking sequence of the electrodes and the organic material layers of the organic electroluminescent device according to exemplary embodiments of the present application. However, the scope of the present invention is not intended to be limited by these drawings, and the structure of the organic electroluminescent device known in the art may also be applied to the present invention.

According to FIG. 1, an organic electroluminescent device in which a positive electrode 200, an organic material layer 300, and a negative electrode 400 are sequentially stacked on a substrate 100 is illustrated. However, the organic electroluminescent device is not limited only to such a structure, and as illustrated in FIG. 2, an organic electroluminescent device in which a negative electrode, an organic material layer, and a positive electrode are sequentially stacked on a substrate may also be implemented.

FIG. 3 exemplifies a case where the organic material layer is a multilayer. The organic electroluminescent device according to FIG. 3 includes a hole injection layer 301, a hole transporting layer 302, a light emitting layer 303, an electron transporting layer 304, and an electron injection layer 305. However, the scope of the present application is not limited by the stacking structure as described above, and if necessary, the other layers except for the light emitting layer may be omitted, and another necessary functional layer may be further added.

The organic electroluminescent device of the present specification may be manufactured by the materials and methods known in the art, except that one or more layers of the organic material layers include the compound of the present specification, that is, the compound of Formula 1.

When the organic electroluminescent device includes a plurality of organic material layers, the organic material layers may be formed of the same material or different materials.

The organic electroluminescent device of the present specification may be manufactured by the materials and methods known in the art, except that one or more layers of the organic material layers include the compound of Formula 1, that is, the compound represented by Formula 1.

For example, the organic electroluminescent device of the present specification may be manufactured by sequentially stacking a first electrode, an organic material layer, and a second electrode on a substrate. In this case, the organic electroluminescent device may be manufactured by depositing a metal or a metal oxide having conductivity, or an alloy thereof on a substrate to form a positive electrode by using a physical vapor deposition (PVD) method such as sputtering or e-beam evaporation, forming an organic material layer including a hole injection layer, a hole transporting layer, a light emitting layer, and an electron transporting layer thereon, and then depositing a material, which may be used as a negative electrode, thereon. In addition to the method as described above, an organic light emitting device may be made by subsequently depositing a negative electrode material, an organic material layer, and a positive electrode material on a substrate.

The compound of Formula 1 may be formed as an organic material layer by not only a vacuum deposition method, but also a solution application method when an organic electroluminescent device is manufactured. Here, the solution application method means spin coating, dip coating, doctor blading, inkjet printing, screen printing, a spray method, roll coating, and the like, but is not limited thereto.

In addition to the method as described above, an organic electroluminescent device may also be made by sequentially stacking a negative electrode material, an organic material layer, and a positive electrode material on a substrate (International Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection material is a layer which injects holes from an electrode, and is preferably a compound which has a capability of transporting holes, and thus has an effect of injecting holes at a positive electrode and an excellent effect of injecting holes into a light emitting layer or a light emitting material, prevents excitons, which are produced from the light emitting layer, from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transporting layer is a layer which receives holes from a hole injection layer and transports holes to a light emitting layer, and a hole transporting material is suitably a material which may receive holes from a positive electrode or a hole injection layer to transfer the holes to a light emitting layer, and has high mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transporting layer and an electron transporting layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specific examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine|[x2] compound, a boron complex, a fluoranthene compound, a metal complex, and the like. Specifically, the aromatic amine derivative is a condensed aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting material is a material which receives electrons from an electron injection layer and transports the electrons to a light emitting layer, and an electron transporting material is a material which may inject electrons well from a negative electrode and may transfer the electrons to the light emitting layer, and is suitably a material which has high mobility for the electrons. Specific examples thereof include: an Al complex of 8-hydroxyquinoline; a complex including Alq$_3$; an organic radical compound; a hydroxyflavone-metal complex, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons, which are produced from the light emitting layer, from moving to the hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane|[x3], anthrone and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato)aluminum, tris (2-methyl-8-hydroxyquinolinato)aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato)chlorogallium, bis(2-methyl-8-quinolinato) (o-cresolato) gallium, bis(2-methyl-8-quinolinato) (1-naphtholato)aluminum, bis(2-methyl-8-quinolinato) (2-naphtholato) gallium, and the like, but are not limited thereto.

The organic electroluminescent device according to the present specification may be a top emission type, a bottom emission type, or a dual emission type according to the material to be used.

In an exemplary embodiment of the present specification, the compound of Formula 1 may be included in an organic solar cell or an organic transistor in addition to the organic electroluminescent device.

The preparation of the compound represented by Formula 1 and the organic electroluminescent device including the same will be specifically described in the following Examples. However, the following Examples are provided for exemplifying the present specification, and the scope of the present specification is not limited thereby.

PREPARATION EXAMPLES

In order to synthesize the compound represented by Formula 1, a compound of the following Formulae a to c may be used as a starting material.

Preparation Example 1

Preparation of Starting Material Represented by Formula a

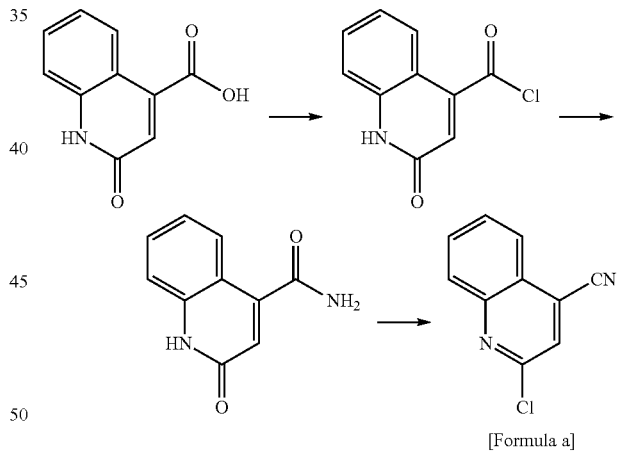

[Formula a]

2-oxo-1,2-dihydroquinoline-4-carboxylic acid (3.78 g, 20 mmol), thionyl chloride (1.60 mL, 22 mmol), and 20 mL of benzene were stirred under nitrogen atmosphere. Dimethylformamide (0.6 ml) was slowly added dropwise thereto, the resulting mixture was stirred at the same temperature for 2 hours, and then the solvent was removed under reduced pressure and vacuum dried to prepare a white solid (4.11 g).

The white solid (4.11 g) was stirred with benzene under nitrogen atmosphere at 0° C. 28% ammonia water (1.3 mL) and water (10 mL) were added thereto, the temperature was increased to normal temperature, and the resulting mixture was further stirred for 12 hours. The product was extracted with chloroform, the moisture was removed over anhydrous magnesium sulfate (MgSO$_4$), and then the solvent was removed under reduced pressure to prepare a white solid (3.53 g) having an amide functional group.

The white solid (3.53 g), phosphorus oxychloride (POCl$_3$, 20 Ml), phosphorus pentachloride (PCl$_5$, 7.81 g, 37.5 mmol), and 1,4-dioxane (10 mL) were refluxed under nitrogen atmosphere. The mixture was refluxed for 8 hours, and then cooled to 0° C., and the reaction was terminated with an aqueous sodium carbonate solution. The product was extracted with chloroform, the moisture was removed over anhydrous magnesium sulfate (MgSO$_4$), and then the solvent was removed under reduced pressure. The obtained solid was filtered, washed with ethanol, and then vacuum dried to obtain 2.08 g (a yield of 59%) of Formula a.

MS: [M+H]$^+$=189

Preparation Example 2

Preparation of Starting Material Represented by Formula b

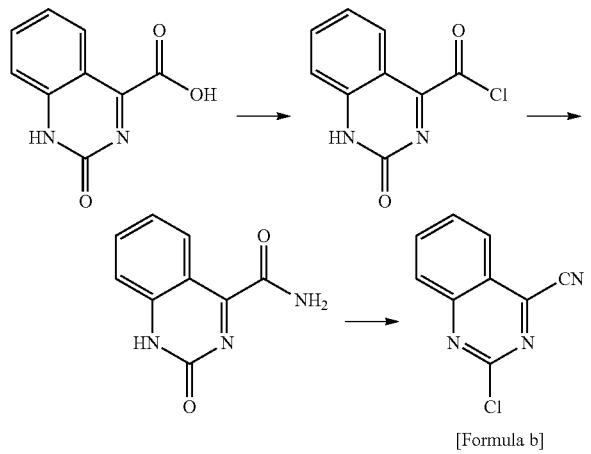

[Formula b]

2-oxo-1,2-dihydroquinazoline-4-carboxylic acid (3.80 g, 20 mmol), thionyl chloride (1.60 mL, 22 mmol), and 20 mL of benzene were stirred under nitrogen atmosphere. Dimethylformamide (0.6 mL) was slowly added dropwise thereto, the resulting mixture was stirred at the same temperature for 2 hours, and then the solvent was removed under reduced pressure and vacuum dried to prepare a white solid (4.11 g).

The white solid (4.11 g) was stirred with benzene under nitrogen atmosphere at 0° C. 28% ammonia water (1.3 mL) and water (10 mL) were added thereto, the temperature was increased to normal temperature, and the resulting mixture was further stirred for 12 hours. The product was extracted with chloroform, the moisture was removed over anhydrous magnesium sulfate (MgSO$_4$), and then the solvent was removed under reduced pressure to prepare a white solid (3.53 g) having an amide functional group.

The white solid (3.53 g), phosphorus oxychloride (POCl$_3$, 20 Ml), phosphorus pentachloride (PCl$_5$, 7.81 g, 37.5 mmol), and 1,4-dioxane (10 mL) were refluxed under nitrogen atmosphere. The mixture was refluxed for 8 hours, and then cooled to 0° C., and the reaction was terminated with an aqueous sodium carbonate solution. The product was extracted with chloroform, the moisture was removed over anhydrous magnesium sulfate (MgSO$_4$), and then the solvent was removed under reduced pressure. The obtained solid was filtered, washed with ethanol, and then vacuum dried to obtain 2.19 g (a yield of 58%) of Formula b.

MS: [M+H]$^+$=190

Preparation Example 3

Preparation of Starting Material Represented by Formula c

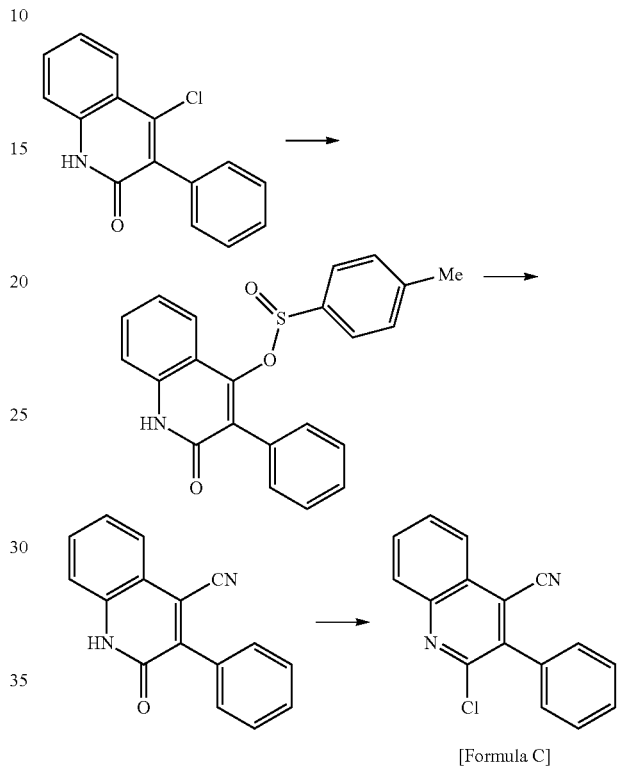

[Formula C]

4-chloro-3-phenylquinolin-2(1H)-one (5.11 g, 20 mmol) was dissolved in dimethyl formaldehyde (DMF 1 L), and then sodium p-toluenesulfinate (5.34 g, 30 mmol) was added thereto, and the resulting mixture was stirred at 120° C. for 20 hours. The temperature was lowered to normal temperature, water was introduced to obtain a solid, and then the solid was filtered and vacuum dried to obtain 5.25 g (a yield of 70%) of a yellow solid.

5.25 g of the yellow solid was dissolved in dimethyl formaldehyde (DMF 100 mL), and then potassium cyanide (KCN, 13.6 g) was added thereto, and the resulting mixture was stirred at 70° C. under nitrogen conditions for 6 hours. The temperature was lowered to normal temperature, water was introduced to obtain a solid, and then diluted hydrochloric acid was continuously introduced. The produced solid was filtered and vacuum dried to obtain 2.06 g (a yield of 60%) of a yellow solid.

The yellow solid (2.06 g), phosphorus oxychloride (POCl$_3$, 10 mL), and 1,4-dioxane (10 mL) were refluxed under nitrogen atmosphere. The mixture was refluxed for 8 hours, and then cooled to 0° C., and the reaction was terminated with an aqueous sodium carbonate solution. The product was extracted with chloroform, the moisture was removed over anhydrous magnesium sulfate (MgSO$_4$), and then the solvent was removed under reduced pressure. The obtained solid was filtered, washed with ethanol, and then vacuum dried to obtain 2.04 g (a yield of 92%) of Formula c.

MS: [M+H]$^+$=275

Preparation Example 4

Preparation of Compound A

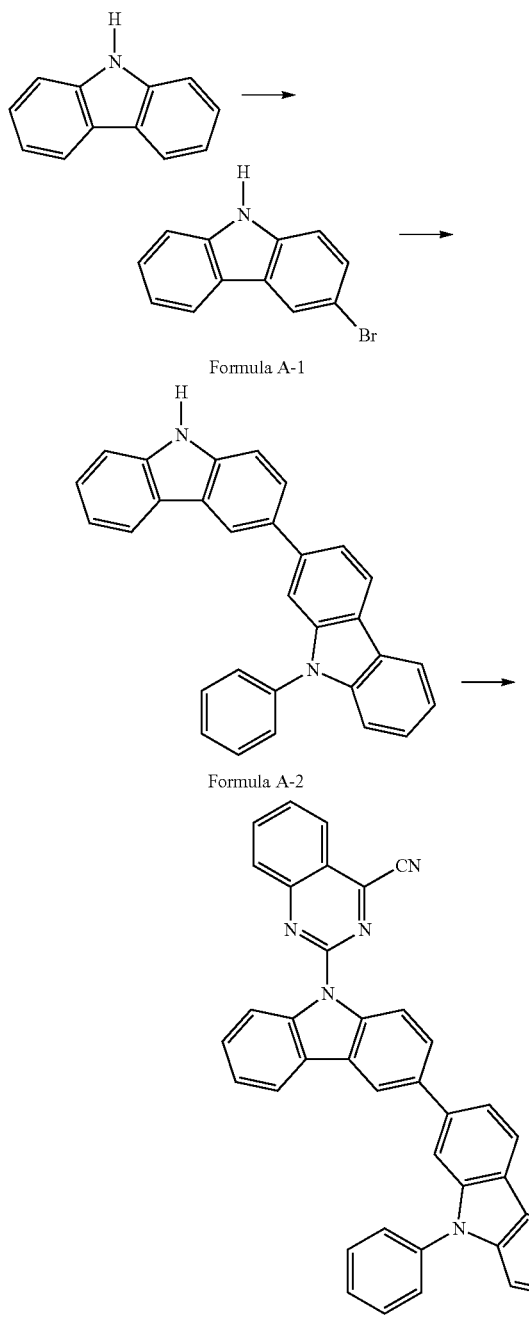

Formula A-1

Formula A-2

Formula A

Preparation of Compound A-1

16.7 g (0.1 mol) of carbazole was dissolved in tetrahydrofuran (THF, 500 mL), and then the resulting solution was stirred at 0° C. for 10 minutes. N-bromosuccinimide (NBS, 18.68 g, 0.105 mol) was added thereto, and the resulting mixture was stirred at normal temperature for 12 hours, and then was extracted with distilled water and ethyl acetate. The organic layer was dried over anhydrous magnesium sulfate| [x4] (MgSO$_4$), and then the solvent was removed, and silica gel column chromatography was performed to obtain 22.4 g (91%) of Compound A-1.

Preparation of Compound A-2

22.4 g (91 mmol) of Compound A-1, 31.3 g (109 mmol) of 9-phenyl-9H-carbazole-2-boronic acid|[x5], Pd(PPh$_3$)$_4$ (5.25 g, 4.5 mmol), 60 mL of 2 M K$_2$CO$_3$ aqueous solution, 300 mL of toluene, and 90 mL of ethanol were put into a container, and the resulting mixture was stirred under reflux for 12 hours. The mixture was washed with distilled water and extracted with chloroform. The organic layer was dried over anhydrous magnesium sulfate (MgSO$_4$), and then the solvent was removed, and silica gel column chromatography was performed to obtain 29.7 g (72.8 mmol, 80%) of Compound A-2.

Preparation of Compound A

60% sodium hydride (1.16 g, 29 mmol) and 40 mL of dehydrated dimethylformamide were added to a nitrogen-substituted flask, and the resulting mixture was stirred. 100 mL of dimethylformamide was added to Compound A-2 (11.84 g, 28 mmol) obtained above to dissolve the compound, and then the resulting solution was added dropwise to the same flask for 15 minutes. After the addition dropwise was completed, the resulting mixture was continuously stirred for 30 minutes. 100 mL of dimethylformamide was added to the starting material (5.69 g, 30 mmol) represented by Formula b to dissolve the starting material, and then the resulting solution was added dropwise to the same flask for 10 minutes. And then, after the addition dropwise was completed, the resulting mixture was continuously stirred for 4 hours. And then, 0.6 L of water was added thereto to filter and collect the crystals precipitated. The filtered and collected crystals were dispersed in ethanol and the dispersion was stirred overnight, and then filtered and vacuum dried to obtain 14.60 g (26 mmol, a yield of 87%) of Compound A.

MS: [M+H]$^+$=562

Preparation Example 5

Preparation of Compound B

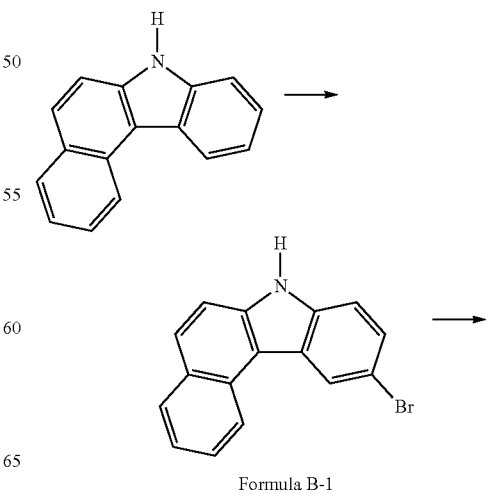

Formula B-1

-continued

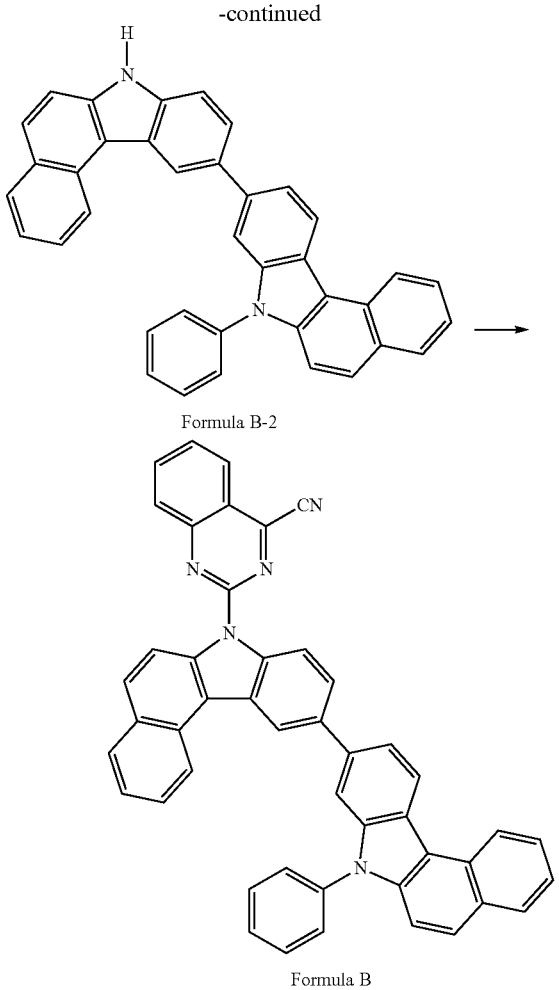

Formula B-2

Formula B

Preparation of Formula B-1

20.4 g (0.1 mol) of 7H-benzo[c]carbazole was dissolved in tetrahydrofuran (THF, 500 mL), and then the resulting solution was stirred at 0° C. for 10 minutes. N-bromosuccinimide (NBS, 18.68 g, 0.105 mol) was added thereto, and the resulting mixture was stirred at normal temperature for 12 hours, and then was extracted with distilled water and ethyl acetate. The organic layer was dried over anhydrous magnesium sulfate (MgSO$_4$), and then the solvent was removed, and silica gel column chromatography was performed to obtain 25.4 g (86%) of Compound B-1.

Preparation of Formula B-2

23.7 g (80 mmol) of Compound B-1, 32.3 g (96 mmol) of 7-phenyl-7H-benzo[c]carbazol-9-boronic acid|[x6], ??Pd (PPh$_3$)$_4$ (5.25 g, 4.5 mmol), 80 mL of 2 M K$_2$CO$_3$ aqueous solution, 400 mL of toluene, and 160 mL of ethanol were put into a container, and the resulting mixture was stirred under reflux for 12 hours. The mixture was washed with distilled water and extracted with chloroform. The organic layer was dried over anhydrous magnesium sulfate (MgSO$_4$), and then the solvent was removed, and silica gel column chromatography was performed to obtain 33.4 g (65.6 mmol, 82%) of Compound B-2.

Preparation of Compound B

60% sodium hydride (1.20 g, 30 mmol) and 40 mL of dehydrated dimethylformamide were added to a nitrogen-substituted flask, and the resulting mixture was stirred. 100 mL of dimethylformamide was added to the starting material (5.12 g, 27 mmol) represented by Formula b to dissolve the starting material, and then the resulting solution was added dropwise to the same flask for 10 minutes. After the addition dropwise was completed, the resulting mixture was continuously stirred for 30 minutes. And then, 100 mL of dimethylformamide was added to Compound B-2 (14.24 g, 28 mmol) obtained above to dissolve the compound, and then the resulting solution was added dropwise to the same flask for 30 minutes. After the addition dropwise was completed, the resulting mixture was continuously stirred for 4 hours. And then, 0.6 L of water was added thereto to filter and collect the crystals precipitated. The filtered and collected crystals were dispersed in ethanol and the dispersion was stirred overnight, and then filtered and vacuum dried to obtain 14.55 g (22 mmol, a yield of 81%) of Compound B.

MS: [M+H]$^+$=662

Preparation Example 6

Preparation of Compound C

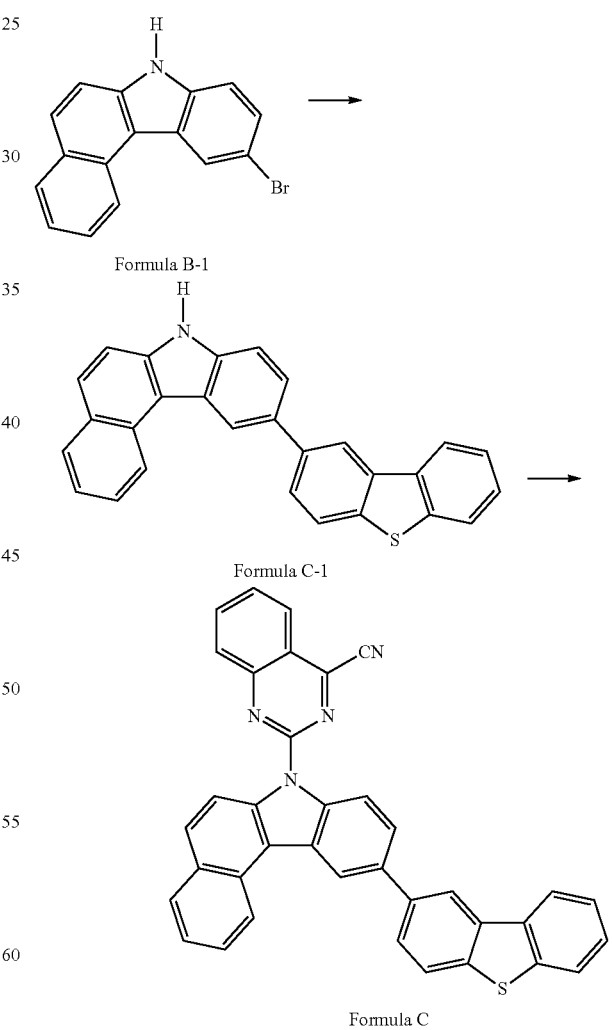

Formula B-1

Formula C-1

Formula C 17.7 g (60 mmol) of Compound B-1 synthesized in Preparation Example 5, dibenzothiophene-2-boronic acid (17.1 g, 75 mmol), Pd(PPh$_3$)$_4$ (3.46 g, 3 mmol), 60 mL of 2

M $K_2CO_3$ aqueous solution, 300 mL of toluene, and 120 mL of ethanol were put into a container, and the resulting mixture was stirred under reflux for 12 hours. The mixture was washed with distilled water and extracted with chloroform. The organic layer was dried over anhydrous magnesium sulfate ($MgSO_4$), and then the solvent was removed, and silica gel column chromatography was performed to obtain 19.4 g (65.6 mmol, 81%) of Compound C-1.

Preparation of Compound C

60% sodium hydride (0.80 g, 20 mmol) and 30 mL of dehydrated dimethylformamide were added to a nitrogen-substituted flask, and the resulting mixture was stirred. 60 mL of dimethylformamide was added to the starting material (3.22 g, 17 mmol) represented by Formula b to dissolve the starting material, and then the resulting solution was added dropwise to the same flask for 10 minutes. After the addition dropwise was completed, the resulting mixture was continuously stirred for 30 minutes. And then, 60 mL of dimethylformamide was added to Compound C-1 (7.20 g, 18 mmol) obtained above to dissolve the compound, and then the resulting solution was added dropwise to the same flask for 30 minutes. After the addition dropwise was completed, the resulting mixture was continuously stirred for 4 hours. And then, 0.4 L of water was added thereto to filter and collect the crystals precipitated. The filtered and collected crystals were dispersed in ethanol and the dispersion was stirred overnight, and then filtered and vacuum dried to obtain 7.54 g (12 mmol, a yield of 70%) of Compound C. MS: $[M+H]^+$ =540

Preparation Example 7

Preparation of Compound D

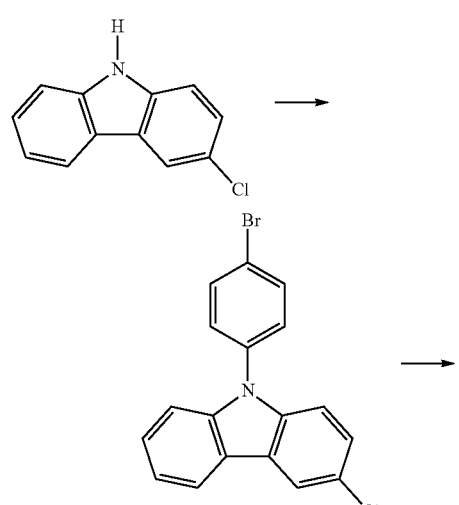

Formula D-1

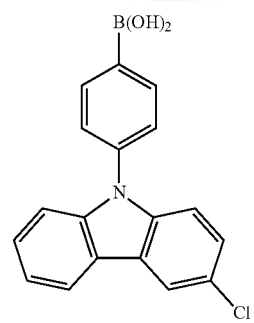

Formula D-2

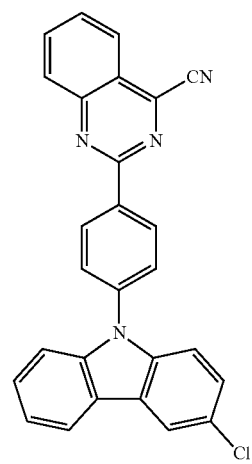

Formula D-3

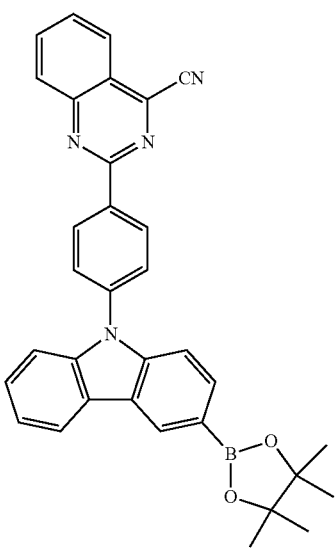

Formula D-4

-continued

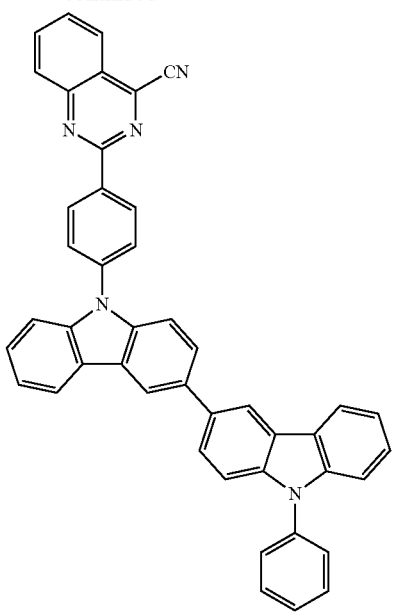

Compound D 20.1 g (100 mmol) of 3-chloro-9H-carbazole and 43.5 g (184 mmol) of 1-bromo-4-iodobenzene were dissolved in 500 mL of toluene, and then 9.2 g (48 mmol) of CuI, 6.5 mL (96 mmol) of diaminoethane, and 9.1 g (288 mmol) of tripotassium phosphate were added thereto, and the resulting mixture was refluxed for 24 hours. The mixture was cooled to normal temperature, and then the reaction was terminated with hydrochloric acid diluted with water, extraction with chloroform was performed, and then the extract was washed with distilled water. The obtained organic layer was dried over anhydrous magnesium sulfate (MgSO$_4$), and then the solvent was removed, and silica gel column chromatography was performed to obtain 19.6 g (55.0 mmol, 55%) of Compound D-1.

Preparation of Formula D-2

18.2 g (51 mmol) of Compound D-1 was dissolved in 300 mL of THF, the resulting solution was cooled to −78° C., and then 25.0 mL of n-BuLi (2.5 M in hexane) was slowly added thereto. The resulting mixture was stirred at −78° C. for 2 hours, and then 8.5 mL of B(OMe)$_3$ was added thereto, the mixture was stirred while being warmed, and then an aqueous ammonium chloride solution was introduced to the mixture to terminate the reaction. Extraction was performed with chloroform, and then the extract was washed with distilled water. The obtained organic layer was dried over anhydrous magnesium sulfate (MgSO$_4$), and then the solvent was removed, and silica gel column chromatography was performed to obtain 11.1 g (55.0 mmol, 68%) of Compound D-2.

Preparation of Formula D-3

2.84 g (15 mmol) of Compound b and 4.50 g (14 mmol) of Compound D-2 were mixed with 100 mL of tetrahydrofuran (THF) and 40 mL of water, and then 0.86 g (0.75 mmol) of Pd(PPh$_3$)$_4$ and 4.14 g of potassium carbonate (K$_2$CO$_3$) were added thereto. The mixture was stirred for 8 hours while being refluxed, and then the mixture was cooled to room temperature, and the reaction was terminated with 20 mL of an aqueous ammonium chloride solution. The mixture was extracted with chloroform, and then was washed with distilled water. The obtained organic layer was dried over anhydrous magnesium sulfate (MgSO$_4$), and then the solvent was removed, and silica gel column chromatography was performed to obtain 5.0 g (11.7 mmol, 78%) of Compound D-3.

Preparation of Formula D-4

Compound D-3 (4.30 g, 10 mmol), bis(pinacolato)diboron (3.04 g, 12 mmol), and potassium acetate (2.94 g, 30 mmol) were mixed under nitrogen atmosphere, 40 mL of dioxane was added thereto, and the resulting mixture was heated while being stirred. Bis(dibenzylideneacetone)palladium (0.457 g, 0.5 mmol) and tricyclohexylphosphine (0.28 g, 1.0 mmol) were added to the mixture while being refluxed, and the mixture was stirred for 10 hours while being heated. After the reaction was terminated, the mixture was lowered to normal temperature, and then filtered. The filtrate was extracted with distilled water and chloroform, and the organic layer was dried with anhydrous magnesium sulfate. The organic layer was distilled under reduced pressure, and then recrystallized with ethanol to obtain 4.12 g (7.9 mmol, 79%) of Compound D-4.

Preparation of Compound D

Compound D-4 (5.22 g, 10.0 mmol) and the material represented by Formula A-1 (3.86 g, 12.0 mmol) synthesized in Preparation Example 4 were completely dissolved in 50 mL of tetrahydrofuran under nitrogen atmosphere, and then 25 Ml of 2 M of an aqueous potassium carbonate solution was added thereto, tetrakistriphenylphosphinopalladium (1.10 g, 1.0 mmol) was introduced thereto, and then the resulting mixture was stirred for 2 hours while being heated. The temperature was lowered to normal temperature, the reaction was terminated, and then the potassium carbonate solution was removed to filter the white solid. The filtered white solid was washed once with tetrahydrofuran and ethanol, respectively, to prepare 5.50 g (8 mmol, 80%) of Compound D.

MS: [M+H]$^+$=688

Preparation Example 8

Preparation of Compound E

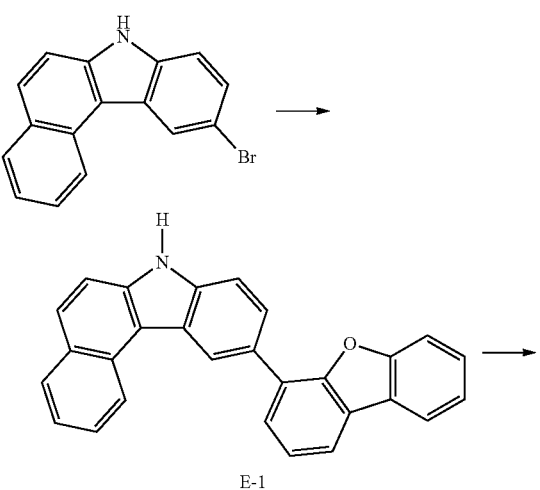

E-1

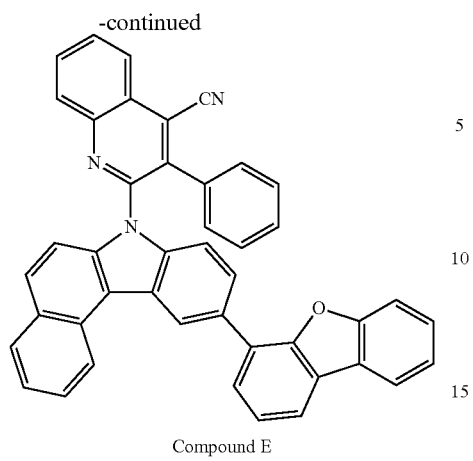

Compound E

Preparation of Formula E-1

200 mL of tetrahydrofuran was introduced into 14.8 g (50 mmol) of Compound B-1 synthesized in Preparation Example 5 and dibenzo[b,d]furan-4-ylboronic acid (12.7 g, 60 mmol), and then Pd(PPh$_3$)$_4$ (2.89 g, 2.5 mmol) and 100 mL of 2 M K$_2$CO$_3$ aqueous solution were added thereto, and the resulting mixture was stirred for 12 hours while being refluxed. The temperature was cooled to normal temperature to perform extraction with chloroform and distilled water. The organic layer was dried over anhydrous magnesium sulfate (MgSO$_4$), and then the solvent was removed, and silica gel column chromatography was performed to obtain 16.1 g (42 mmol, 84%) of Compound E-1.

Preparation of Compound E 5.3 g (20 mmol) of the compound represented by Formula c, 7.6 g (40 mmol) of CuI, 19.5 g (60 mmol) of Cs$_2$CO$_3$, 0.716 mL (6 mmol) of trans 1,2-diaminocyclohexane, and 130 mL of 1,2-dichlorobenzene were added to 11.5 g (30 mmol) of Compound E-1, and the resulting mixture was stirred at 180° C. for 12 hours while being refluxed.

Thereafter, the temperature was cooled to normal temperature, the organic layer was extracted with chloroform while being washed with distilled water, and then the organic layer was dried over anhydrous magnesium sulfate (MgSO$_4$), and then the solvent was removed, and silica gel column chromatography was performed to obtain 12.4 g (20.4 mmol, 68%) of Compound E.

MS: [M+H]$^+$=612

Preparation Example 9

Preparation of Compound F

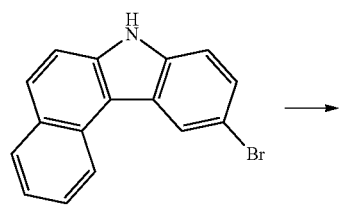

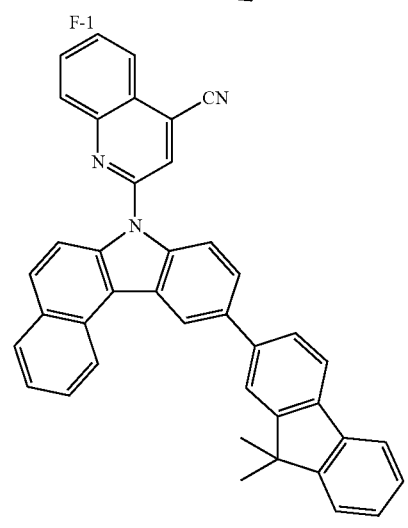

F-1

Compound F 200 mL of tetrahydrofuran was introduced into 14.8 g (50 mmol) of Compound B-1 synthesized in Preparation Example 5 and (9,9-dimethyl-9H-fluoren-2-yl)boronic acid (14.3 g, 60 mmol), and then Pd(PPh$_3$)$_4$ (2.89 g, 2.5 mmol) and 100 mL of 2 M K$_2$CO$_3$ aqueous solution were added thereto, and the resulting mixture was stirred for 12 hours while being refluxed. The temperature was cooled to normal temperature to perform extraction with chloroform and distilled water. The organic layer was dried over anhydrous magnesium sulfate (MgSO$_4$), and then the solvent was removed, and silica gel column chromatography was performed to obtain 16.0 g (39 mmol, 78%) of Compound F-1.

Preparation of Compound F 5.3 g (20 mmol) of the compound represented by Formula b, 7.6 g (40 mmol) of CuI, 19.5 g (60 mmol) of Cs$_2$CO$_3$, 0.716 mL (6 mmol) of trans 1,2-diaminocyclohexane, and 130 mL of 1,2-dichlorobenzene were added to 12.3 g (30 mmol) of Compound F-1, and the resulting mixture was stirred at 180° C. for 12 hours while being refluxed. Thereafter, the temperature was cooled to normal temperature, the organic layer was extracted with chloroform while being washed with distilled water, and then the organic layer was dried over anhydrous magnesium sulfate (MgSO$_4$), and then the solvent was removed, and silica gel column chromatography was performed to obtain 10.9 g (19.5 mmol, 65%) of Compound F.

MS: [M+H]$^+$=562.

Preparation Example 10

Preparation of Compound G

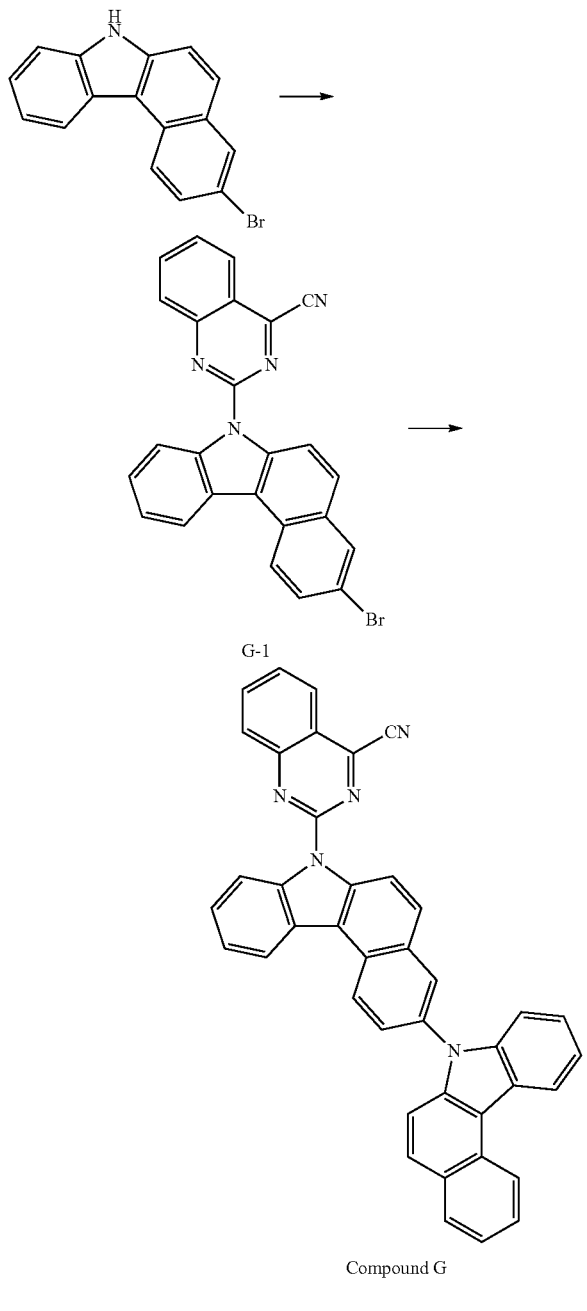

Compound G

Preparation of Formula G-1

60% sodium hydride (0.80 g, 20 mmol) and 30 mL of dehydrated dimethylformamide were added to a nitrogen-substituted flask, and the resulting mixture was stirred. 60 mL of dimethylformamide was added to 3-bromo-7H-benzo[c]carbazole (5.0 g, 17 mmol) to dissolve the compound, and then the resulting solution was added dropwise to the same flask for 10 minutes. After the addition dropwise was completed, the resulting mixture was continuously stirred for 30 minutes. 60 mL of dimethylformamide was added to the compound (3.41 g, 18 mmol) represented by Formula b to dissolve the compound, and then the resulting solution was added dropwise to the same flask for 30 minutes. After the addition dropwise was completed, the resulting mixture was continuously stirred for 4 hours. And then, 0.4 L of water was added thereto to filter and collect the crystals precipitated. The filtered and collected crystals were dispersed in ethanol and the dispersion was stirred overnight, and then filtered and vacuum dried to obtain 5.95 g (13.2 mmol, a yield of 78%) of a material of Compound G-1.

Preparation of Compound G 0.21 g (0.94 mmol) of palladium acetate (II), xylene (20 mL), and 0.76 g (3.76 mmol) of tri-tert-butylphosphine were added to a container, and the resulting mixture was stirred at 60° C. for 30 minutes. The solution was delivered to a xylene solution (180 mL) of G-1 (8.1 g, 18 mmol), 7H-benzo[c]carbazole (3.9 g, 18 mmol), and tert-butoxy sodium (7.7 g, 80 mmol), which was heated to 60° C. under nitrogen flow. Thereafter, the mixture was warmed up to 130° C., and stirred for 5 hours while being heated. The temperature was cooled to room temperature, and then 200 mL of water was added thereto. The organic layer was extracted with chloroform, and then the organic layer was dried over anhydrous magnesium sulfate ($MgSO_4$), and then the solvent was removed, and silica gel column chromatography was performed to obtain 8.0 g (13.7 mmol, 76%) of Compound G.

MS: $[M+H]^+=586$

Preparation Example 11

Preparation of Compound H

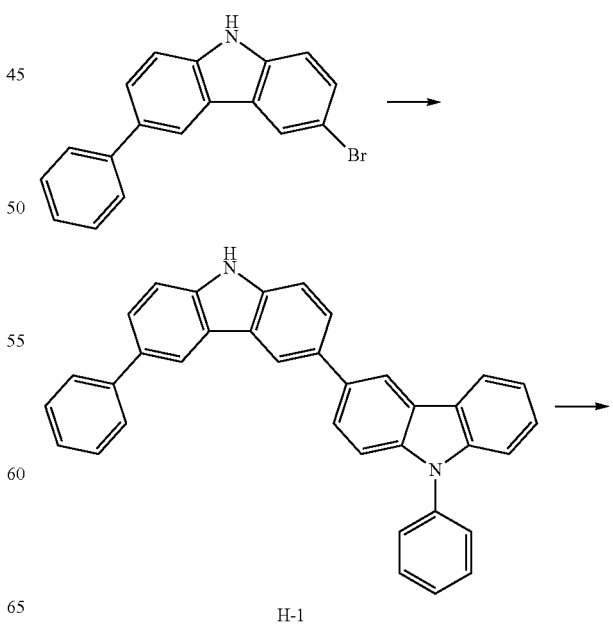

H-1

137

-continued

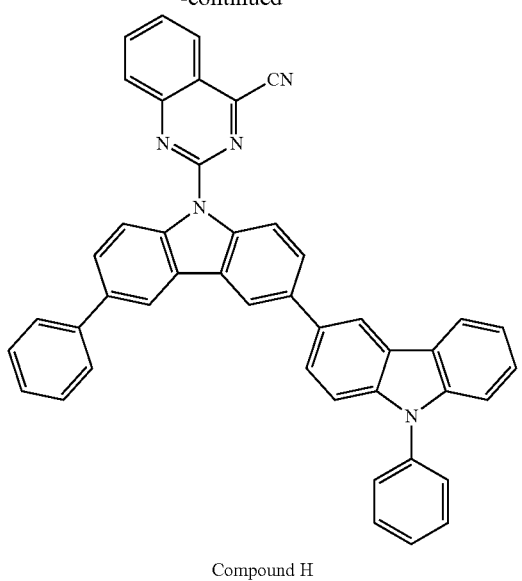

Compound H

Preparation of Formula H-1

300 mL of tetrahydrofuran was introduced into 16.1 g (50 mmol) of 3-bromo-6-phenyl-9H-carbazole and 9-phenyl-3-carbazole boronic acid pinacolate (22.1 g, 60 mmol), and then Pd(PPh$_3$)$_4$ (2.89 g, 2.5 mmol) and 100 mL of 2 M K$_2$CO$_3$ aqueous solution were added thereto, and the resulting mixture was stirred for 12 hours while being refluxed. The temperature was cooled to normal temperature to perform extraction with chloroform and distilled water. The organic layer was dried over anhydrous magnesium sulfate (MgSO$_4$), and then the solvent was removed, and silica gel column chromatography was performed to obtain 17.4 g (39 mmol, 72%) of Compound H-1.

Preparation of Compound H

60% sodium hydride (0.80 g, 20 mmol) and 30 mL of dehydrated dimethylformamide were added to a nitrogen-substituted flask, and the resulting mixture was stirred. 80 mL of dimethylformamide was added to the compound of Formula H-1 (8.2 g, 17 mmol) to dissolve the compound, and then, the resulting solution was added dropwise to the same flask for 10 minutes. After the addition dropwise was completed, the resulting mixture was continuously stirred for 30 minutes. 60 mL of dimethylformamide was added to the compound (3.41 g, 18 mmol) represented by Formula b to dissolve the compound, and then the resulting solution was added dropwise to the same flask for 30 minutes. After the addition dropwise was completed, the resulting mixture was continuously stirred for 4 hours. And then, 0.4 L of water was added thereto to filter and collect the crystals precipitated. The filtered and collected crystals were dispersed in ethanol and the dispersion was stirred overnight, and then filtered and vacuum dried to obtain 6.72 g (10.5 mmol, a yield of 62%) of a material of Compound H.

MS: [M+H]$^+$=638

138

Preparation Example 12

Preparation of Compound I

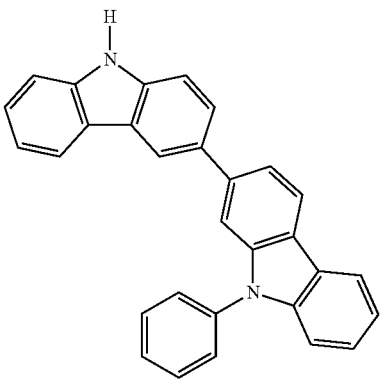

Formula A-2

→

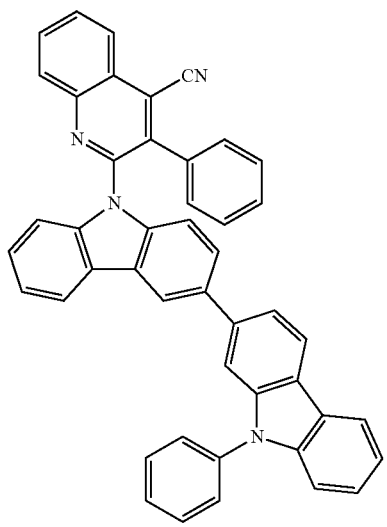

Compound I

Preparation of Compound I 5.3 g (20 mmol) of the compound represented by Formula c, 7.6 g (40 mmol) of CuI, 19.5 g (60 mmol) of Cs$_2$CO$_3$, 0.716 mL (6 mmol) of trans 1,2-diaminocyclohexane, and 130 mL of 1,2-dichlorobenzene were added to 12.3 g (30 mmol) of Compound A-2, and the resulting mixture was stirred at 180° C. for 12 hours while being refluxed. Thereafter, the temperature was cooled to normal temperature, the organic layer was extracted with chloroform while being washed with distilled water, and then the organic layer was dried over anhydrous magnesium sulfate (MgSO$_4$), and then the solvent was removed, and silica gel column chromatography was performed to obtain 9.2 g (14.4 mmol, 48%) of Compound I.

MS: [M+H]$^+$=637

Preparation Example 13

Preparation of Compound J

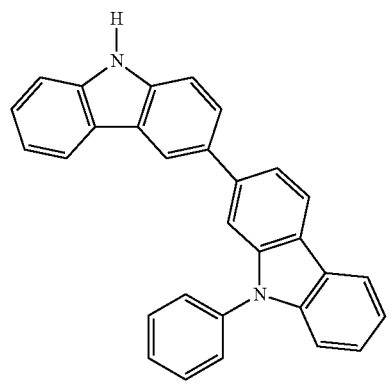

Formula A-2

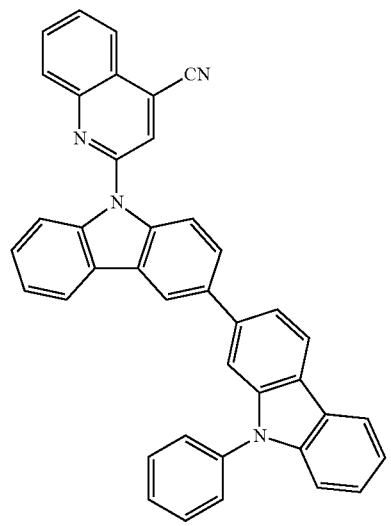

Compound J

Preparation of Compound J 3.8 g (20 mmol) of the compound represented by Formula a, 7.6 g (40 mmol) of CuI, 19.5 g (60 mmol) of $Cs_2CO_3$, 0.716 mL (6 mmol) of trans 1,2-diaminocyclohexane, and 130 mL of 1,2-dichlorobenzene were added to 12.3 g (30 mmol) of Compound A-2, and the resulting mixture was stirred at 180° C. for 12 hours while being refluxed. Thereafter, the temperature was cooled to normal temperature, the organic layer was extracted with chloroform while being washed with distilled water, and then the organic layer was dried over anhydrous magnesium sulfate ($MgSO_4$), and then the solvent was removed, and silica gel column chromatography was performed to obtain 7.1 g (12.6 mmol, 42%) of Compound J.

MS: $[M+H]^+=561$

Preparation Example 14

Preparation of Compound K

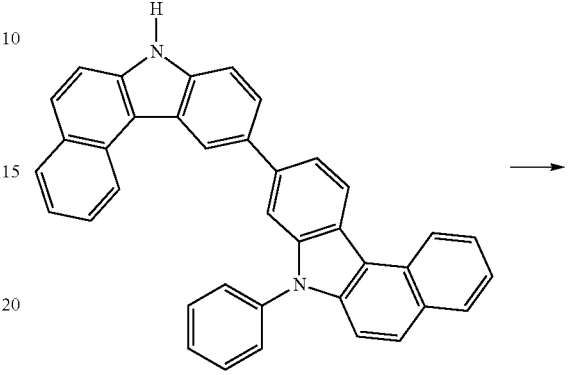

Formula B-2

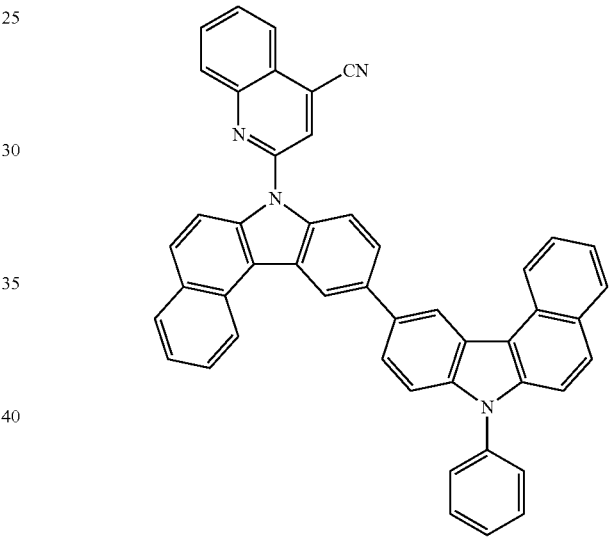

Compound K

Preparation of Compound K 3.8 g (20 mmol) of the compound represented by Formula a, 7.6 g (40 mmol) of CuI, 19.5 g (60 mmol) of $Cs_2CO_3$, 0.716 mL (6 mmol) of trans 1,2-diaminocyclohexane, and 130 mL of 1,2-dichlorobenzene were added to 15.3 g (30 mmol) of Compound B-2, and the resulting mixture was stirred at 180° C. for 12 hours while being refluxed. Thereafter, the temperature was cooled to normal temperature, the organic layer was extracted with chloroform while being washed with distilled water, and then the organic layer was dried over anhydrous magnesium sulfate ($MgSO_4$), and then the solvent was removed, and silica gel column chromatography was performed to obtain 11.1 g (16.8 mmol, 56%) of Compound K.

MS: $[M+H]^+=661$

Preparation Example 15

Preparation of Compound L

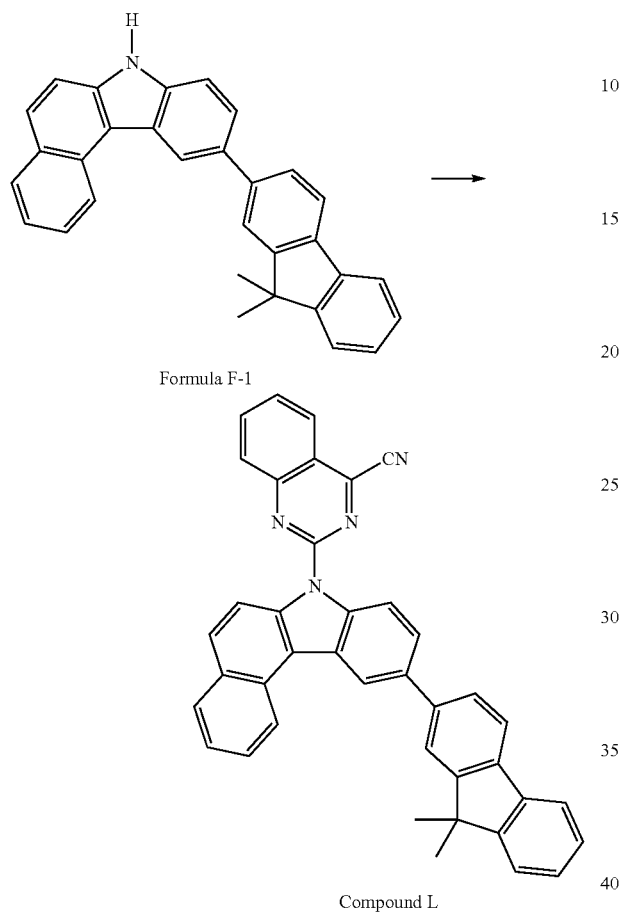

Formula F-1

Compound L

Preparation of Compound L

60% sodium hydride (0.80 g, 20 mmol) and 30 mL of dehydrated dimethylformamide were added to a nitrogen-substituted flask, and the resulting mixture was stirred. 80 mL of dimethylformamide was added to the compound of Formula F-1 (7.0 g, 17 mmol) to dissolve the compound, and then the resulting solution was added dropwise to the same flask for 10 minutes. After the addition dropwise was completed, the resulting mixture was continuously stirred for 30 minutes. 60 mL of dimethylformamide was added to the compound (3.41 g, 18 mmol) represented by Formula b to dissolve the compound, and then the resulting solution was added dropwise to the same flask for 30 minutes. After the addition dropwise was completed, the resulting mixture was continuously stirred for 4 hours. And then, 0.4 L of water was added thereto to filter and collect the crystals precipitated. The filtered and collected crystals were dispersed in ethanol and the dispersion was stirred overnight, and then filtered and vacuum dried to obtain 5.74 g (10.2 mmol, a yield of 60%) of a material of Compound H. MS: $[M+H]^+=563$

Preparation Example 16

Preparation of Compound M

Preparation of Compound M

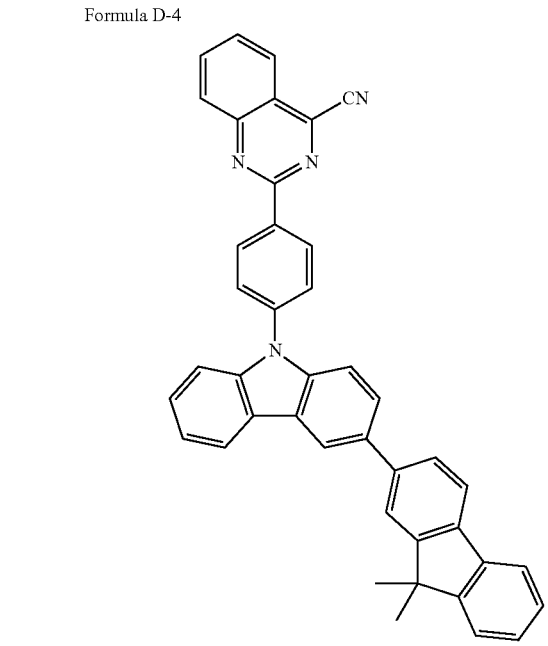

Formula D-4

Compound M

Compound D-4 (5.22 g, 10.0 mmol) and the material represented by 2-bromo-9,9-dimethyl-9H-fluorene (3.27 g, 12.0 mmol) were completely dissolved in 50 mL of tetrahydrofuran under nitrogen atmosphere, and then 25 mL of 2 M of an aqueous potassium carbonate solution was added thereto, tetrakistriphenylphosphinopalladium (1.10 g, 1.0 mmol) was introduced, and then the resulting mixture was stirred for 2 hours while being heated. The temperature was lowered to normal temperature, the reaction was terminated, and then the potassium carbonate solution was removed to filter the white solid. The filtered white solid was washed once with tetrahydrofuran and ethanol, respectively, to prepare 3.53 g (6 mmol, 60%) of Compound M.

MS: [M+H]$^+$=589

Preparation Example 17

Preparation of Compound N

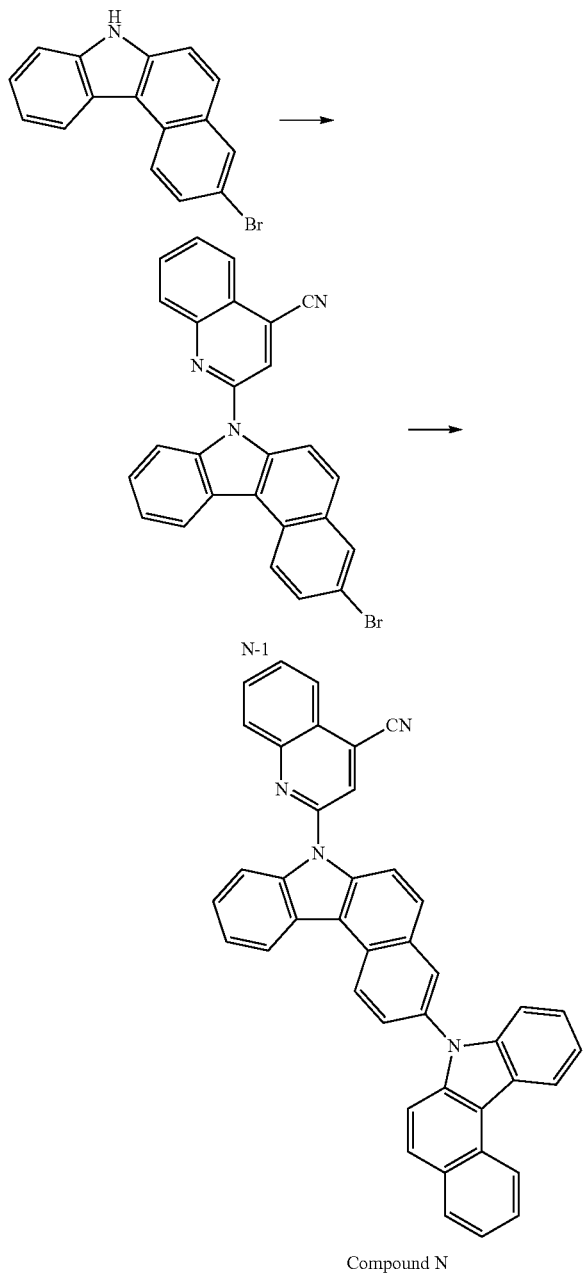

Preparation of Formula N-1

60% sodium hydride (0.80 g, 20 mmol) and 30 mL of dehydrated dimethylformamide were added to a nitrogen-substituted flask, and the resulting mixture was stirred. 60 mL of dimethylformamide was added to 3-bromo-7H-benzo[c]carbazole (5.0 g, 17 mmol) to dissolve the compound, and then the resulting solution was added dropwise to the same flask for 10 minutes. After the addition dropwise was completed, the resulting mixture was continuously stirred for 30 minutes. 60 mL of dimethylformamide was added to the compound (3.40 g, 18 mmol) represented by Formula a to dissolve the compound, and then the resulting solution was added dropwise to the same flask for 30 minutes. After the addition dropwise was completed, the resulting mixture was continuously stirred for 4 hours. And then, 0.4 L of water was added thereto to filter and collect the crystals precipitated. The filtered and collected crystals were dispersed in ethanol and the dispersion was stirred overnight, and then filtered and vacuum dried to obtain 5.02 g (11.2 mmol, a yield of 66%) of a material of Compound N-1.

Preparation of Compound N 0.21 g (0.94 mmol) of palladium acetate (II), xylene (20 mL), and 0.76 g (3.76 mmol) of tri-tert-butylphosphine were added to a container, and the resulting mixture was stirred at 60° C. for 30 minutes. The solution was delivered to a xylene solution (180 mL) of N-1 (8.1 g, 18 mmol), 7H-benzo[c]carbazole (3.9 g, 18 mmol), and tert-butoxy sodium (7.7 g, 80 mmol), which was heated to 60° C. under nitrogen flow. Thereafter, the mixture was warmed up to 130° C., and stirred for 5 hours while being heated. The mixture was cooled to room temperature, and then 200 mL of water was added thereto. The organic layer was extracted with chloroform, and then the organic layer was dried over anhydrous magnesium sulfate (MgSO$_4$), and then the solvent was removed, and silica gel column chromatography was performed to obtain 7.4 g (12.6 mmol, 70%) of Compound N.

MS: [M+H]$^+$=585

Experimental Examples 1 to 14

The compounds synthesized in the Preparation Examples were subjected to high-purity sublimation purification in a typically known method, and then red organic light emitting devices were manufactured by the following method.

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted repeatedly twice using distilled water for 10 minutes. After the washing using distilled water was completed, ultrasonic washing was conducted using isopropyl alcohol, acetone, and methanol solvents in this order, and drying was then conducted.

The substrate was mounted on a vacuum chamber, and then the base pressure was allowed to be 1×10$^{-6}$ torr, and then for the organic material, DNTPD (700 Å), NPB (300 Å), and Compounds A to N prepared by the present invention were used as hosts (90 wt %) on the ITO, Dp-6 (10 wt %) was co-deposited as a dopant, and films were formed in the sequence of Alq3 (350 Å), LiF (5 Å), and Al (1,000 Å). In the aforementioned procedure, the deposition rates of the organic material, LiF, and aluminum were maintained at 1 Å/sec, 0.2 Å/sec, and 3 to 7 Å/sec, respectively.

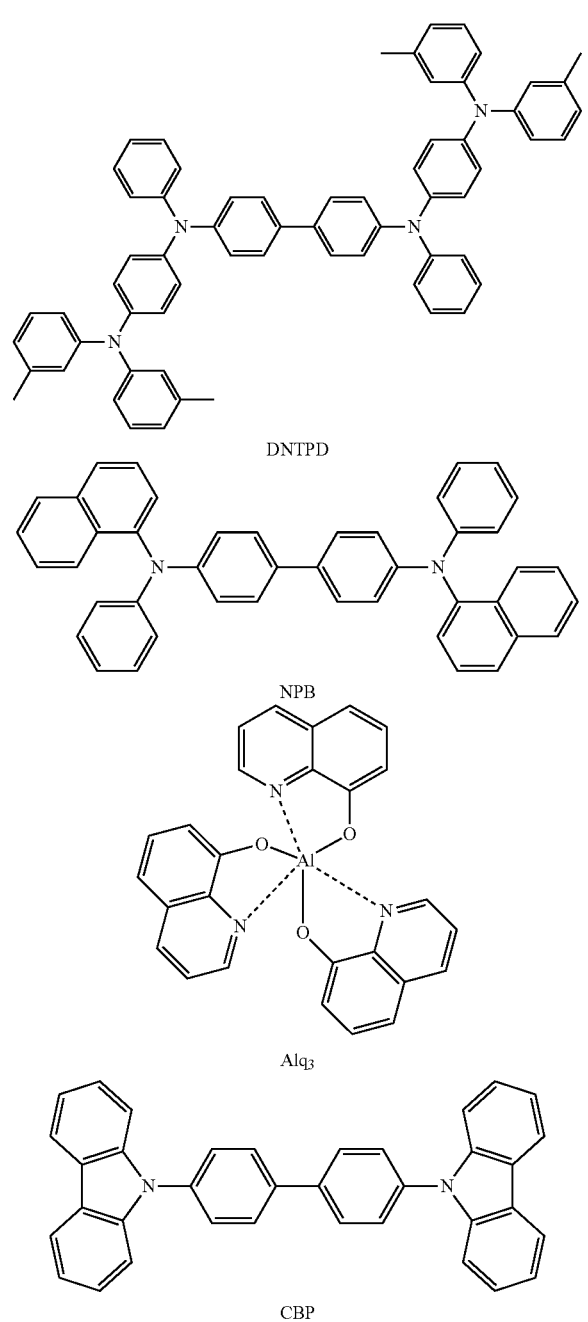

DNTPD

NPB

Alq3

CBP

Comparative Example 1

For the organic light emitting devices for the Comparative Examples, an organic light emitting device was manufactured in the same manner as in Experimental Examples 1 to 14, except that CBP, which is frequently used as a general phosphorescent host material, was used instead of the compounds prepared in the Preparation Examples of the present specification as a host of the light emitting layer in the device structures of Experimental Examples 1 to 14.

Comparative Example 2

For the organic light emitting devices for the Comparative Examples, an organic light emitting device was manufactured in the same manner as in Experimental Examples 1 to 14, except that the following compound O-1 was used instead of the compounds prepared in the Preparation Examples of the present specification as a host of the light emitting layer in the device structures of Experimental Examples 1 to 14.

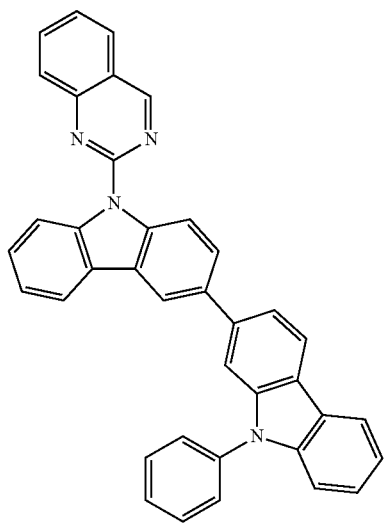 [SMILES: c1ccc(-n2c3ccccc3c3ccc(-c4ccc5c(c4)c4ccccc4n5-c4ncc5ccccc5n4)cc32)cc1]

Comparative Example 3

For the organic light emitting devices for the Comparative Examples, an organic light emitting device was manufactured in the same manner as in Experimental Examples 1 to 15, except that the following compound O-2 was used instead of the compounds prepared in the Preparation Examples of the present specification as a host of the light emitting layer in the device structures of Experimental Examples 1 to 15.

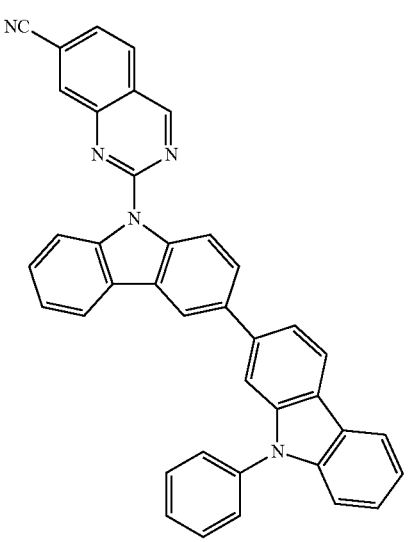 [SMILES: N#Cc1ccc2cnc(-n3c4ccccc4c4cc(-c5ccc6c7ccccc7n(-c7ccccc7)c6c5)ccc43)nc2c1]

The driving voltage, current efficiency, power efficiency, and service life of the organic light emitting devices prepared in Experimental Examples 1 to 14 and Comparative Examples 1 to 3 were measured, and the results are shown in the following Table 1.

TABLE 1

| | Compound | Driving voltage (V) | Current efficiency (cd/A) | Power efficiency (lm/w) | Service life (T95@10 mA) | x-coordinate | y-coordinate |
|---|---|---|---|---|---|---|---|
| Experimental Example 1 | A | 4.70 | 24.98 | 14.91 | 226 | 0.661 | 0.332 |
| Experimental Example 2 | B | 4.89 | 23.35 | 11.75 | 192 | 0.656 | 0.343 |
| Experimental Example 3 | C | 4.80 | 23.03 | 13.76 | 222 | 0.662 | 0.334 |
| Experimental Example 4 | D | 5.59 | 21.48 | 15.30 | 158 | 0.666 | 0.331 |
| Experimental Example 5 | E | 4.83 | 23.60 | 13.86 | 162 | 0.652 | 0.334 |
| Experimental Example 6 | F | 4.86 | 22.88 | 12.88 | 188 | 0.661 | 0.330 |
| Experimental Example 7 | G | 4.74 | 23.91 | 13.59 | 226 | 0.660 | 0.334 |
| Experimental Example 8 | H | 4.88 | 23.64 | 13.24 | 182 | 0.660 | 0.333 |
| Experimental Example 9 | I | 4.77 | 23.64 | 13.89 | 166 | 0.658 | 0.334 |
| Experimental Example 10 | J | 4.98 | 20.36 | 16.31 | 136 | 0.667 | 0.332 |
| Experimental Example 11 | K | 4.82 | 22.46 | 13.24 | 214 | 0.662 | 0.334 |
| Experimental Example 12 | L | 5.02 | 24.04 | 12.46 | 115 | 0.664 | 0.332 |
| Experimental Example 13 | M | 5.34 | 20.22 | 12.58 | 176 | 0.652 | 0.332 |
| Experimental Example 14 | N | 4.76 | 24.94 | 15.78 | 206 | 0.664 | 0.334 |
| Comparative Example 1 | CBP | 5.54 | 17.04 | 11.04 | 58 | 0.652 | 0.331 |
| Comparative Example 2 | O-1 | 5.68 | 16.94 | 11.02 | 54 | 0.652 | 0.330 |
| Comparative Example 3 | O-2 | 5.80 | 16.84 | 10.84 | 56 | 0.664 | 0.326 |

Referring to Table 1, it can be confirmed that Compounds A to N, which are experimental examples in which the compound of the present invention was used as a light emitting layer host material, had the reduced driving voltage, and the improved current efficiency and service life as compared to Comparative Examples 1 to 3.

What is claimed is:
1. A compound represented by the following Formula 1:

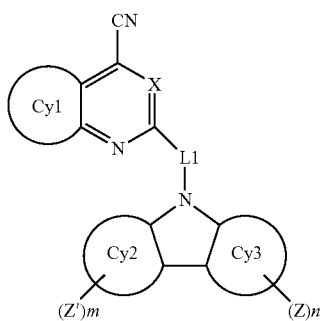

[Formula 1]

in Formula 1,
Cy1 to Cy3 are the same as or different from each other, and are each independently a substituted or unsubstituted aromatic hydrocarbon ring having 6 to 30 carbon atoms; or a substituted or unsubstituted heterocyclic group,
X is N or CR,
L1 is a direct bond; a substituted or unsubstituted divalent aromatic hydrocarbon ring group having 6 to 30 carbon atoms; or a substituted or unsubstituted divalent heterocyclic group having 6 to 30 carbon atoms,
Z and Z' are the same as or different from each other,
at least one of Z and Z' is represented by any one of the following Formulae 2 to 6,

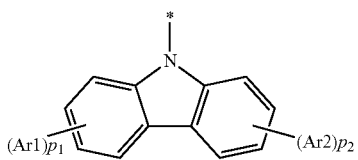

[Formula 2]

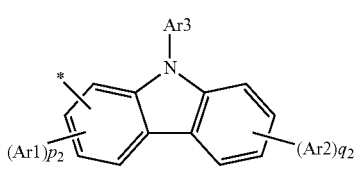

[Formula 3]

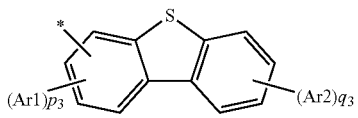

[Formula 4]

-continued

[Formula 5]
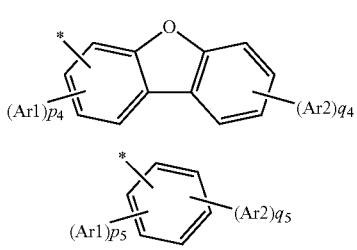

[Formula 6]
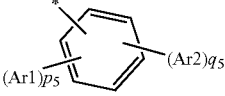

n and m are each independently 0 or 1,
at least one of n and m is 1,
$p_1$ and $q_1$ are each independently an integer of 1 to 4,
$p_2$ to $p_4$ are each independently an integer of 1 to 3, and $q_2$ to $q_4$ are each independently an integer of 1 to 4,
$p_5$ and $q_5$ are each independently an integer of 1 to 5, and p+q is 5 or less,
when $p_1$ to $p_5$ are each independently an integer of 2 or more, a plurality of Ar1's is the same as or different from each other,
when $q_1$ to $q_5$ are each independently an integer of 2 or more, a plurality of Ar2's is the same as or different from each other, and
R and Ar1 to Ar3 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphineoxide group; a substituted or unsubstituted aryl group; or a substituted or unsubstituted heterocyclic group, or optionally combine with an adjacent group to form a ring.

2. The compound of claim 1, wherein Cy1 is a substituted or unsubstituted monocyclic aromatic hydrocarbon ring having 6 to 30 carbon atoms; or a substituted or unsubstituted monocyclic heterocyclic group including one or more N's.

3. The compound of claim 1, wherein Cy1 is a substituted or unsubstituted benzene.

4. The compound of claim 1, wherein Cy2 is a substituted or unsubstituted benzene; or a substituted or unsubstituted naphthalene.

5. The compound of claim 1, wherein Cy3 is a substituted or unsubstituted benzene; or a substituted or unsubstituted naphthalene.

6. The compound of claim 1, wherein L is a direct bond; a substituted or unsubstituted phenylene group; or a substituted or unsubstituted divalent naphthalene group.

7. The compound of claim 1, wherein Formula 6 is represented by a substituted or unsubstituted phenyl group; a substituted or unsubstituted naphthyl group; a substituted or unsubstituted fluorenyl group; or a substituted or unsubstituted phenanthrene group.

8. The compound of claim 1, wherein m is 0.

9. The compound of claim 1, wherein at least one of Z and Z' is represented by any one of Formulae 2 and 6 and the following Formulae 7 to 18:

[Formula 7]
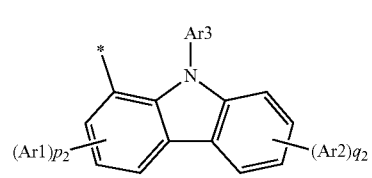

[Formula 8]
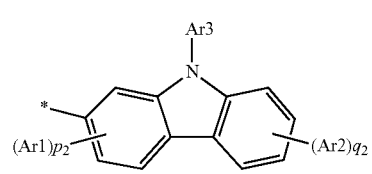

[Formula 9]
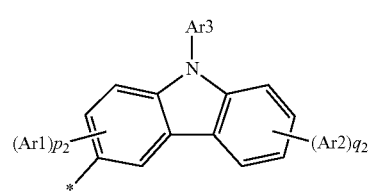

[Formula 10]
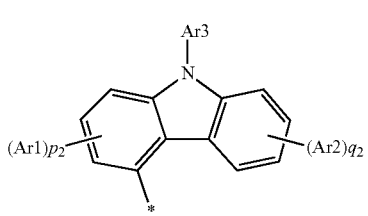

[Formula 11]
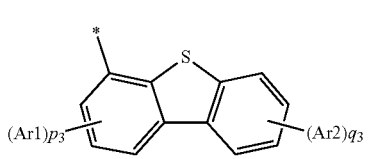

[Formula 12]
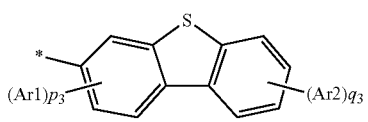

[Formula 13]
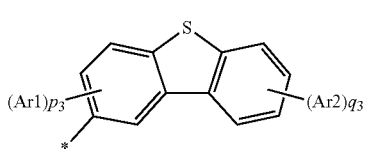

[Formula 14]
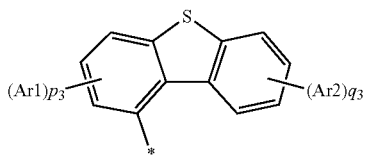

[Formula 15]
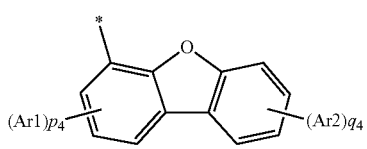
[Formula 16]
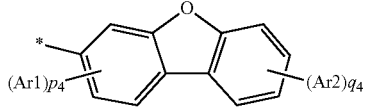
[Formula 17]
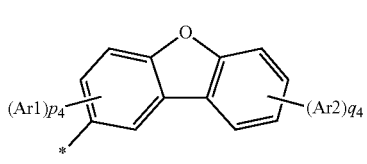
[Formula 18]
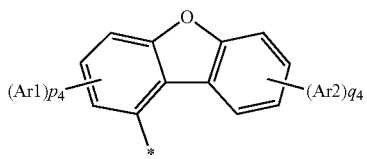
in Formulae 7 to 18,
$p_2$ to $p_4$, $q_2$ to $q_4$, and Ar1 to Ar3 are the same as those defined in claim 1.
10. The compound of claim 1, wherein the compound represented by Formula 1 is represented by any one of the following Formulae 1-1 to 1-7,
provided that m is 0:
[Formula 1-1]
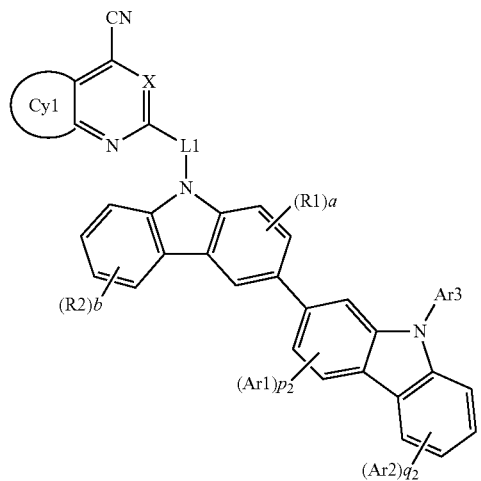
[Formula 1-2]
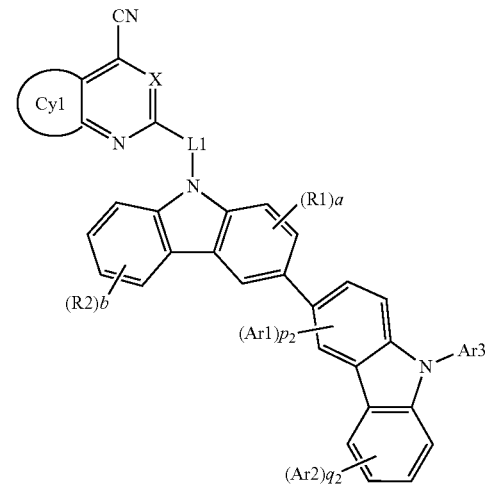
[Formula 1-3]
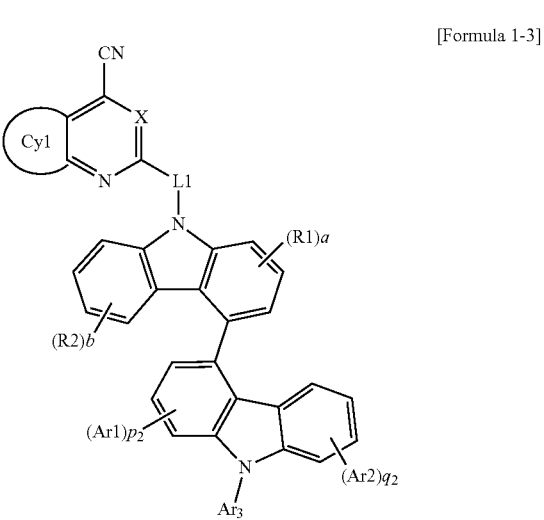
[Formula 1-4]
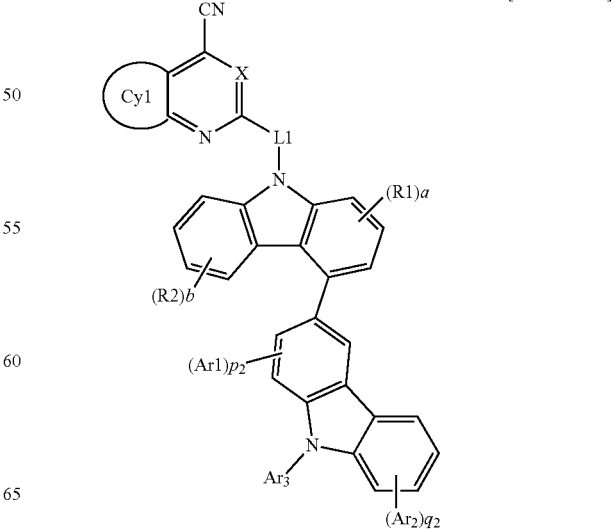

-continued

[Formula 1-5]

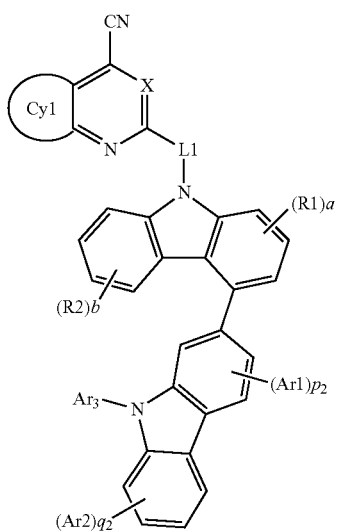

[Formula 1-6]

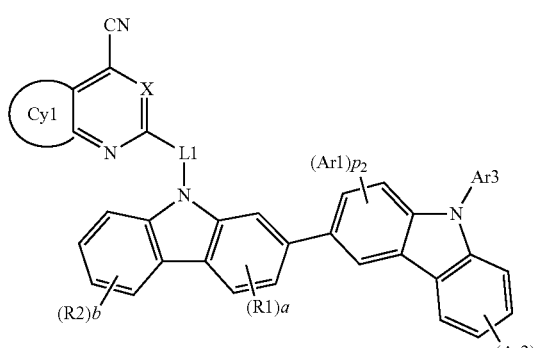

[Formula 1-7]

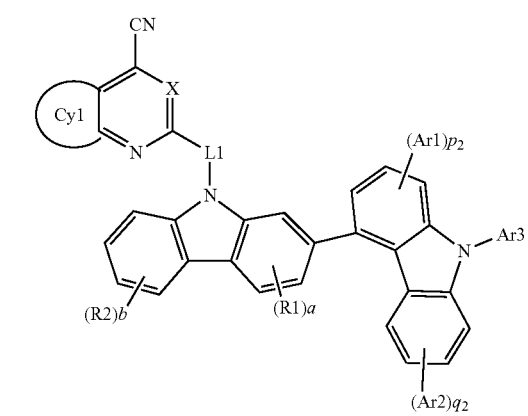

in Formulae 1-1 to 1-7,

Cy1, X, L1, Ar1 to Ar3, $p_2$, and $q_2$ are the same as those defined in Formula 1, R1 and R2 are the same as or different from each other, and the same as the definition of Ar1 to Ar3, a is an integer of 1 to 3, when a is an integer of 2 or more, a plurality of R1's is the same as or different from each other, b is an integer of 1 to 4, and when b is an integer of 2 or more, a plurality of R2's is the same as or different from each other.

11. The compound of claim 1, wherein the compound represented by Formula 1 is represented by the following Formula 1-8 or 1-9:

[Formula 1-8]

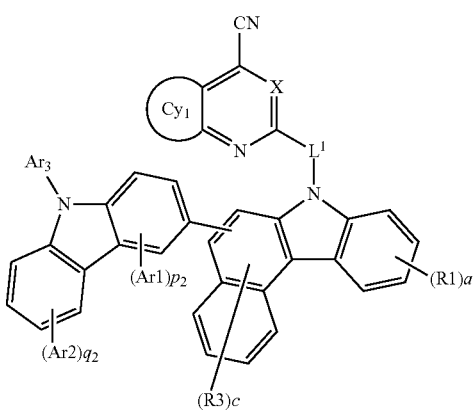

[Formula 1-9]

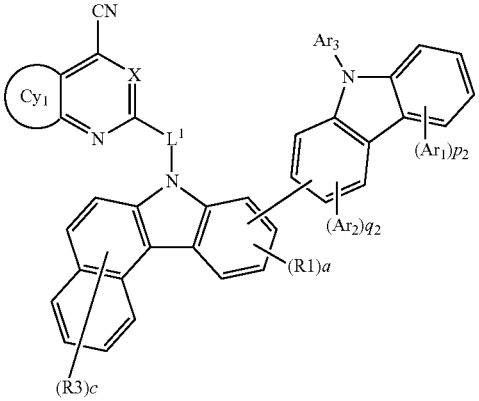

in Formulae 1-8 and 1-9,

Cy1, X, L1, Ar1 to Ar3, $p_2$, and $q_2$ are the same as those defined in Formula 1, R1 and R3 are the same as or different from each other, and the same as the definition of Ar1 to Ar3, a is an integer of 1 to 4, when a is an integer of 2 or more, a plurality of R1's is the same as or different from each other, c is an integer of 1 to 5, and when c is an integer of 2 or more, a plurality of R3's is the same as or different from each other.

12. The compound of claim 1, wherein the compound represented by Formula 1 is selected from the following structural formulae:

155
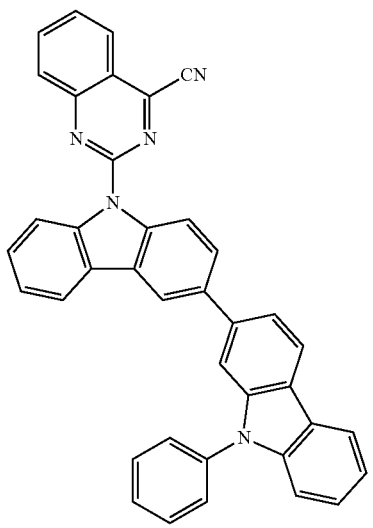
156
-continued
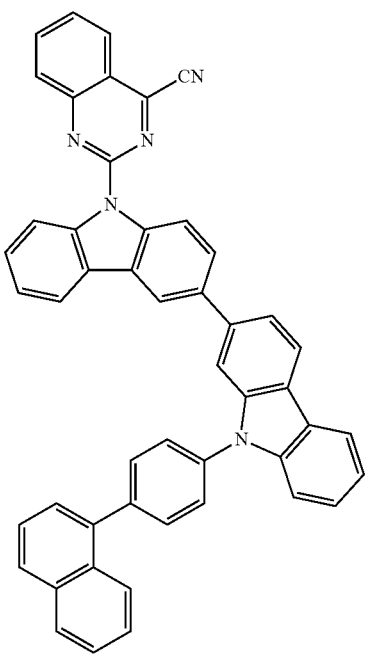
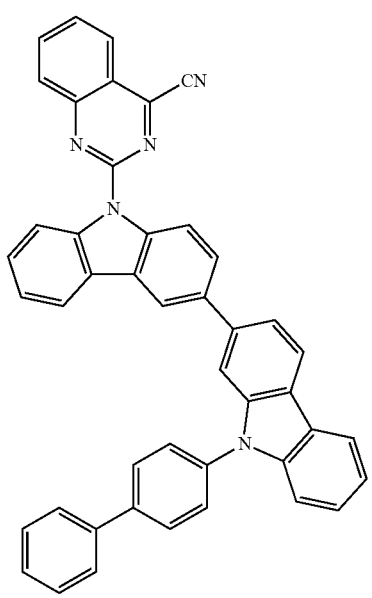

157
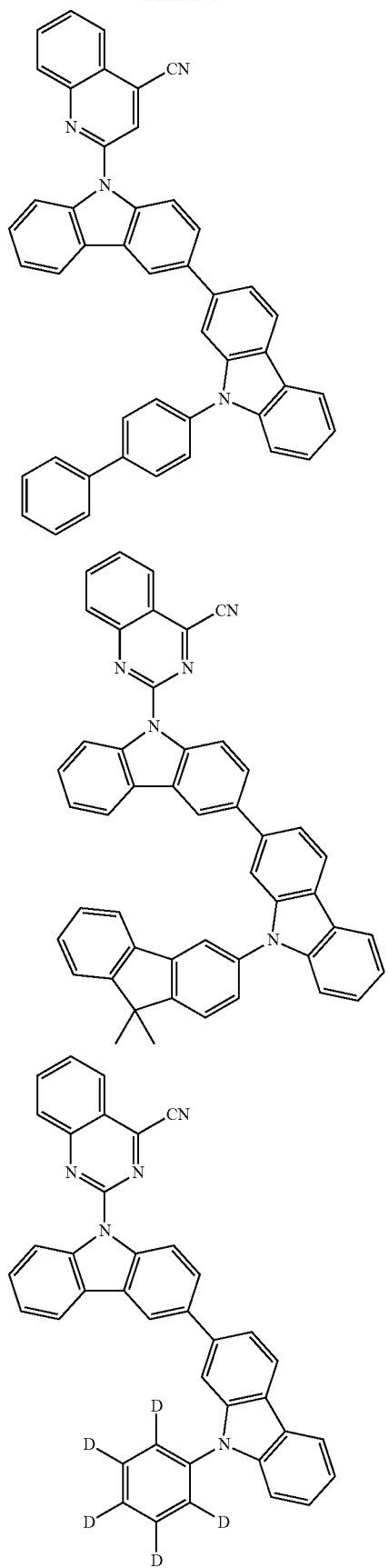
158

159
-continued
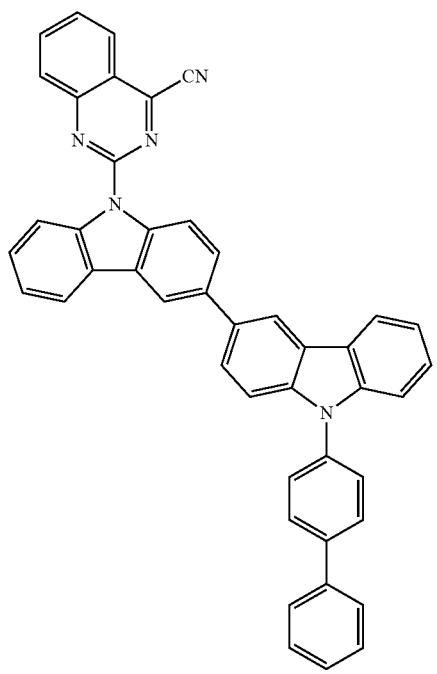
160
-continued
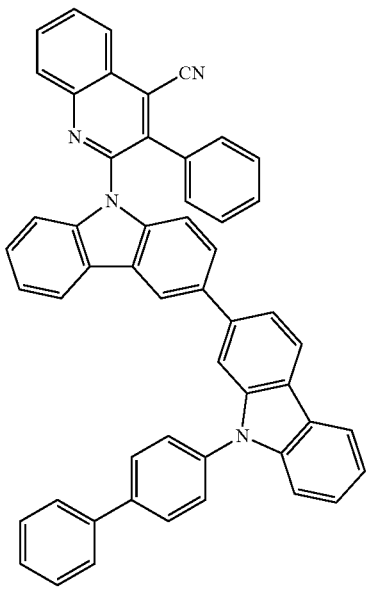
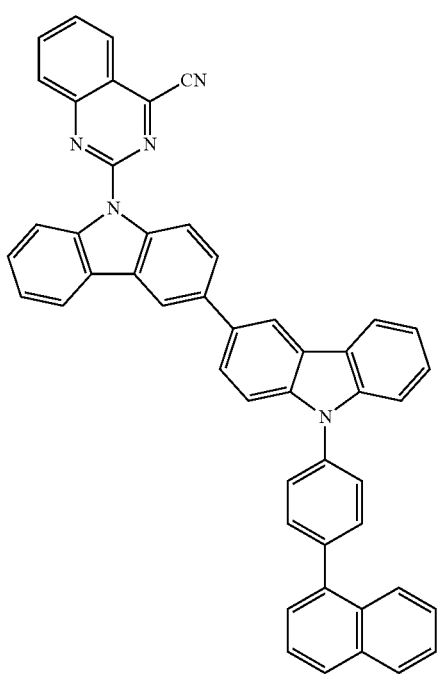
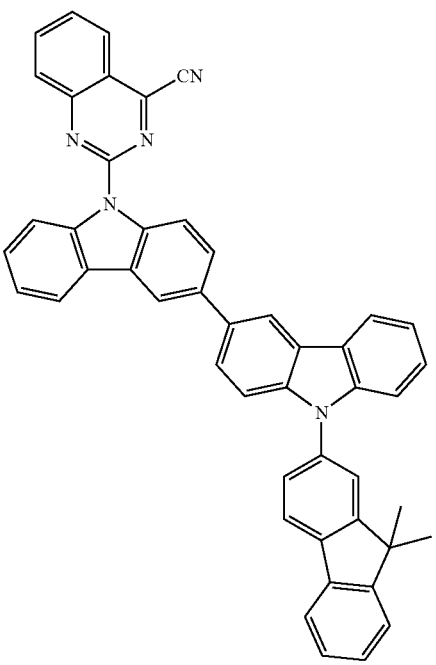

161
-continued
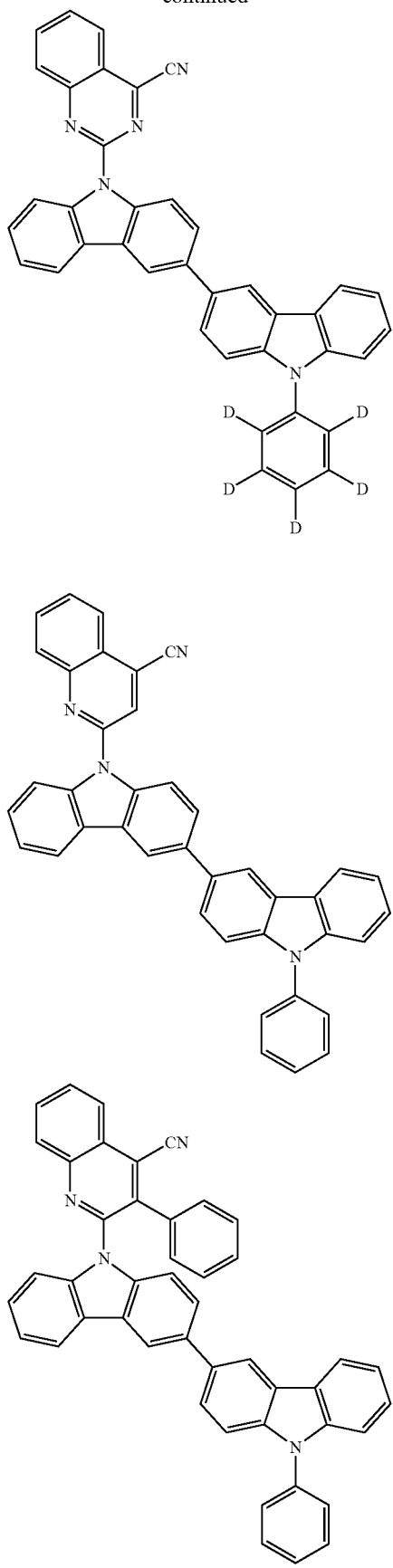
162
-continued
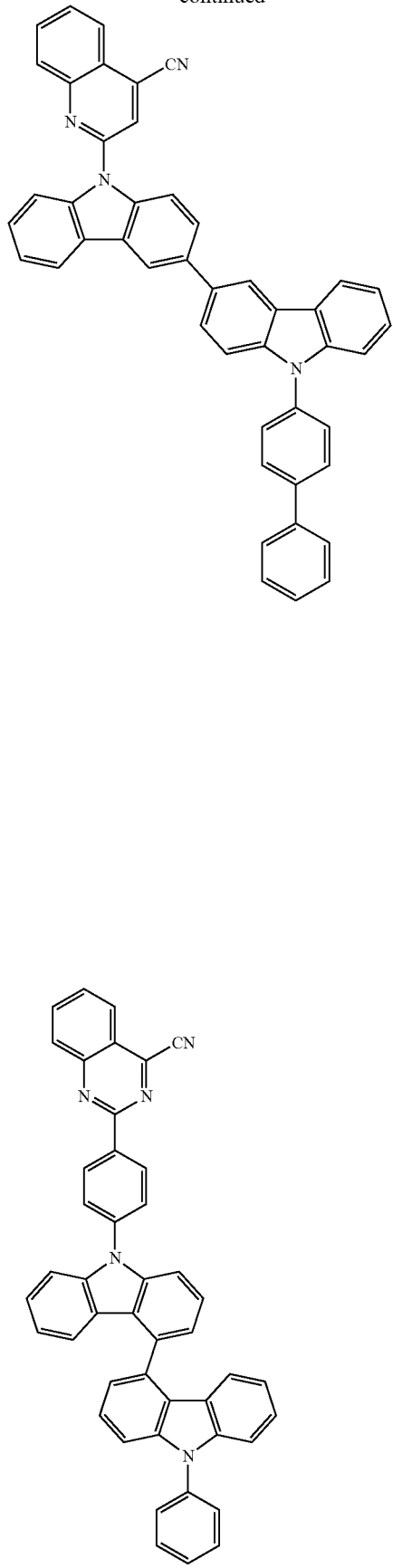

163
-continued
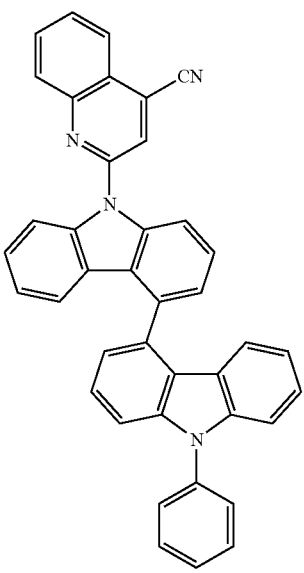
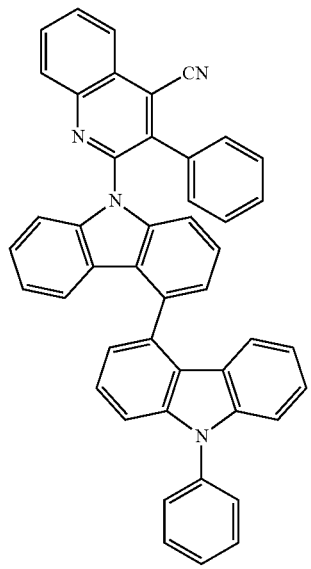
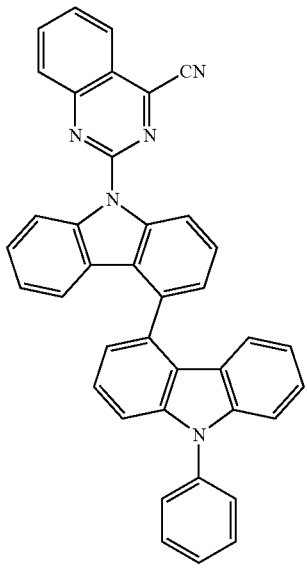
164
-continued
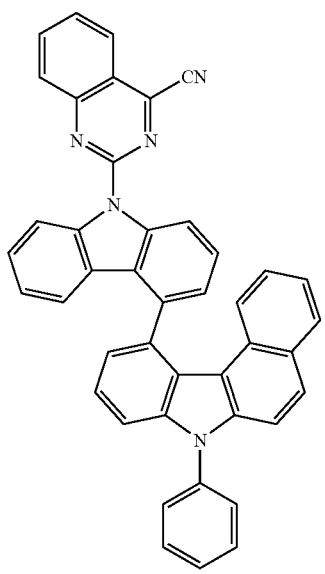
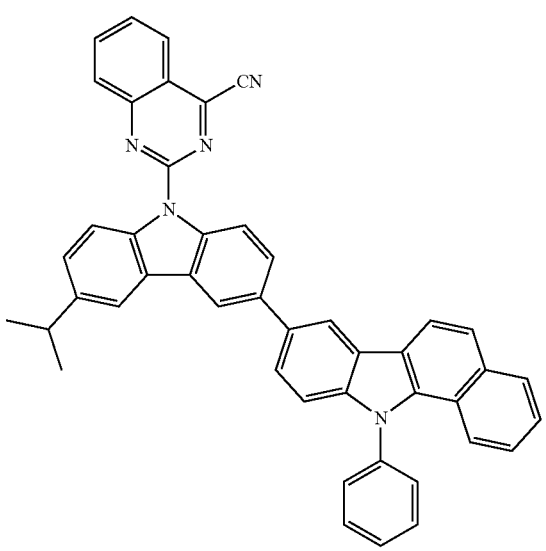

165
-continued
166
-continued
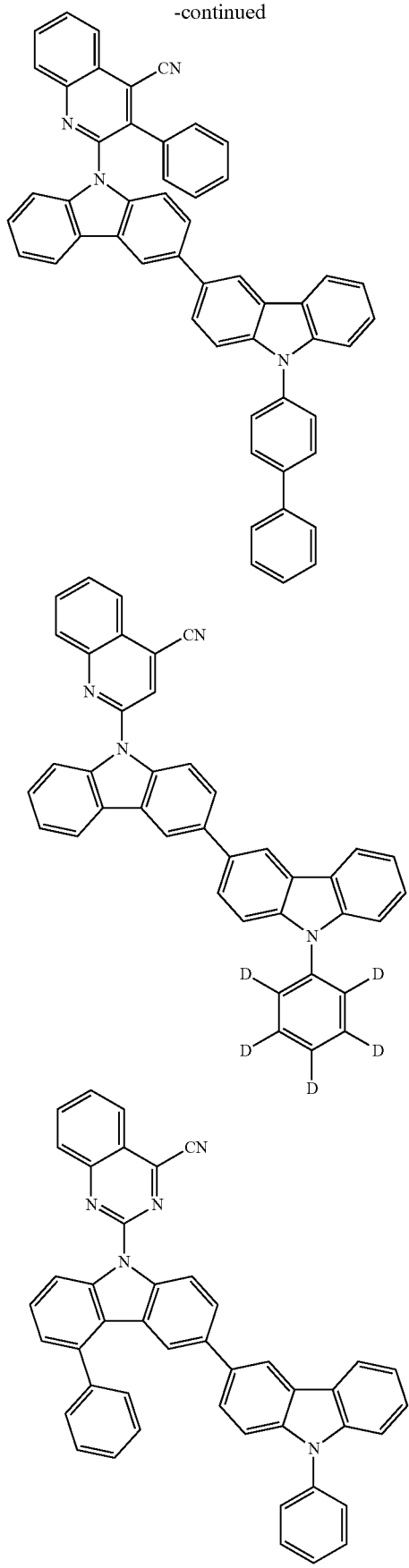
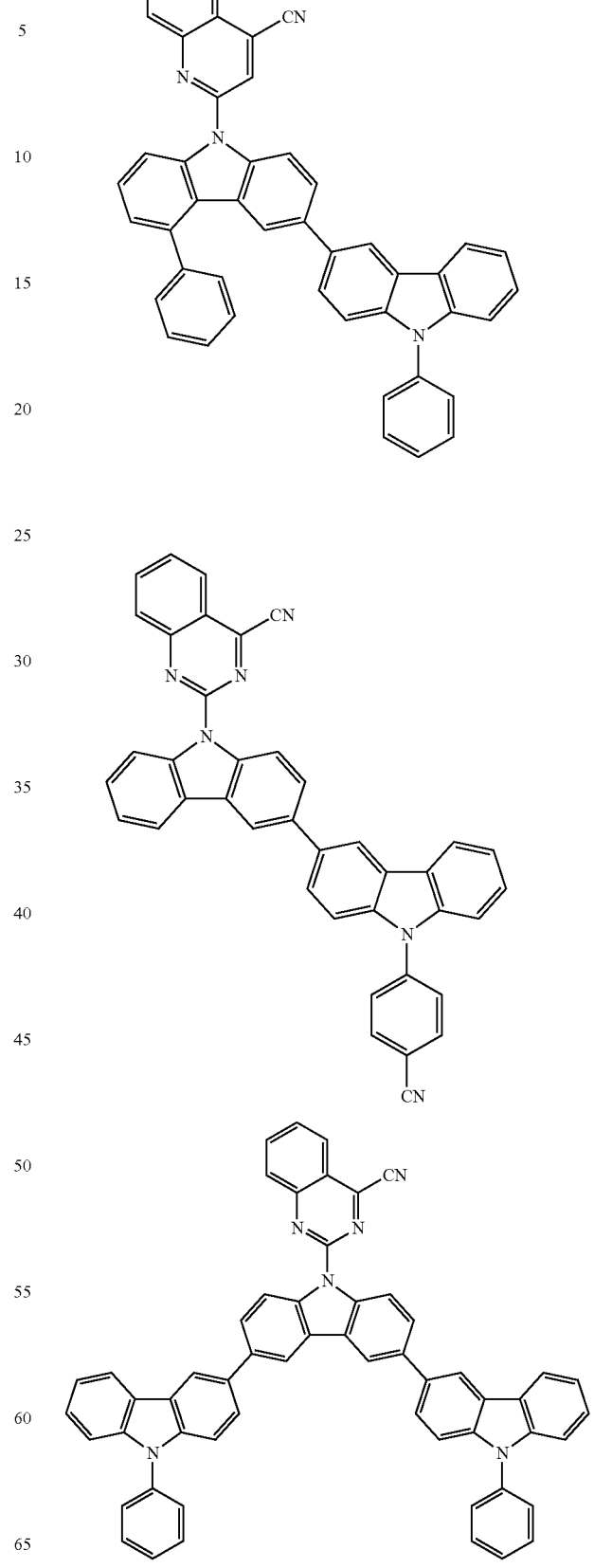

167
-continued
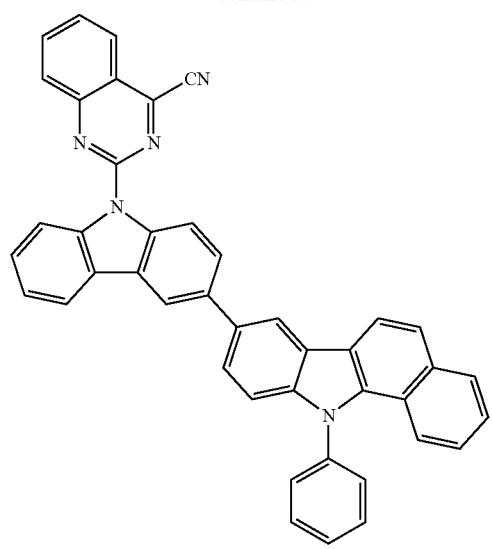
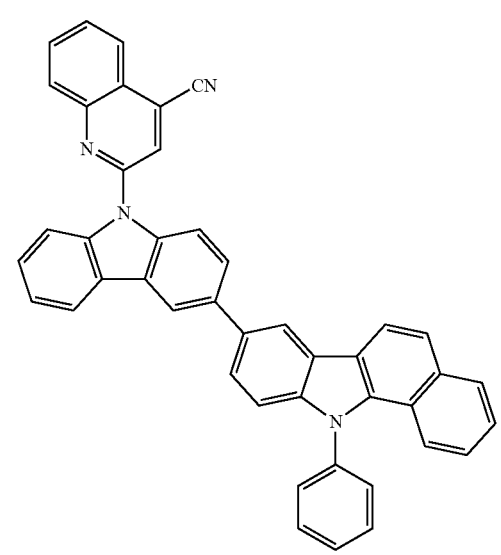
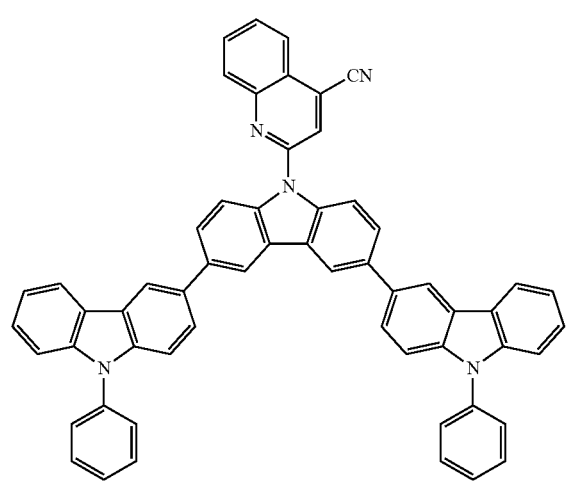
168
-continued
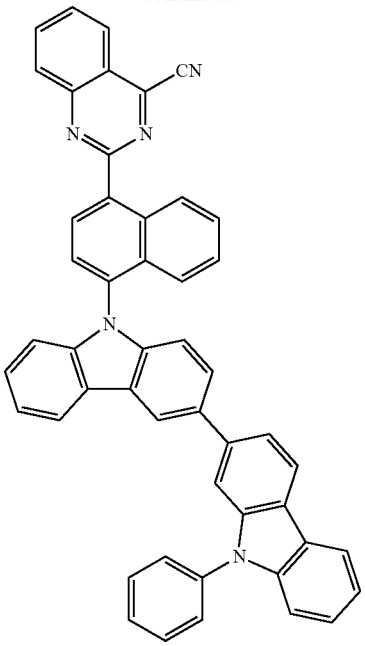
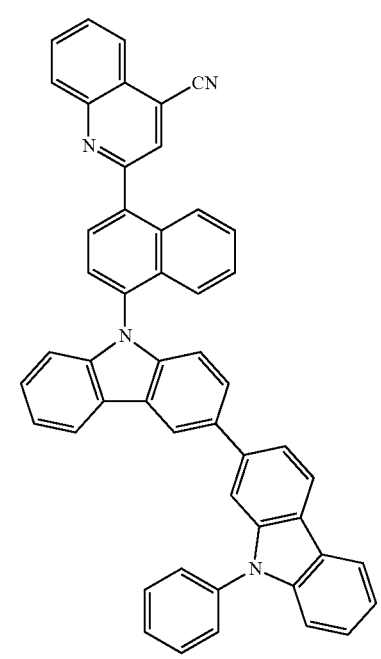

169
-continued
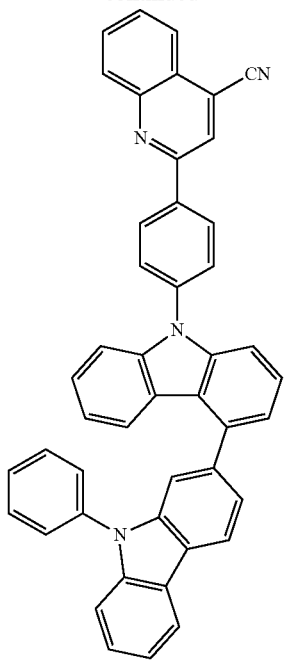
170
-continued
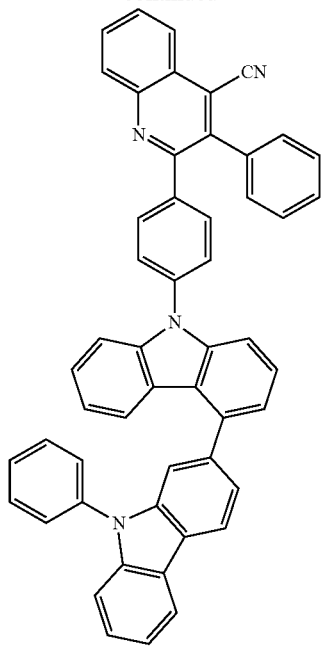
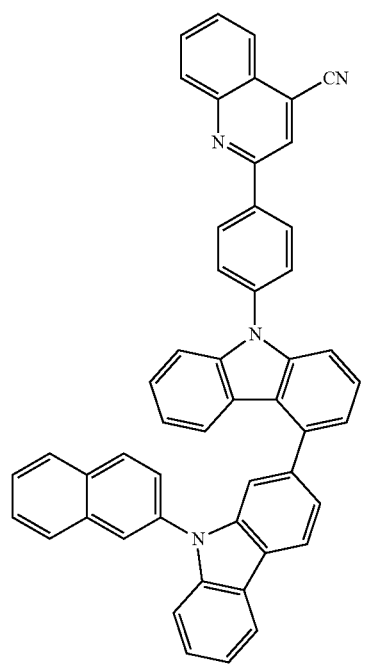
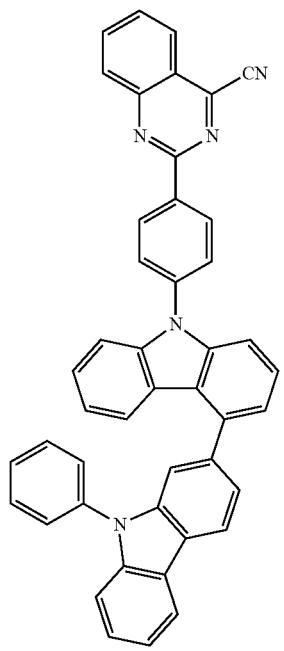

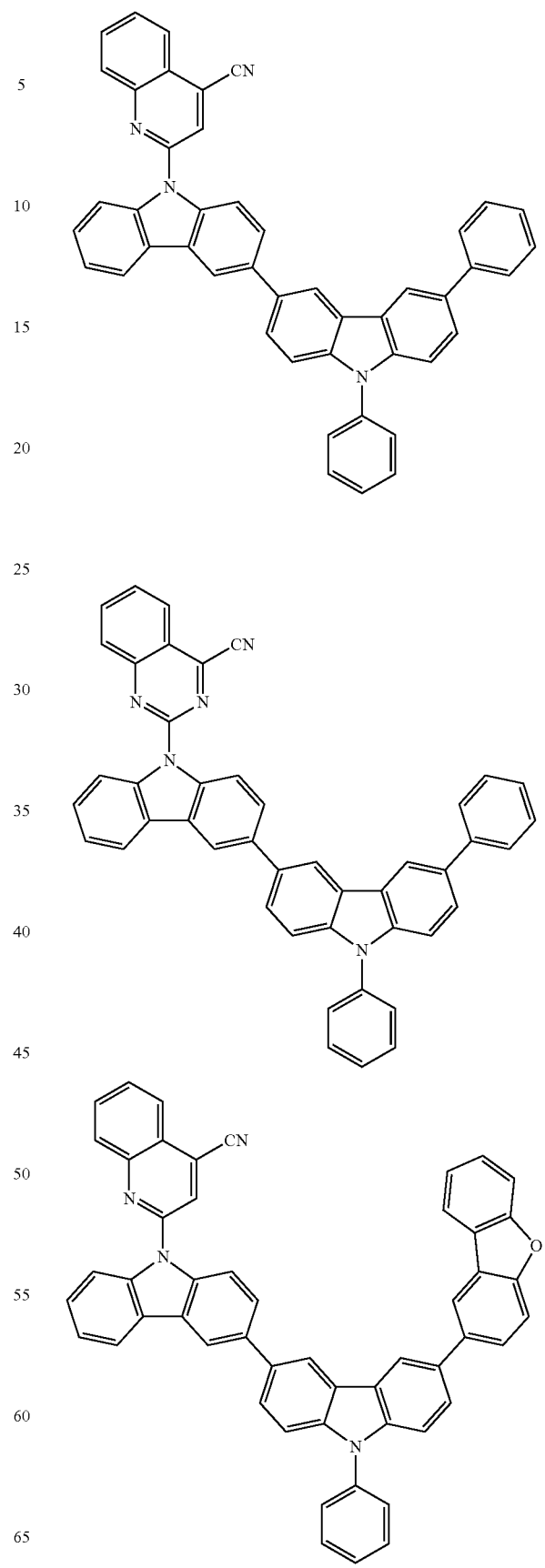

173
-continued
174
-continued
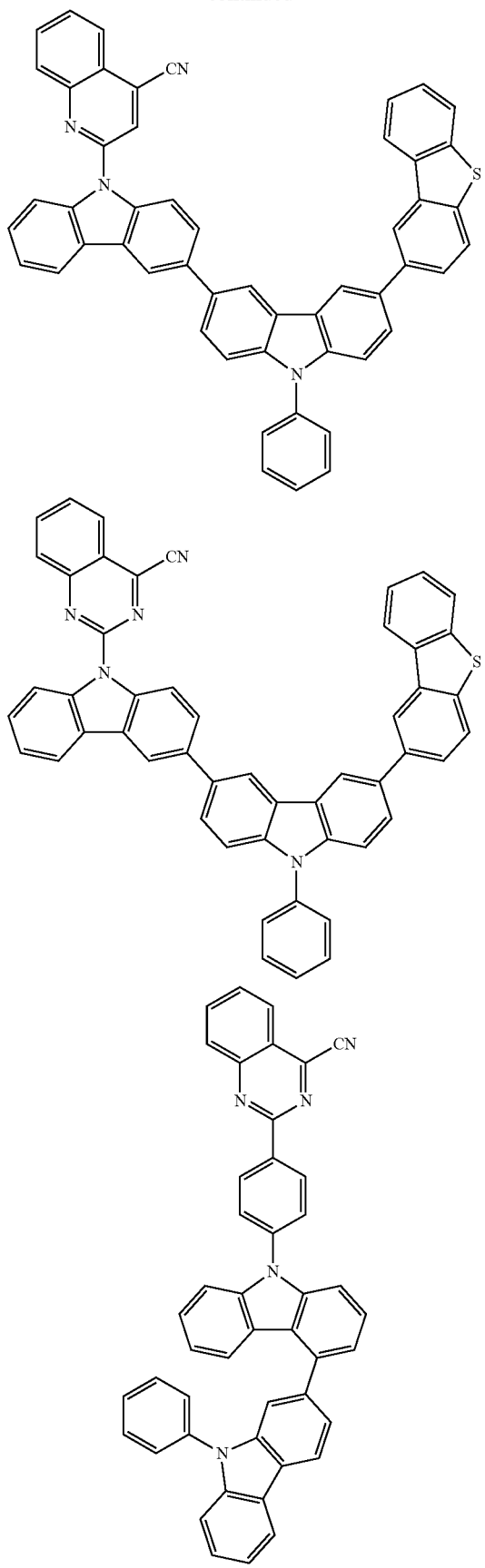
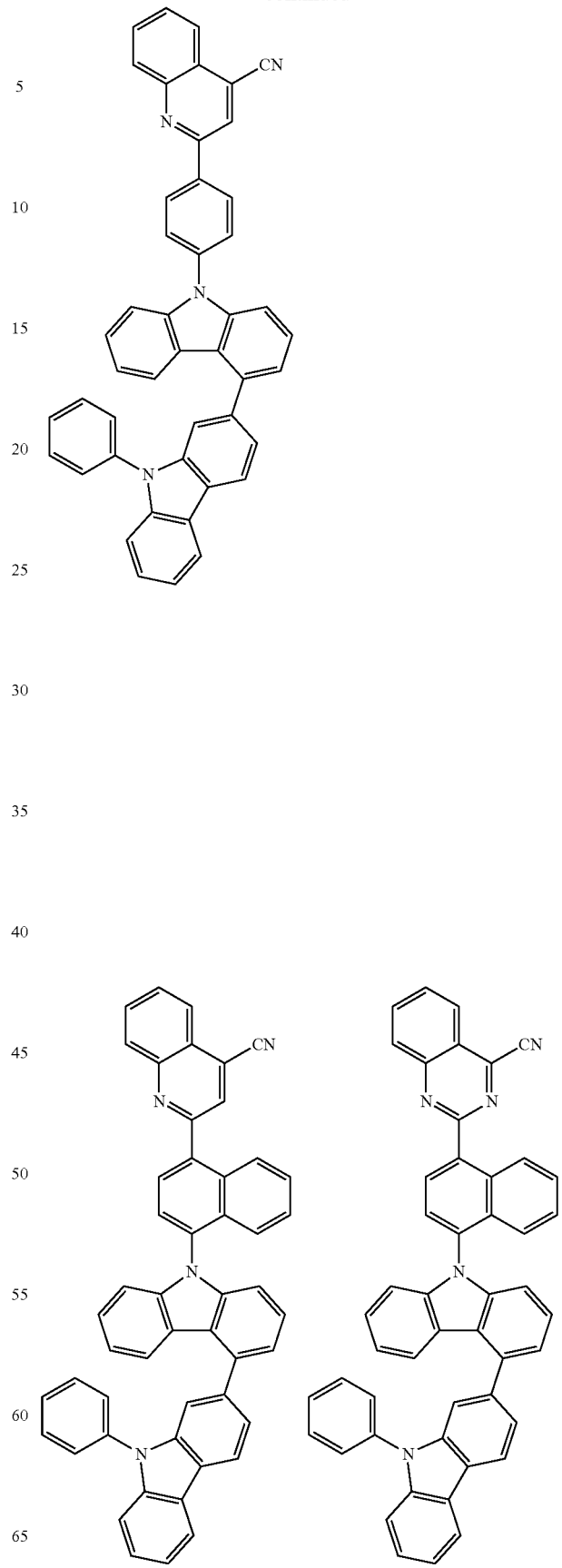

175
-continued
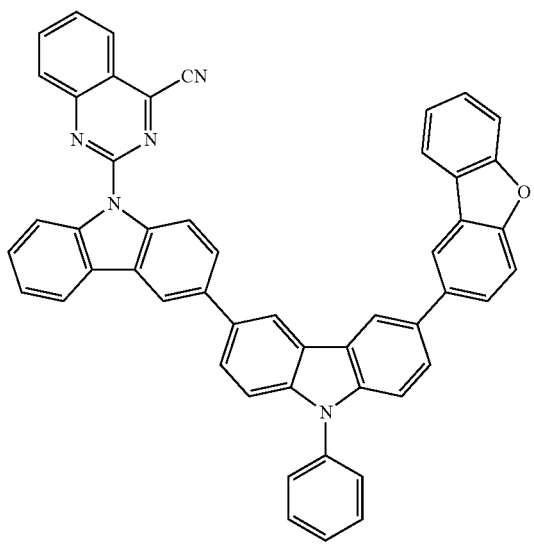
176
-continued
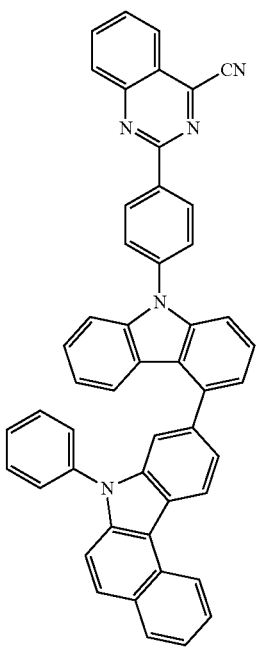
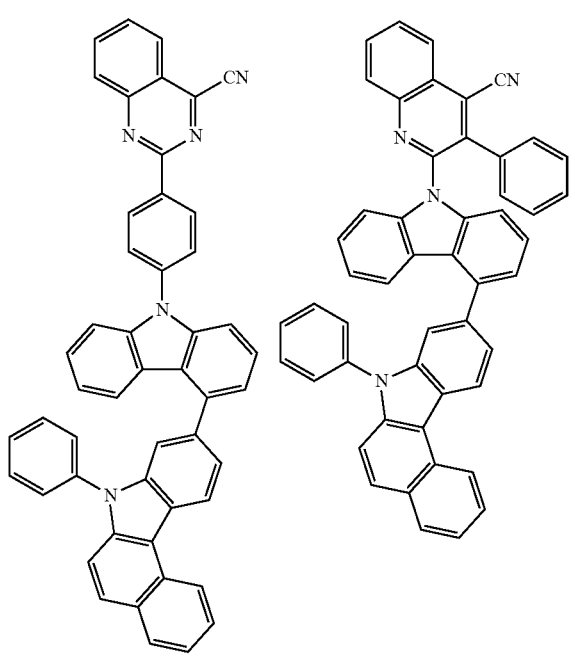
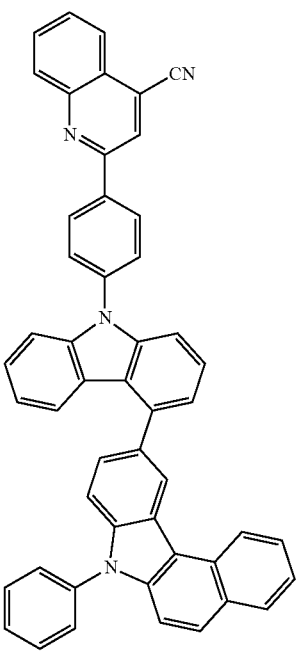

177
-continued
178
-continued
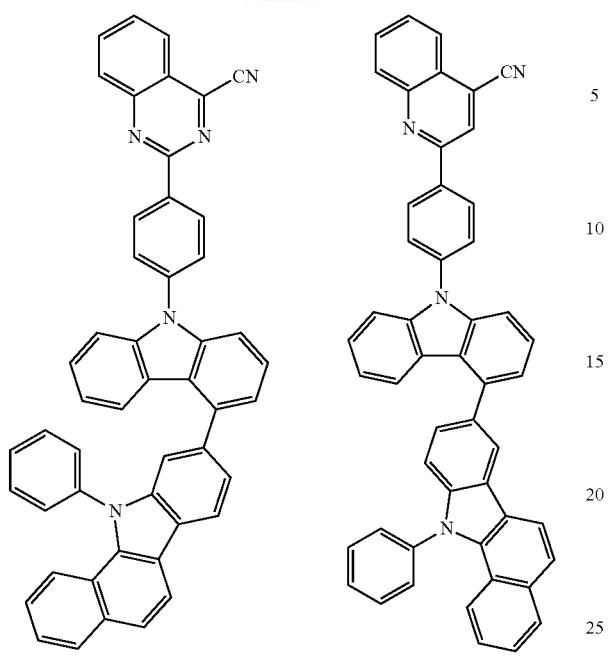
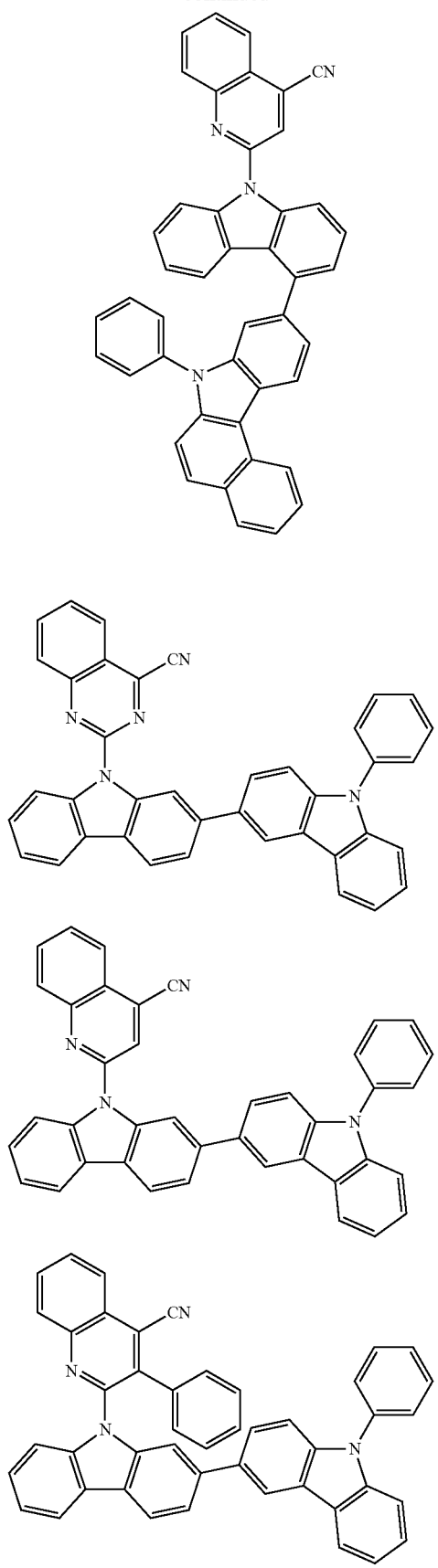

179
-continued
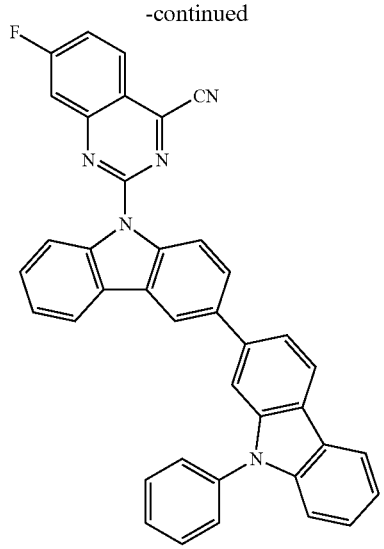
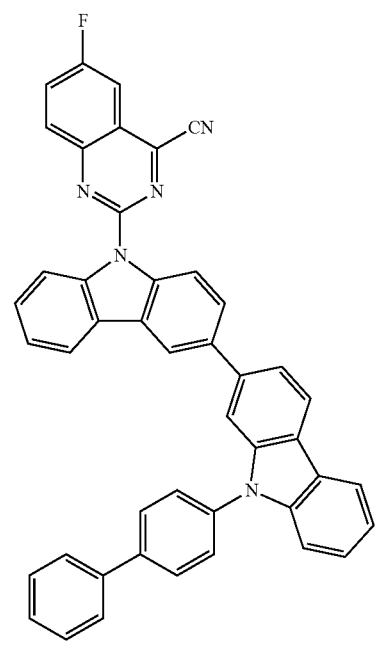
180
-continued
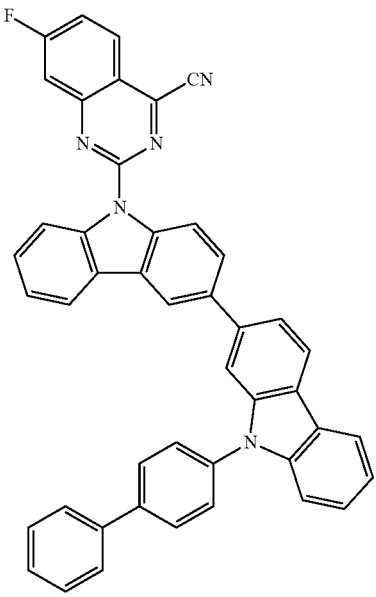
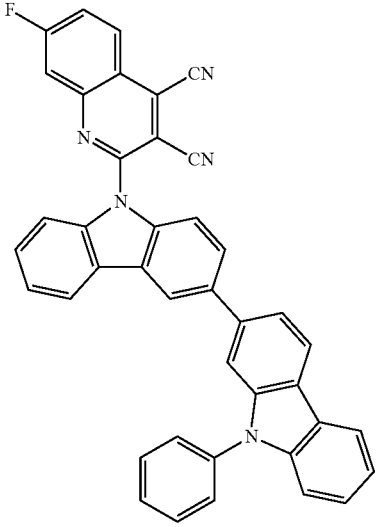

181
-continued
182
-continued
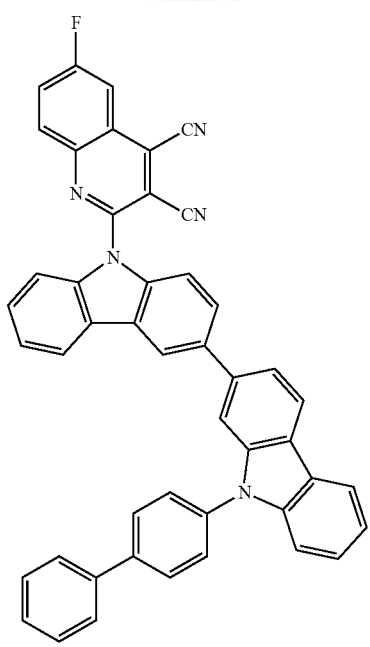
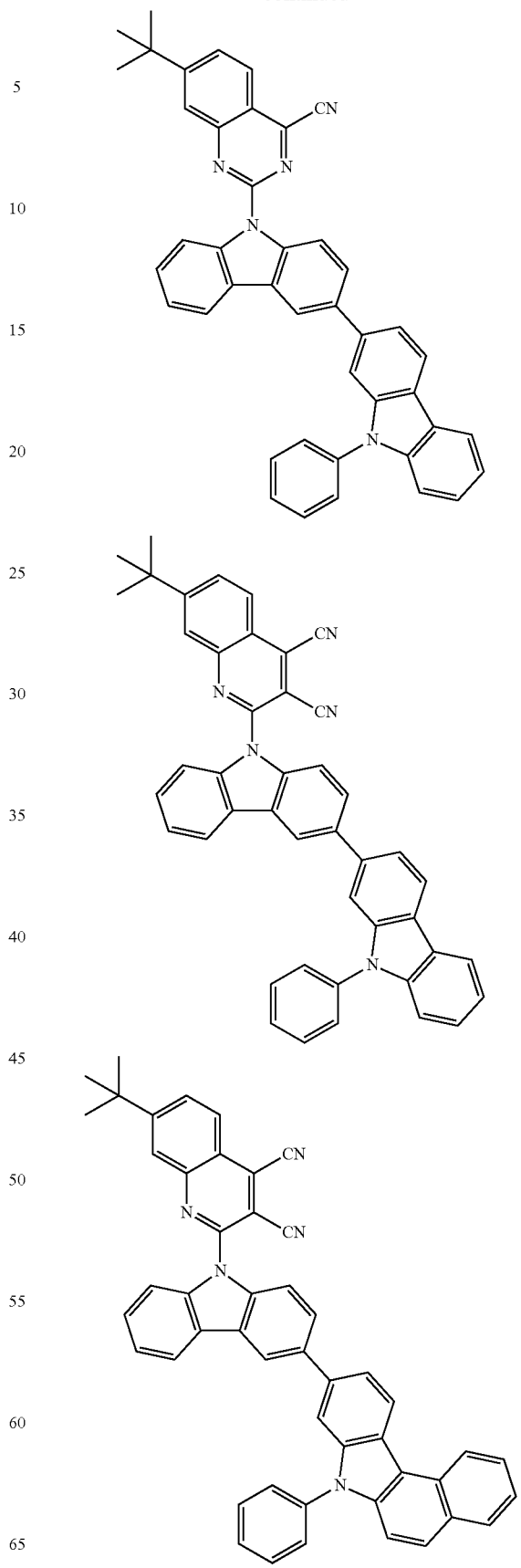
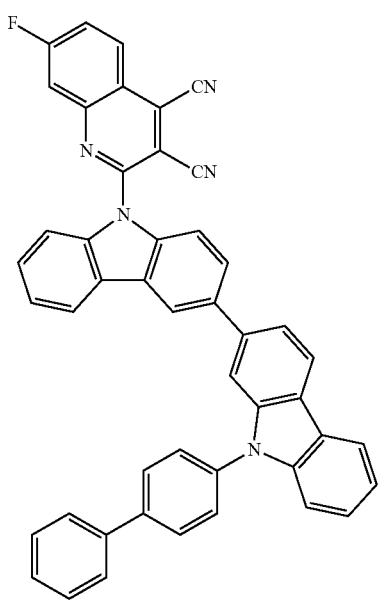

183
-continued
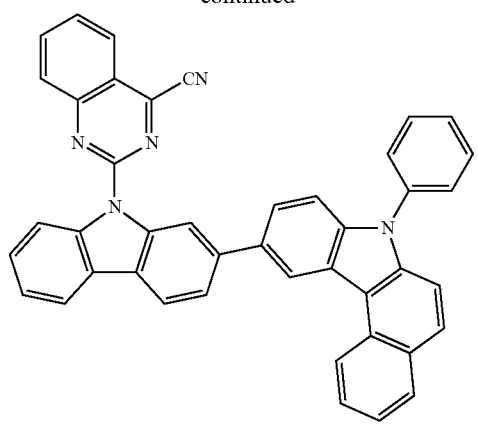
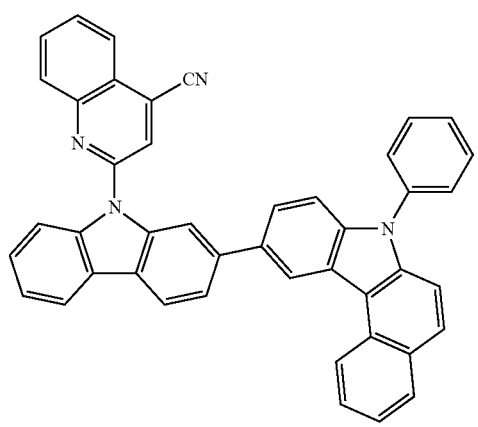
184
-continued
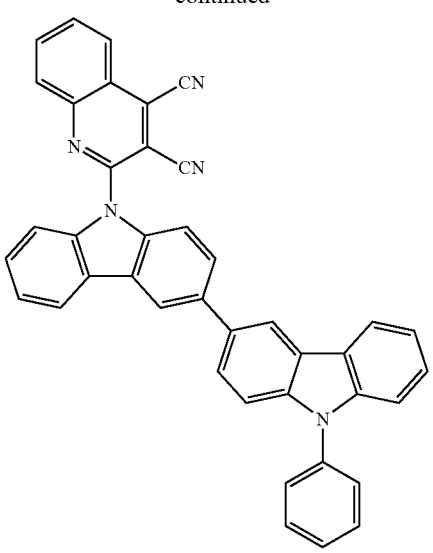
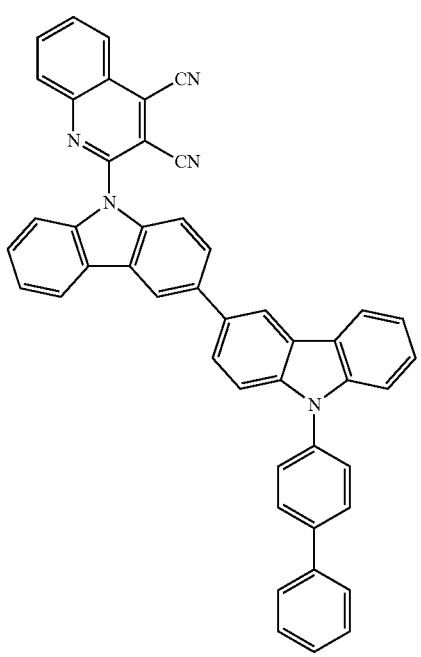

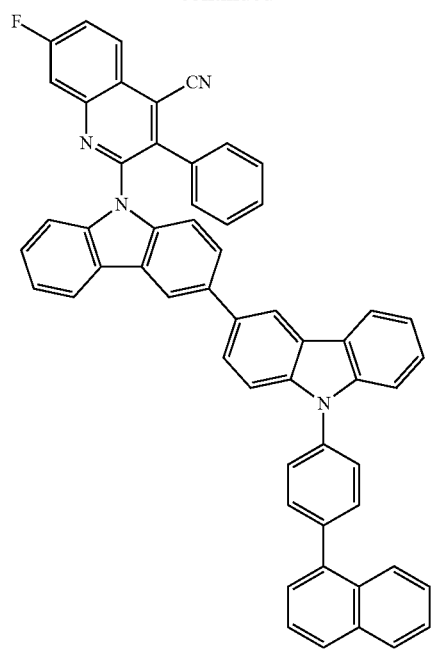
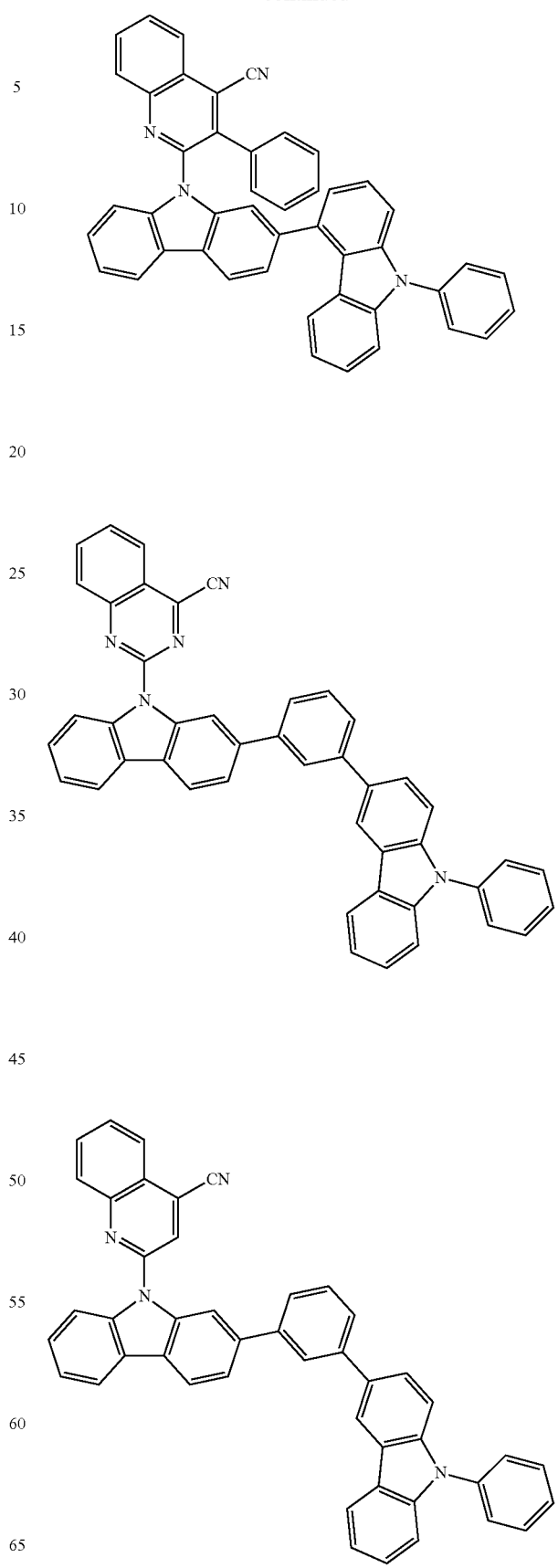

187
-continued
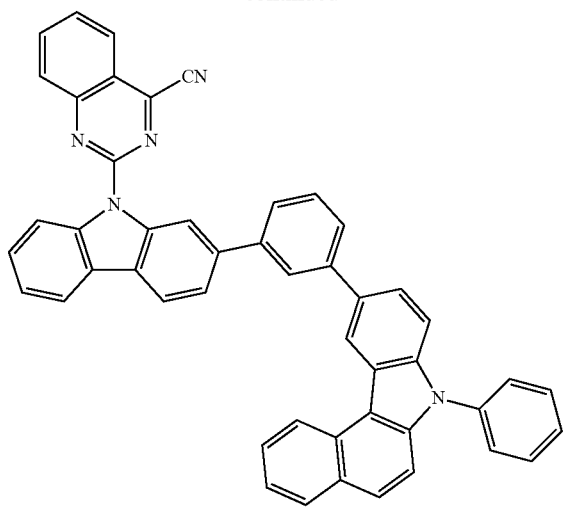
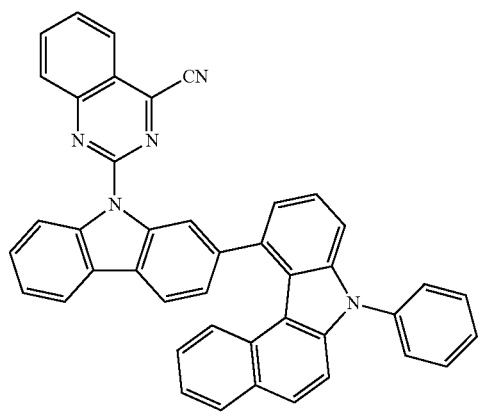
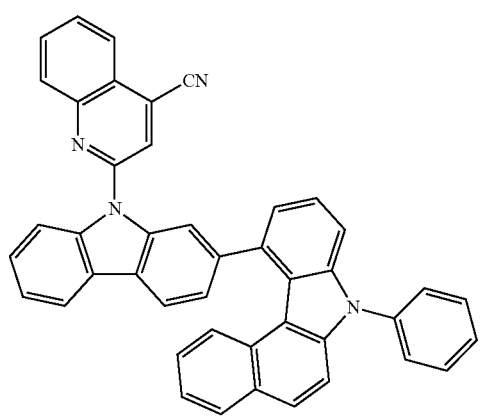
188
-continued
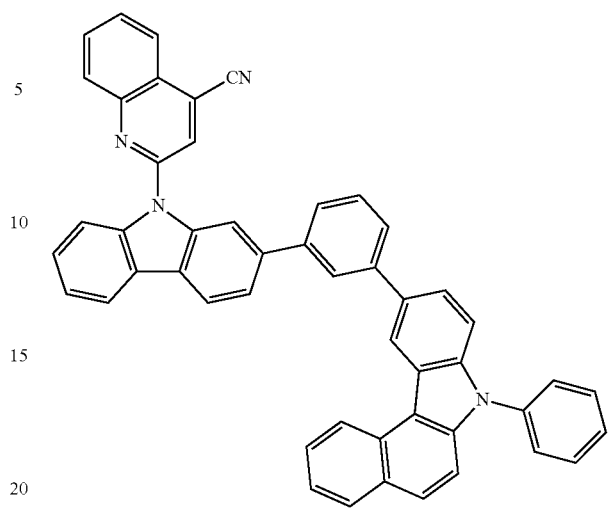
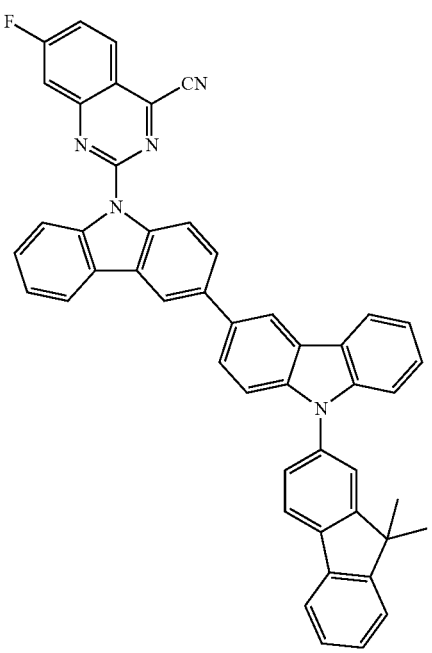

189
-continued
190
-continued
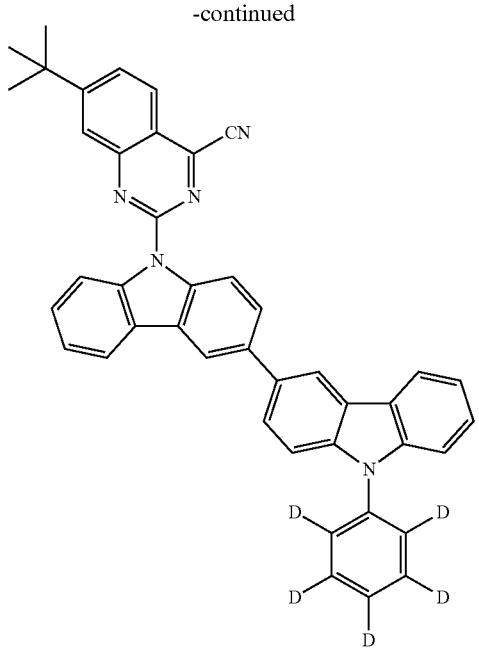
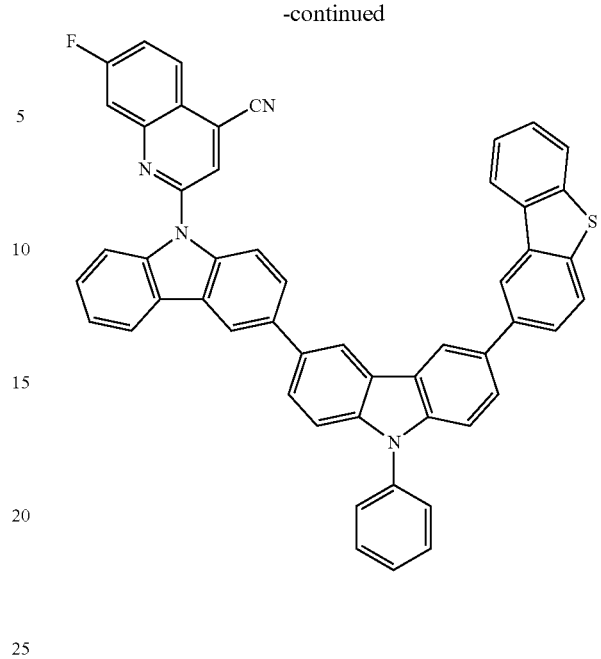
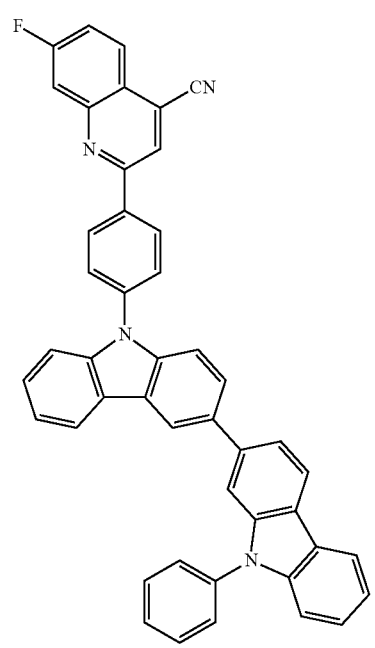
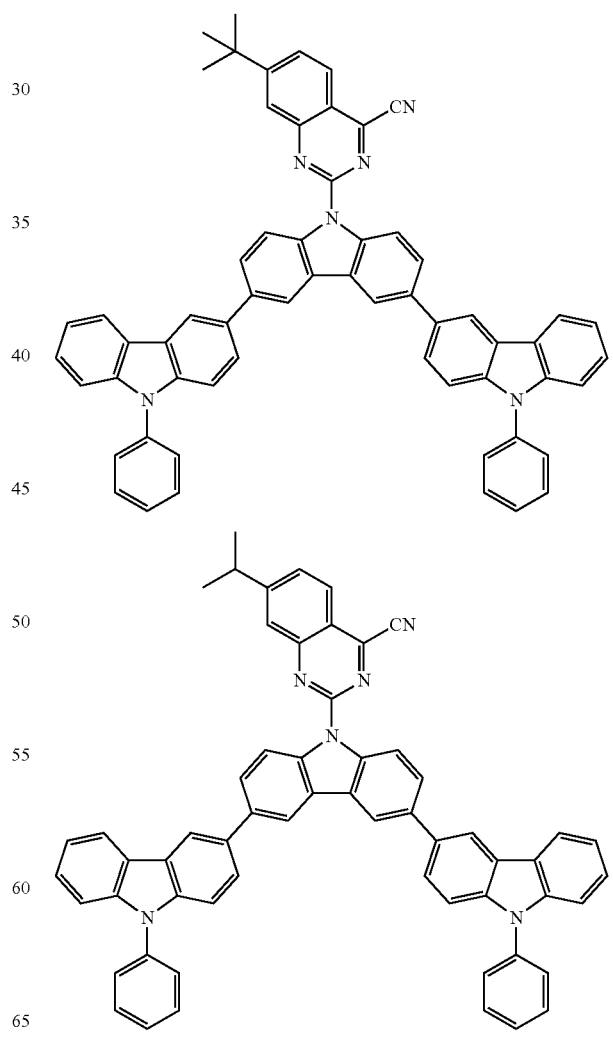

191
-continued
192
-continued
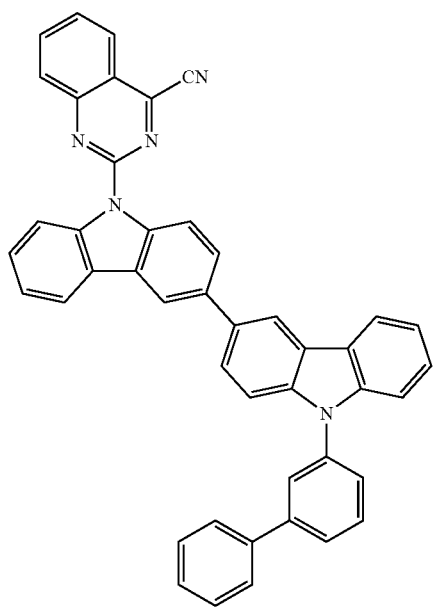
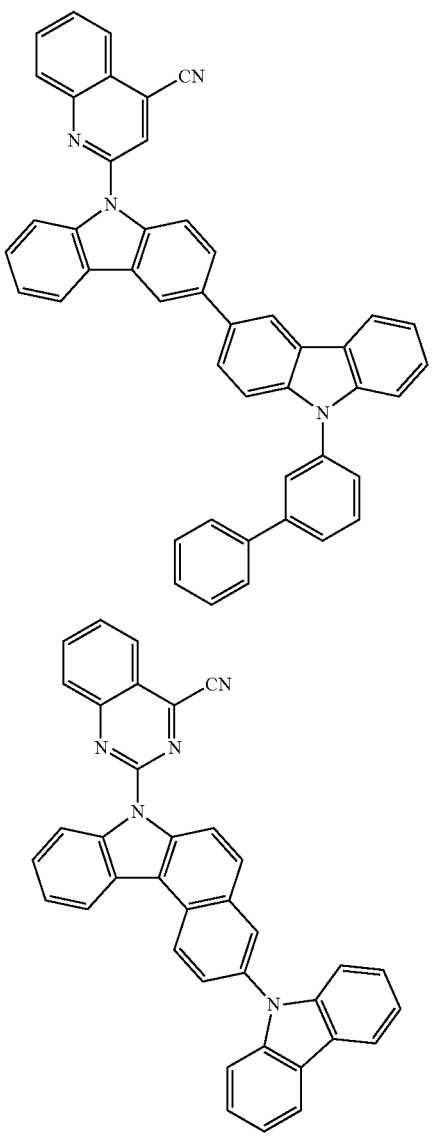
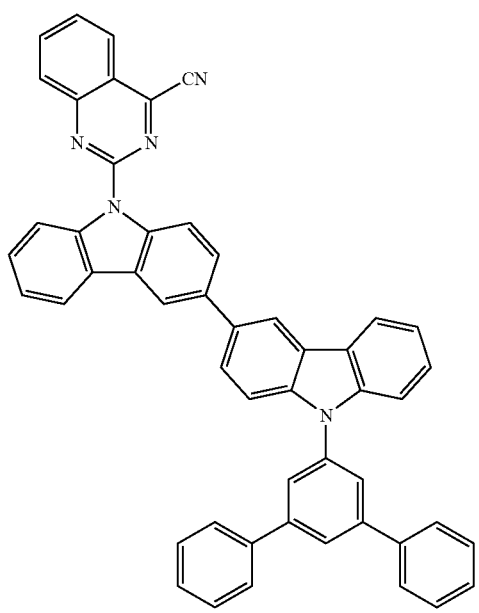

193
-continued
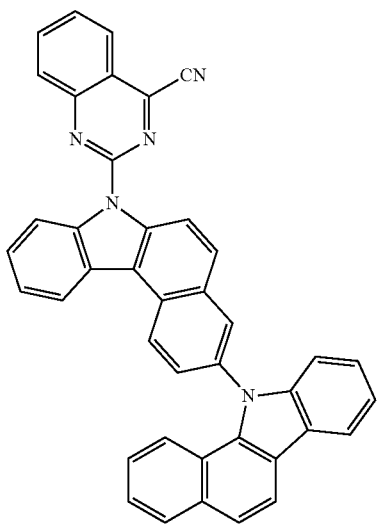
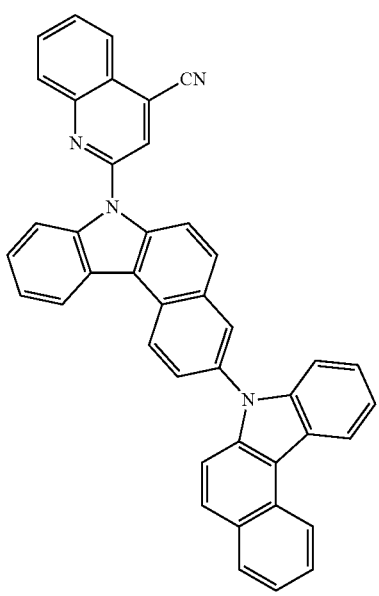
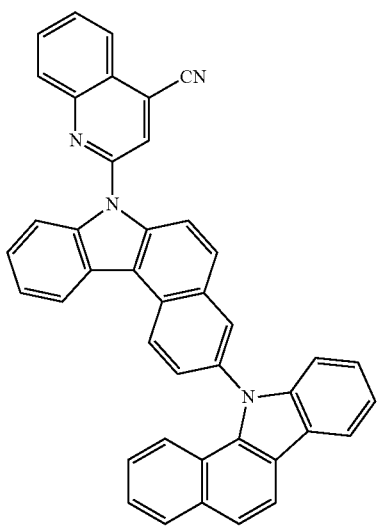
194
-continued
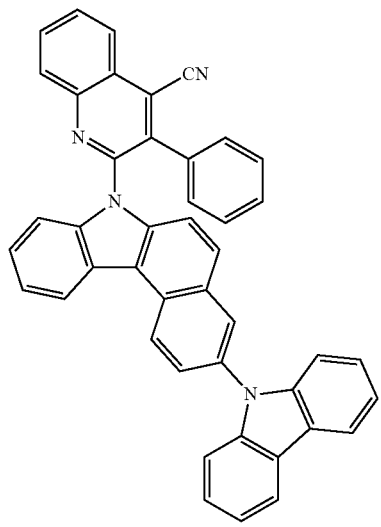
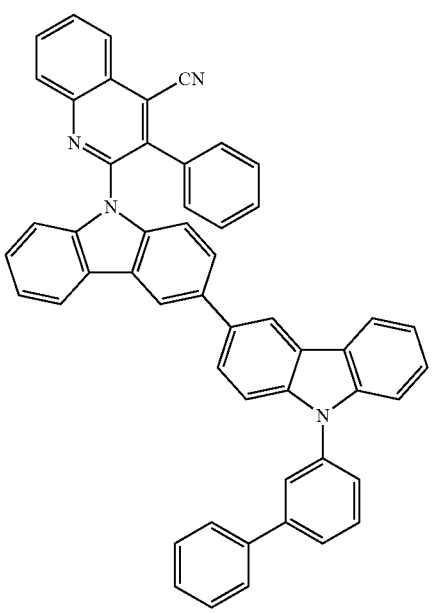

195
-continued
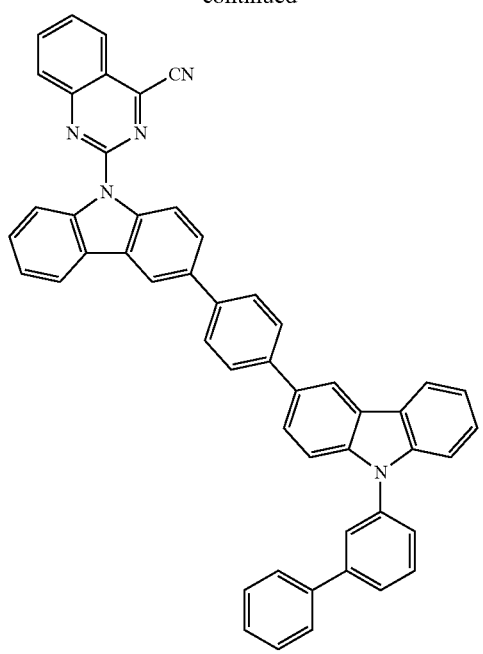
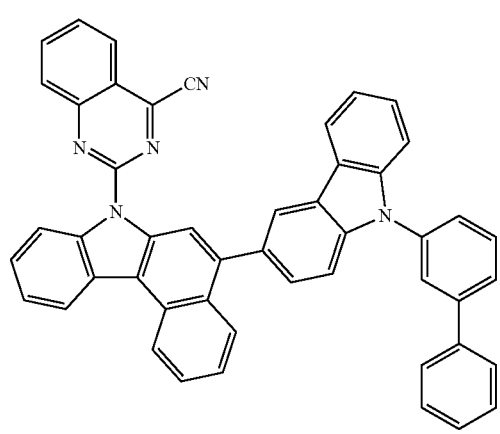
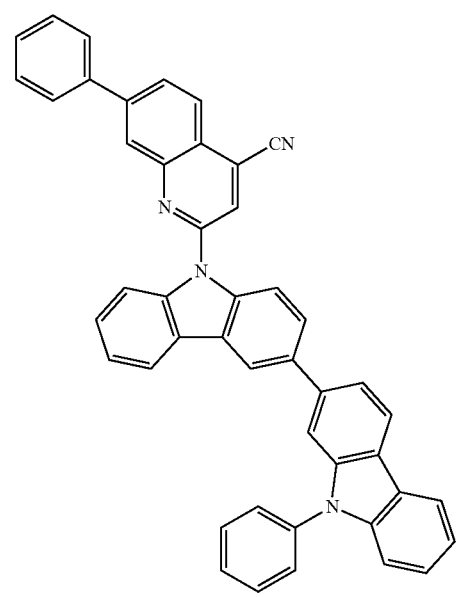
196
-continued
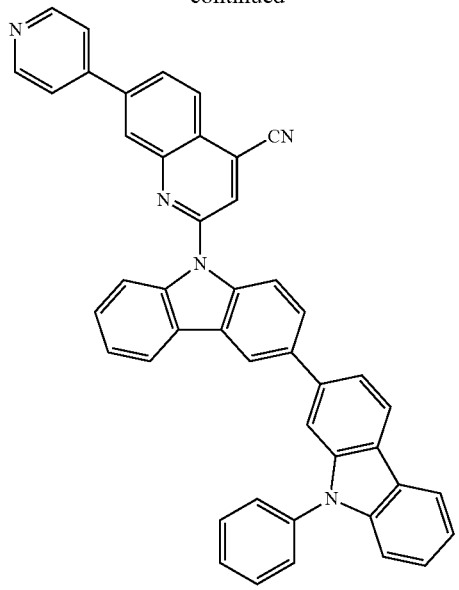
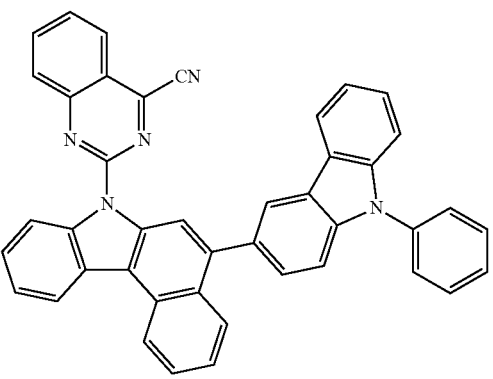
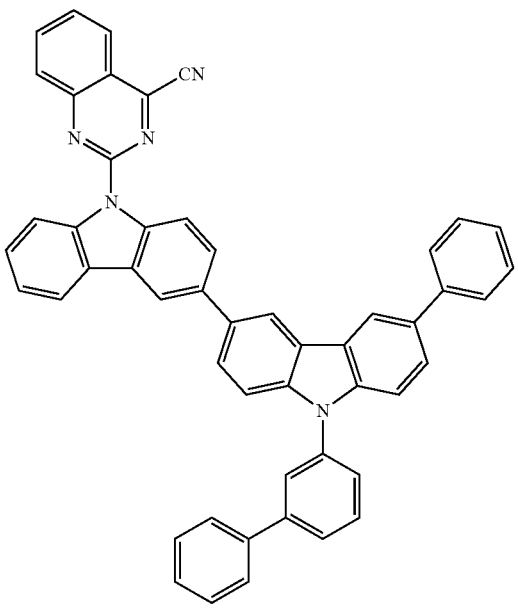

197
-continued
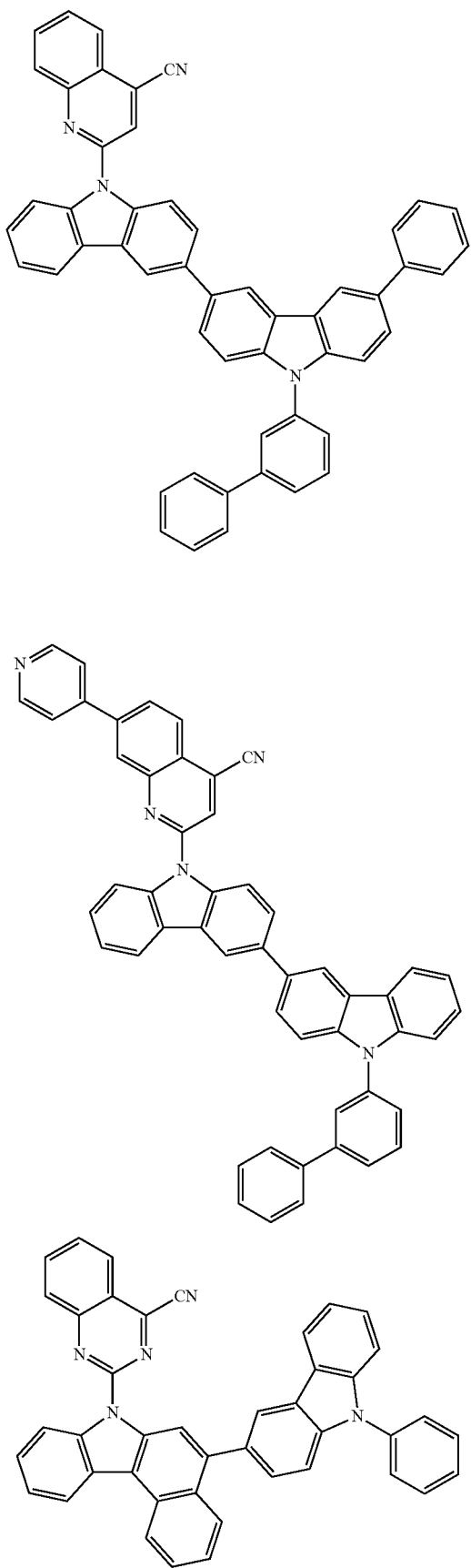
198
-continued
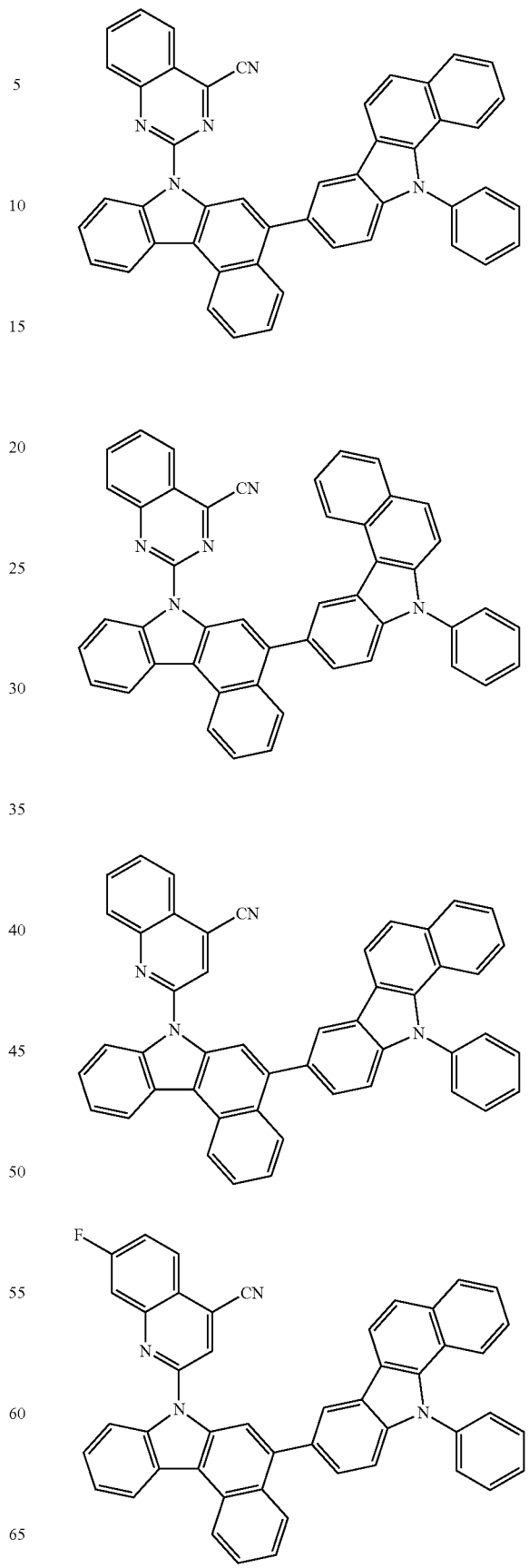

199
-continued
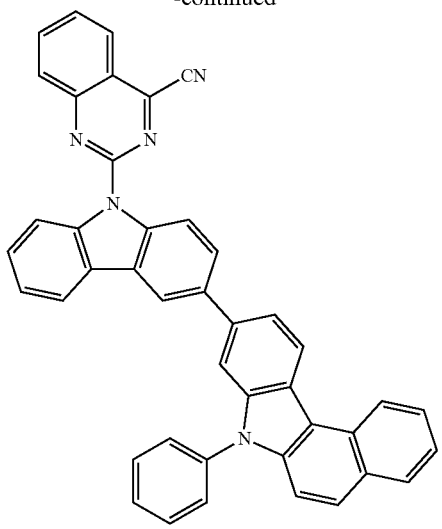
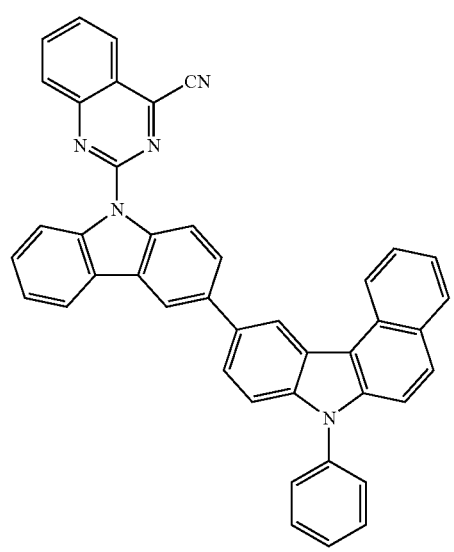
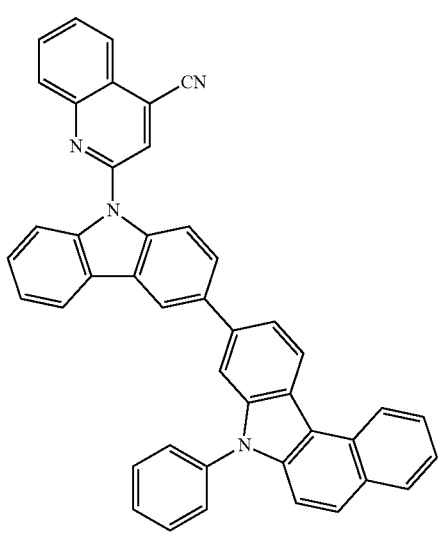
200
-continued
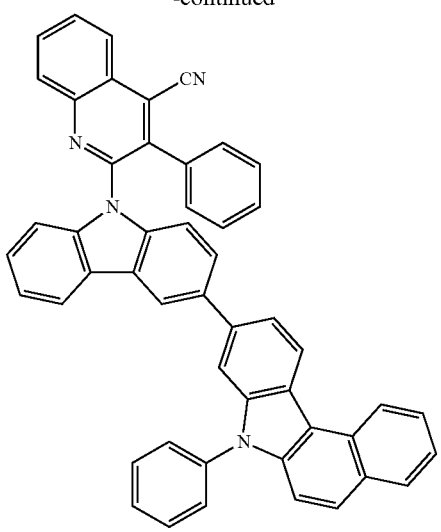
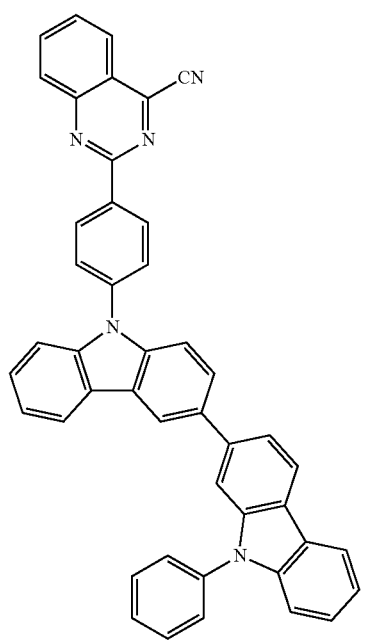

201
-continued
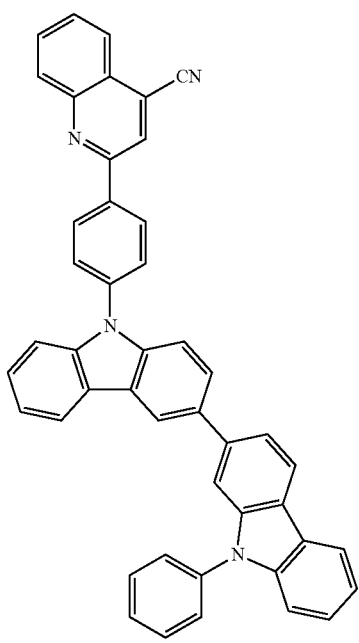
202
-continued
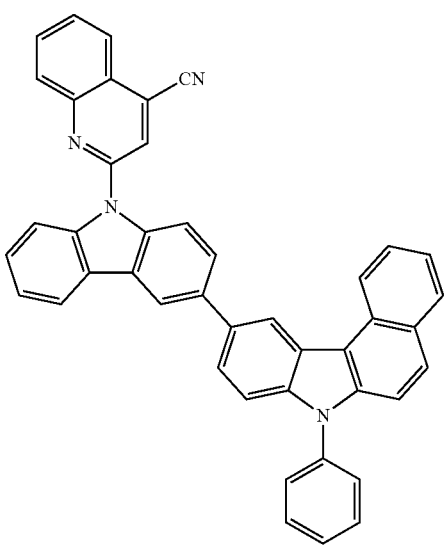
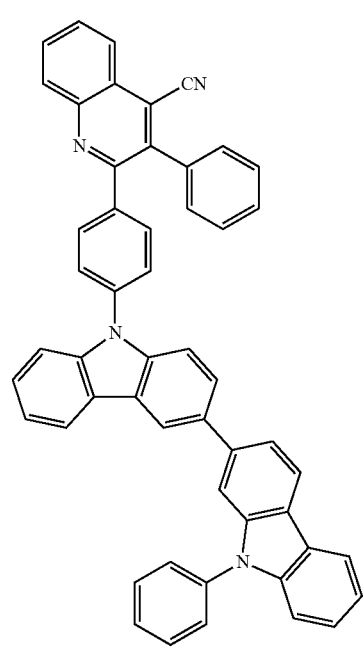
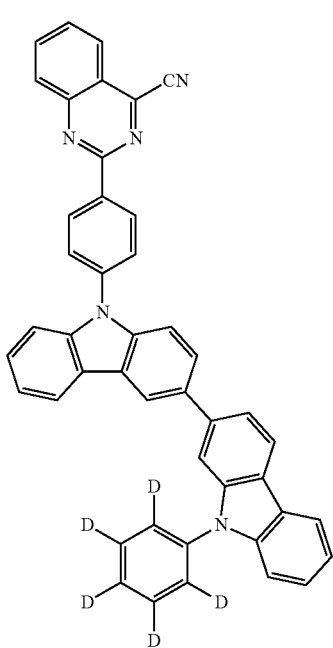

203
-continued
204
-continued
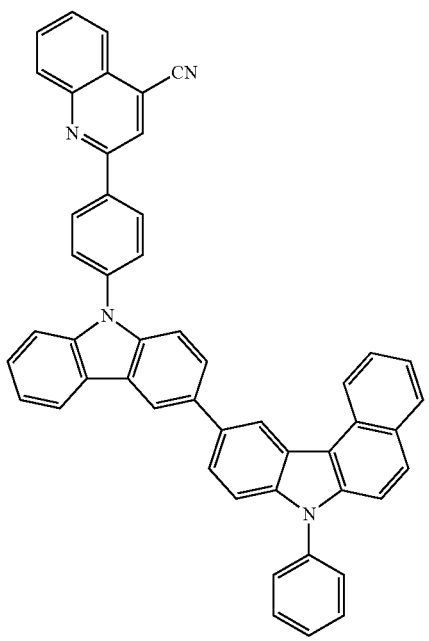
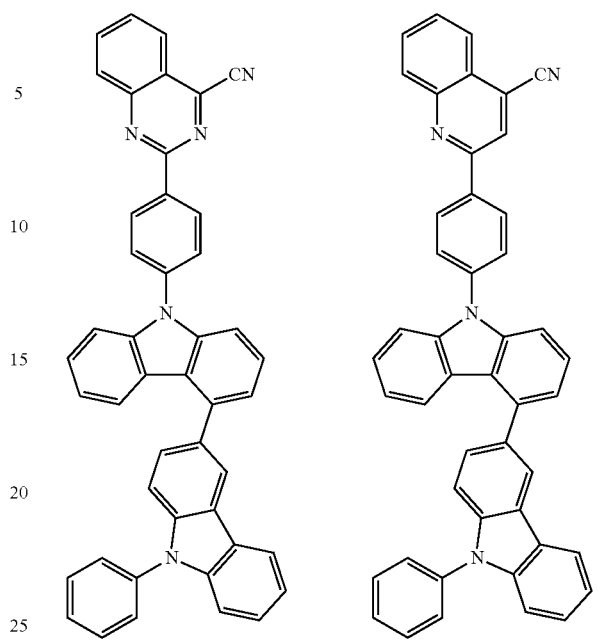
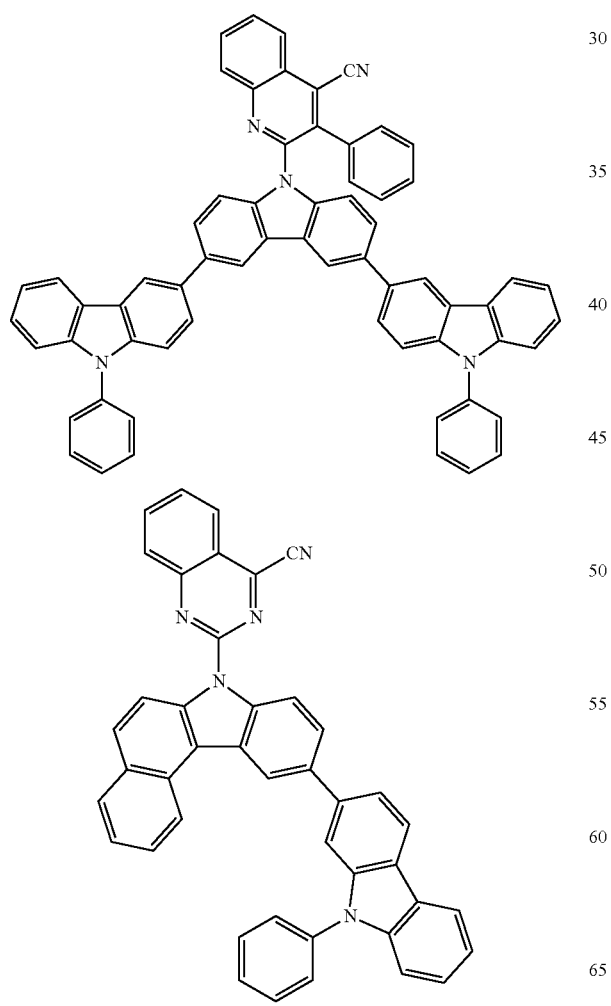
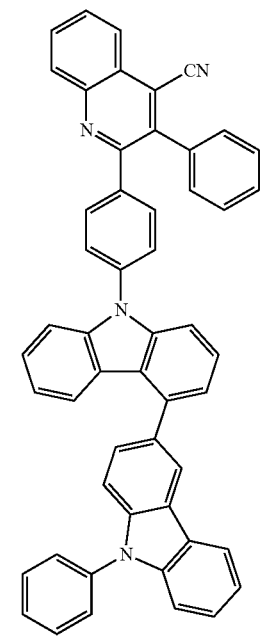

205
-continued
206
-continued
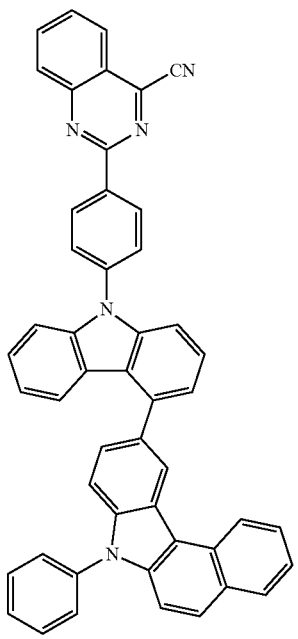
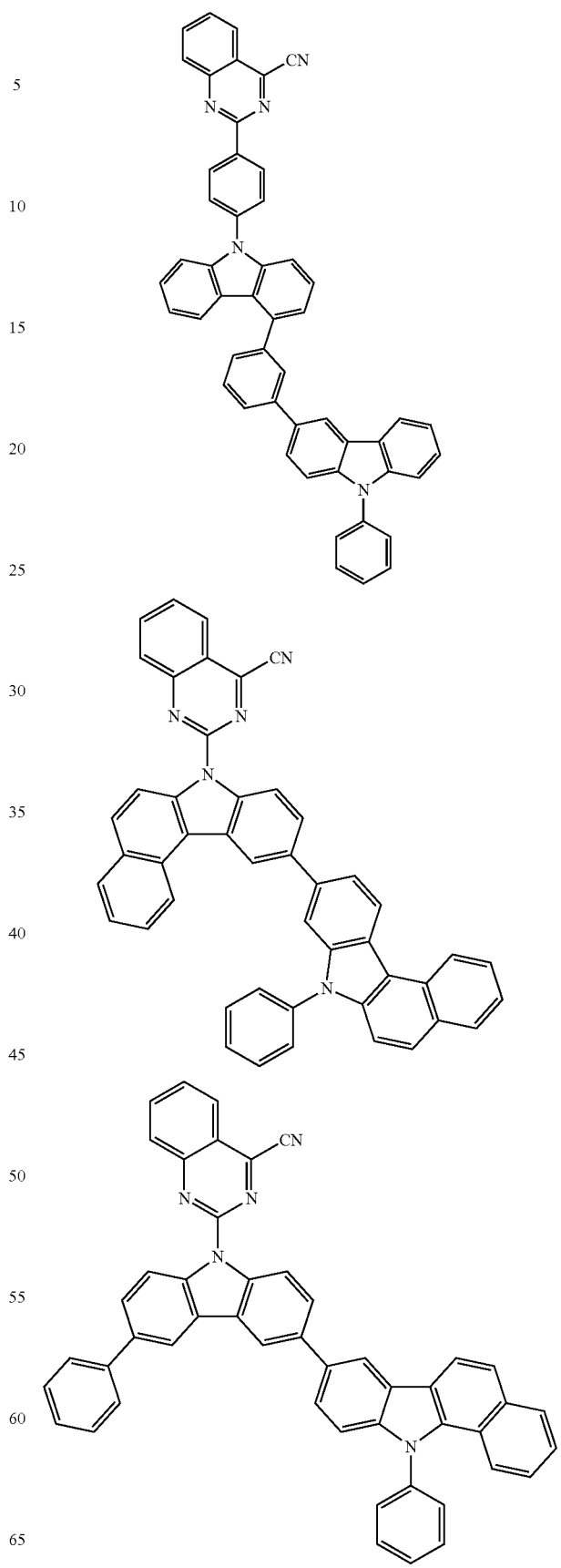

207
-continued
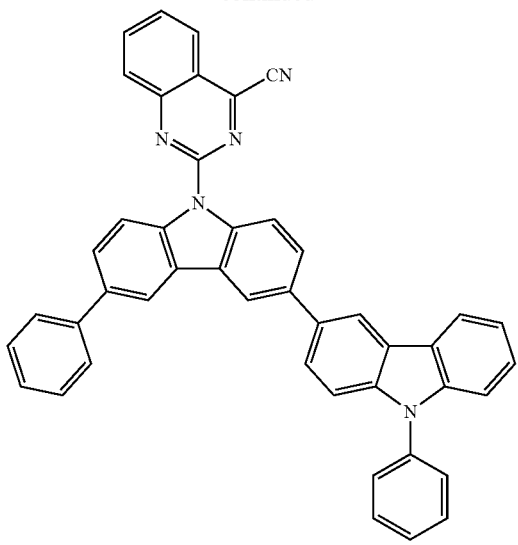
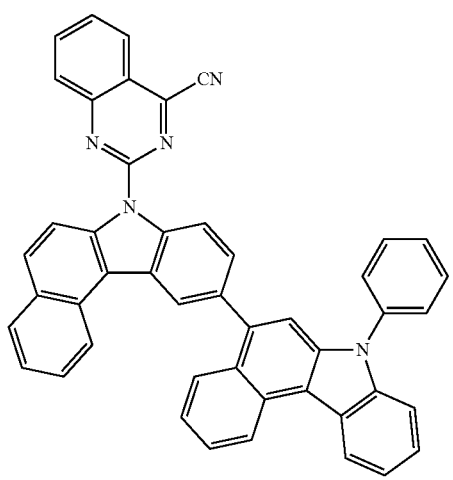
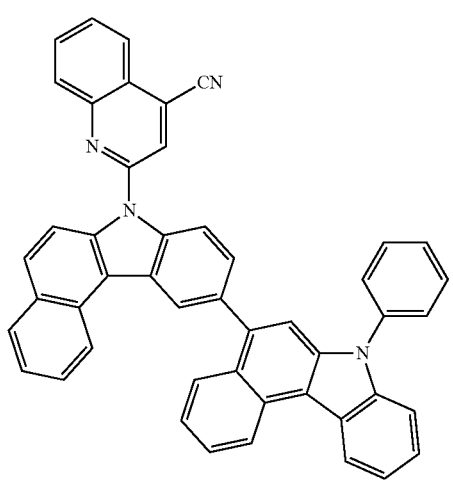
208
-continued
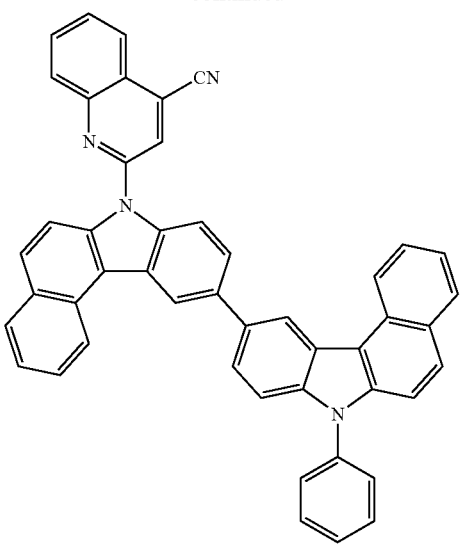
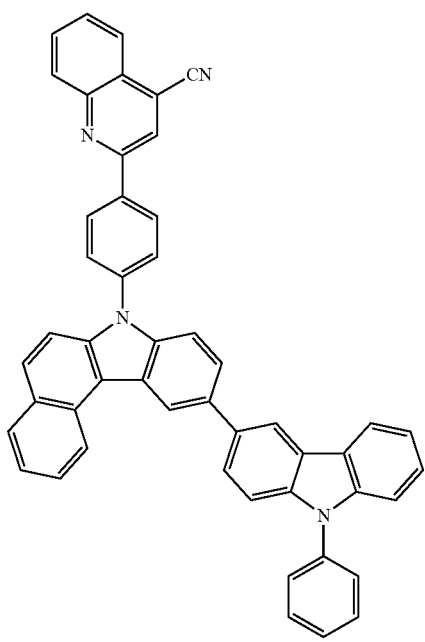
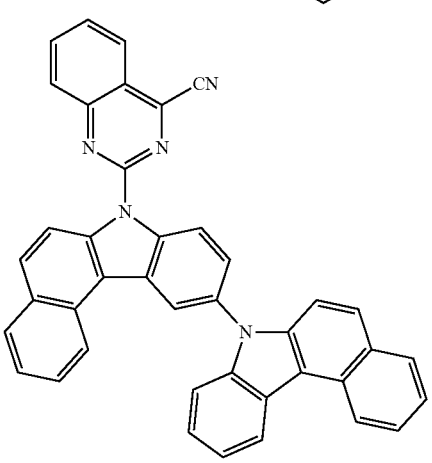

209
-continued
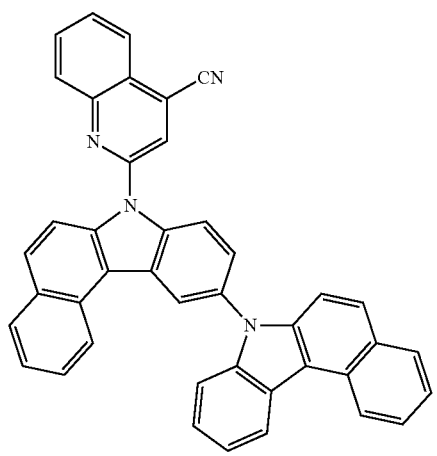
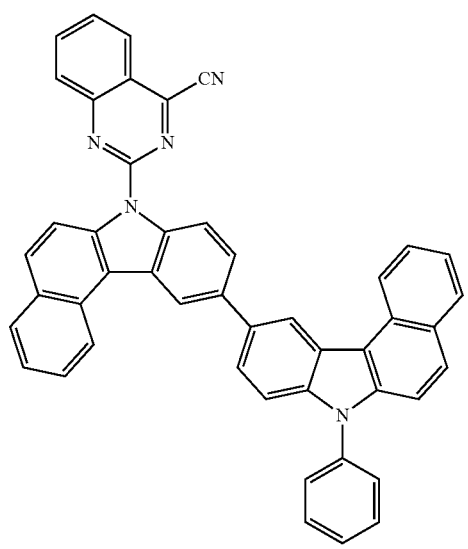
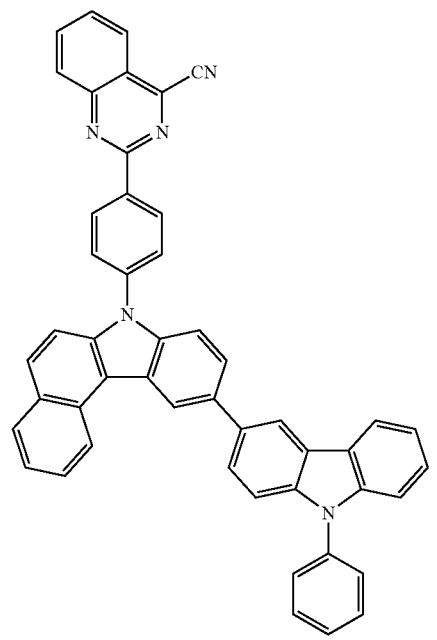
210
-continued
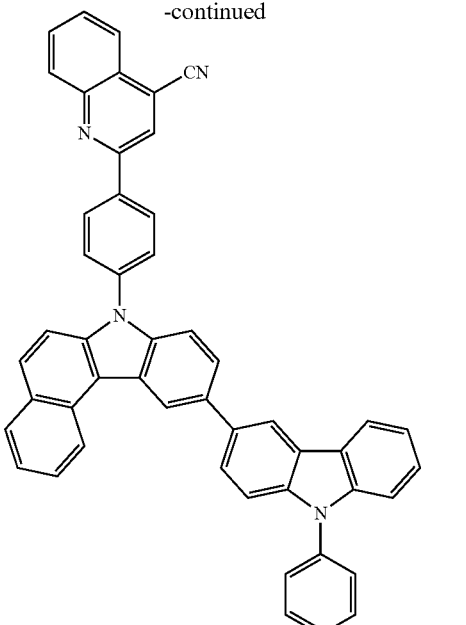
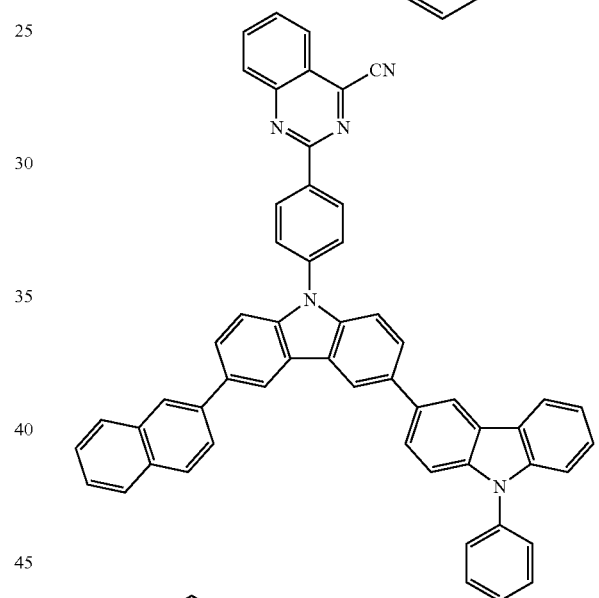
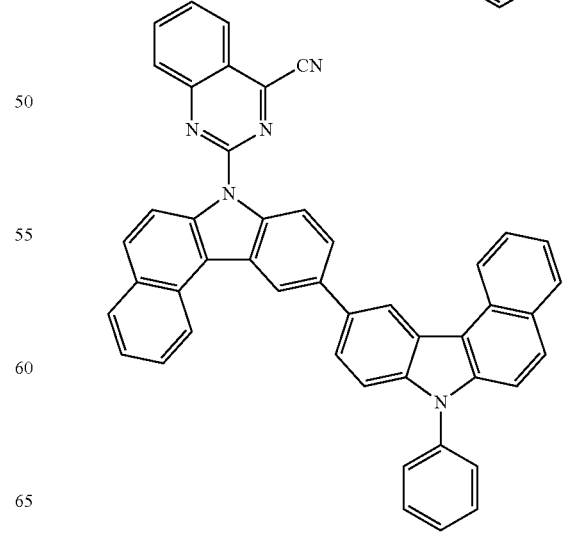

211
-continued
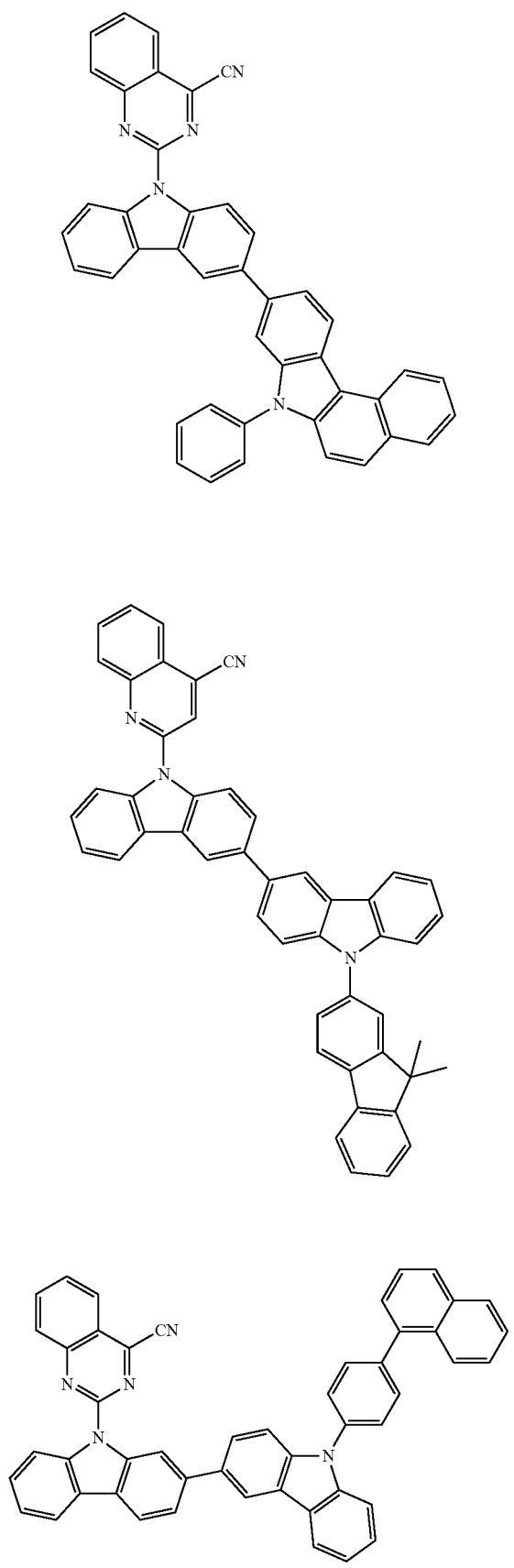
212
-continued
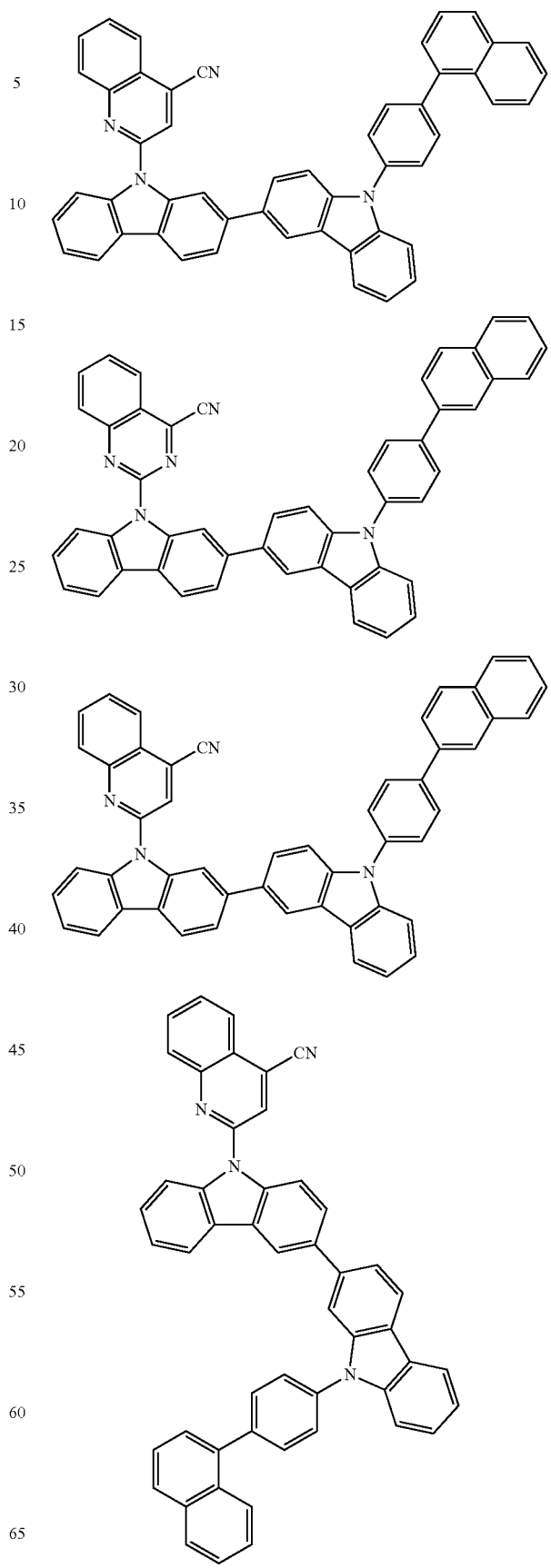

213
-continued
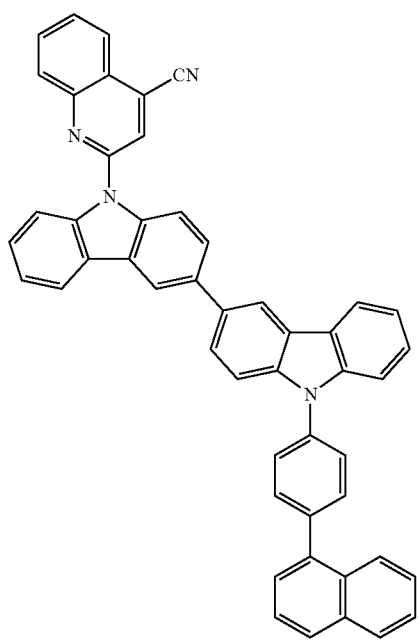
214
-continued
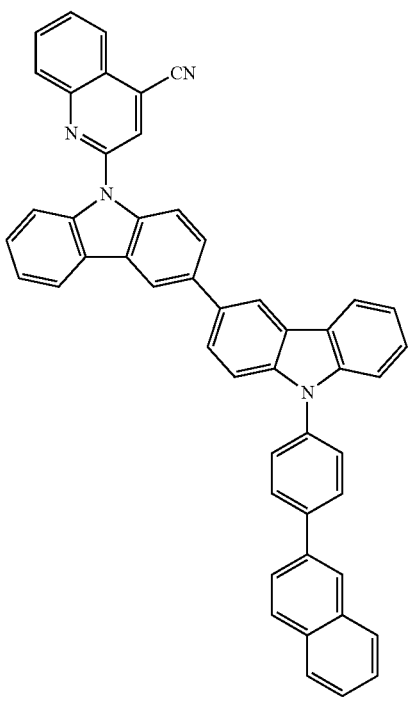
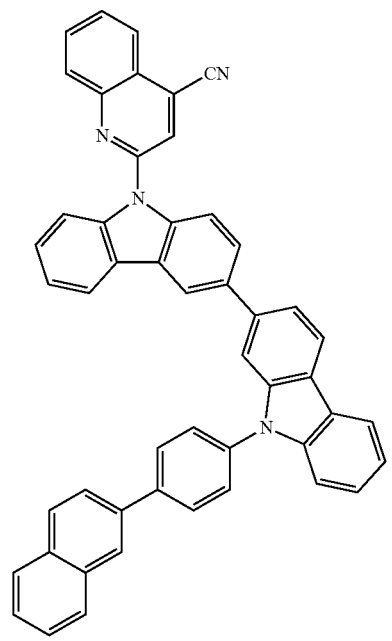
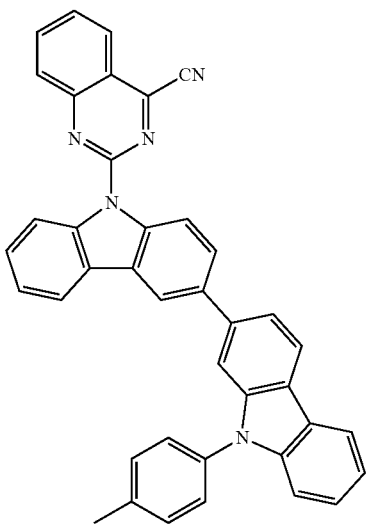

215
-continued
216
-continued
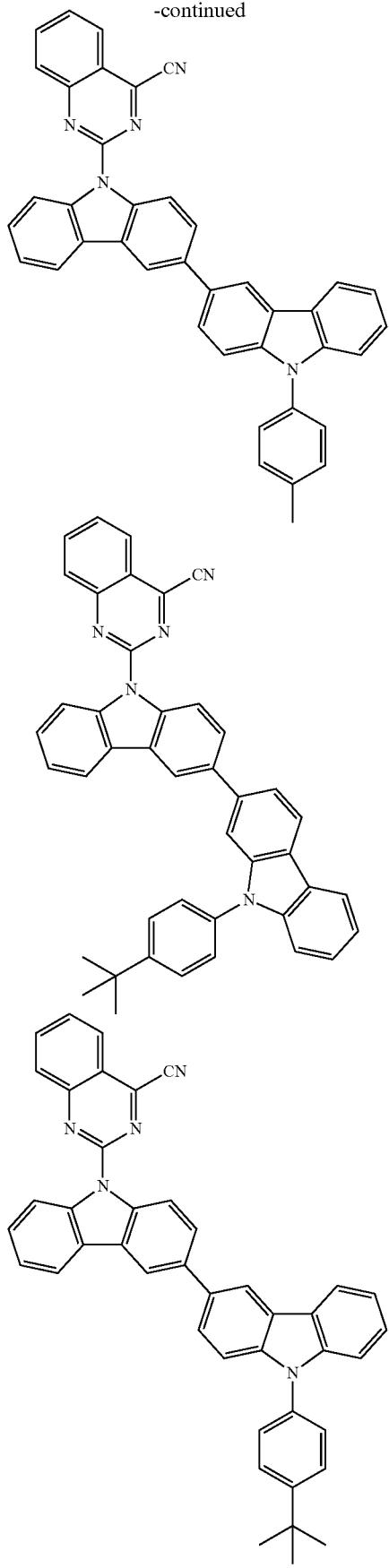
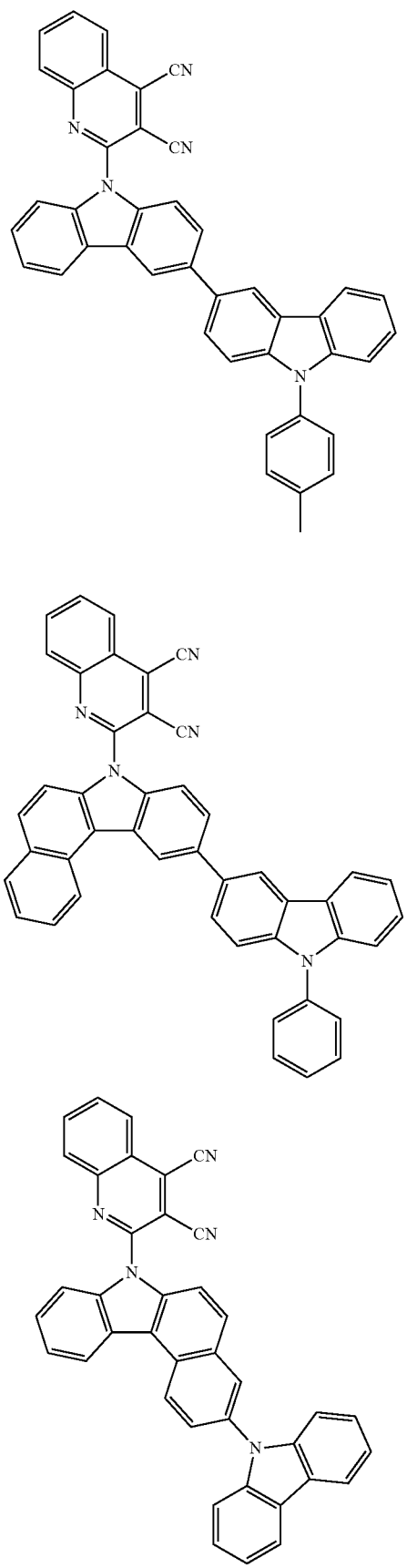

217
-continued
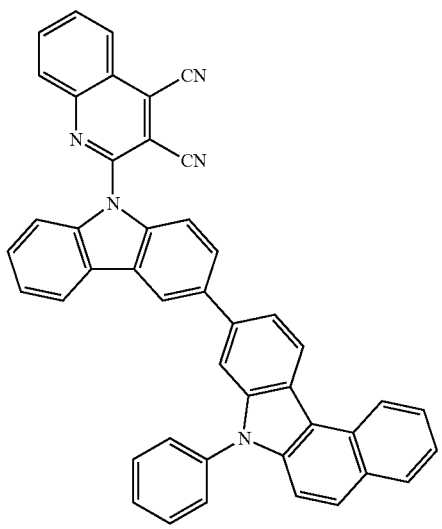
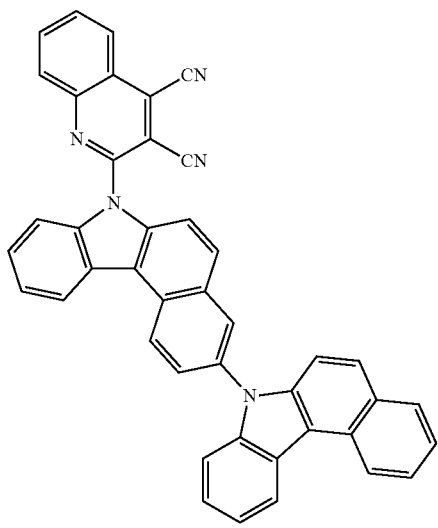
13. The compound of claim 1, wherein the compound represented by Formula 1 is selected from the following structural formulae:
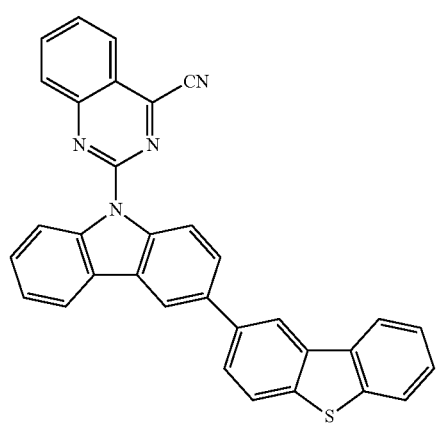
218
-continued
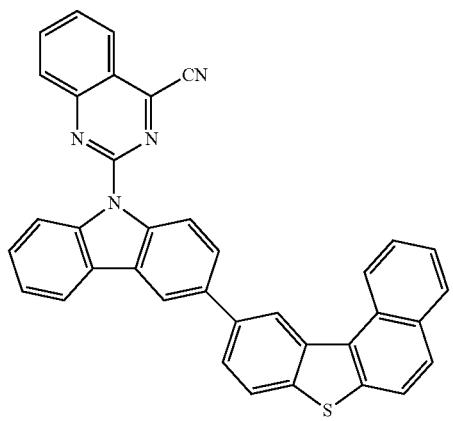
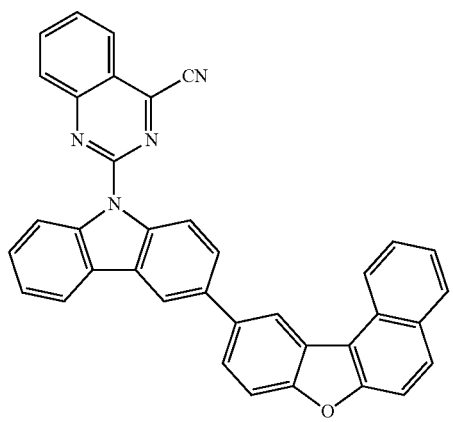
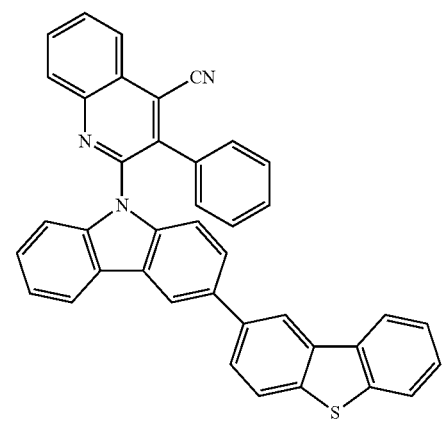
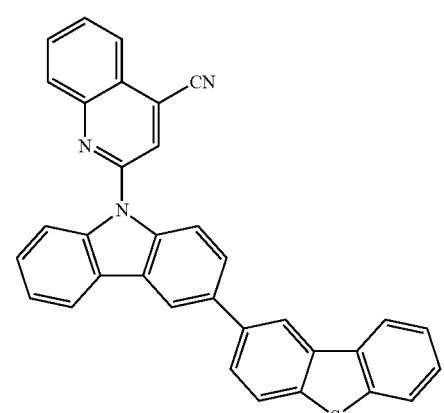

219
-continued
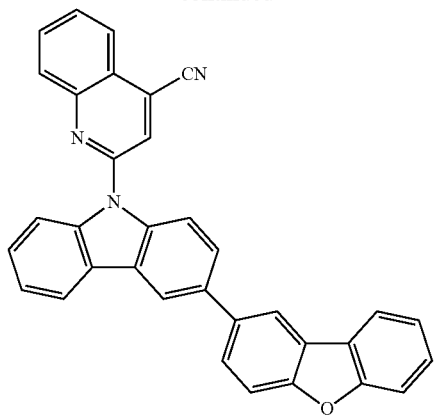
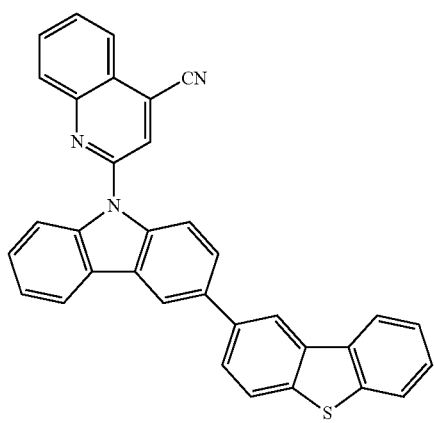
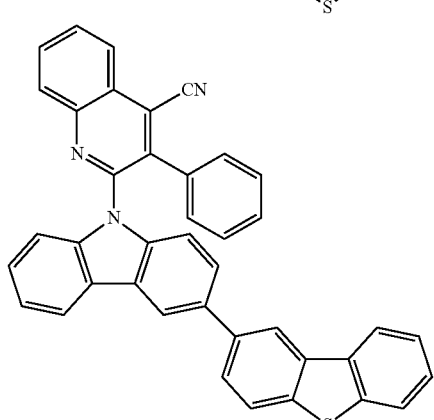
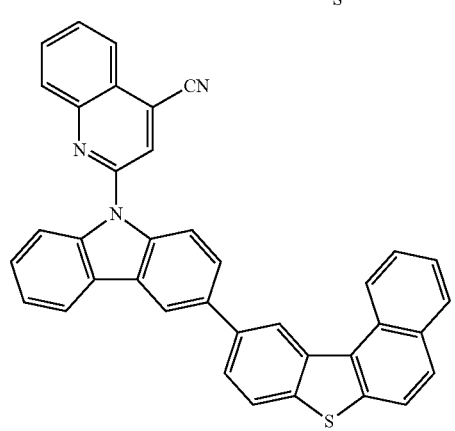
220
-continued
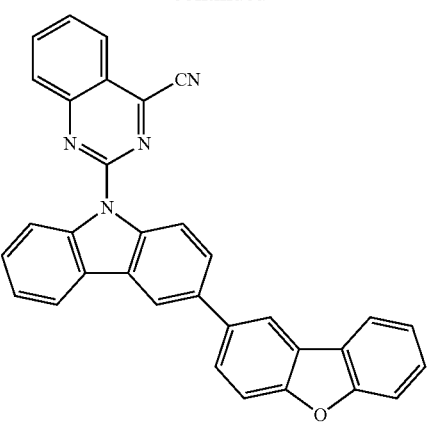
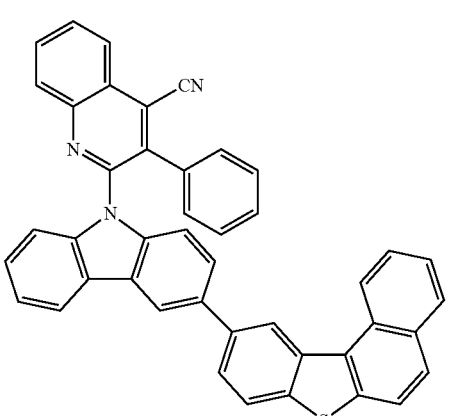

221
-continued
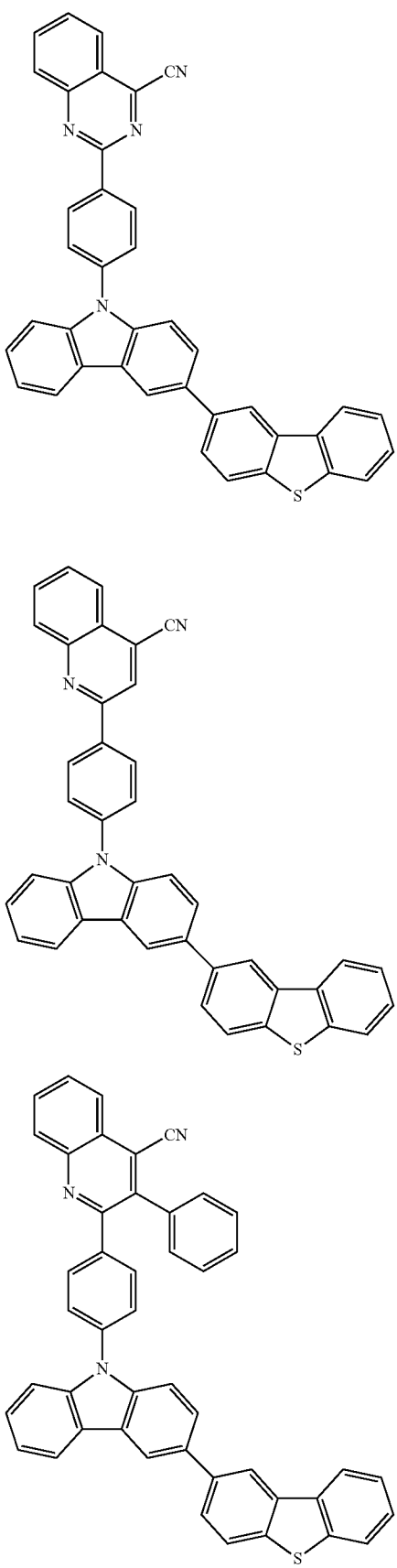
222
-continued
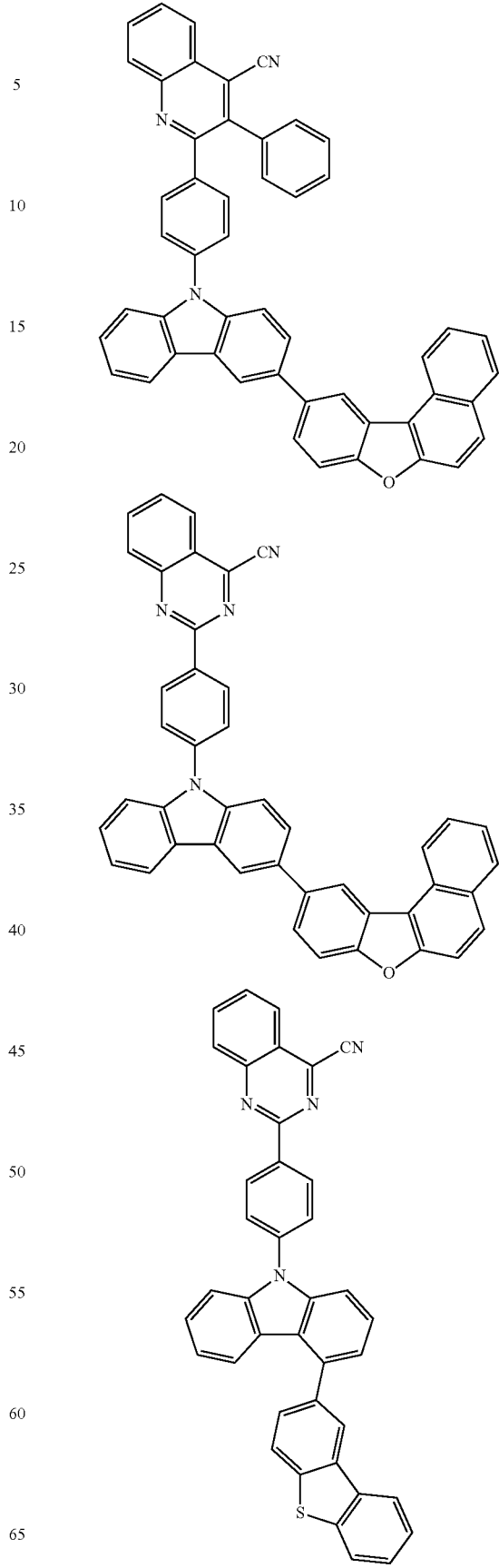

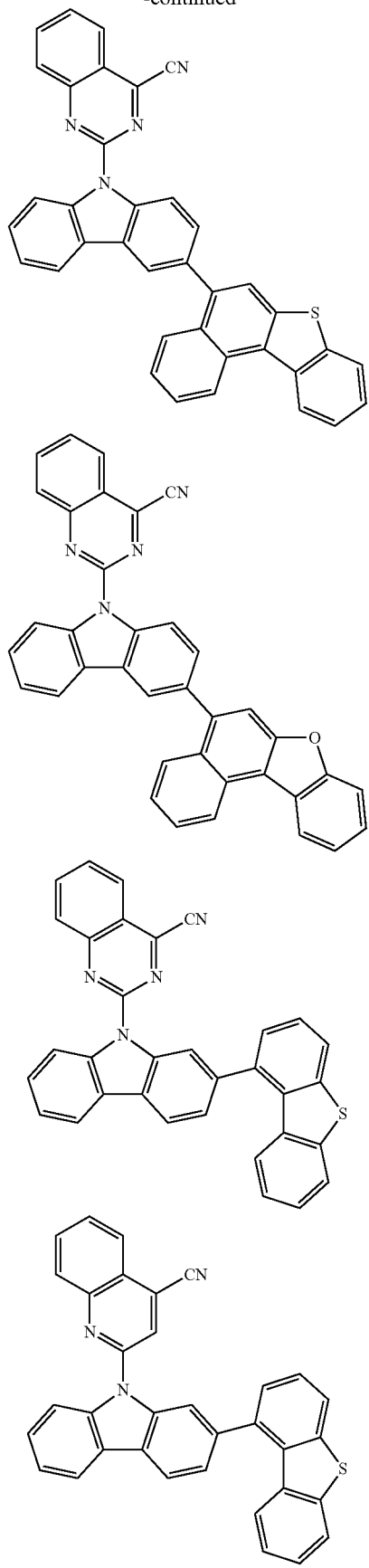
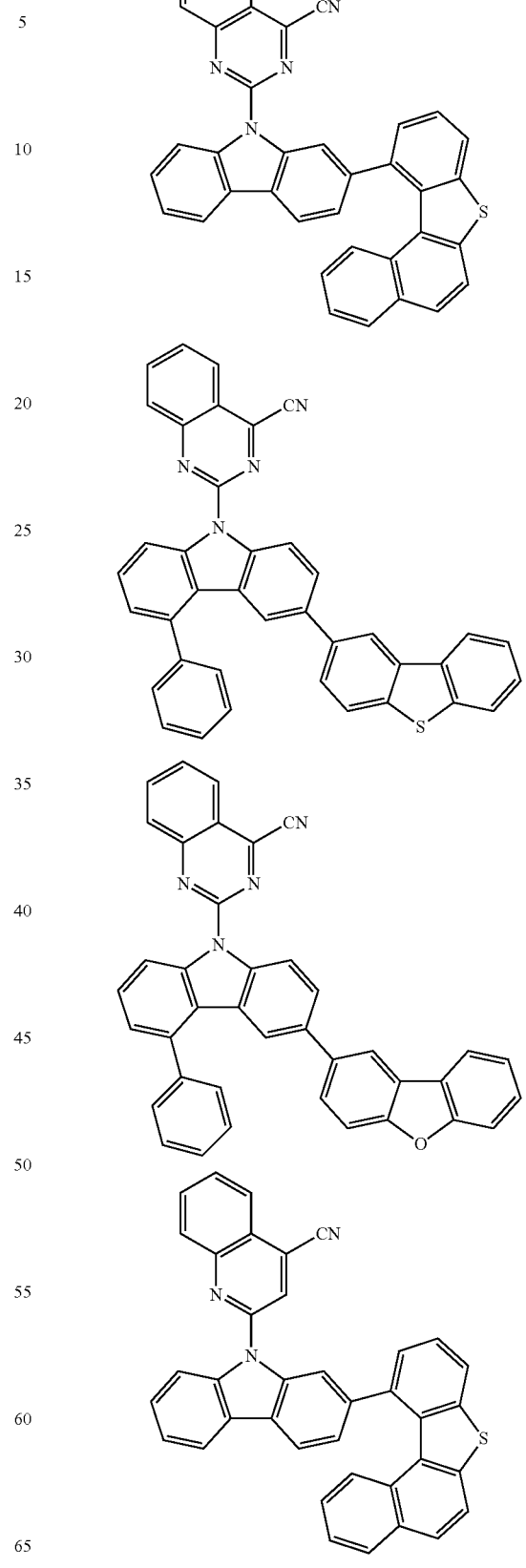

225
-continued
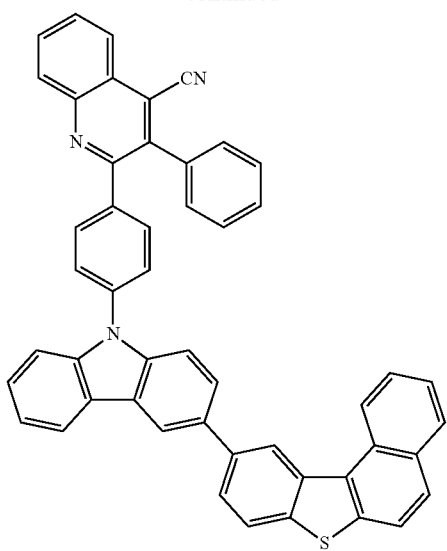
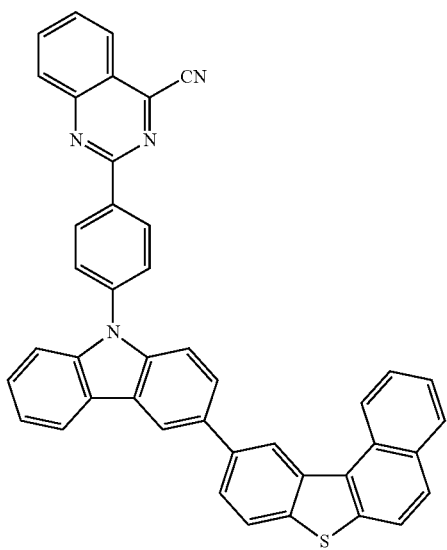
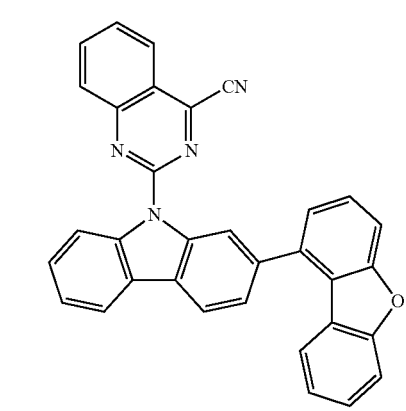
226
-continued
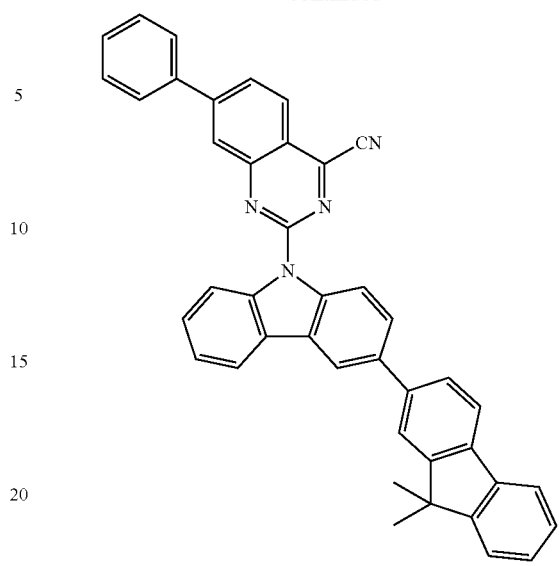
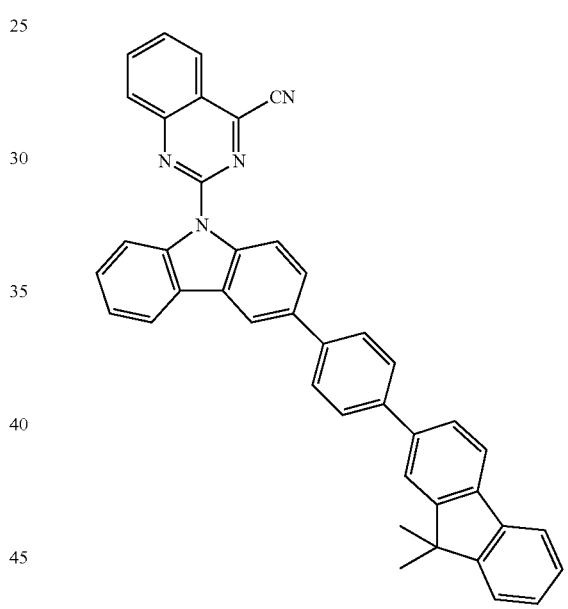
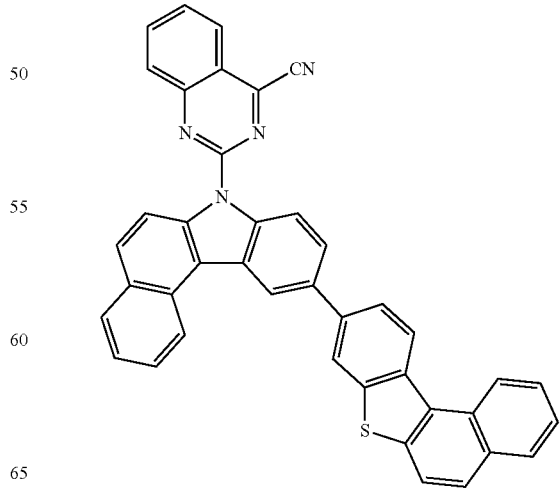

227
-continued
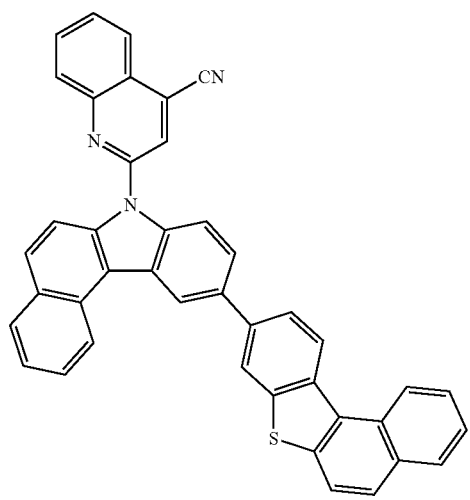
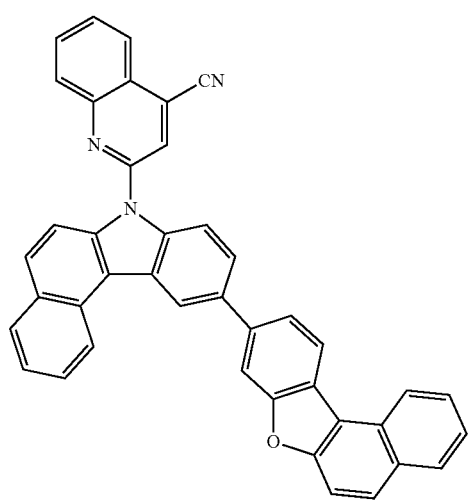
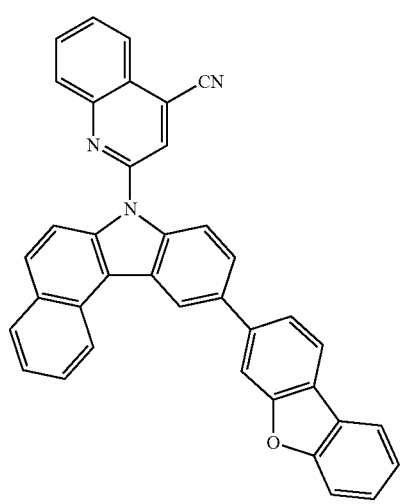
228
-continued
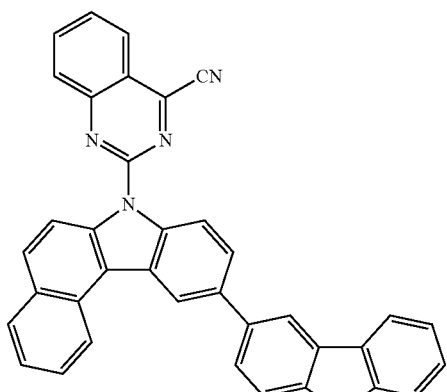
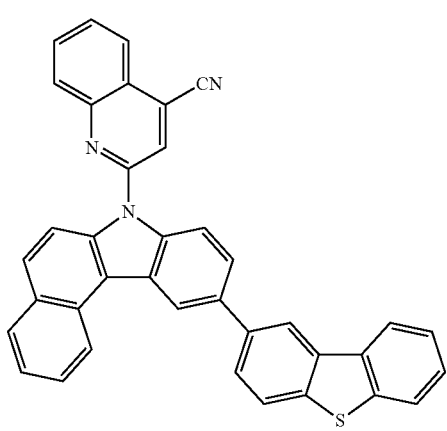
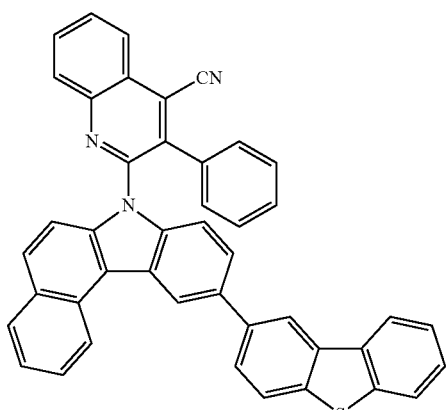
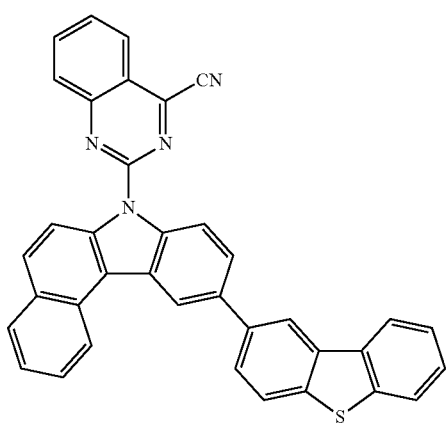

-continued
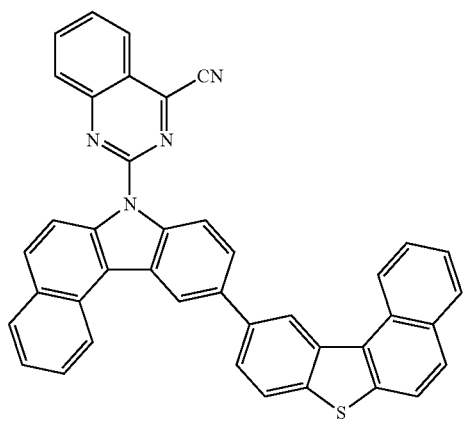
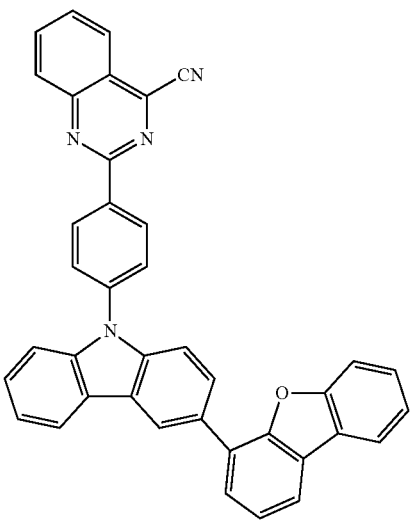
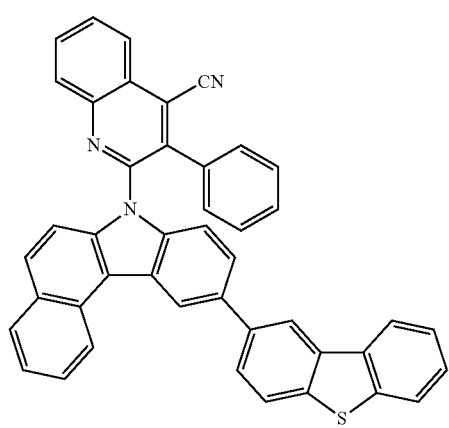
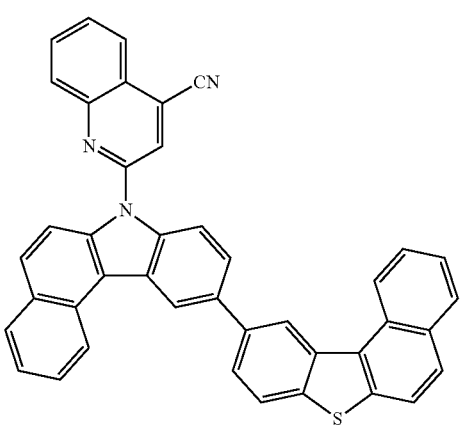
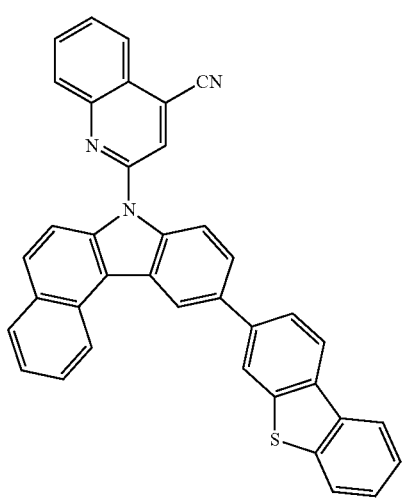
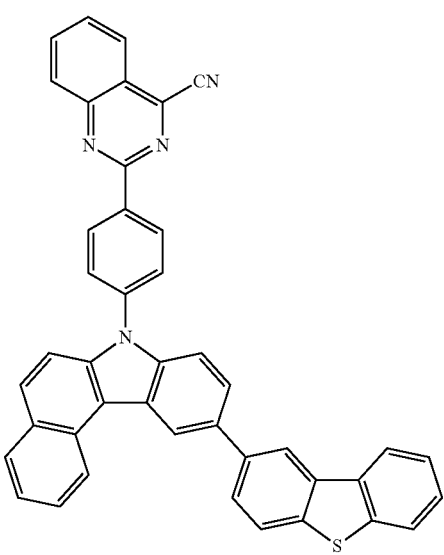

231
-continued
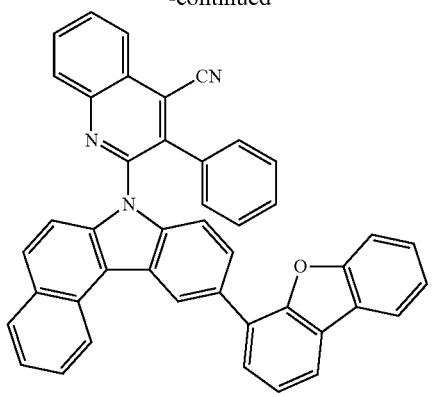
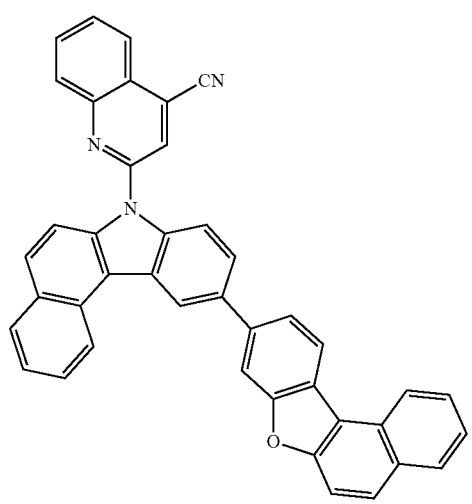
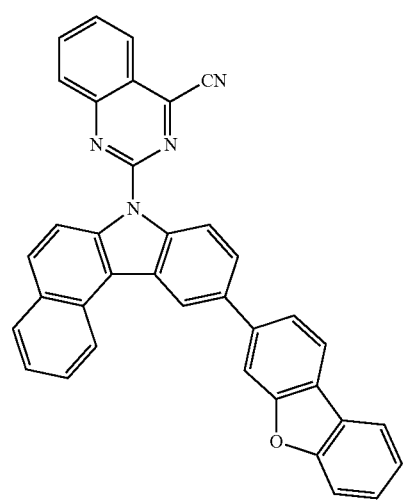
232
-continued
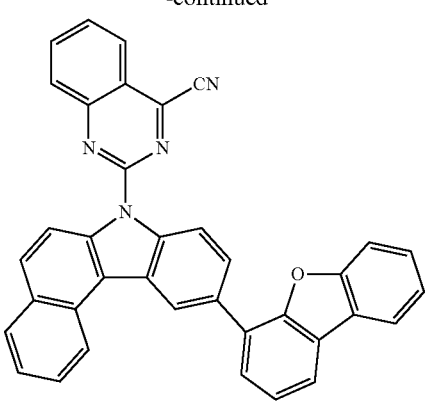
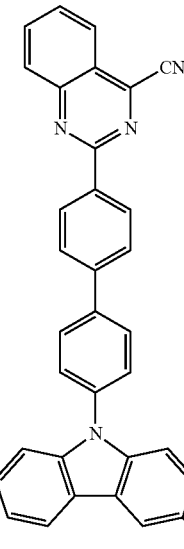
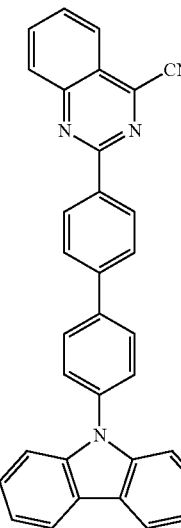

233
-continued
234
-continued
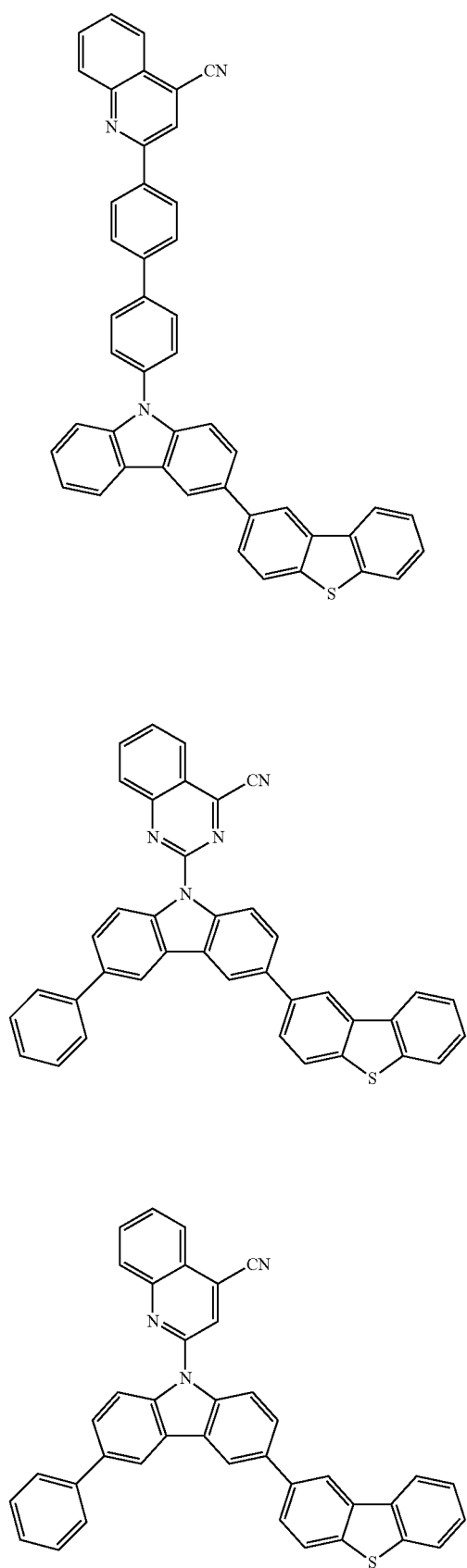
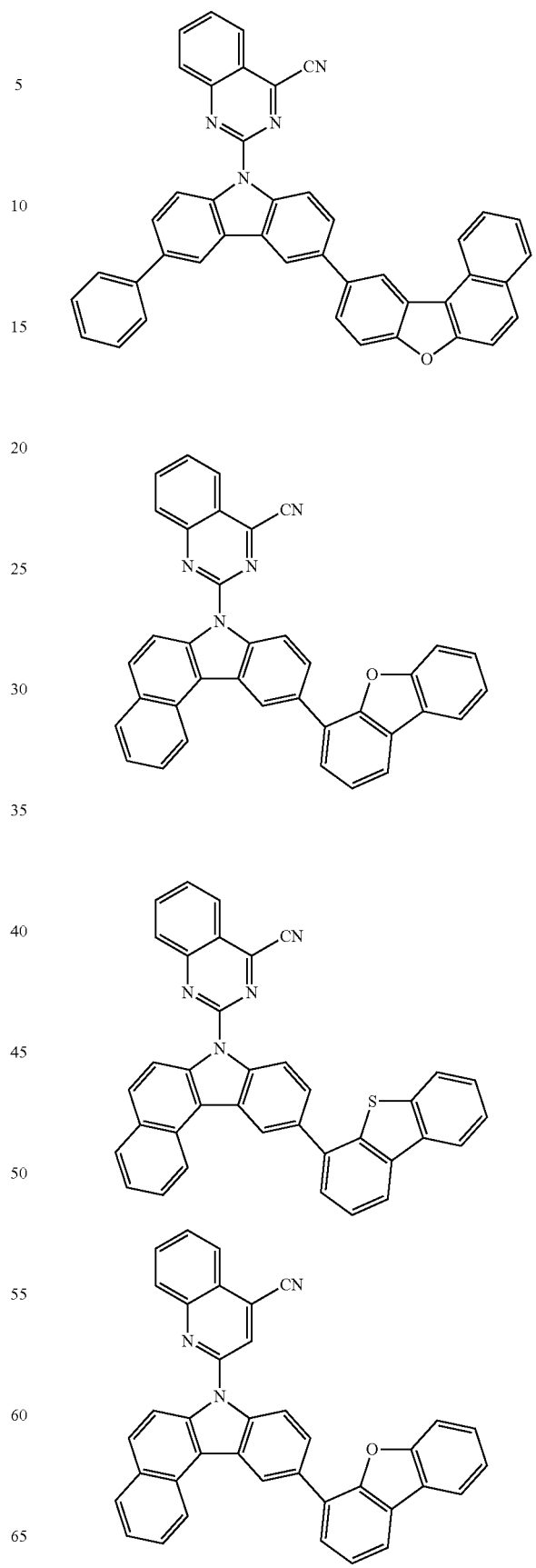

235
-continued
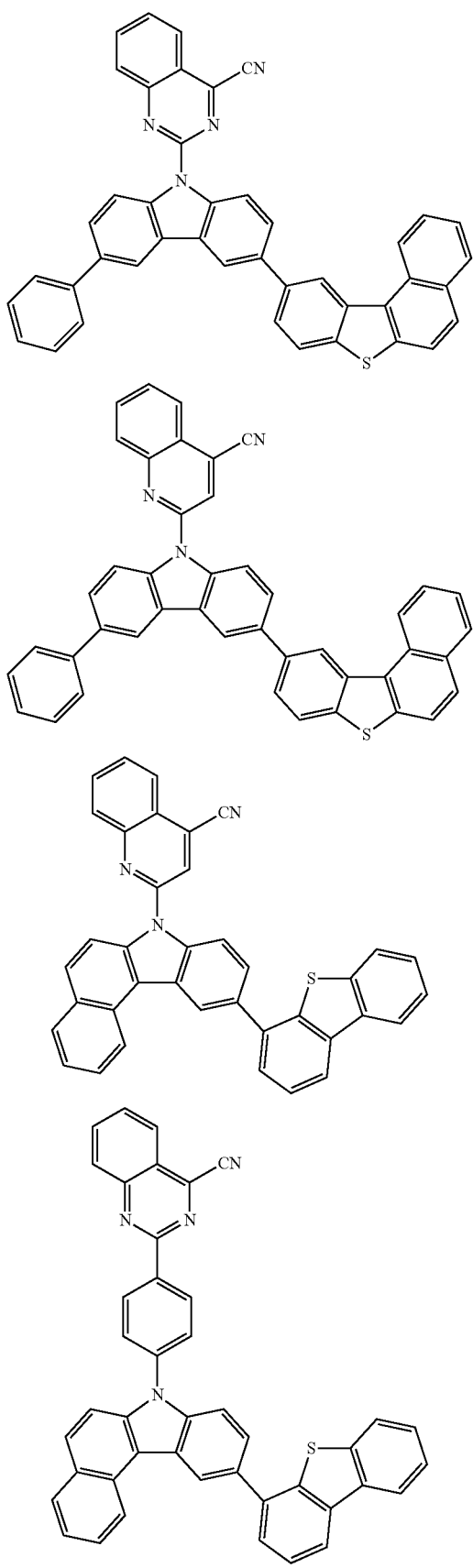
236
-continued
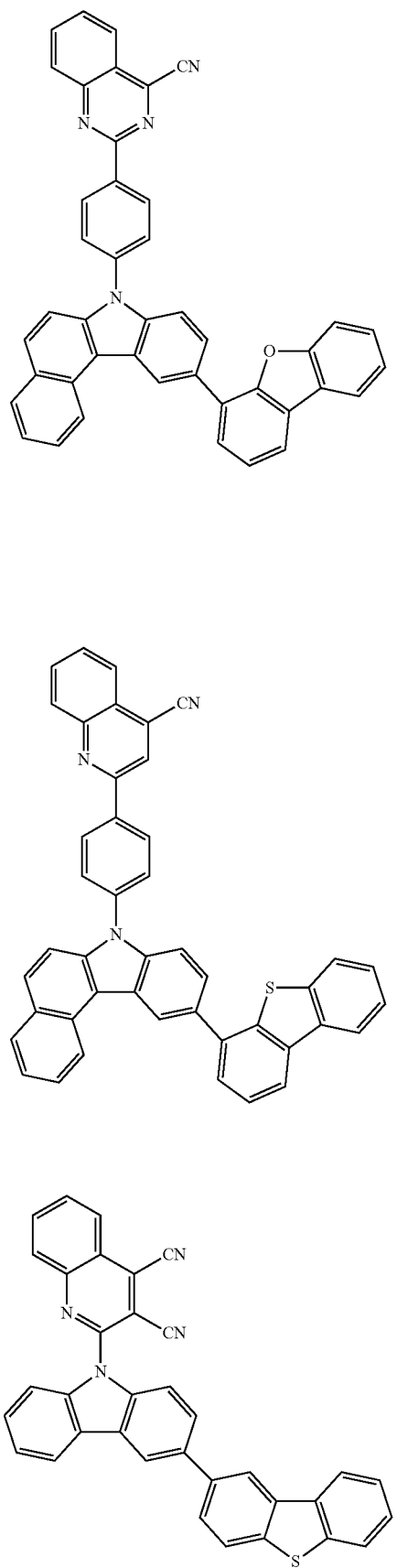

237
-continued
238
-continued
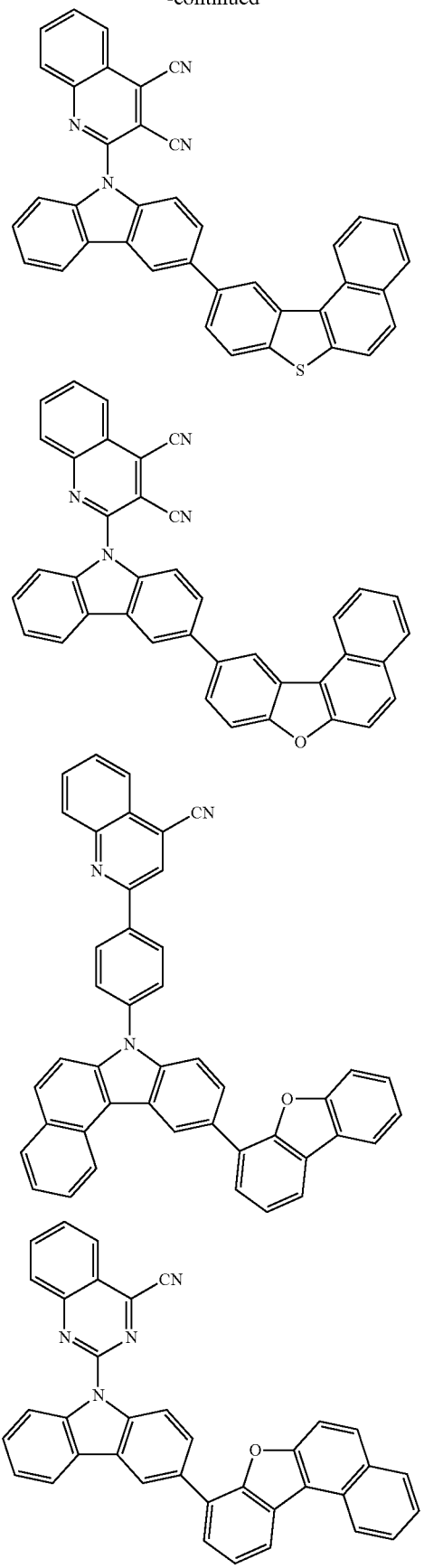
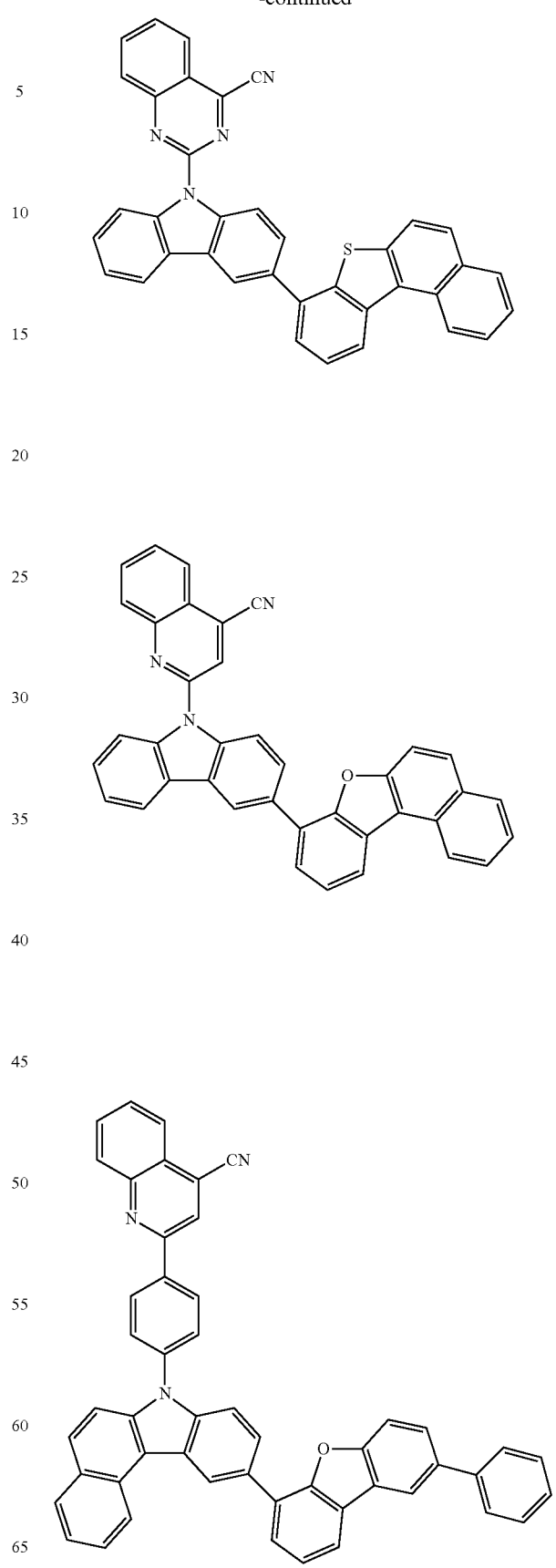

239
-continued
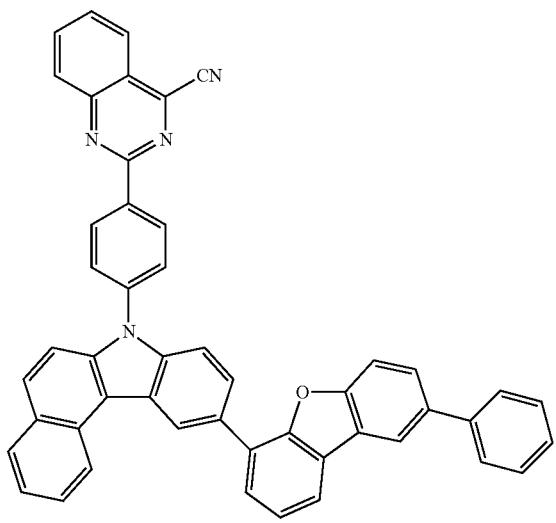
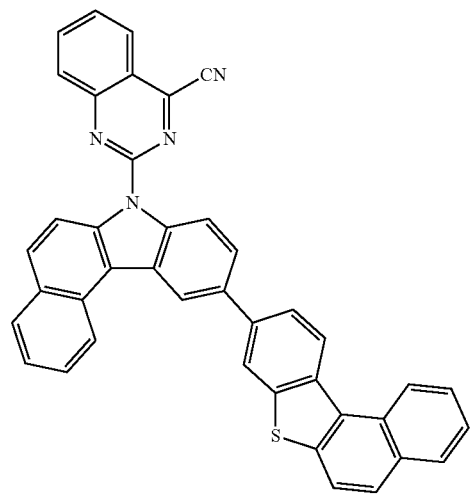
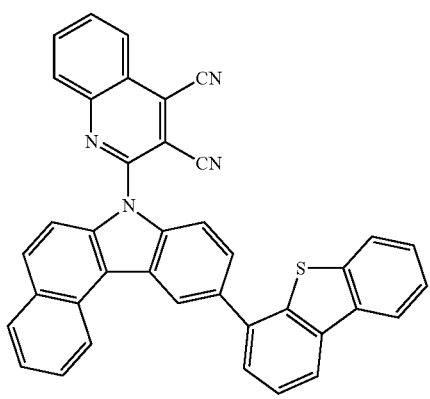
240
-continued
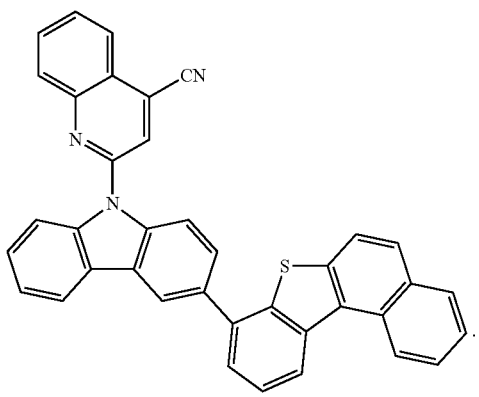 [SMILES: N#Cc1cc(-n2c3ccccc3c3cc(-c4cccc5c4sc4ccc6ccccc6c45)ccc32)nc2ccccc12]
14. The compound of claim 1, wherein the compound represented by Formula 1 is selected from the following structural formulae:
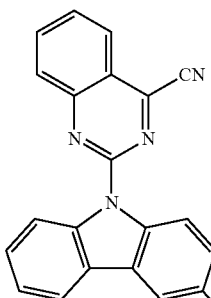
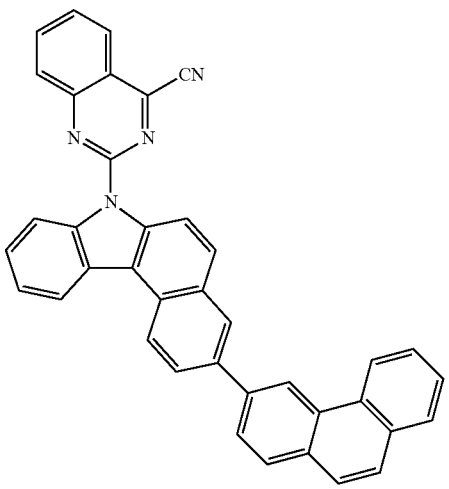

241
-continued
242
-continued
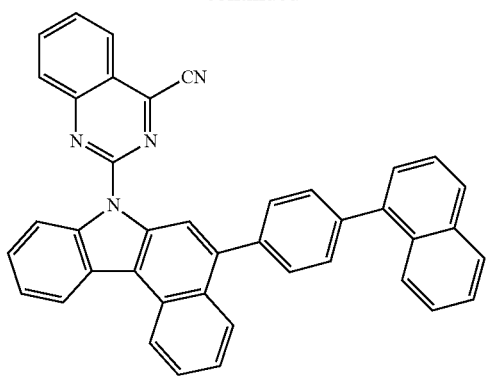
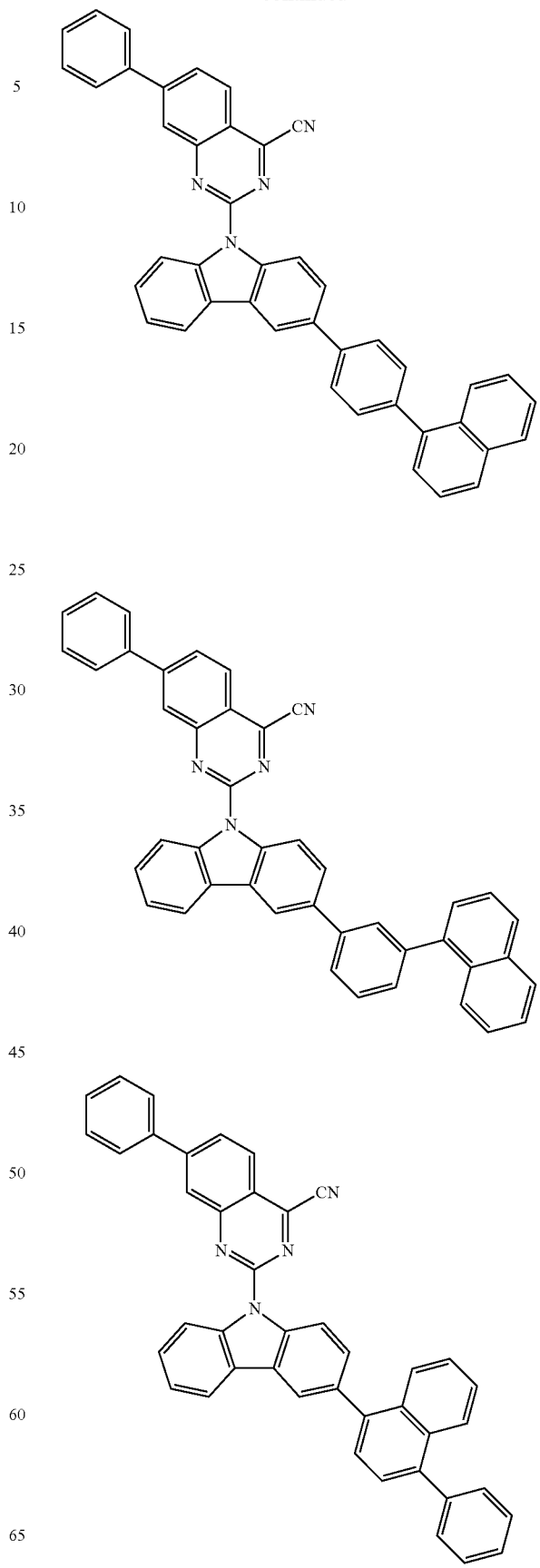

243
-continued
244
-continued
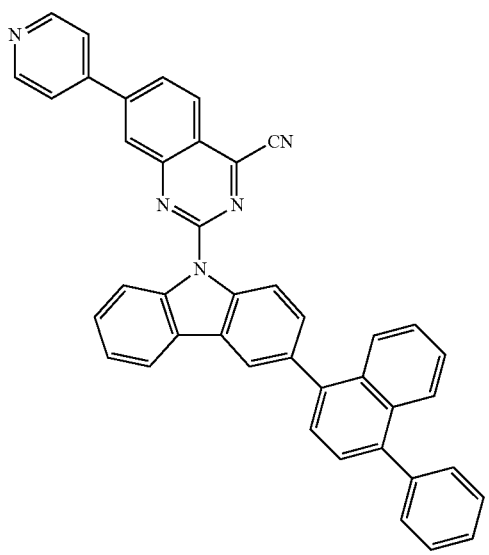
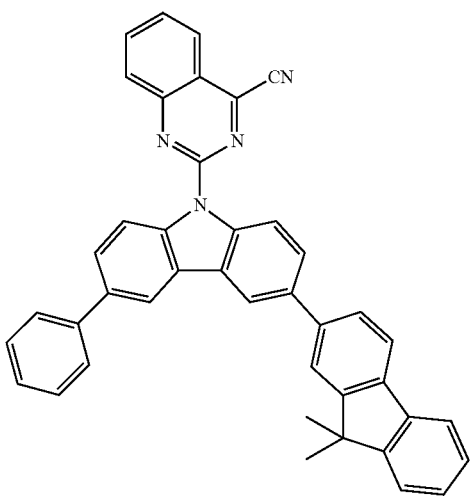
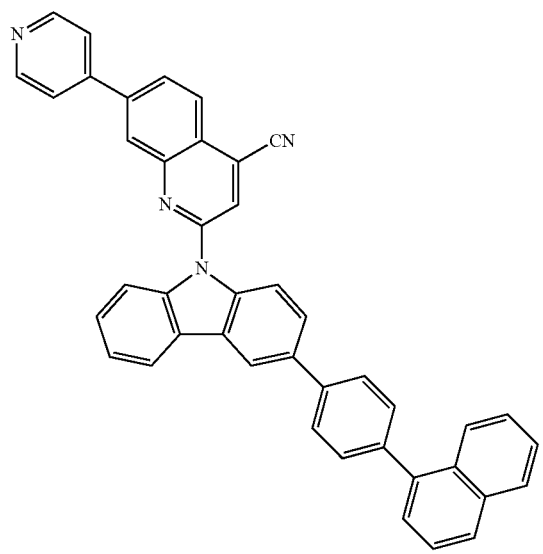
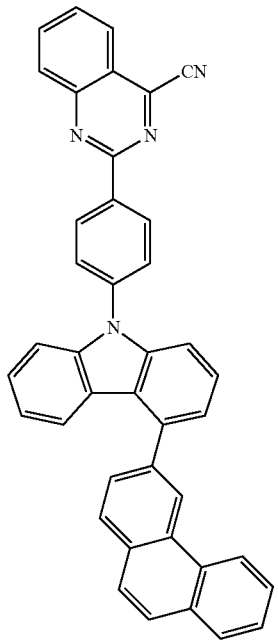

245
-continued
246
-continued
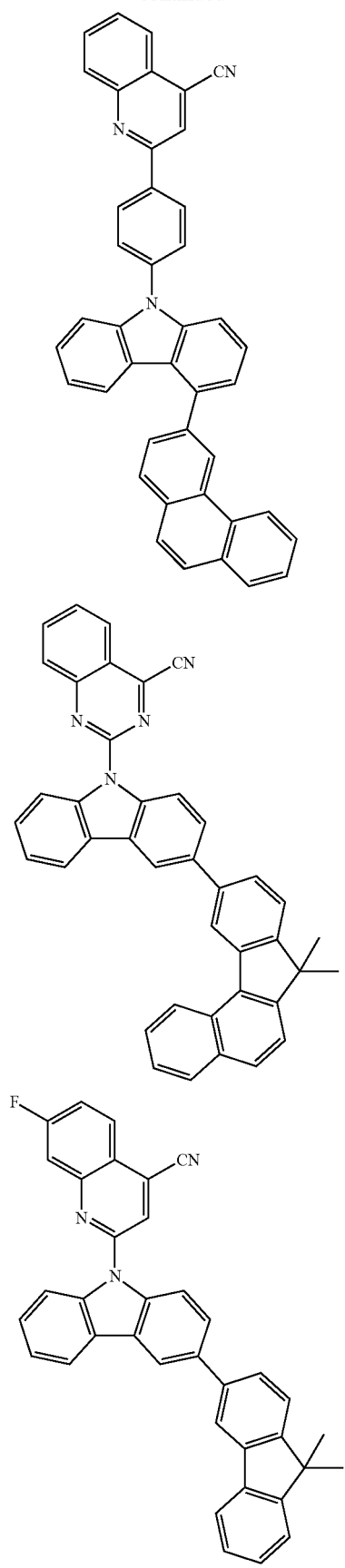
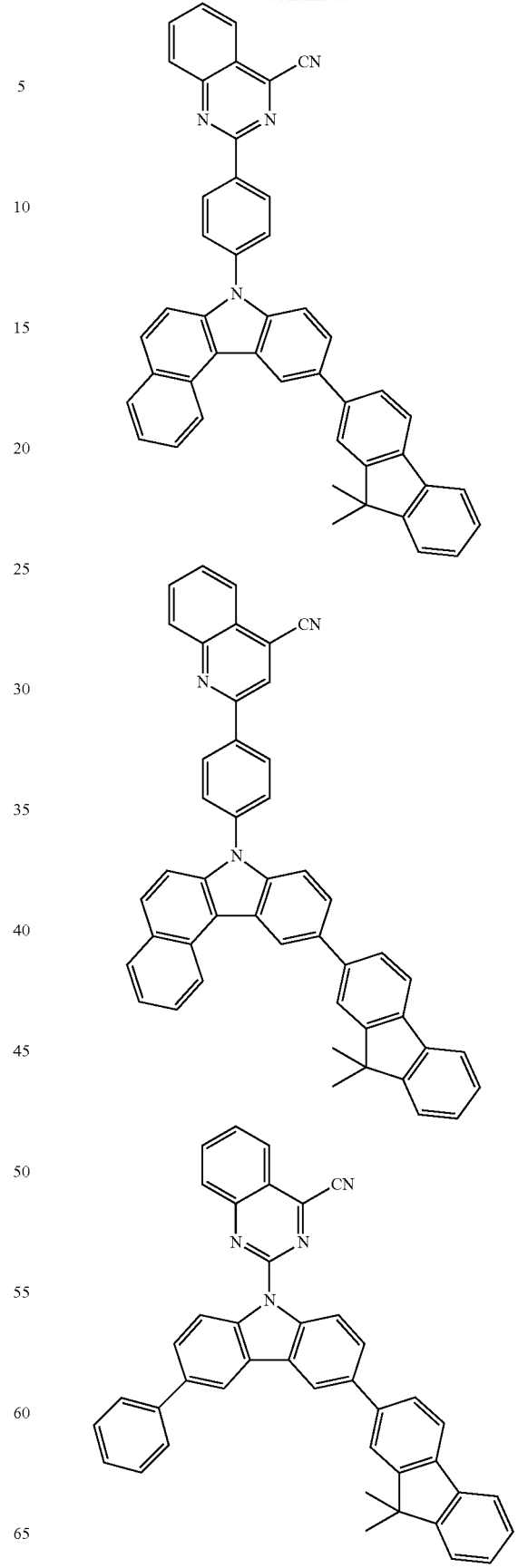

247
-continued
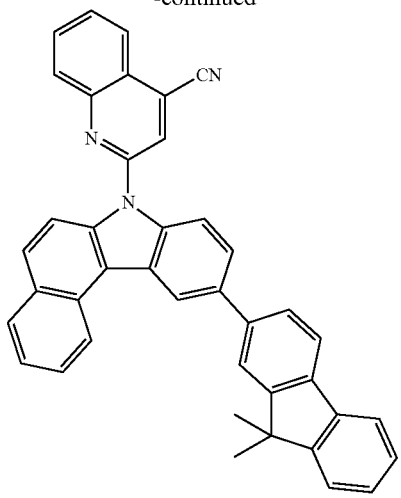
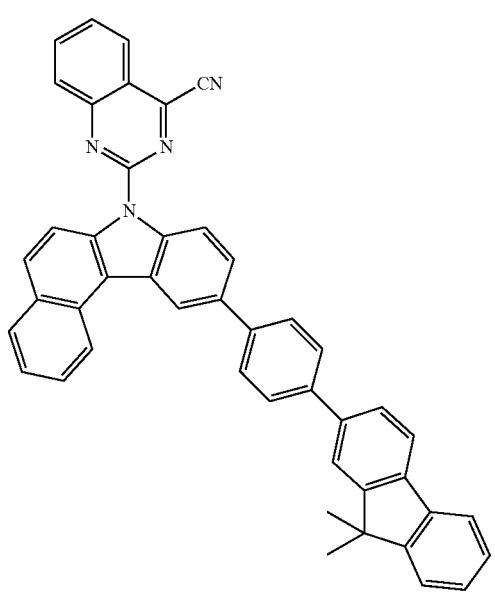
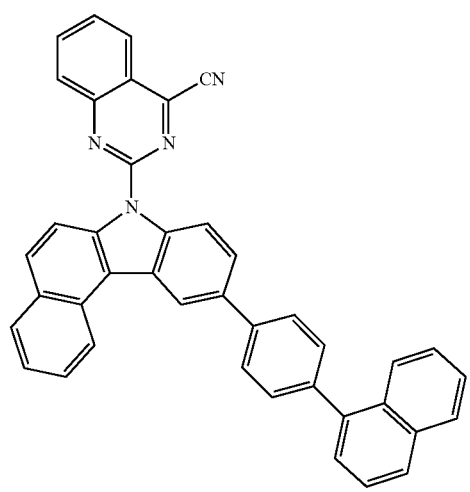
248
-continued
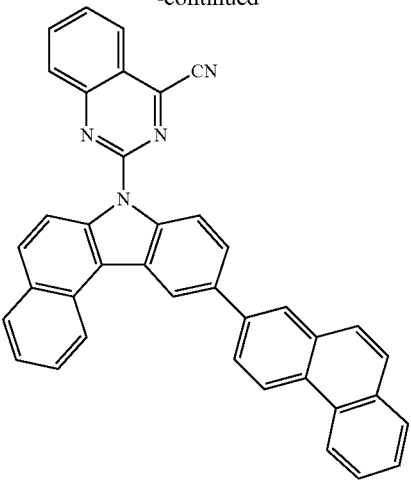
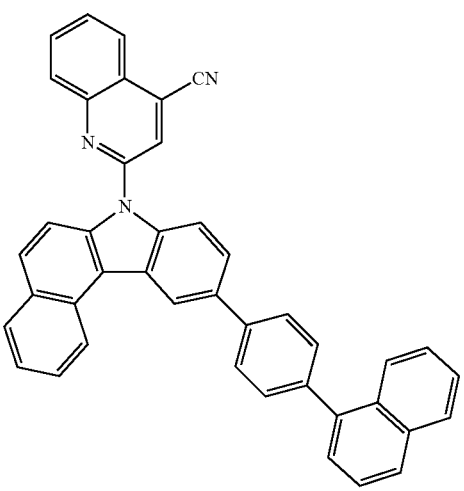
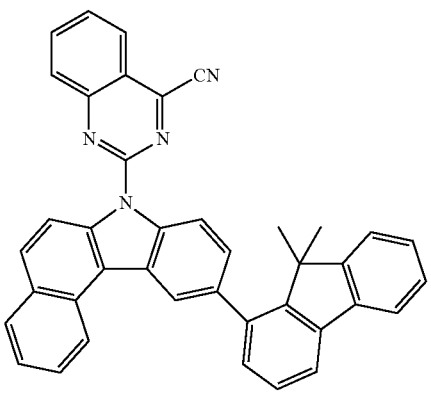

249
-continued
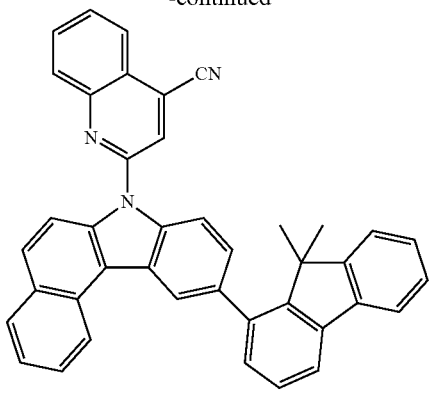
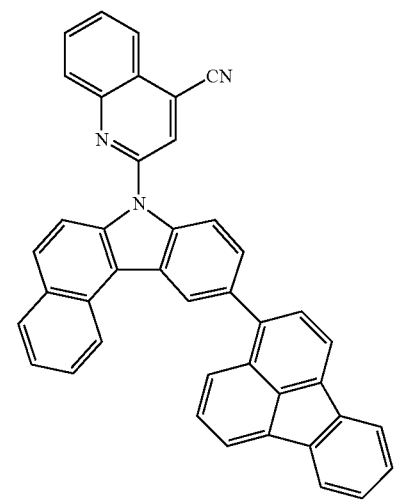
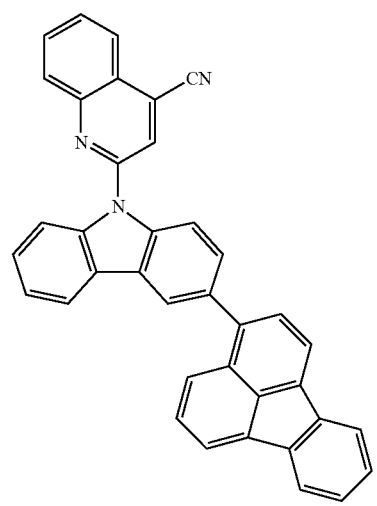
250
-continued
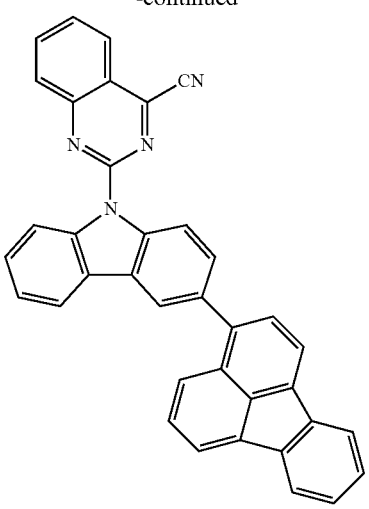
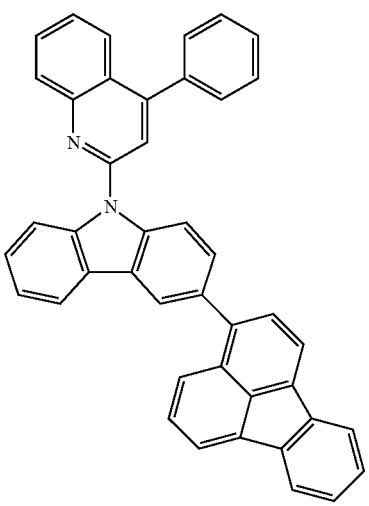
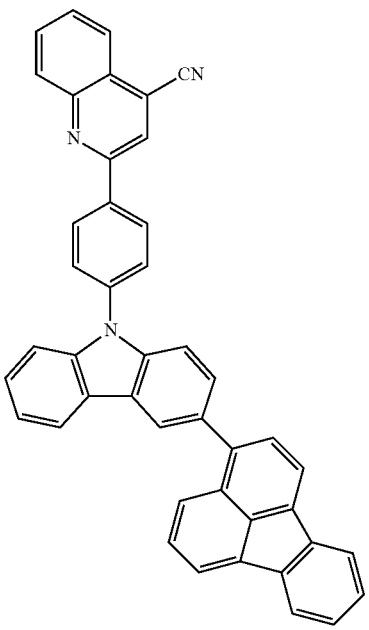

251
-continued
252
-continued
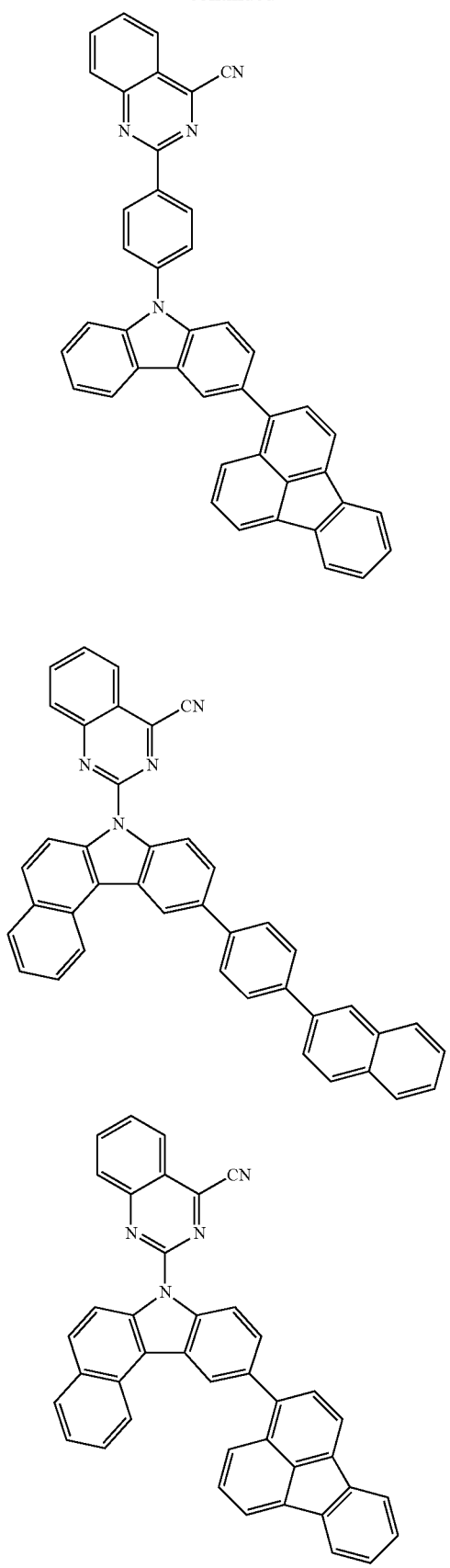
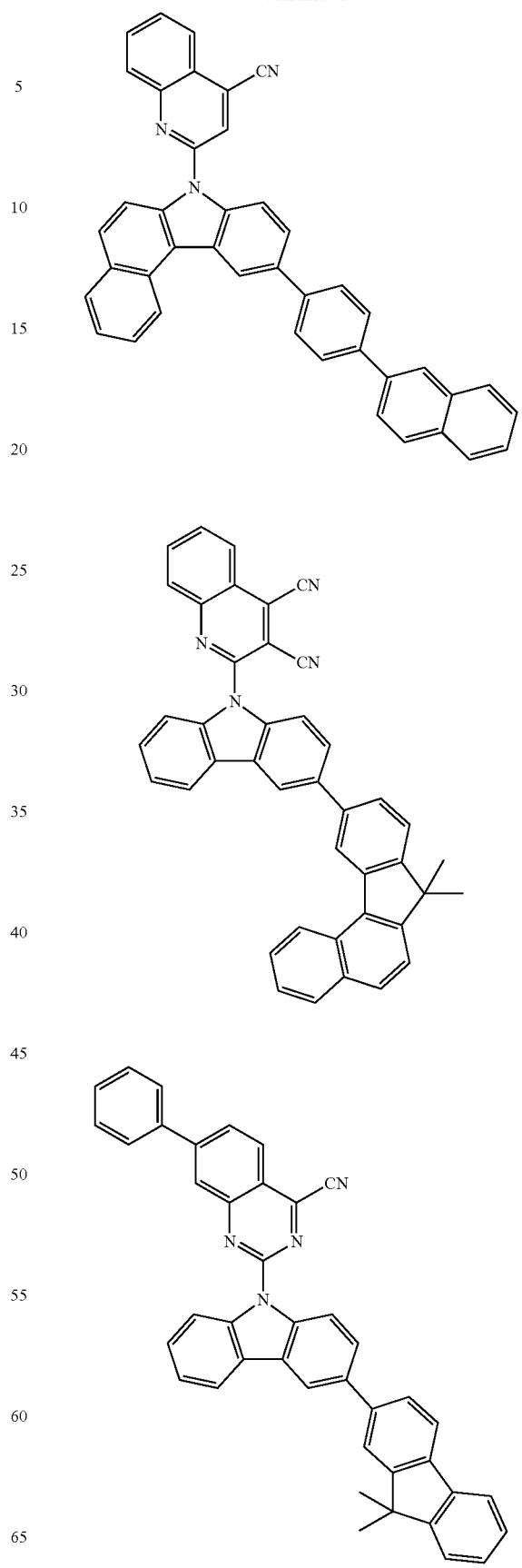

253
-continued

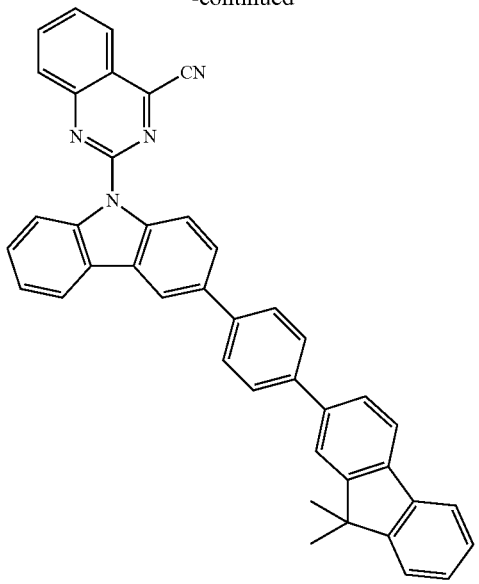

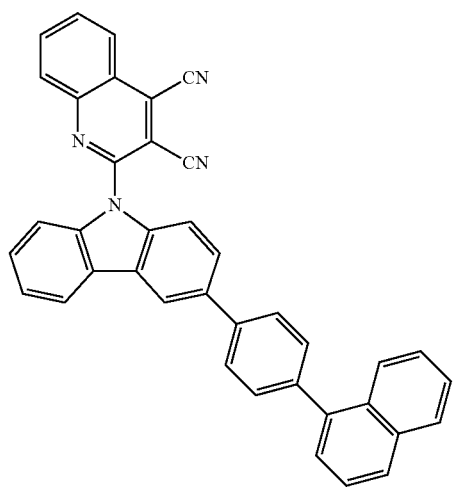

254
-continued

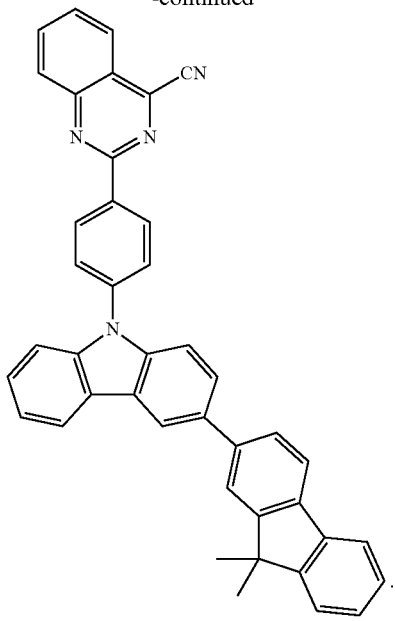

15. An organic electroluminescent device, comprising:
a first electrode;
a second electrode provided to face the first electrode; and
one or more organic material layers provided between the first electrode and the second electrode,
wherein at least one of the organic material layers comprises the compound of claim 1.

16. The organic electroluminescent device of claim 15, wherein the organic material layer comprising the compound is a light emitting layer.

17. The organic electroluminescent device of claim 15, wherein the organic material layer comprising the compound is an electron injection layer, an electron transporting layer, or an electron injection and transporting layer.

18. The organic electroluminescent device of claim 15, wherein the organic material layer comprising the compound is a hole injection layer, a hole transporting layer, or a hole injection and transporting layer.

19. The organic electroluminescent device of claim 15, wherein the compound is a phosphorescent host material or a fluorescent host material.

* * * * *